(12) United States Patent
Quan et al.

(10) Patent No.: US 8,828,983 B2
(45) Date of Patent: Sep. 9, 2014

(54) MACROCYCLES AS FACTOR XIA INHIBITORS

(75) Inventors: Mimi L. Quan, Yardley, PA (US); Carl P. Decicco, New Hope, PA (US); James R. Corte, Lawrenceville, NJ (US); Cailan Wang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/577,666

(22) PCT Filed: Feb. 10, 2011

(86) PCT No.: PCT/US2011/024308
§ 371 (c)(1),
(2), (4) Date: Aug. 8, 2012

(87) PCT Pub. No.: WO2011/100402
PCT Pub. Date: Aug. 18, 2011

(65) Prior Publication Data
US 2012/0309960 A1     Dec. 6, 2012

Related U.S. Application Data

(60) Provisional application No. 61/303,423, filed on Feb. 11, 2010, provisional application No. 61/405,338, filed on Oct. 21, 2010.

(51) Int. Cl.
| C07D 487/06 | (2006.01) |
| C07D 498/06 | (2006.01) |
| C07D 471/08 | (2006.01) |
| C07D 471/18 | (2006.01) |
| C07D 487/08 | (2006.01) |
| C07D 487/18 | (2006.01) |
| C07D 498/08 | (2006.01) |
| A61K 31/395 | (2006.01) |

(52) U.S. Cl.
USPC .......................................... 514/183; 540/460

(58) Field of Classification Search
USPC .......................................... 540/460; 514/183
See application file for complete search history.

(56) References Cited

FOREIGN PATENT DOCUMENTS

| WO | WO 99/15530 | 4/1999 |
| WO | WO 2004/080971 | 9/2004 |
| WO | WO 2004/094372 | 11/2004 |
| WO | WO 2005/099709 | 10/2005 |
| WO | WO 2005/123050 | 12/2005 |
| WO | WO 2005/123680 | 12/2005 |
| WO | WO 2006/076575 | 7/2006 |
| WO | WO 2006/089005 | 8/2006 |
| WO | WO 2007/070816 | 6/2007 |
| WO | WO 2007/070818 | 6/2007 |
| WO | WO 2007/070826 | 6/2007 |
| WO | WO 2008/076805 | 6/2008 |
| WO | WO 2008/079836 | 7/2008 |
| WO | WO 2008/157162 | 12/2008 |
| WO | WO 2009/114677 | 9/2009 |
| WO | WO 2011/100401 | 8/2011 |
| WO | WO 2011/100402 | 8/2011 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/118805 | 8/2013 |
| WO | WO 2013/174937 | 11/2013 |

OTHER PUBLICATIONS

Boger, D.L. et al., "Thermal Atropisomerism of Aglucovancomycin Derivatives: Preparation of (M, M, M)- and (P, M, M)-Aglucovancomycins", J. Am. Chem. Soc., vol. 120, No. 35, pp. 8920-8926 (1998).

Chan, J.C.Y. et al., "The Characterization of Mice with a Targeted Combined Deficiency of Protein C and Factor XI", American Journal of Pathology, vol. 158, No. 2, pp. 469-479 (2001).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor XI deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

(Continued)

Primary Examiner — Bruck Kifle
(74) Attorney, Agent, or Firm — Hong Liu

(57) ABSTRACT

The present invention provides compounds of Formula (I): or a stereoisomer, a tautomer, or a pharmaceutically acceptable salt thereof, wherein all the variables are as defined herein. These compounds are selective factor XIa inhibitors or dual inhibitors of fXIa and plasma kallikrein. This invention also relates to pharmaceutical compositions comprising these compounds and methods of treating thromboembolic and/or inflammatory disorders using the same.

(I)

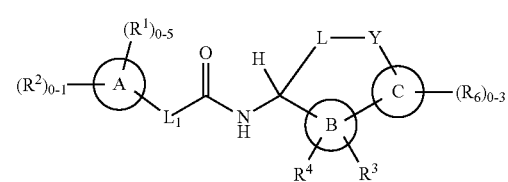

14 Claims, No Drawings

(56) References Cited

OTHER PUBLICATIONS

Meijers, J.C.M. et al., "High Levels of Coagulation Factor XI as a Risk Factor for Venous Thrombosis", The New England Journal of Medicine, vol. 342, pp. 696-701 (2000).

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$ -Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Rosen, E.D. et al., "FXI is Essential for Thrombus Formation Following $FeCl_3$-Induced Injury of the Carotid Artery in the Mouse", Thromb. Haemost., vol. 87, pp. 774-776 (2002).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

MACROCYCLES AS FACTOR XIA INHIBITORS

FIELD OF THE INVENTION

The present invention relates generally to novel macrocyclic compounds, and their analogues thereof, which are inhibitors of factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for antithrombotic therapy.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two, other agent(s).

These and other features of the invention will be set forth in expanded form as the disclosure continues.

DETAILED DESCRIPTION OF THE INVENTION

I. Compounds of the Invention

In a first aspect, the present invention provides, inter alia, a compound of Formula (I):

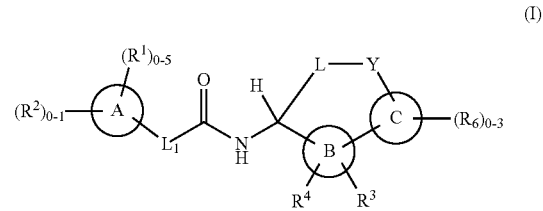

or a stereoisomer, a tautomer, a pharmaceutically acceptable salt, a solvate, or a prodrug thereof, wherein:

ring A is independently a $C_{3-10}$ carbocycle or a 5- to 10-membered heterocycle comprising: carbon atoms and 1-4 heteroatoms selected from N, NH, N($C_{1-4}$ alkyl), O, and $S(O)_p$;

ring B is independently a benzene ring or a 5- to 6-membered heteroaryl comprising: carbon atoms and 1-4 heteroatoms selected from N, O, and $S(O)_p$;

ring C is independently a benzene ring or a 5- to 10-membered heterocycle comprising: carbon atoms and 1-4 heteroatoms selected from N, NH, N($C_{1-4}$ alkyl), O, and $S(O)_p$;

$L_1$ is independently selected from the group consisting of: a bond, —$CHR^5$—, —$CHR^5CHR^5$—, —$CR^5$=$CR^5$—, —C≡C—, —$OCH_2$—, —$CHR^5NH$—, —$CH_2O$—, —$SCH_2$—, —$SO_2CH_2$—, —$CH_2NH$—, and —$CR^5R^5$—;

L is independently selected from the group consisting of: —$C_{1-6}$ alkylene-($C_{3-8}$ carbocycle)-$C_{0-4}$ alkylene-, and —$C_{1-6}$ alkylene-(5- to 6-membered heterocycle)-$C_{0-4}$ alkylene-; wherein said heterocycle comprises: carbon atoms and 1-4 heteroatoms selected from N, NH, N($C_{1-4}$ alkyl), O, and $S(O)_p$; wherein said alkylene is substituted with 0-2 $R^7$ and optionally one or more of the carbon atoms of said alkylene may be replaced by O, S, NH, N($C_{1-4}$ alkyl), CO, CONH, NHCO, OCONH, NHCO$_2$, SO$_2$NH, NHSO$_2$, CON($C_{1-4}$ alkyl), or N($C_{1-4}$ alkyl)CO; wherein said carbocycle and heterocycle are substituted with 0-2 $R^{7a}$;

Y is independently selected from the group consisting of: $CH_2$, CH($C_{1-4}$ alkyl), C($C_{1-4}$ alkyl)$_2$, O, S, NH, N($C_{1-4}$ alkyl), N(CO$_2$($C_{1-4}$ alkyl)), —CONH—, —NHCO—, —CONHCH$_2$—, —CON($C_{1-4}$ alkyl)CH$_2$—, —OCONH—, —OCON($C_{1-4}$ alkyl)-, —NHCONH—, —SO$_2$NH—, —NHCO$_2$—, and —NHSO$_2$—;

$R^1$ is, independently at each occurrence, selected from the group consisting of: halogen, $C_{1-6}$ alkyl, $C_{1-4}$ alkoxy, $C_{1-4}$ alkylthio, OH, $C_{1-4}$haloalkyl, OCH$_2$F, OCHF$_2$, OCF$_3$, CN, NH$_2$, —NH($C_{1-4}$ alkyl), —N($C_{1-4}$ alkyl)$_2$, —CO$_2$($C_{1-4}$ alkyl), —CO($C_{1-4}$ alkyl), —CH$_2$NH$_2$, —CONH$_2$, —CONH ($C_{1-4}$ alkyl), —$CH_2NHCO_2(C_{1-4}$ alkyl), —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —$C(=NH)NH_2$, and phenyl substituted with 0-2 $R^a$;

$R^2$ is independently a 5- to 7-membered heterocycle comprising carbon atoms and 1-4 heteroatoms selected from N, NH, $N(C_{1-4}$ alkyl), O, and $S(O)_p$, wherein said heterocycle is substituted with 0-2 $R^{2a}$;

$R^{2a}$ is, independently at each occurrence, selected from the group consisting of: halogen, $C_{1-4}$ alkyl, —$CH_2OH$, $C_{1-4}$ alkoxy, OH, $CF_3$, $OCF_3$, CN, $NH_2$, $CO_2H$, $CO_2(C_{1-4}$ alkyl), $COC_{1-4}$ alkyl, —$CONH_2$, —$CONH(C_{1-4}$ alkyl), —$CON(C_{1-4}$ alkyl)$_2$, —$SO_2(C_{1-4}$ alkyl), —$SO_2NH_2$, —$SO_2NH(C_{1-4}$ alkyl), and —$SO_2N(C_{1-4}$ alkyl)$_2$;

$R^3$ is independently selected from the group consisting of: H, halogen, OH, $NH_2$, CN, $CF_3$, $C_{1-4}$ alkyl, $C_{1-4}$ alkoxy, —$CH_2OH$, $CO_2H$, $CO_2(C_{1-4}$ alkyl), —$C(O)NH_2$, —$C(O)NH(C_{1-4}$ alkyl), —$C(O)N(C_{1-4}$ alkyl)$_2$, —$CH_2CO_2H$, and $C_{3-6}$ cycloalkyl;

$R^4$ is independently selected from the group consisting of: H, and $C_{1-4}$ alkyl;

$R^5$ is, independently at each occurrence, selected from the group consisting of: H, halogen, OH, and $C_{1-4}$ alkyl;

$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, $NH(C_{1-4}$alkyl), —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2CH_2CH(C_{1-4}$alkyl)$O(C_{1-4}$ alkyl), —$NHCO_2(CH_2)_2OH$, —$NHCO_2(CH_2)_2NH_2$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2NH(CH_2)_2OH$, —$SO_2NH(CH_2)_2O(C_{1-4}$ alkyl), —$C(O)NH(CH_2)_2O(C_{1-4}$alkyl), —$CONH_2$, —$CONH(C_{1-4}$ alkyl), —$CON(C_{1-4}$ alkyl)$_2$, —$CH_2CONH_2$, and

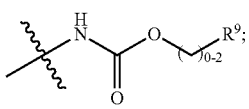

$R^7$ and $R^{7a}$ are, independently at each occurrence, selected from the group consisting of: halogen, OH, $NH_2$, $CH_2NH_2$, $CH_2F$, $CHF_2$, $CF_3$, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2O(CH_2)_{1-4}O(C_{1-4}$ alkyl), $CO_2H$, $CO_2(C_{1-4}$ alkyl), $CH_2CO_2H$, $CH_2CO_2(C_{1-4}$ alkyl), $CONH_2$, $CONH(C_{1-4}$ alkyl), $CON(C_{1-4}$ alkyl)$_2$, —$OCO(C_{1-4}$ alkyl), —$CON(C_{1-4}$ alkyl)$(CH_2)_2N(C_{1-4}$alkyl)$_2$, $C_{1-4}$ alkyl, —$(CO)_{0-1}(CH_2)_{0-1}$—$C_{3-6}$ carbocycle, and —$(CO)_{0-1}(CH_2)_{0-1}$-(4- to 6-membered heterocycle comprising carbon atoms and 1-4 heteroatoms selected from N, NH, $N(C_{1-4}$ alkyl), O, and $S(O)_p$; wherein said carbocycle and heterocycle are substituted with 0-2 $R^8$;

$R^8$ is, independently at each occurrence, selected from the group consisting of: halogen, OH, $CHF_2$, $CF_3$, $C_{1-4}$ alkoxy, $CH_2OH$, $CO_2H$, $CO_2(C_{1-4}$ alkyl), $CONH_2$, and $C_{1-4}$ alkyl;

$R^9$ is a 4- to 6-membered heterocycle comprising: carbon atoms and 1-4 heteroatoms selected from N, NH, $N(C_{1-4}$ alkyl), $N(CO_2(C_{1-4}$ alkyl)), O, and $S(O)_p$;

$R^a$ is, independently at each occurrence, selected from the group consisting of: halogen, OH, $CF_3$, $C_{1-4}$ alkoxy, and $C_{1-4}$ alkyl;

p is, independently at each occurrence, selected from the group consisting of: 0, 1, and 2.

In a second aspect, the present invention provides compounds of Formula (I), or a stereoisomer, a tautomer, a pharmaceutically acceptable salt, a solvate, or a prodrug thereof, within the scope of the first aspect, wherein:

ring A is independently a 6-membered carbocycle, a 9- to 10-membered carbocycle, or a 5- to 10-membered heterocycle comprising: carbon atoms and 1-3 heteroatoms selected from N, NH, $N(C_{1-4}$ alkyl), O, and $S(O)_p$;

ring B is independently selected from the group consisting of: imidazole, oxazole, oxadiazole, triazole, pyridine, pyridazine, pyrimidine, and benzene; and ring C is independently selected from the group consisting of: benzene, pyridine, indazole, indole, benzimidazole, quinoline, isoquinoline and quinazoline.

In a third aspect, the present invention provides compounds of Formula (I), or a stereoisomer, a tautomer, a pharmaceutically acceptable salt, a solvate, or a prodrug thereof, within the scope of the first or second aspect, wherein:

ring A is independently selected from the group consisting of: benzene, cyclohexane, indane, tetrahydronaphthalene, naphthalene, dihydroisoxazole, isoxazole, pyrazole, imidazole, triazole, piperidine, indazole, indole, benzimidazole, quinoline, isoquinoline, tetrahydroquinoline, and tetrahydroisoquinoline;

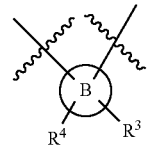

is independently selected from the group consisting of:

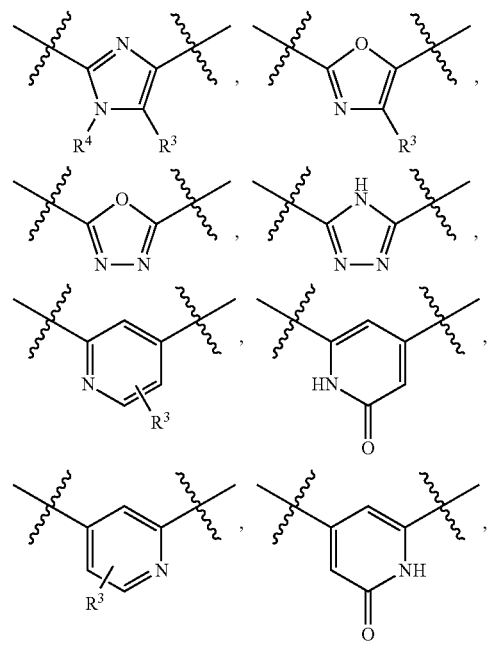

-continued
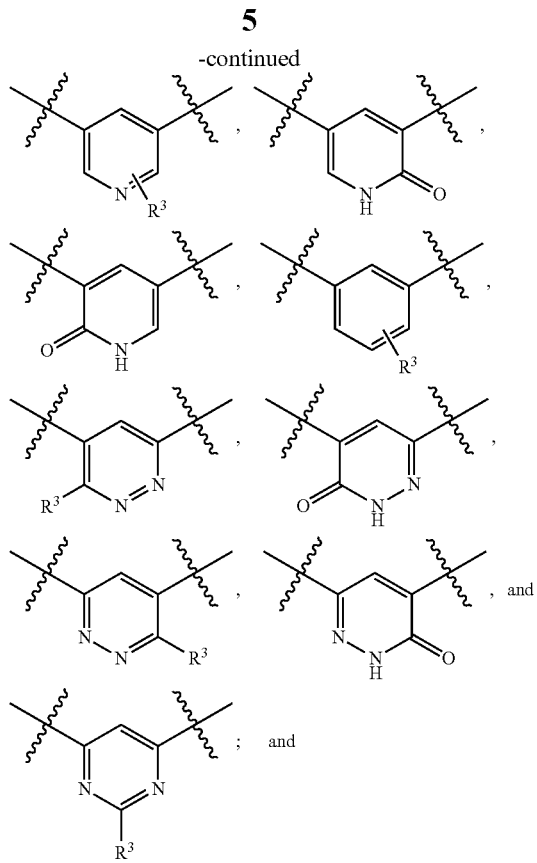
and
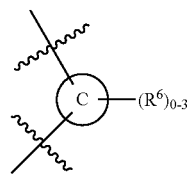
is independently selected from the group consisting of:
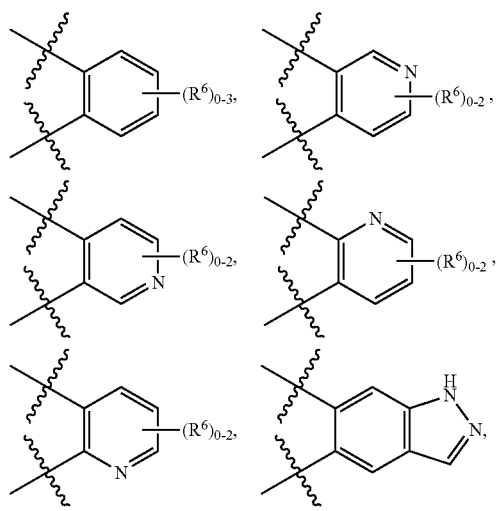
-continued
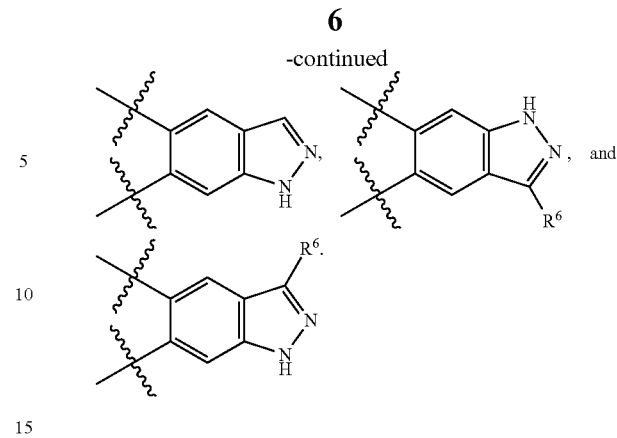
In a fourth aspect, the present invention provides compounds of Formula (II):
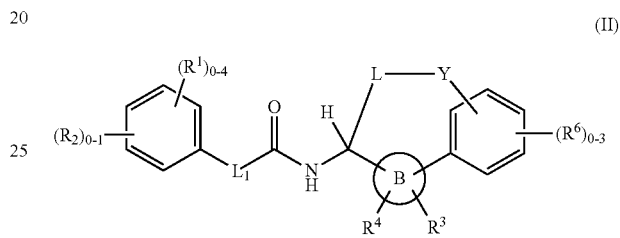
(II)
or a stereoisomer, a tautomer, a pharmaceutically acceptable salt, a solvate, or a prodrug thereof, wherein:
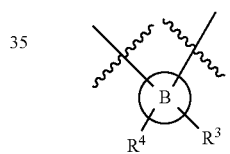
is independently selected from the group consisting of:
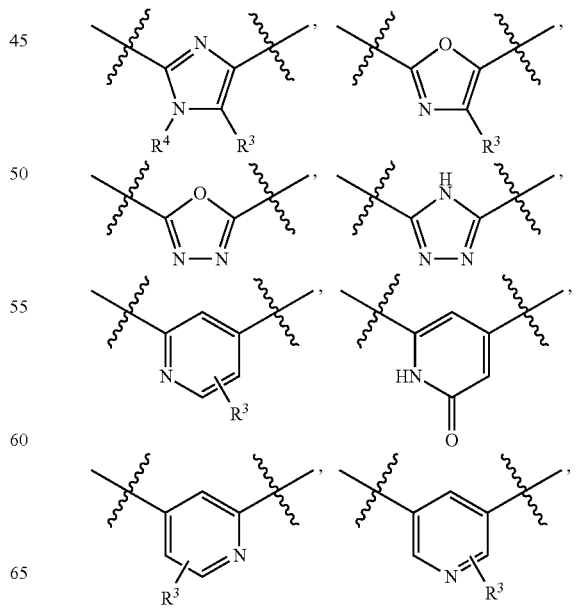

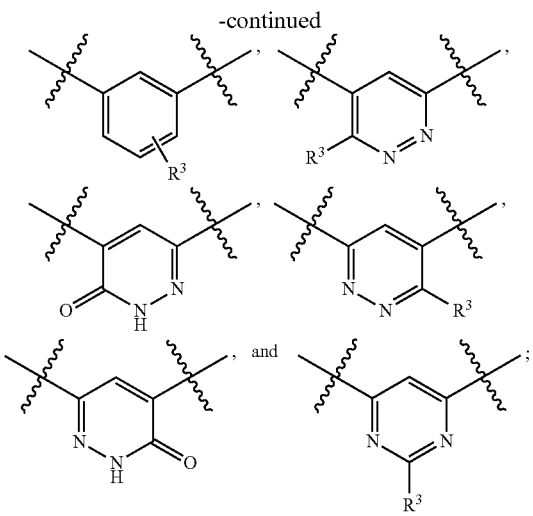

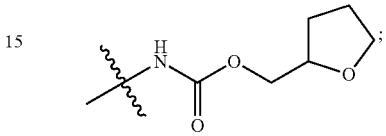

L₁ is independently selected from the group consisting of: a bond, —CHR⁵CHR⁵—, —CR⁵═CHR⁵—, —C≡C—, —OCH₂—, —CHR⁵NH—, —CH₂O—, —SCH₂—, —SO₂CH₂—, —CH₂NH—, and —CR⁵R⁵—;

L is independently selected from the group consisting of: —C₁₋₆ alkylene-(C₃₋₈ carbocycle)-C₀₋₄ alkylene-, and —C₁₋₆ alkylene-(5- to 6-membered heterocycle)-C₀₋₄ alkylene-; wherein said heterocycle comprises: carbon atoms and 1-4 heteroatoms selected from N, NH, N(C₁₋₄ alkyl), O, and S(O)$_p$; wherein said alkylene is substituted with 0-2 R⁷ and optionally one or more of the carbon atoms of said alkylene may be replaced by O, S, NH, N(C₁₋₄ alkyl), CO, CONH, NHCO, OCONH, SO₂NH, or CON(C₁₋₄ alkyl); wherein said carbocycle and heterocycle are substituted with 0-2 R⁷ᵃ;

Y is independently selected from the group consisting of: CH₂, CH(C₁₋₄ alkyl), C(C₁₋₄ alkyl)₂, O, S, NH, N(C₁₋₄ alkyl), N(CO₂(C₁₋₄ alkyl)), —CONH—, —NHCO—, —CONHCH₂—, —CON(C₁₋₄ alkyl)CH₂—, —OCONH—, —OCON(C₁₋₄ alkyl)-, —NHCONH—, and —SO₂NH—;

R¹ is, independently at each occurrence, selected from the group consisting of: halogen, C₁₋₆ alkyl, C₁₋₄ alkoxy, C₁₋₄ alkylthio, OH, CH₂F, CHF₂, CF₃, OCH₂F, OCHF₂, OCF₃, CN, NH₂, NH(C₁₋₄ alkyl)₂, N(C₁₋₄ alkyl)₂, CO₂(C₁₋₄ alkyl), CO(C₁₋₄ alkyl), —OCH₂CO₂H, —CH₂NH₂, —CONH₂, —CONH(C₁₋₄ alkyl), —CH₂NHCO₂(C₁₋₄ alkyl), —SO₂NH₂, and —C(═NH)NH₂;

R² is independently a 5- to 6-membered heterocycle comprising carbon atoms and 1-4 heteroatoms selected from N, NH, O, and S(O)$_p$, wherein said heterocycle is substituted with 0-2 R²ᵃ;

R²ᵃ is, independently at each occurrence, selected from the group consisting of: halogen, C₁₋₄ alkyl, —CH₂OH, C₁₋₄ alkoxy, OH, CF₃, OCF₃, CN, NH₂, CO₂H, CO₂(C₁₋₄ alkyl), COC₁₋₄ alkyl, —CONH₂, —CONH(C₁₋₄ alkyl), and —CON(C₁₋₄ alkyl)₂;

R³ is independently selected from the group consisting of: H, halogen, OH, NH₂, CN, CF₃, C₁₋₄ alkyl, C₁₋₄ alkoxy, —CH₂OH, CO₂H, CO₂(C₁₋₄ alkyl), —C(O)NH₂, —C(O)NH (C₁₋₄ alkyl), —C(O)N(C₁₋₄ alkyl)₂, and —CH₂CO₂H;

R⁴ is independently selected from the group consisting of: H and C₁₋₄ alkyl;

R⁵ is, independently at each occurrence, selected from the group consisting of: H, halogen, OH, and C₁₋₄ alkyl;

R⁶ is, independently at each occurrence, selected from the group consisting of: halogen, C₁₋₄ alkyl, CN, OH, CF₃, CO₂H, CO₂(C₁₋₄ alkyl), —CH₂CO₂H, —(CH₂)₂CO₂H, —CH₂CO₂(C₁₋₄ alkyl), —(CH₂)₂CO₂(C₁₋₄ alkyl), NH₂, NH(C₁₋₄ alkyl), —CH₂NH₂, —NHCO(C₁₋₄ alkyl), —NHCO₂(C₁₋₄ alkyl), —NHCO₂(CH₂)₂O(C₁₋₄ alkyl), —NHCO₂(CH₂)₃O(C₁₋₄ alkyl), —NHCO₂CH₂CH(C₁₋₄ alkyl)O(C₁₋₄ alkyl), —NHCO₂(CH₂)₂OH, —NHCO₂(CH₂)₂NH₂, —NHCO₂CH₂CO₂H, —CH₂NHCO₂(C₁₋₄ alkyl), —NHC(O)NH(C₁₋₄ alkyl), —NHC(O)N(C₁₋₄ alkyl)₂, —NHSO₂(C₁₋₄ alkyl), —SO₂NH(CH₂)₂OH, —SO₂NH(CH₂)₂O(C₁₋₄ alkyl), —C(O)NH(CH₂)₂O(C₁₋₄ alkyl), CONH₂, CONH(C₁₋₄ alkyl), CON(C₁₋₄ alkyl)₂, —CH₂CONH₂, and

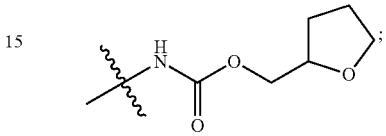

R⁷ and R⁷ᵃ are, independently at each occurrence, selected from the group consisting of: halogen, OH, CHF₂, CF₃, C₁₋₄ alkoxy, CH₂OH, CH₂O(C₁₋₄ alkyl), CO₂H, CO₂(C₁₋₄ alkyl), CH₂CO₂H, CH₂CO₂(C₁₋₄ alkyl), CONH₂, CONH(C₁₋₄ alkyl), CON(C₁₋₄ alkyl)₂, —OCO(C₁₋₄ alkyl), —CON(C₁₋₄ alkyl)(CH₂)₂N(C₁₋₄ alkyl)₂, C₁₋₄ alkyl, and —(CO)₀₋₁-(4- to 6-membered heterocycle comprising carbon atoms and 1-4 heteroatoms selected from N, NH, N(C₁₋₄ alkyl), O, and S(O)$_p$; wherein said heterocycle is substituted with 0-2 R⁸;

R⁸ is, independently at each occurrence, selected from the group consisting of: halogen, OH, CHF₂, CF₃, C₁₋₄ alkoxy, and C₁₋₄ alkyl; and p is, independently at each occurrence, selected from the group consisting of: 0, 1, and 2.

In a fifth aspect, the present invention provides compounds of Formula (IIa) or Formula (IIb):

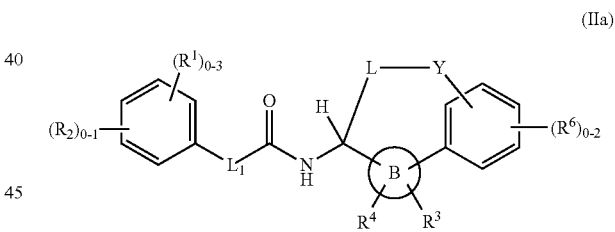

(IIa)

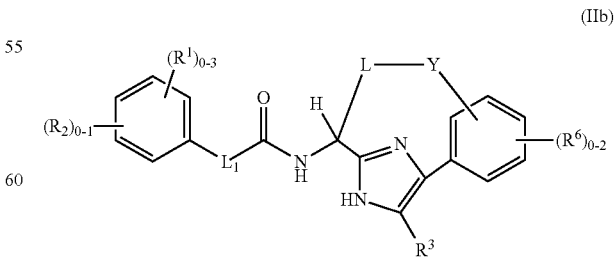

(IIb)

or a stereoisomer, a tautomer, a pharmaceutically acceptable salt, a solvate, or a prodrug thereof, within the scope of the fourth aspect.

In a sixth aspect, the present invention provides compounds of Formula (IIc) or Formula (IId):

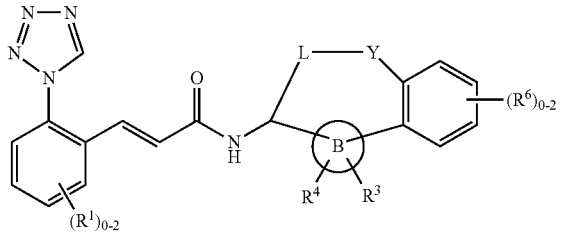
(IIc)

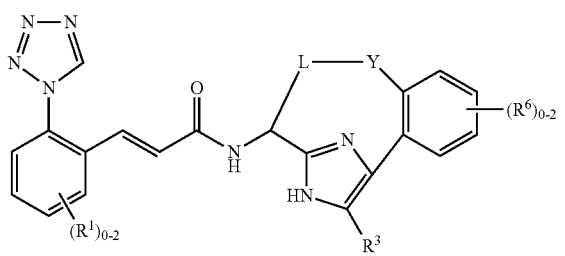
(IId)

or a stereoisomer, a tautomer, a pharmaceutically acceptable salt, a solvate, or a prodrug thereof, within the scope of the fourth aspect.

In a seventh aspect, the present invention provides compounds of Formula (IIe) or Formula (IIf):

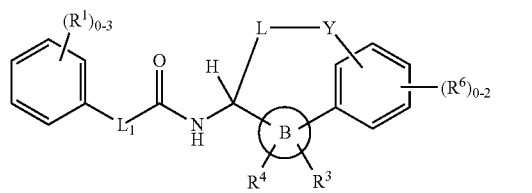
(IIe)

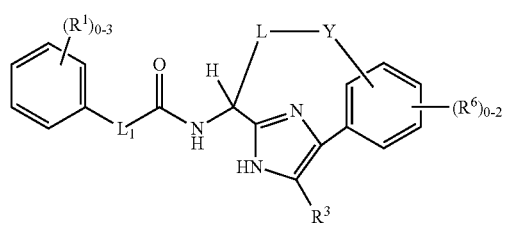
(IIf)

or a stereoisomer, a tautomer, a pharmaceutically acceptable salt, a solvate, or a prodrug thereof, within the scope of the fourth aspect.

In an eighth aspect, the present invention includes compounds of Formula (I), (II), (IIa), (IIb), (IIc), (IId), (IIe) or (IIf) a stereoisomer, a tautomer, a pharmaceutically acceptable salt, a solvate, or a prodrug thereof, within the scope of any of the above aspects, wherein:

$L_1$ is independently selected from the group consisting of: a bond, —$CH_2CH_2$—, —CH═CH—, —C(Me)═CH—, —C≡C—, and —$CH_2NH$—;

L is independently selected from the group consisting of: —$(CH_2)_{1-2}$-(phenylene)-$(CH_2)_{0-3}$—, —$CH_2$—O— $(CH_2)_{1-4}$-(phenylene)-$(CH_2)_{0-3}$—, —$(CH_2)_{1-2}$-(phenylene)-$CONH(CH_2)_{0-2}$—, —$(CH_2)_{1-2}$-phenylene-$CON(C_{1-4}$ alkyl)$(CH_2)_{0-2}$—, —$(CH_2)_{1-2}$-(pyridinylene)-$(CH_2)_{0-3}$—, —$CH_2$-pyrimidinylene-$(CH_2)_{0-3}$—,

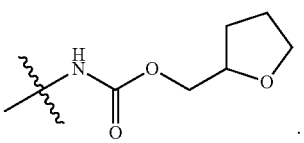 [SMILES: *NC(=O)OCC1CCCO1]
, and wherein each ring moiety is substituted with 0-2 $R^{7a}$;

Y is independently selected from the group consisting of: $CH_2$, $CH(C_{1-4}$ alkyl), $C(C_{1-4}$ alkyl)$_2$, O, S, NH, N($C_{1-4}$ alkyl), N($CO_2(C_{1-4}$ alkyl)), —CONH—, —NHCO—, —CONHCH$_2$—, —CON($C_{1-4}$ alkyl)$CH_2$—, —OCONH—, —NHCONH—, and —$SO_2NH$—;

$R^1$ is, independently at each occurrence, selected from: halogen, CN, OH, $CH_2F$, $CHF_2$, $CF_3$, $OCH_2F$, $OCHF_2$, $OCF_3$, $C_{1-4}$ alkyl, $C_{1-4}$ alkoxy, $CO(C_{1-4}$ alkyl), $NH_2$, $NH(C_{1-4}$ alkyl)$_2$, $N(C_{1-4}$ alkyl)$_2$, —C(═NH)$NH_2$, —C(O)$NH_2$, —$CH_2NH_2$, —$CH_2NHCO_2(C_{1-4}$ alkyl), and —$SO_2NH_2$;

$R^3$ is independently selected from the group consisting of: H, halogen, OH, $NH_2$, CN, $CF_3$, $C_{1-4}$ alkyl, $C_{1-4}$ alkoxy, —$CH_2OH$, $CO_2H$, $CO_2(C_{1-4}$ alkyl), —C(O)$NH_2$, —C(O)NH ($C_{1-4}$ alkyl), —C(O)N($C_{1-4}$ alkyl)$_2$, and —$CH_2CO_2H$; and $R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2CH_2CH(C_{1-4}$ alkyl)$O(C_{1-4}$ alkyl), —$NHCO_2(CH_2)_2OH$, —$NHCO_2(CH_2)_2NH_2$, —$NHCO_2CH_2CO_2H$, —$CH_2NHCO_2(C_{1-4}$ alkyl), —NHC(O)NH($C_{1-4}$ alkyl), —NHC(O)N($C_{1-4}$ alkyl)$_2$, —$NHSO_2$ ($C_{1-4}$ alkyl), —$SO_2NH(CH_2)_2OH$, —$SO_2NH(CH_2)_2O(C_{1-4}$ alkyl), $CONH_2$, $CONH(C_{1-4}$ alkyl), $CON(C_{1-4}$ alkyl)$_2$, and In a ninth aspect, the present invention includes compounds of Formula (I), (II), (IIa), (IIb), (IIc), (IId), (IIe) or (IIf) or a stereoisomer, a tautomer, a pharmaceutically acceptable salt, a solvate, or a prodrug thereof, within the scope of any of the above aspects, wherein:

$L_1$ is independently selected from the group consisting of: a bond, —$CH_2CH_2$— and —CH═CH—;

$R^1$ is, independently at each occurrence, selected from the group consisting of: halogen, CN, $C_{1-4}$ alkyl, OH, $C_{1-4}$ alkoxy, $CH_2F$, $CHF_2$, $CF_3$, $OCH_2F$, $OCHF_2$, $OCF_3$, $CO(C_{1-4}$ alkyl), $NH_2$, $NH(C_{1-4}$ alkyl)$_2$, $N(C_{1-4}$ alkyl)$_2$, —$CH_2NH_2$, —$CH_2NHCO_2(C_{1-4}$ alkyl), and —C(═NH)$NH_2$;

$R^3$ is independently selected from the group consisting of: H, halogen, CN, $CF_3$, $CO_2H$, $CO_2(C_{1-4}$ alkyl$)$, and $C_{1-4}$ alkyl; and $R^6$ is, independently at each occurrence, selected from the group consisting of: halogen, $C_{1-4}$ alkyl, CN, OH, $CF_3$, $CO_2H$, $CO_2(C_{1-4}$ alkyl$)$, —$CH_2CO_2H$, —$CH_2CO_2(C_{1-4}$ alkyl$)$, $NH_2$, —$CH_2NH_2$, —$NHCO(C_{1-4}$ alkyl$)$, —$NHCO_2(C_{1-4}$ alkyl$)$, —$CH_2NHCO_2(C_{1-4}$ alkyl$)$, —$CONH_2$, —$NHCO_2(CH_2)_2OH$, —$NHCO_2(CH_2)_2O(C_{1-4}$ alkyl$)$, —$NHCO_2CH_2CO_2H$, —$NHCO_2CH_2CH(C_{1-4}$ alkyl$)O(C_{1-4}$ alkyl$)$, and

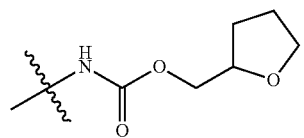

In a tenth aspect, the present invention includes compounds of Formula (I), (II), (IIa), (IIb), (IIc), (IId), (IIe) or (IIf) or a stereoisomer, a tautomer, a pharmaceutically acceptable salt, a solvate, or a prodrug thereof, within the scope of any one of the above aspects, wherein:

L is independently selected from the group consisting of: —$CH_2$-phenylene-$(CH_2)_{0-3}$—, —$CH_2$—O—$(CH_2)_{2-4}$-phenylene-$(CH_2)_{0-1}$—, —$CH_2$-phenylene-$CONH(CH_2)_{0-2}$—, —$CH_2$-phenylene-$CON(C_{1-4}$ alkyl$)(CH_2)_{0-2}$—, —$CH_2$-pyridinylene-$(CH_2)_{0-3}$—, —$CH_2$-pyrimidinylene-$(CH_2)_{0-3}$—,

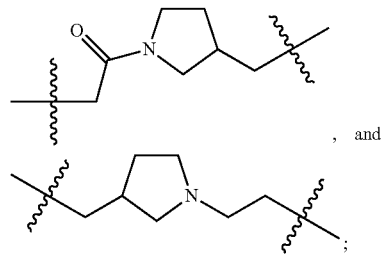

wherein each ring moiety is substituted with 0-1 $R^{7a}$;

Y is independently selected from the group consisting of: $CH_2$, O, NH, $N(C_{1-4}$ alkyl$)$, $N(CO_2(C_{1-4}$ alkyl$))$, —CONH—, —NHCO—, —$CONHCH_2$—, —$CON(C_{1-4}$ alkyl$)CH_2$—, —OCONH—, —NHCONH—, and —$SO_2NH$—; and $L_1$ is independently selected from the group consisting of: a bond and —CH=CH—;

$R^1$ is, independently at each occurrence, selected from the group consisting of: halogen, $C_{1-4}$ alkyl, OH, $C_{1-4}$ alkoxy, $CO(C_{1-4}$ alkyl$)$, CN, $CH_2F$, $CHF_2$, $OCHF_2$, $NH_2$, $N(C_{1-4}$ alkyl$)_2$, —$CH_2NH_2$, —$CH_2NHCO_2(C_{1-4}$ alkyl$)$, and —C(=NH)$NH_2$;

$R^3$ is independently selected from the group consisting of: H, halogen, $C_{1-4}$ alkyl, and CN;

$R^6$ is, independently at each occurrence, selected from the group consisting of: halogen, $NH_2$, $CO_2H$, $CO_2(C_{1-4}$ alkyl$)$, $CONH_2$, $CONH(C_{1-4}$ alkyl$)$, $CON(C_{1-4}$ alkyl$)_2$, —$NHCO_2(C_{1-4}$ alkyl$)$, —$CH_2NHCO_2(C_{1-4}$ alkyl$)$, —$NHCO_2CH_2CO_2H$, —$NHCO_2(CH_2)_2OH$, —$NHCO_2(CH_2)_2O(C_{1-4}$ alkyl$)$, —$NHCO_2CH_2CH(C_{1-4}$ alkyl$)O(C_{1-4}$ alkyl$)$, and

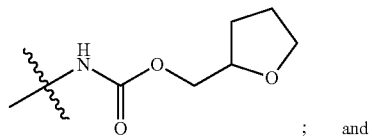 [SMILES: *NC(=O)OCC1CCCO1 ; ";"]

; and $R^{7a}$ is independently selected from the group consisting of: halogen, $C_{1-4}$ alkyl, and $N(C_{1-4}$ alkyl$)_2$.

In an 11th aspect, the present invention includes compounds of Formula (III) or Formula (IIIa):

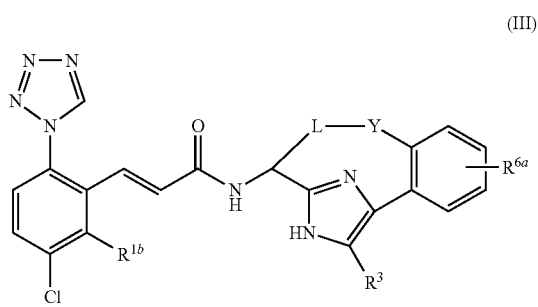

(III)

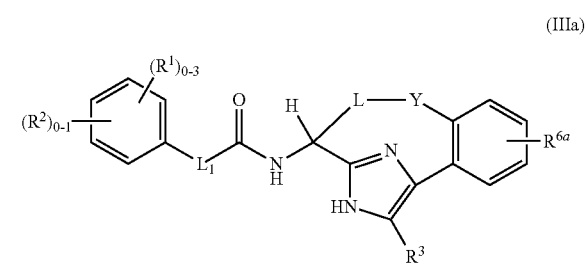

(IIIa)

or a stereoisomer, a tautomer, a pharmaceutically acceptable salt, a solvate, or a prodrug thereof, wherein:

L is independently selected from the group consisting of:

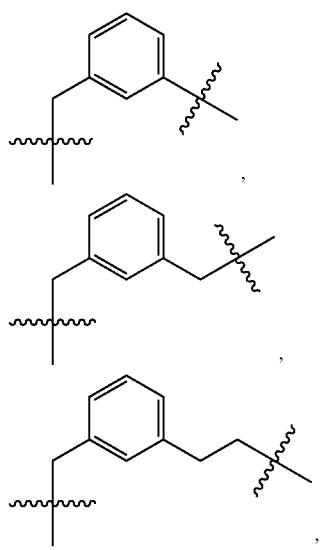

-continued

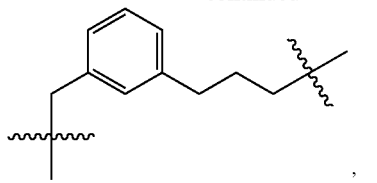,

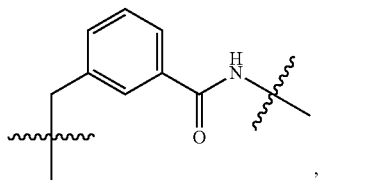,

,

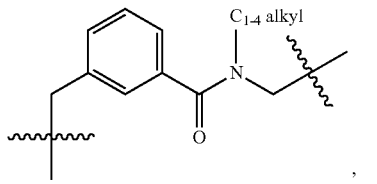,

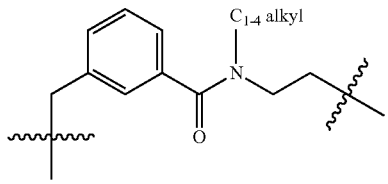,

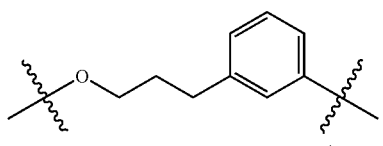,

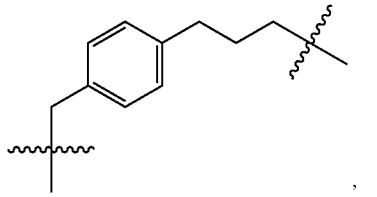,

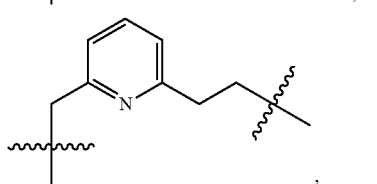,

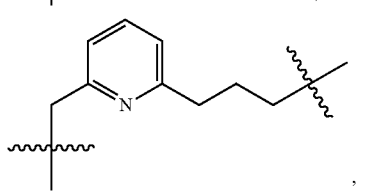,

-continued

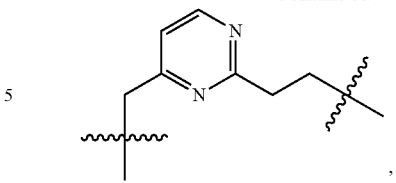,

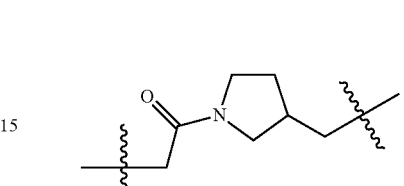, and

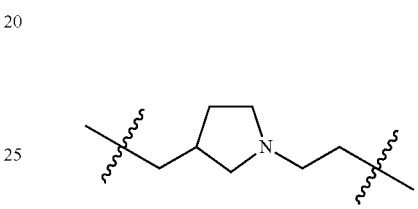;

wherein each ring moiety is substituted with 0-1 $R^{7a}$;

Y is independently selected from the group consisting of: $CH_2$, O, NH, $N(C_{1-4}$ alkyl), $N(CO_2(C_{1-4}$ alkyl)), —CONH—, —NHCO—, —CONHCH$_2$—, —CON($C_{1-4}$ alkyl)CH$_2$—, —OCONH—, —NHCONH—, and —SO$_2$NH—;

$L_1$ is independently selected from the group consisting of: a bond and —CH=CH—;

$R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, $NH_2$, $N(C_{1-4}$ alkyl)$_2$, —CH$_2$NH$_2$, —CH$_2$NHCO$_2$($C_{1-4}$ alkyl), and —C(=NH)NH$_2$;

$R^{1b}$ is independently selected from the group consisting of: H and halogen;

$R^2$ is independently a 5-membered heterocycle selected from: triazolyl and tetrazolyl;

$R^3$ is independently selected from the group consisting of: H, halogen, $C_{1-4}$ alkyl, and CN;

$R^{6a}$ is independently selected from the group consisting of: H, halogen, NH$_2$, CO$_2$H, CONH$_2$, CO$_2$($C_{1-4}$ alkyl), —NHCO$_2$($C_{1-4}$ alkyl), —NHCO$_2$(CH$_2$)$_2$OH, —NHCO$_2$(CH$_2$)$_2$O($C_{1-4}$ alkyl), —NHCO$_2$CH$_2$CO$_2$H, —NHCO$_2$CH$_2$CH($C_{1-4}$ alkyl)O($C_{1-4}$ alkyl), and

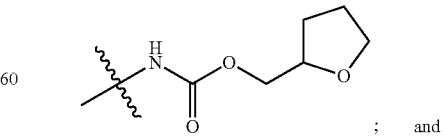; and and $R^{7a}$ is independently selected from the group consisting of: halogen, $C_{1-4}$ alkyl, and N($C_{1-4}$ alkyl)$_2$.

In a 12th aspect, the present invention includes compounds of Formula (IIIb) or Formula (IIIc):

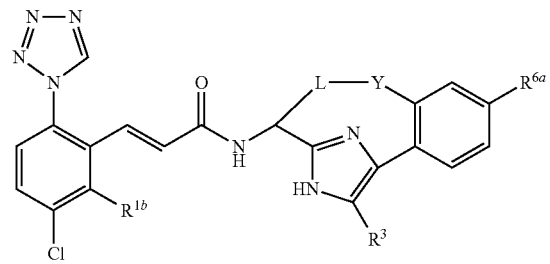
(IIIb)

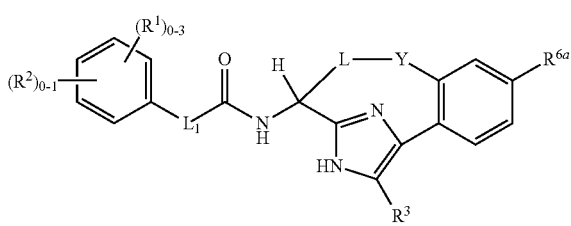
(IIIc)

or a stereoisomer, a tautomer, a pharmaceutically acceptable salt, a solvate, or a prodrug thereof, wherein:

L is independently selected from the group consisting of:

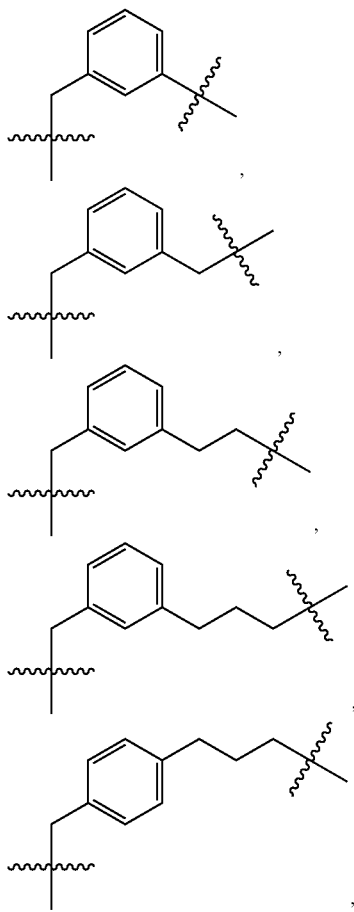

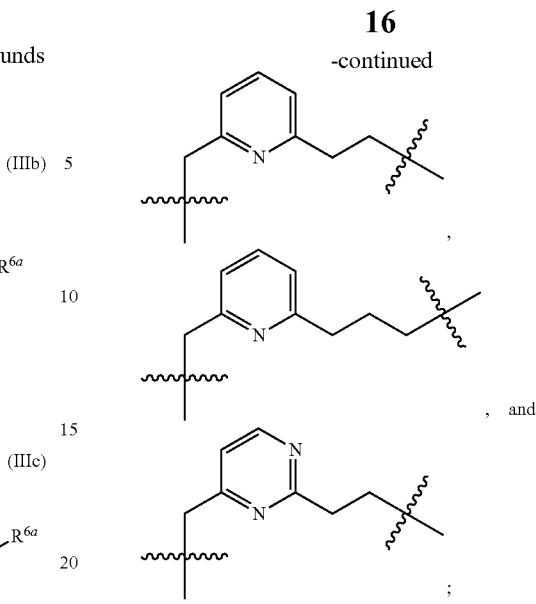

wherein each ring moiety is substituted with 0-1 $R^{7a}$;

Y is independently selected from the group consisting of: $CH_2$, O, NH, —CONH—, —NHCO—, —CONHCH$_2$—, —CON($C_{1-4}$ alkyl)CH$_2$—, —OCONH—, —NHCONH—, and —SO$_2$NH—;

$L_1$ is independently selected from the group consisting of: a bond and —CH=CH—;

$R^1$ is, independently at each occurrence, selected from the group consisting of: halogen, $C_{1-4}$ alkyl, OH, $C_{1-4}$ alkoxy, CO($C_{1-4}$ alkyl), CN, CH$_2$F, CHF$_2$, OCHF$_2$, —CH$_2$NH$_2$, —CH$_2$NHCO$_2$($C_{1-4}$ alkyl), and —C(=NH)NH$_2$;

$R^{1b}$ is independently selected from the group consisting of: H and halogen;

$R^3$ is independently selected from the group consisting of: H, halogen, $C_{1-4}$ alkyl, and CN;

$R^{6a}$ is independently selected from the group consisting of: H, halogen, NH$_2$, CO$_2$H, CONH$_2$, —NHCO$_2$($C_{1-4}$ alkyl), —NHCO$_2$(CH$_2$)$_2$OH, —NHCO$_2$(CH$_2$)$_2$O($C_{1-4}$ alkyl), —NHCO$_2$CH$_2$CH($C_{1-4}$ alkyl)O($C_{1-4}$ alkyl), and

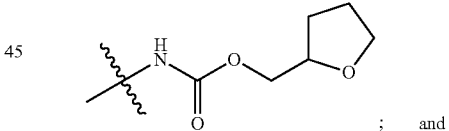

and $R^{7a}$ is independently selected from the group consisting of: halogen, $C_{1-4}$ alkyl, and N($C_{1-4}$ alkyl)$_2$.

In a 13th aspect, the present invention includes compounds of Formula (IIIc):

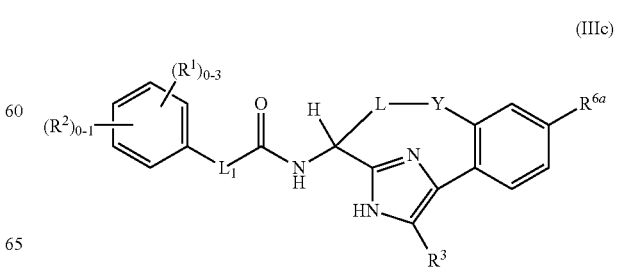
(IIIc)

or a stereoisomer, a tautomer, a pharmaceutically acceptable salt, a solvate, or a prodrug thereof, wherein:

L-Y is independently selected from the group consisting of:

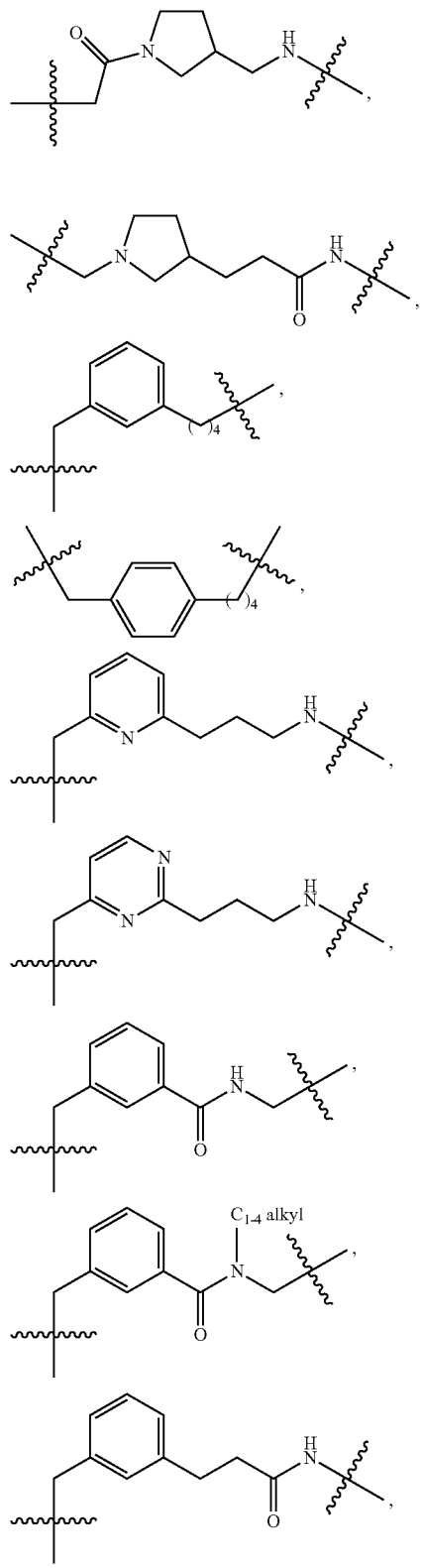

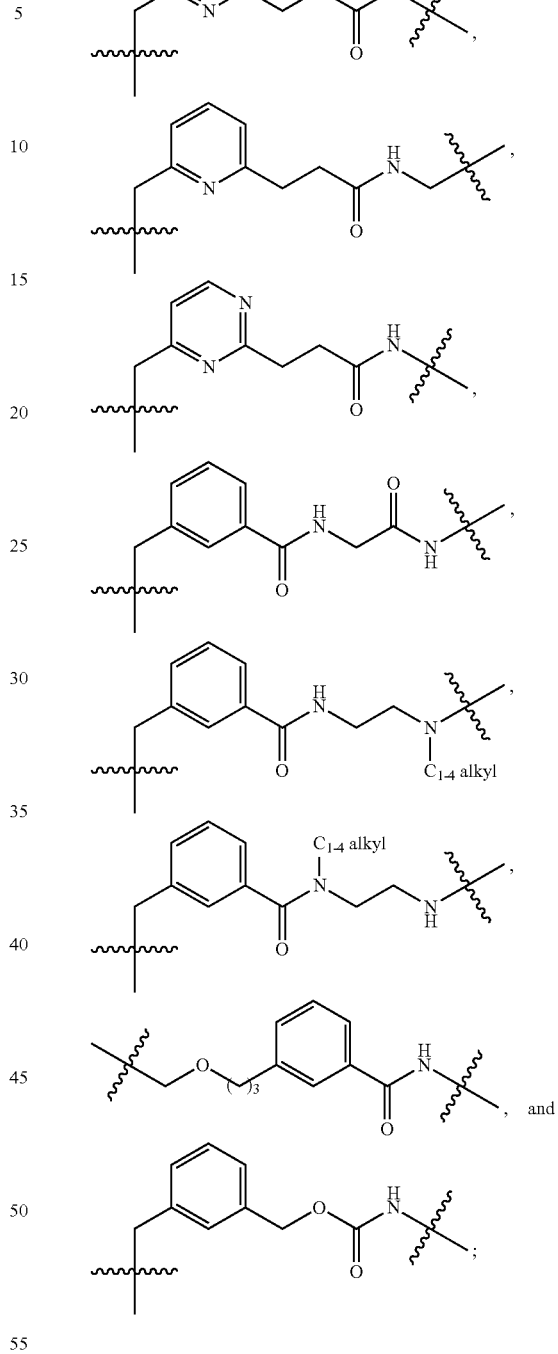

wherein each ring moiety is substituted with 0-1 $R^{7a}$;

$L_1$ is independently selected from the group consisting of: a bond and —CH═CH—;

$R^1$ is, independently at each occurrence, selected from the group consisting of: halogen, $C_{1-4}$ alkyl, $C_{1-4}$ alkoxy, $CO(C_{1-4}$ alkyl), CN, $CHF_2$, and $OCHF_2$;

$R^{1b}$ is independently selected from the group consisting of: H and halogen;

$R^2$ is independently a 5-membered heterocycle selected from: pyrazolyl, imidazolyl, triazolyl, and tetrazolyl;

$R^3$ is independently selected from the group consisting of: H and halogen;

$R^{6a}$ is independently selected from the group consisting of: H, halogen, $NH(C_{1-4}$ alkyl), and $NHCO_2(C_{1-4}$ alkyl); and $R^{7a}$ is independently selected from the group consisting of: halogen, $C_{1-4}$ alkyl, $N(C_{1-4}$ alkyl)$_2$.

In a 14th aspect, the present invention includes compounds of Formula (IIIc) or a stereoisomer, a tautomer, a pharmaceutically acceptable salt, a solvate, or a prodrug thereof, within the scope of the 13th aspect, wherein:

L-Y is independently selected from the group consisting of:

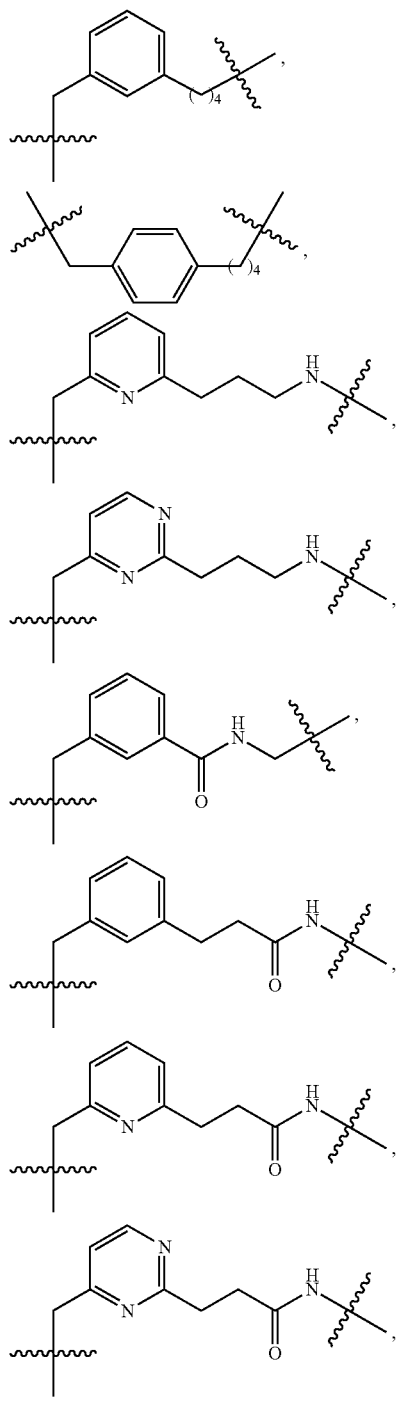

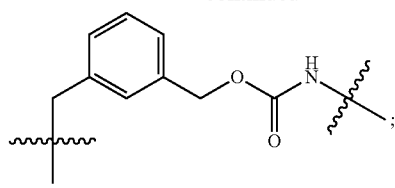

wherein each ring moiety is substituted with 0-1 $R^{7a}$;

$R^2$ is independently triazolyl or tetrazolyl; and $R^{6a}$ is independently selected from the group consisting of: H, halogen, and $NHCO_2(C_{1-4}$ alkyl).

In a 15th aspect, the present invention includes compounds of Formula (IIIc) or a stereoisomer, a tautomer, a pharmaceutically acceptable salt, a solvate, or a prodrug thereof, within the scope of the 13th aspect or 14th aspect, wherein:

L-Y is independently selected from the group consisting of:

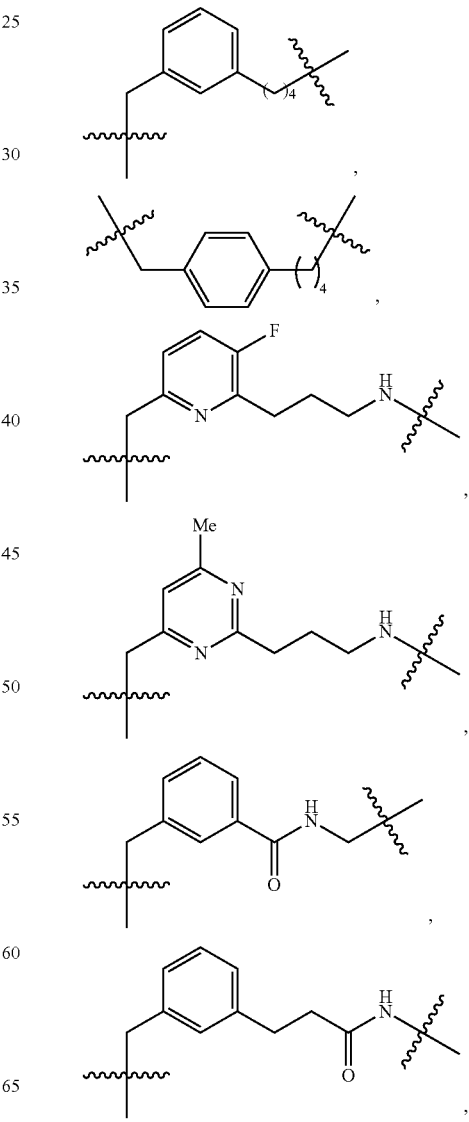

-continued

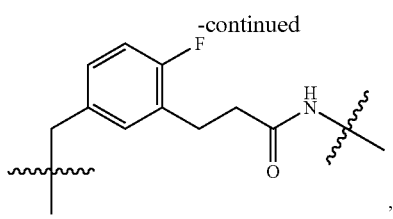
,

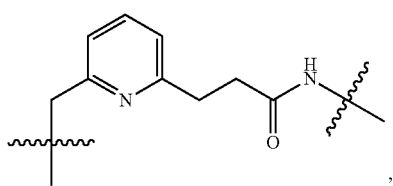
,

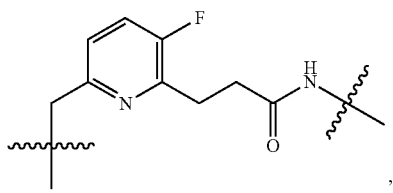
,

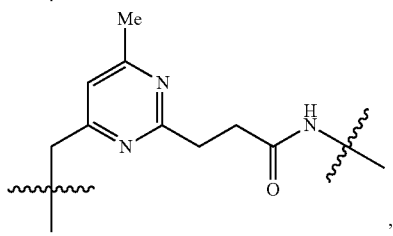
,

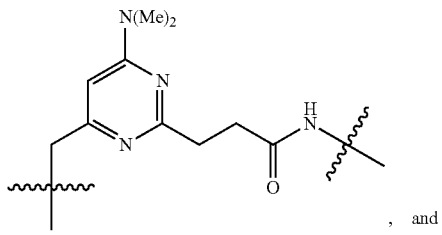
, and

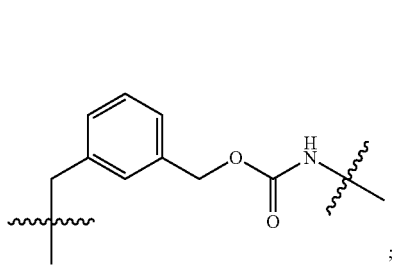
;

$R^1$ is independently selected from the group consisting of: F, Cl, Me, OMe, COMe, CN, $CHF_2$, and $OCHF_2$;

$R^{1b}$ is independently selected from the group consisting of: H and F;

$R^2$ is tetrazolyl;

$R^3$ is independently selected from the group consisting of: H and Cl; and $R^{6a}$ is independently selected from the group consisting of: H, F, and $NHCO_2Me$.

In a 16th aspect, the present invention includes compounds of Formula (V):

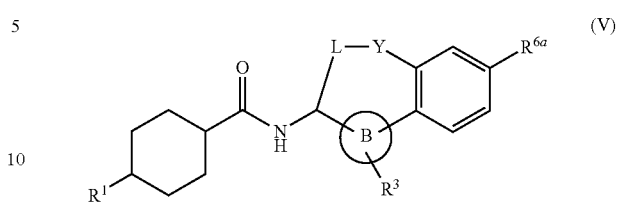

or a stereoisomer, a tautomer, a pharmaceutically acceptable salt, a solvate, or a prodrug thereof, within the scope of the first, second or third aspect, wherein:

ring B is independently selected from the group consisting of: imidazole and pyridine; and $R^1$ is independently selected from the group consisting of: $C_{1-4}$ alkyl and $CH_2NH_2$.

In another aspect, the present invention includes compounds of Formula (V): or a stereoisomer, a tautomer, a pharmaceutically acceptable salt, a solvate, or a prodrug thereof, wherein:

ring B is independently selected from the group consisting of:

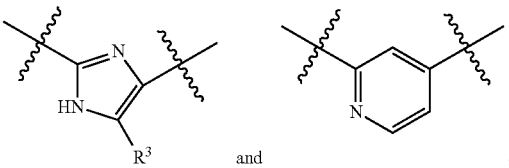
and          ;

L is independently —$CH_2$-2,6-(3-F-pyridinylene)-$(CH_2)_2$—;

Y is independently selected from the group consisting of: —$CH_2$—, —CONH—, and NH;

$R^3$ is independently selected from the group consisting of: H, F, Cl, and Me; and $R^{6a}$ is independently selected from the group consisting of: H and —$NHCO_2Me$.

In a 17th aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the 24th aspect.

In another aspect, the present invention provides compounds of Formula (I), (II), (IIa), (IIc), or (IIe), or a stereoisomer, a tautomer, a pharmaceutically acceptable salt, a solvate, or a prodrug thereof, within the scope of the fourth aspect, wherein:

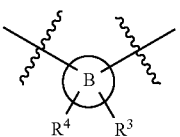

is independently selected from the group consisting of:

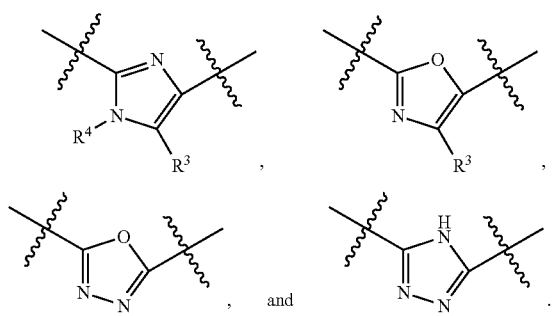

In another aspect wherein:

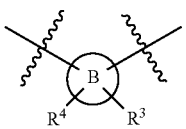

is independently selected from the group consisting of:

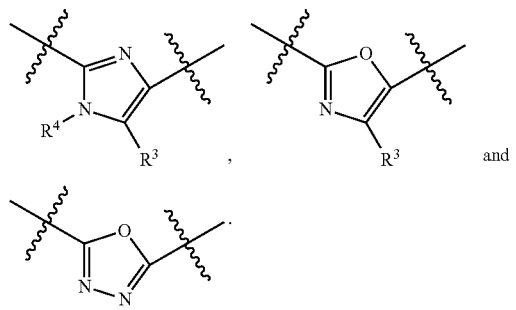

In another aspect, wherein:

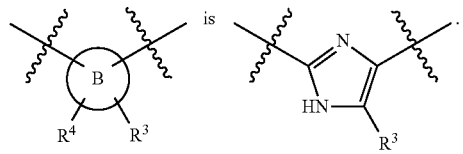

In another aspect, the present invention provides compounds of Formula (I), (II), (IIa), (IIc), or (IIe), or a stereoisomer, a tautomer, a pharmaceutically acceptable salt, a solvate, or a prodrug thereof, within the scope of the fourth aspect, wherein:

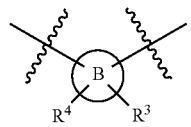

is independently selected from the group consisting of:

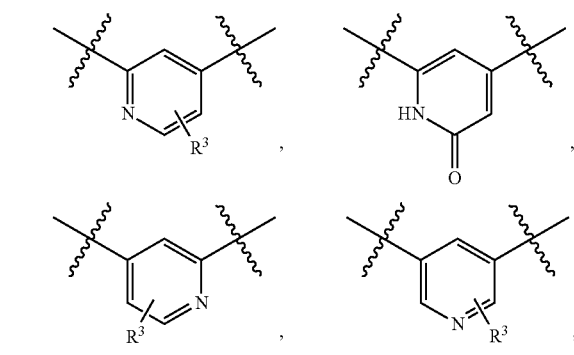

In another aspect wherein:

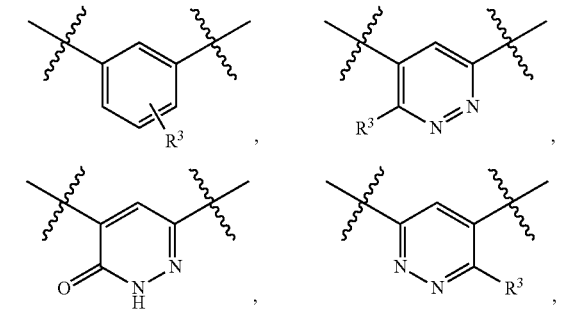

is independently selected from the group consisting of:

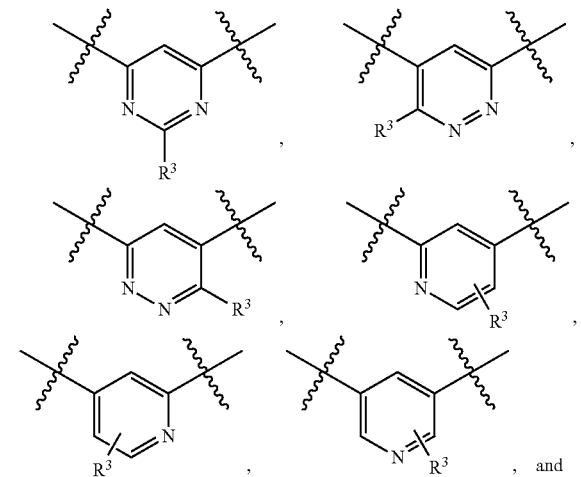

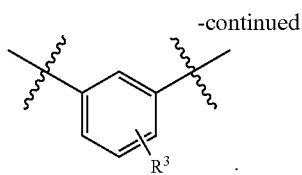

In another aspect wherein:

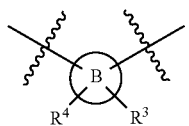

is independently selected from the group consisting of:

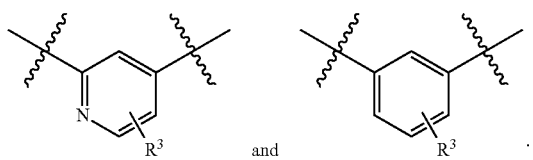

In another aspect wherein:

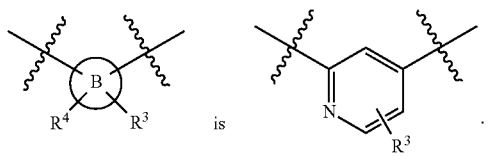

In another aspect wherein:

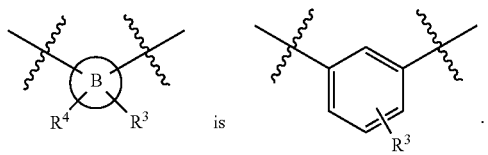

In another aspect, the present invention includes compounds of Formula (I), (II), (IIa), or (IIb), a stereoisomer, a tautomer, a pharmaceutically acceptable salt, a solvate, or a prodrug thereof, within the scope of any of the above aspects, wherein:

$R^2$ is independently a 5-membered heterocycle substituted with 0-1 $R^{2a}$, wherein said heterocycle is selected from: pyrazolyl, imidazolyl, triazolyl, and tetrazolyl; and $R^{2a}$ is, independently at each occurrence, selected from the group consisting of: halogen, OH, $NH_2$, $CH_2OH$, $CO_2H$, $C_{1-4}$ alkyl, —$CONH_2$, —$CONH(C_{1-4}$ alkyl), and —$CON(C_{1-4}$ alkyl)$_2$.

In another aspect, the present invention includes compounds of Formula (I), (II), (IIa), or (IIb), a stereoisomer, a tautomer, a pharmaceutically acceptable salt, a solvate, or a prodrug thereof, within the scope of any of the above aspects, wherein:

$R^2$ is independently selected from the group consisting of: triazolyl and tetrazolyl.

In another embodiment, ring A is independently selected from the group consisting of: phenyl, cyclohexyl, and 5,6,7,8-tetrahydroisoquinolinyl.

In another embodiment, ring A is phenyl.

In another embodiment, ring A is cyclohexyl.

In another embodiment, ring A is tetrahydroisoquinoline.

In another aspect, ring A is

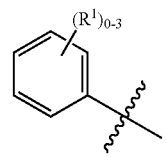

wherein $R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, $NH_2$, $N(C_{1-4}$ alkyl)$_2$, —$CH_2NH_2$, —$CH_2NHCO_2(C_{1-4}$ alkyl), and —$C(=NH)NH_2$.

In another aspect, ring A is

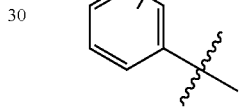

independently selected from the group consisting of:

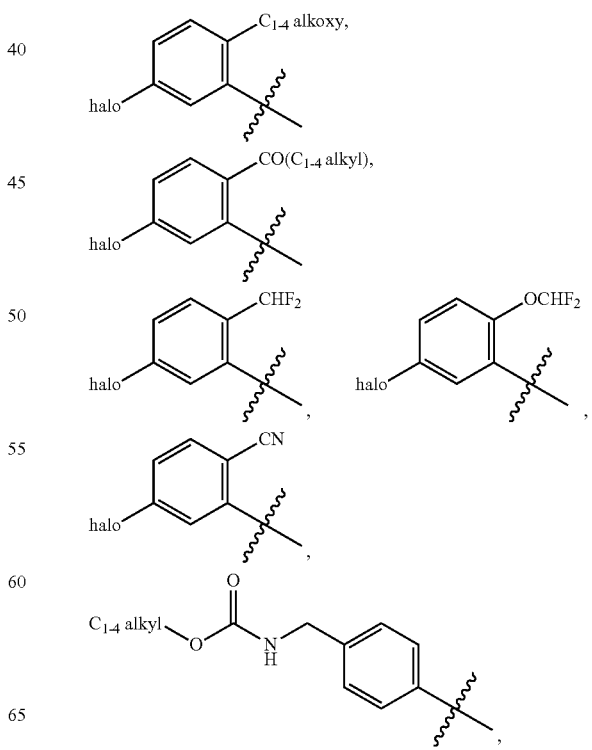

-continued
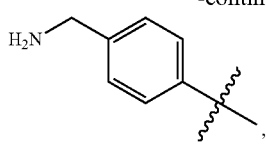,
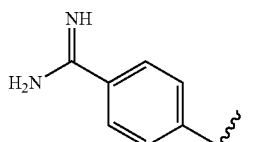,
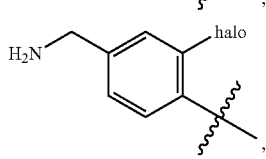,
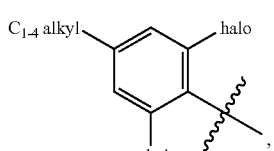,
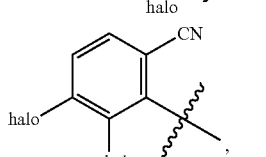,
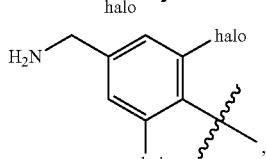,
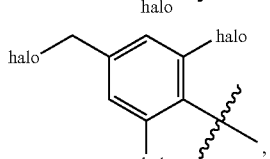,
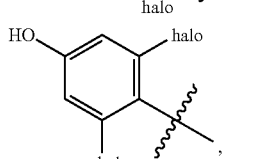,
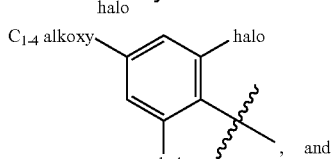, and
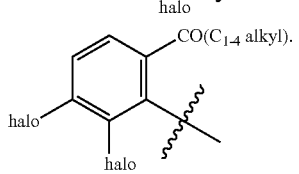.
In another embodiment, ring B is independently selected from the group consisting of: imidazole, oxadiazole, pyridine, pyridazine, and benzene.
In another embodiment,
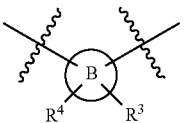
is independently selected from the group consisting of:
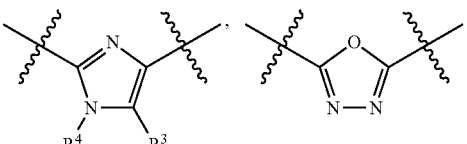,
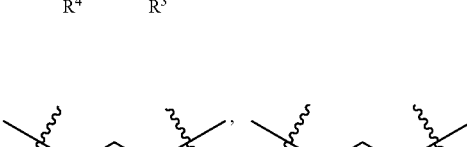,
, and
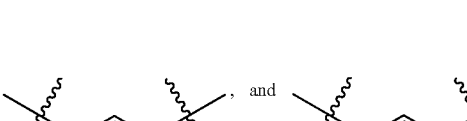.
In another embodiment,
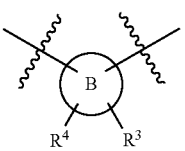
is independently selected from the group consisting of:
.
In another embodiment,
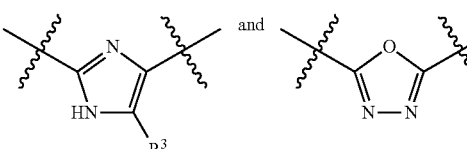 is 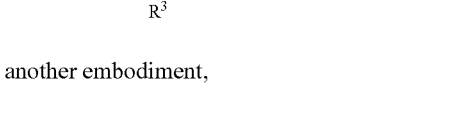.
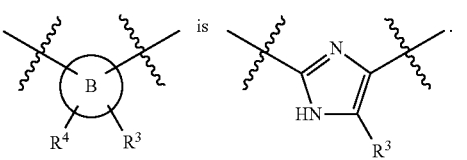

In another embodiment,

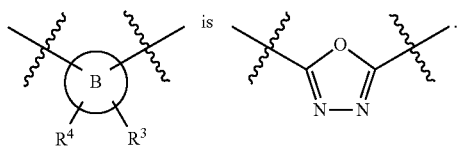

In another embodiment,

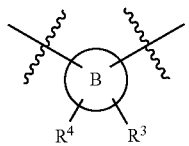

is independently selected from the group consisting of:

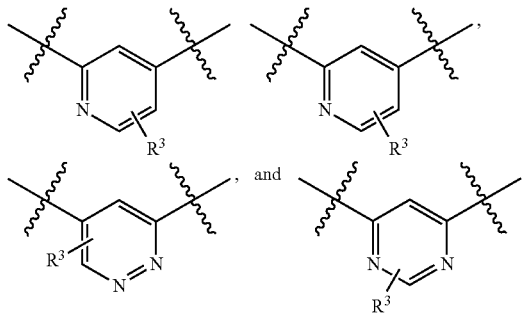

In another embodiment,

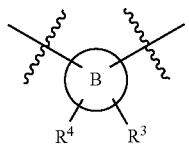

is independently selected from the group consisting of:

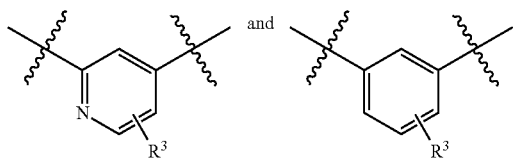

In another embodiment,

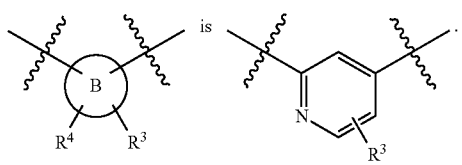

In another embodiment,

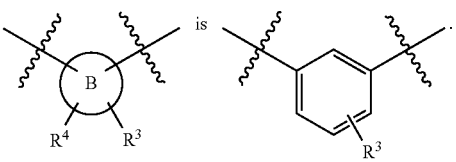

In another embodiment,

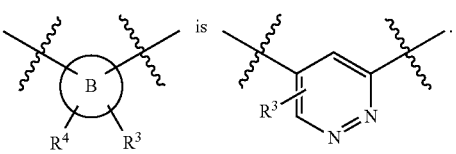

In another embodiment,

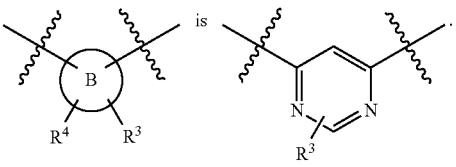

In another embodiment, $L_1$ is independently selected from the group consisting of: a bond, —$CH_2CH_2$—, —CH=CH—, —C(Me)=CH—, —C≡C—, and —$CH_2NH$—.

In another embodiment, $L_1$ is independently selected from the group consisting of: a bond, —$CH_2CH_2$—, —CH=CH—, and —C(Me)=CH.

In another embodiment, $L_1$ is independently selected from the group consisting of: a bond, —$CH_2CH_2$— and —CH=CH—.

In another embodiment, $L_1$ is a bond.

In another embodiment, $L_1$ is —CH=CH—.

In another embodiment, L is independently selected from the group consisting of: —$(CH_2)_{1-2}$-(phenylene)-$(CH_2)_{0-3}$—, —$CH_2$—O—$(CH_2)_{1-4}$-(phenylene)-$(CH_2)_{0-3}$—, —$(CH_2)_{1-2}$-(phenylene)-$CONH(CH_2)_{0-2}$—, —$(CH_2)_{1-2}$-Phenylene-$CON(C_{1-4}$ alkyl)$(CH_2)_{0-2}$—, —$(CH_2)_{1-2}$-(pyridinylene)-$(CH_2)_{0-3}$—, —$CH_2$-pyrimidinylene-$(CH_2)_{0-3}$—,

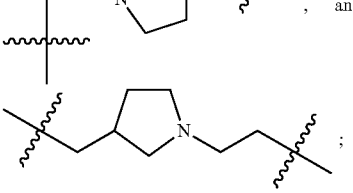

wherein each ring moiety is substituted with 0-2 $R^{7a}$.

In another embodiment, L is independently selected from the group consisting of: —$(CH_2)_{1-2}$-(phenylene)-$(CH_2)_{0-3}$—, —$(CH_2)_{1-2}$-(pyridinylene)-$(CH_2)_{0-3}$—, —$CH_2O(CH_2)_{1-3}$-(phenylene)-$(CH_2)_{0-3}$—, —$(CH_2)_{1-2}$-(phenylene)-$CONHCH_2$—, and

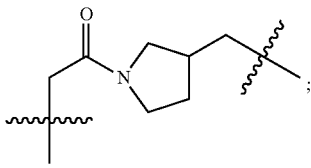 [SMILES: *CC(=O)N1CCC(C*)C1]

wherein said phenylene and pyridinylene are optionally substituted with 1-2 $R^7$; optionally one or more of the carbon atoms of said alkylene and alkenylene may be replaced by O, S, NH, N($C_{1-4}$ alkyl), CONH—, or CON($C_{1-4}$ alkyl).

In another embodiment, L is independently selected from the group consisting of: —$(CH_2)_{1-2}$-(phenylene)-$(CH_2)_{0-3}$—, —$(CH_2)_{1-2}$-(pyridinylene)-$(CH_2)_{0-3}$—, —$CH_2$—O—$(CH_2)_{1-3}$-(phenylene)-$(CH_2)_{0-3}$—, —$(CH_2)_{1-2}$-(phenylene)-$CONHCH_2$—, and

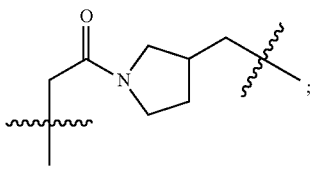 [SMILES: *CC(=O)N1CCC(C*)C1]

wherein said phenylene and pyridinylene are optionally substituted with 1-2 $R^7$; optionally one or two of the carbon atoms of said alkylene and alkenylene may be replaced by O, NH, N($C_{1-4}$ alkyl), CONH, or CON($C_{1-4}$ alkyl).

In another embodiment, L is independently selected from the group consisting of: —$(CH_2)_{1-2}$-(phenylene)-$(CH_2)_{0-3}$—, —$(CH_2)_{1-2}$-(pyridinylene)-$(CH_2)_{0-3}$—, —$CH_2$—O—$(CH_2)_{1-3}$-(phenylene)-$(CH_2)_{0-3}$—, —$(CH_2)_{1-2}$-(phenylene)-$CONHCH_2$—, and

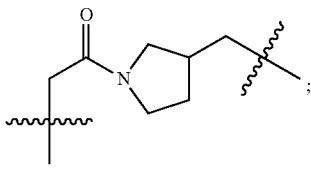 [SMILES: *CC(=O)N1CCC(C*)C1]

wherein said phenylene and pyridinylene are optionally substituted with 1-2 $R^7$.

In another embodiment, L is independently selected from the group consisting of: —$(CH_2)_{1-2}$-(phenylene)-$(CH_2)_{0-3}$—, —$CH_2$—O—$(CH_2)_{1-3}$-(phenylene)-$(CH_2)_{0-3}$—, and —$(CH_2)_{1-2}$-(phenylene)-$CONHCH_2$—; wherein said phenylene is optionally substituted with 1-2 $R^7$.

In another embodiment, L is —$(CH_2)_{1-2}$-(pyridinylene)-$(CH_2)_{0-3}$—; wherein said pyridinylene is optionally substituted with 1-2 $R^7$.

In another embodiment, Y is independently selected from the group consisting of: —$CH_2$—, O, NH, N($C_{1-4}$ alkyl), —NHCO—, —CONH—, —$CONHCH_2$—, —CON($C_{1-4}$ alkyl)$CH_2$—, —OCONH—, —NHCONH—, and —$SO_2NH$—.

In another embodiment, Y is independently selected from the group consisting of: —$CH_2$—, O, NH, NMe, —CONH—, —NHCO—, —$CONHCH_2$—, —$CONMeCH_2$—, —OCONH—, —NHCONH—, and —$SO_2NH$—.

In another embodiment, Y is —CONH—.

In another embodiment, $R^1$ is, independently at each occurrence, selected from the group consisting of: halogen, $C_{1-6}$ alkyl, $C_{1-4}$ alkoxy, $C_{1-4}$ alkylthio, OH, $CH_2F$, $CHF_2$, $CF_3$, $OCH_2F$, $OCHF_2$, $OCF_3$, CN, $NH_2$, NH($C_{1-4}$ alkyl)$_2$, N($C_{1-4}$ alkyl)$_2$, $CO_2$($C_{1-4}$ alkyl), CO($C_{1-4}$ alkyl), —$OCH_2CO_2H$, —$CH_2NH_2$, —$CONH_2$, —CONH($C_{1-4}$ alkyl), —$CH_2NHCO_2$($C_{1-4}$ alkyl), —$SO_2NH_2$, and —C(=NH)$NH_2$.

In another embodiment, $R^1$ is, independently at each occurrence, selected from the group consisting of: halogen, $C_{1-6}$ alkyl, $C_{1-4}$ alkoxy, $C_{1-4}$ alkylthio, OH, $CHF_2$, $CF_3$, $OCF_3$, CN, $NH_2$, $CO_2$($C_{1-4}$ alkyl), CO($C_{1-4}$ alkyl), —$OCH_2CO_2H$, —$CH_2NH_2$, —$CONH_2$, —CONH($C_{1-4}$ alkyl), —$SO_2NH_2$, and —C(=NH)$NH_2$.

In another embodiment, $R^1$ is, independently at each occurrence, selected from: halogen, CN, OH, $CH_2F$, $CHF_2$, $CF_3$, $OCH_2F$, $OCHF_2$, $OCF_3$, $C_{1-4}$ alkyl, $C_{1-4}$ alkoxy, CO($C_{1-4}$ alkyl), $NH_2$, NH($C_{1-4}$ alkyl)$_2$, N($C_{1-4}$ alkyl)$_2$, —C(=NH)$NH_2$, —C(O)$NH_2$, —$CH_2NH_2$, —$CH_2NHCO_2$($C_{1-4}$ alkyl), and —$SO_2NH_2$.

In another embodiment, $R^1$ is, independently at each occurrence, selected from: halogen, CN, OH, $OCF_3$, $CHF_2$, $CF_3$, $C_{1-4}$ alkyl, $C_{1-4}$ alkoxy, CO($C_{1-4}$ alkyl), $NH_2$, —C(=NH)$NH_2$, —C(O)$NH_2$, —$CH_2NH_2$, and —$SO_2NH_2$.

In another embodiment, $R^1$ is selected from the group consisting of: halogen, $C_{1-4}$ alkyl, $CHF_2$, and CO($C_{1-4}$ alkyl).

In another embodiment, $R^2$ is a 5-membered heterocycle substituted with 0-1 $R^{2a}$, wherein said heterocycle is independently selected from: pyrazolyl, imidazolyl, triazolyl, and tetrazolyl.

In another embodiment, $R^2$ is independently selected from the group consisting of: triazolyl and tetrazolyl.

In another embodiment, $R^2$ is tetrazolyl.

In another embodiment, $R^3$ is independently selected from the group consisting of: H, $C_{1-4}$ alkyl, and halogen.

In another embodiment, $R^3$ is independently selected from the group consisting of: H and halogen.

In another embodiment, $R^3$ is independently selected from the group consisting of: H and Cl.

In another embodiment, $R^3$ is H.

In another embodiment, $R^3$ is Cl.

In another embodiment, $R^4$ is H.

In another embodiment, $R^5$ is, independently at each occurrence, selected from the group consisting of: H and $C_{1-4}$ alkyl.

In another embodiment, $R^5$ is, independently at each occurrence, selected from the group consisting of: H and methyl.

In another embodiment, $R^6$ is, independently at each occurrence, selected from the group consisting of: halogen, $C_{1-4}$ alkyl, CN, OH, $CF_3$, $CO_2H$, $CO_2$($C_{1-4}$ alkyl), —$CH_2CO_2H$, —$(CH_2)_2CO_2H$, —$CH_2CO_2$($C_{1-4}$ alkyl), —$(CH_2)_2CO_2$($C_{1-4}$ alkyl), $NH_2$, —$CH_2NH_2$, —NHCO($C_{1-4}$ alkyl), —$NHCO_2$($C_{1-4}$ alkyl), —$NHCO_2(CH_2)_2O$($C_{1-4}$ alkyl), —$NHCO_2(CH_2)_3O$($C_{1-4}$ alkyl), —$NHCO_2CH_2CH$($C_{1-4}$ alkyl)O($C_{1-4}$ alkyl), —$NHCO_2(CH_2)_2OH$, —$NHCO_2(CH_2)_2NH_2$, —$NHCO_2CH_2CO_2H$, —$CH_2NHCO_2$($C_{1-4}$ alkyl), —NHC(O)NH($C_{1-4}$ alkyl), —NHC(O)N($C_{1-4}$ alkyl)$_2$, —$NHSO_2$($C_{1-4}$ alkyl), —$SO_2NH(CH_2)_2OH$, —$SO_2NH(CH_2)_2O$($C_{1-4}$ alkyl), —C(O)NH$(CH_2)_2O$($C_{1-4}$ alkyl), $CONH_2$, CONH($C_{1-4}$ alkyl), CON($C_{1-4}$ alkyl)$_2$, —$CH_2CONH_2$, and

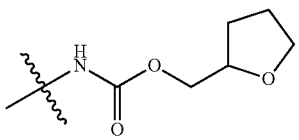

In another embodiment, R⁶ is, independently at each occurrence, selected from the group consisting of: halogen, $C_{1-4}$ alkyl, CN, OH, $CF_3$, $CO_2H$, $CO_2(C_{1-4}$ alkyl), $—CH_2CO_2H$, $—(CH_2)_2CO_2H$, $—CH_2CO_2(C_{1-4}$ alkyl), $—(CH_2)_2CO_2(C_{1-4}$ alkyl), $NH_2$, $—CH_2NH_2$, $—NHCO(C_{1-4}$ alkyl), $—NHCO_2(C_{1-4}$ alkyl), $—NHCO_2(CH_2)_2O(C_{1-4}$ alkyl)$_2$, $—NHCO_2(CH_2)_3O(C_{1-4}$ alkyl), $—NHCO_2(CH_2)_2OH$, $—NHCO_2(CH_2)_2NH_2$, $—CH_2NHCO_2(C_{1-4}$—NHC(O)NH($C_{1-4}$ alkyl), $—NHC(O)N(C_{1-4}$ alkyl)$_2$, $—NHSO_2(C_{1-4}$ alkyl), $—SO_2NH(CH_2)_2OH$, $—SO_2NH(CH_2)_2O(C_{1-4}$ alkyl), and $—CONH_2$.

In another embodiment, R⁶ is, independently at each occurrence, selected from the group consisting of: halogen, $C_{1-4}$ alkyl, CN, OH, $CF_3$, $CO_2H$, $CO_2(C_{1-4}$ alkyl), $—CH_2CO_2H$, $—CH_2CO_2(C_{1-4}$ alkyl), $NH_2$, $—CH_2NH_2$, $—NHCO(C_{1-4}$ alkyl), $—NHCO_2(C_{1-4}$—$CH_2NHCO_2(C_{1-4}$ alkyl), $—CONH_2$, $—NHCO_2(CH_2)_2OH$, $—NHCO_2(CH_2)_2O(C_{1-4}$ alkyl), $—NHCO_2CH_2CO_2H$, $—NHCO_2CH_2CH(C_{1-4}$ alkyl)$O(C_{1-4}$ alkyl), and

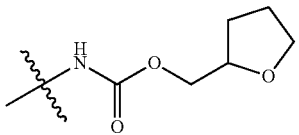

In another embodiment, R⁶ is, independently at each occurrence, selected from the group consisting of: halogen, $NH_2$, $CO_2H$, $CO_2(C_{1-4}$ alkyl), $CONH_2$, $CONH(C_{1-4}$ alkyl), $CON(C_{1-4}$ alkyl)$_2$, $—NHCO_2(C_{1-4}$ alkyl), $—CH_2NHCO_2(C_{1-4}$ alkyl), $—NHCO_2CH_2CO_2H$, $—NHCO_2(CH_2)_2OH$, $—NHCO_2(CH_2)_2O(C_{1-4}$ alkyl), $—NHCO_2CH_2CH(C_{1-4}$ alkyl)$O(C_{1-4}$ alkyl), and

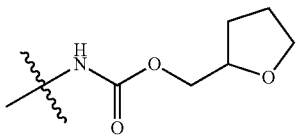

In another embodiment, R⁶ is, independently at each occurrence, selected from the group consisting of: halogen, $C_{1-4}$ alkyl, CN, OH, $CF_3$, $CO_2H$, $CO_2(C_{1-4}$ alkyl), $—CH_2CO_2H$, $—CH_2CO_2(C_{1-4}$ alkyl), $NH_2$, $—CH_2NH_2$, $—NHCO(C_{1-4}$ alkyl), $—NHCO_2(C_{1-4}$ alkyl), $—CH_2NHCO_2(C_{1-4}$ alkyl), and $—CONH_2$.

In another embodiment, R⁶ is, independently at each occurrence, selected from the group consisting of: halogen, $CO_2H$, $CO_2(C_{1-4}$ alkyl), $NH_2$, $NHCO_2(C_{1-4}$ alkyl), and $—CH_2NHCO_2(C_{1-4}$ alkyl).

In another embodiment, R⁶ is, independently at each occurrence, is selected from the group consisting of: halogen, $NH_2$, $NHCO_2(C_{1-4}$ alkyl), and $—CH_2NHCO_2(C_{1-4}$ alkyl).

In another embodiment, R⁶ is, independently at each occurrence, is selected from the group consisting of: F, $NH_2$, $NHCO_2Me$, and $—CH_2NHCO_2Me$.

In another embodiment, $R^{6a}$ is independently selected from the group consisting of: H, halogen, $NH_2$, $CO_2H$, $CONH_2$, $—NHCO_2(C_{1-4}$ alkyl), $—NHCO_2(CH_2)_2OH$, $—NHCO_2(CH_2)_2O(C_{1-4}$ alkyl), $—NHCO_2CH_2CH(C_{1-4}$ alkyl)$O(C_{1-4}$ alkyl), and

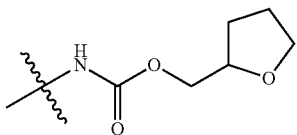

In another embodiment, $R^{6a}$ is independently selected from the group consisting of: H, halogen, $NH(C_{1-4}$ alkyl), and $NHCO_2(C_{1-4}$ alkyl).

In another embodiment, $R^{6a}$ is independently selected from the group consisting of: H, halogen, and $NHCO_2(C_{1-4}$ alkyl).

In another embodiment, $R^{6a}$ is $R^{6a}$ is independently selected from the group consisting of: H, F, and $NHCO_2Me$.

In another embodiment, $R^7$ is independently selected from the group consisting of: halogen, $C_{1-4}$ alkyl, and $N(C_{1-4}$ alkyl)$_2$.

In another embodiment, $R^7$ is independently selected from the group consisting of: halogen, and $C_{1-4}$ alkyl.

In another embodiment, $R^{7a}$ is independently selected from the group consisting of: halogen, $C_{1-4}$ alkyl, and $N(C_{1-4}$ alkyl)$_2$.

In another embodiment, $R^{7a}$ is independently selected from the group consisting of: halogen, and $C_{1-4}$ alkyl.

In another aspect, the present invention provides, inter alia, a compound of Formula (I-1):

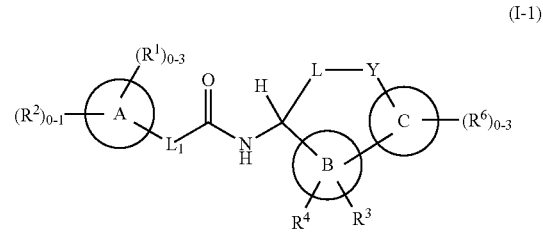

or a stereoisomer, a tautomer, a pharmaceutically acceptable salt, a solvate, or a prodrug thereof, wherein:

ring A is a $C_{3-10}$ carbocycle or a 5- to 10-membered heterocycle comprising: carbon atoms and 1-4 heteroatoms selected from N, O, and $S(O)_p$;

ring B is a benzene ring or a 5- to 6-membered heteroaryl comprising: carbon atoms and 1-4 heteroatoms selected from N, O, and $S(O)_p$;

ring C is a benzene ring or a 5- to 10-membered heterocycle comprising: carbon atoms and 1-4 heteroatoms selected from N, O, and $S(O)_p$;

$L_1$ is selected from the group consisting of: a bond, $—CHR^5CHR^5—$, $—CR^5=CR^5—$, $—C\equiv C—$, $—OCH_2—$, $—CHR^5NH—$, $—CH_2O—$, $—SCH_2—$, $—SO_2CH_2—$, $—CH_2NH—$, and $—CR^5R^5—$;

L is selected from the group consisting of:
$—C_{1-6}$ alkylene-($C_{3-8}$ carbocycle)-$C_{0-4}$ alkylene-, and $—C_{1-6}$ alkylene-(5- to 6-membered heterocycle)-$C_{0-4}$ alkylene-; wherein said heterocycle comprises: carbon atoms and 1-4 heteroatoms selected from N, O, and $S(O)_p$; wherein said carbocycle and heterocycle are optionally substituted with 1-2 R$^7$; optionally one or more of the carbon atoms of said alkylene and alkenylene may be replaced by O, S, NH, N(C$_{1-4}$ alkyl), CO, CONH, NHCO, OCONH, SO$_2$NH, or CON(C$_{1-4}$ alkyl);

Y is selected from the group consisting of: O, S, NH, N(C$_{1-4}$ alkyl), CH$_2$, CH(C$_{1-4}$ alkyl), C(C$_{1-4}$ alkyl)$_2$, —CONH—, —NHCO—, —CONHCH$_2$—, —CON(C$_{1-4}$ alkyl)CH$_2$—, —OCONH—, —OCON(C$_{1-4}$ alkyl)-, —NH-CONH—, —SO$_2$NH—, —NHCO$_2$—, and —NHSO$_2$—;

R$^1$ is, independently at each occurrence, selected from the group consisting of: halogen, C$_{1-6}$ alkyl, C$_{1-4}$ alkoxy, C$_{1-4}$ alkylthio, OH, CHF$_2$, CF$_3$, OCF$_3$, CN, NH$_2$, —CO$_2$(C$_{1-4}$ alkyl), —CO(C$_{1-4}$ alkyl), —CH$_2$NH$_2$, —CONH$_2$, —CONH(C$_{1-4}$ alkyl), —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, and —C(=NH)NH$_2$;

R$^2$ is a 5- to 7-membered heterocycle comprising carbon atoms and 1-4 heteroatoms selected from N, O, and S(O)$_p$, wherein said heterocycle is substituted with 0-2 R$^{2a}$;

R$^{2a}$ is, independently at each occurrence, selected from the group consisting of: C$_{1-4}$ alkyl, —CH$_2$OH, C$_{1-4}$ alkoxy, OH, CF$_3$, OCF$_3$, CN, NH$_2$, CO$_2$H, CO$_2$(C$_{1-4}$ alkyl), COC$_{1-4}$ alkyl, —CONH$_2$, —CONH(C$_{1-4}$ alkyl), —CON(C$_{1-4}$ alkyl)$_2$, —SO$_2$(C$_{1-4}$ alkyl), —SO$_2$NH$_2$, —SO$_2$NH(C$_{1-4}$ alkyl), and —SO$_2$N(C$_{1-4}$ alkyl)$_2$;

R$^3$ is selected from the group consisting of: H, halogen, OH, NH$_2$, CF$_3$, C$_{1-4}$ alkyl, C$_{1-4}$ alkoxy, —CH$_2$OH, CO$_2$H, CO$_2$(C$_{1-4}$ alkyl), —C(O)NH$_2$, —C(O)NH(C$_{1-4}$ alkyl), —C(O)N(C$_{1-4}$ alkyl)$_2$, and —CH$_2$CO$_2$H;

R$^4$ is selected from the group consisting of: H and C$_{1-4}$ alkyl;

R$^5$ is, independently at each occurrence, selected from the group consisting of: H, halogen, OH, and C$_{1-4}$ alkyl;

R$^6$ is, independently at each occurrence, selected from the group consisting of: halogen, C$_{1-4}$ alkyl, CN, OH, CF$_3$, CO$_2$H, CO$_2$(C$_{1-4}$ alkyl), —CH$_2$CO$_2$H, —(CH$_2$)$_2$CO$_2$H, —CH$_2$CO$_2$(C$_{1-4}$ alkyl), —(CH$_2$)$_2$CO$_2$(C$_{1-4}$ alkyl), NH$_2$, —CH$_2$NH$_2$, —NHCO(C$_{1-4}$ alkyl), —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —CH$_2$NHCO$_2$(C$_{1-4}$ alkyl), —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, and —CH$_2$CONH$_2$;

R$^7$ is, independently at each occurrence, selected from the group consisting of: halogen, OH, NH$_2$, —CH$_2$NH$_2$, CHF$_2$, CF$_3$, —NH(C$_{1-4}$ alkyl), —N((C$_{1-4}$ alkyl)$_2$, C$_{1-4}$ alkoxy, and C$_{1-4}$ alkyl; and p is, independently at each occurrence, selected from the group consisting of: 0, 1, and 2.

In another aspect, the present invention provides compounds of Formula (I-1), or a stereoisomer, a tautomer, a pharmaceutically acceptable salt, a solvate, or a prodrug thereof, wherein:

ring A is a 6-membered carbocycle or 5,6,7,8-tetrahydroisoquinoline;

ring B is selected from the group consisting of: imidazole, oxadiazole, pyridine, pyridazine, pyrimidine, and benzene; and ring C is selected from the group consisting of: benzene and pyridine.

In another aspect, the present invention provides compounds of Formula (Ia), or a stereoisomer, a tautomer, a pharmaceutically acceptable salt, a solvate, or a prodrug thereof, wherein:

ring A is selected from the group consisting of: benzene, cyclohexane, and 5,6,7,8-tetrahydroisoquinoline;

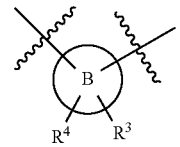

is selected from the group consisting of:

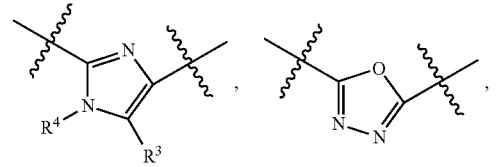

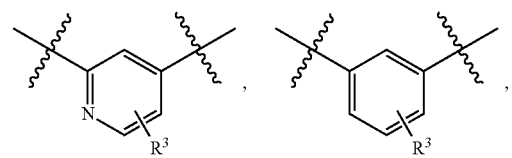

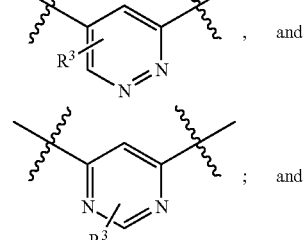

and

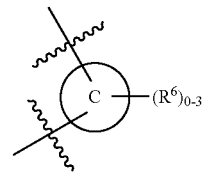

is selected from the group consisting of:

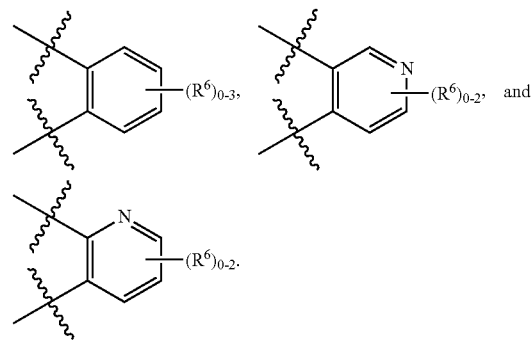

In another aspect, the present invention provides compounds of Formula (II-1):

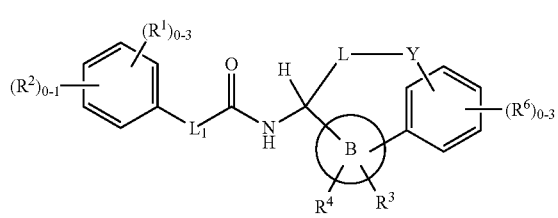
(II-1)

or a stereoisomer, a tautomer, a pharmaceutically acceptable salt, a solvate, or a prodrug thereof, wherein:

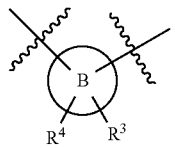

is selected from the group consisting of:

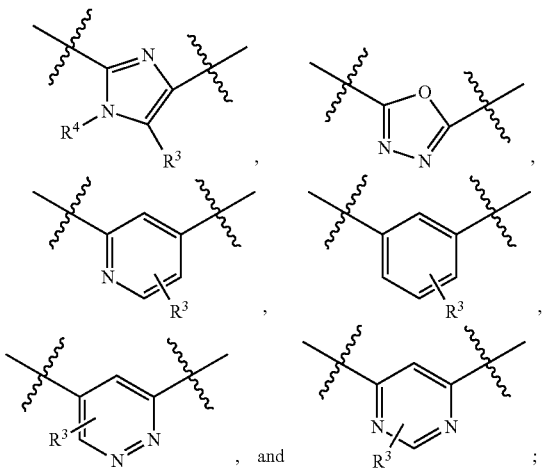

$L_1$ is selected from the group consisting of: a bond, —$CHR^5CHR^5$—, —$CR^5$=$CHR^5$—, —C≡C—, —$OCH_2$—, —$CHR^5NH$—, —$CH_2O$—, —$SCH_2$—, —$SO_2CH_2$—, —$CH_2NH$—, and —$CR^5R^5$—;

L is selected from the group consisting of: —$(CH_2)_{1-2}$-(phenylene)-$(CH_2)_{0-3}$—, —$(CH_2)_{1-2}$-(pyridinylene)-$(CH_2)_{0-3}$—, —$CH_2O(CH_2)_{1-3}$-(phenylene)-$(CH_2)_{0-3}$—, —$(CH_2)_{1-2}$-(phenylene)-$CONHCH_2$—, and

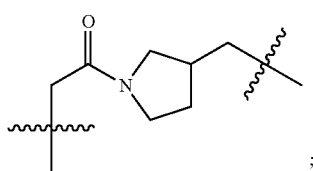 [SMILES: *CC(=O)N1CCC(C*)C1]

wherein said phenylene and pyridinylene are optionally substituted with 1-2 $R^7$; optionally one or two of the carbon atoms of said alkylene and alkenylene may be replaced by O, S, NH, N($C_{1-4}$ alkyl), CONH—, or CON($C_{1-4}$ alkyl);

Y is selected from the group consisting of: $CH_2$, $CH(C_{1-4}$ alkyl), $C(C_{1-4}$ alkyl$)_2$, O, S, NH, N($C_{1-4}$ alkyl), —CONH—, —NHCO—, —$CONHCH_2$—, —CON($C_{1-4}$ alkyl)$CH_2$—, —OCONH—, —OCON($C_{1-4}$ alkyl)-, —NHCONH—, and —$SO_2NH$—;

$R^1$ is, independently at each occurrence, selected from the group consisting of: halogen, $C_{1-6}$ alkyl, $C_{1-4}$ alkoxy, $C_{1-4}$ alkylthio, OH, $CHF_2$, $CF_3$, $OCF_3$, CN, $NH_2$, $CO_2(C_{1-4}$ alkyl), $CO(C_{1-4}$ alkyl), —$OCH_2CO_2H$, —$CH_2NH_2$, —$CONH_2$, —$CONH(C_{1-4}$ alkyl), —$SO_2NH_2$, and —C(=NH)$NH_2$;

$R^2$ is a 5- to 6-membered heterocycle comprising carbon atoms and 1-4 heteroatoms selected from N, O, and S(O)$_p$, wherein said heterocycle is substituted with 0-2 $R^{2a}$;

$R^{2a}$ is, independently at each occurrence, selected from the group consisting of: $C_{1-4}$ alkyl, —$CH_2OH$, $C_{1-4}$ alkoxy, OH, $CF_3$, CN, $NH_2$, $CO_2H$, $CO_2(C_{1-4}$ alkyl), $COC_{1-4}$ alkyl, —$CONH_2$, —$CONH(C_{1-4}$ alkyl), and —$CON(C_{1-4}$ alkyl$)_2$;

$R^3$ is selected from the group consisting of: H, halogen, OH, $NH_2$, $CF_3$, $C_{1-4}$ alkyl, $C_{1-4}$ alkoxy, —$CH_2OH$, $CO_2H$, $CO_2(C_{1-4}$ alkyl), —$C(O)NH_2$, —$C(O)NH(C_{1-4}$ alkyl), —$C(O)N(C_{1-4}$ alkyl$)_2$, and —$CH_2CO_2H$;

$R^4$ is selected from the group consisting of: H and $C_{1-4}$ alkyl;

$R^5$ is, independently at each occurrence, selected from the group consisting of: H, halogen, OH, and $C_{1-4}$ alkyl;

$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$CH_2NHCO_2(C_{1-4}$ alkyl), —$NHC(O)NH(C_{1-4}$ alkyl), —$NHC(O)N(C_{1-4}$ alkyl$)_2$, —$NHSO_2(C_{1-4}$ alkyl), —$SO_2NH(CH_2)_2OH$, —$SO_2NH(CH_2)_2O(C_{1-4}$ alkyl), —$CONH_2$, —$C(O)NH(CH_2)_2O(C_{1-4}$ alkyl), and —$CH_2CONH_2$;

$R^7$ is, independently at each occurrence, selected from the group consisting of: halogen, OH, $CF_3$, $C_{1-4}$ alkoxy and $C_{1-4}$ alkyl; and p is, independently at each occurrence, selected from the group consisting of: 0, 1, and 2.

In another aspect, the present invention provides compounds of Formula (I), (II), (IIa), (IIc), or (IIe), or a stereoisomer, a tautomer, a pharmaceutically acceptable salt, a solvate, or a prodrug thereof, wherein:

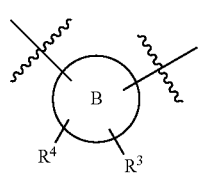

is selected from the group consisting of:

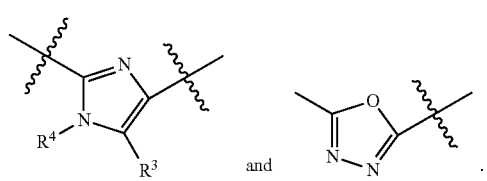

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

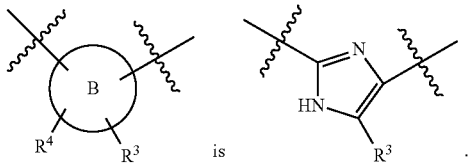 is

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

is selected from the group consisting of:

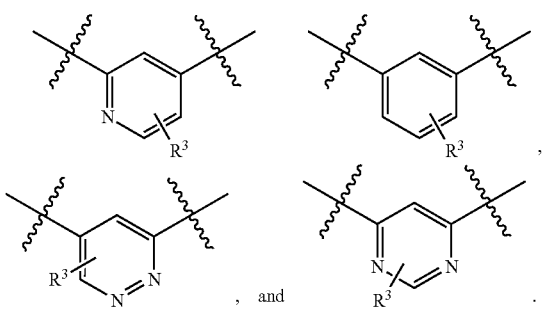

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

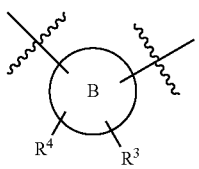

is selected from the group consisting of:

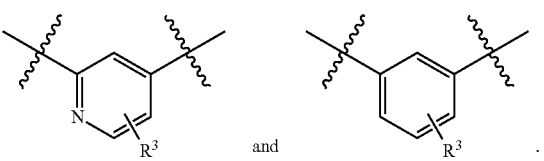

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

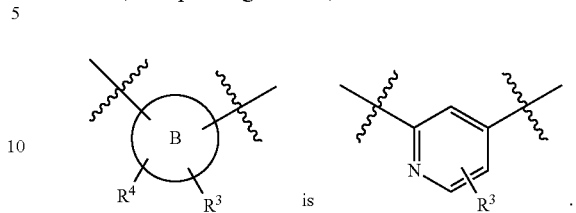 is

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

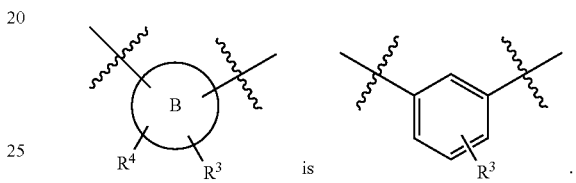 is

In another aspect, the present invention includes compounds of Formula (I-1), (II-1), (IIa), or (IIb), a stereoisomer, a tautomer, a pharmaceutically acceptable salt, a solvate, or a prodrug thereof, wherein:

$R^2$ is a 5-membered heterocycle substituted with 0-1 $R^{2a}$, wherein said heterocycle is selected from: pyrazolyl, imidazolyl, triazolyl, and tetrazolyl; and $R^{2a}$ is, independently at each occurrence, selected from the group consisting of: OH, $NH_2$, $CH_2OH$, $CO_2H$, $C_{1-4}$ alkyl, —$CONH_2$, —$CONH(C_{1-4}$ alkyl), and —$CON(C_{1-4}$ alkyl)$_2$ In another aspect, the present invention includes compounds of Formula (I-1), (II-1), (IIa), or (IIb), a stereoisomer, a tautomer, a pharmaceutically acceptable salt, a solvate, or a prodrug thereof, wherein:

$R^2$ is selected from the group consisting of: triazolyl and tetrazolyl.

In another aspect, the present invention includes compounds of Formula (I-1), (II-1), (IIa), (IIb), (IIc), (IId), (IIe) or (IIf) a stereoisomer, a tautomer, a pharmaceutically acceptable salt, a solvate, or a prodrug thereof, wherein:

$L_1$ is selected from the group consisting of: a bond, —$CH_2CH_2$—, —CH=CH—, —C(Me)=CH—, —C≡C—, and —$CH_2NH$—;

L is selected from the group consisting of: —$(CH_2)_{1-2}$-(phenylene)-$(CH_2)_{0-3}$—, —$(CH_2)_{1-2}$-(pyridinyl)(CH)—$CH_2$—O—$(CH_2)_{1-3}$-(phenylene)-$(CH_2)_{0-3}$—, —$(CH_2)_{1-2}$-(phenylene)-$CONHCH_2$—, and

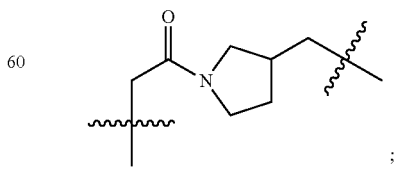

wherein said phenylene and pyridinylene are optionally substituted with 1-2 $R^7$; optionally one or two of the carbon atoms of said alkylene and alkenylene may be replaced by O, NH, N($C_{1-4}$ alkyl), CONH, or CON($C_{1-4}$ alkyl);

Y is selected from the group consisting of: $CH_2$, CH($C_{1-4}$ alkyl), C($C_{1-4}$ alkyl)$_2$, O, S, NH, N($C_{1-4}$ alkyl), —CONH—, —NHCO—, —CONHCH$_2$—, —CON($C_{1-4}$ alkyl)CH$_2$—, —OCONH—, —NHCONH—, and —SO$_2$NH—;

$R^1$ is, independently at each occurrence, selected from: halogen, CN, OH, OCF$_3$, CHF$_2$, CF$_3$, $C_{1-4}$ alkyl, $C_{1-4}$ alkoxy, CO($C_{1-4}$ alkyl), NH$_2$, —C(=NH)NH$_2$, —C(O)NH$_2$, —CH$_2$NH$_2$, and —SO$_2$NH$_2$;

$R^3$ is selected from the group consisting of: H, halogen, OH, NH$_2$, CF$_3$, $C_{1-4}$ alkyl, $C_{1-4}$ alkoxy, —CH$_2$OH, CO$_2$H, CO$_2$($C_{1-4}$ alkyl), —C(O)NH$_2$, —C(O)NH($C_{1-4}$ alkyl), —C(O)N($C_{1-4}$ alkyl)$_2$, and —CH$_2$CO$_2$H; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —(CH$_2$)$_2$CO$_2$H, —CH$_2$CO$_2$($C_{1-4}$ alkyl), —(CH$_2$)$_2$CO$_2$($C_{1-4}$ alkyl), NH$_2$, —CH$_2$NH$_2$, —NHCO($C_{1-4}$ alkyl), —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —CH$_2$NHCO$_2$($C_{1-4}$ alkyl), —NHC(O)NH($C_{1-4}$ alkyl), —NHC(O)N($C_{1-4}$ alkyl)$_2$, —NHSO$_2$($C_{1-4}$ alkyl), —SO$_2$NH(CH$_2$)$_2$OH, —SO$_2$NH(CH$_2$)$_2$O($C_{1-4}$ alkyl), and —CONH$_2$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

$L_1$ is selected from the group consisting of: a bond, —CH$_2$CH$_2$— and —CH=CH—;

$R^1$ is, independently at each occurrence, selected from the group consisting of: halogen, CN, $C_{1-4}$ alkyl, CHF$_2$, CF$_3$, CO($C_{1-4}$ alkyl), NH$_2$, —CH$_2$NH$_2$, and —C(=NH)NH$_2$;

$R^3$ is selected from the group consisting of: H, halogen, CF$_3$, CO$_2$H, CO$_2$($C_{1-4}$ alkyl), and $C_{1-4}$ alkyl; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —CH$_2$CO$_2$($C_{1-4}$ alkyl), NH$_2$, —CH$_2$NH$_2$, —NHCO($C_{1-4}$ alkyl), —NHCO$_2$($C_{1-4}$ alkyl), —CH$_2$NHCO$_2$($C_{1-4}$ alkyl), and —CONH$_2$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

$L_1$ is selected from the group consisting of: a bond, —CH$_2$CH$_2$— and —CH=CH—;

L is selected from the group consisting of: —CH$_2$-1,3-phenylene-, —CH$_2$-1,4-phenylene-, —CH$_2$-1,3-(4-halo-phenylene)-, —CH$_2$-1,4-(3-halo-phenylene)-, —CH$_2$-1,4-phenylene-(CH$_2$)$_2$—, —CH$_2$-1,3-(4-halo-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$—O—(CH$_2$)$_3$-1,3-phenylene-, —CH$_2$-1,3-phenylene-CONHCH$_2$—, —CH$_2$-2,6-pyridinylene-(CH$_2$)$_2$—, —CH$_2$-2,6-(3-halo-pyridinylene)-(CH$_2$)$_2$—, and

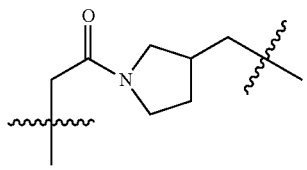

;

Y is selected from the group consisting of: —CH$_2$—, O, NH, N($C_{1-4}$ alkyl), —NHCO—, —CONH—, —CONHCH$_2$—, —CON($C_{1-4}$ alkyl)CH$_2$—, —OCONH—, —NHCONH—, and —SO$_2$NH—;

$R^3$ is selected from the group consisting of: H, $C_{1-4}$ alkyl, and halogen; and $R^6$ is, independently at each occurrence, selected from the group consisting of: halogen, CO$_2$H, CO$_2$($C_{1-4}$ alkyl), NH$_2$, NHCO$_2$($C_{1-4}$ alkyl), and —CH$_2$NHCO$_2$($C_{1-4}$ alkyl).

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —CH$_2$-1,3-phenylene-, —CH$_2$-1,4-phenylene-, —CH$_2$-1,3-(4-halo-phenylene)-, —CH$_2$-1,4-phenylene-(CH$_2$)$_2$—, —CH$_2$-1,3-(4-halo-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$—O—(CH$_2$)$_3$-1,3-phenylene-, —CH$_2$-1,3-phenylene-CON-HCH$_2$—, —CH$_2$-2,6-pyridinylene-(CH$_2$)$_2$—, —CH$_2$-2,6-(3-halo-pyridinylene)-(CH$_2$)$_2$—, and

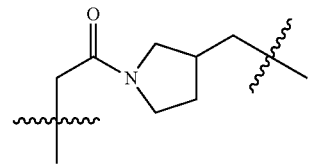

;

Y is selected from the group consisting of: CH$_2$, O, NH, N($C_{1-4}$ alkyl), —NHCO—, —CONH—, —CONHCH$_2$—, —CON($C_{1-4}$ alkyl)CH$_2$—, —OCONH—, —NHCONH—, and —SO$_2$NH—;

$R^1$ is selected from the group consisting of: halogen, $C_{1-4}$ alkyl, CHF$_2$, CN, and CO($C_{1-4}$ alkyl);

$R^3$ is selected from the group consisting of: H, $C_{1-4}$ alkyl, and halogen; and $R^6$ is, independently at each occurrence, is selected from the group consisting of: halogen, NH$_2$, NHCO$_2$($C_{1-4}$ alkyl), and —CH$_2$NHCO$_2$($C_{1-4}$ alkyl).

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —CH$_2$-1,3-phenylene-, —CH$_2$-1,4-phenylene-, —CH$_2$-1,3-phenylene-(CH$_2$)$_2$—, —CH$_2$-1,3-(4-F-phenylene)-, —CH$_2$-1,4-phenylene-(CH$_2$)$_2$—, —CH$_2$-1,3-(4-F-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$—O—(CH$_2$)$_3$-1,3-phenylene-, —CH$_2$-1,3-phenylene-CONHCH$_2$—, —CH$_2$-2,6-pyridinylene-(CH$_2$)$_2$—, —CH$_2$-2,6-(3-F-pyridinylene)-(CH$_2$)$_2$—, and

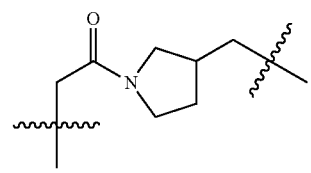

;

Y is selected from the group consisting of: CH$_2$, O, NH, NMe, —CONH—, —NHCO—, —CONHCH$_2$—, —CONMeCH$_2$—, —OCONH—, —NHCONH—, and —SO$_2$NH—;

$R^1$ is selected from the group consisting of: H, F, Cl, Me, COMe, and $CHF_2$;

$R^3$ is selected from the group consisting of: H, Me, and Cl; and $R^6$ is, independently at each occurrence, selected from the group consisting of: F, $NH_2$, $NHCO_2Me$, and —$CH_2NHCO_2Me$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, within the scope of any one of the above aspects, wherein:

L is selected from the group consisting of: —$CH_2$-1,3-phenylene-, —$CH_2$-1,3-phenylene-$(CH_2)_2$—, —$CH_2$-1,3-(4-F-phenylene)-, —$CH_2$-1,3-(4-F-phenylene)-$(CH_2)_2$—, —$CH_2$-1,3-phenylene-$(CH_2)_3$—, —$CH_2$-1,4-phenylene-$(CH_2)_3$—, —$CH_2$-2,6-pyridinylene-$(CH_2)_2$—, and —$CH_2$-2,6-(3-F-pyridinylene)-$(CH_2)_2$—;

Y is selected from the group consisting of: $CH_2$, O, NH, —CONH—, —NHCO—, —CONHCH$_2$—, —CONMeCH$_2$—, —OCONH—, —NHCONH—, and —$SO_2NH$—; and $R^3$ is selected from the group consisting of: H and Cl.

In another aspect, the present invention includes compounds of Formula (IIe) or (IIf) or a stereoisomer, a tautomer, a pharmaceutically acceptable salt, a solvate, or a prodrug thereof, wherein:

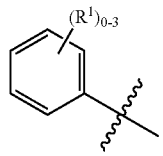

is selected from the group consisting of:

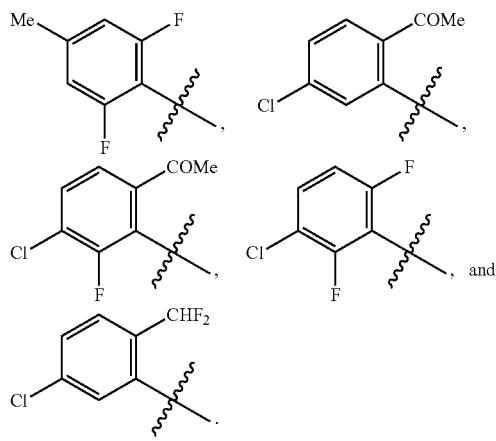

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —$CH_2$-1,3-phenylene-, —$CH_2$-1,4-phenylene-, —$CH_2$-1,3-phenylene-$(CH_2)_2$—, —$CH_2$-1,3-(4-F-phenylene)-, —$CH_2$-1,4-phenylene-$(CH_2)_2$—, —$CH_2$-1,3-(4-F-phenylene)-$(CH_2)_2$—, —$CH_2$-1,3-phenylene-$(CH_2)_3$—, —$CH_2$-1,4-phenylene-$(CH_2)_3$—, —$CH_2$—O—$(CH_2)_3$-1,3-phenylene-, —$CH_2$-1,3-phenylene-$CONHCH_2$—, —$CH_2$-2,6-pyridinylene-$(CH_2)_2$—, —$CH_2$-2,6-(3-F-pyridinylene)-$(CH_2)_2$—, and

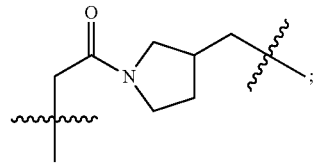 [SMILES: *CC(=O)N1CCC(C*)C1]

Y is selected from the group consisting of: $CH_2$, O, NH, NMe, —CONH—, —NHCO—, —CONHCH$_2$—, —CONMeCH$_2$—, —OCONH—, —NHCONH—, and —$SO_2NH$—;

$R^1$ is selected from the group consisting of: H, F, Cl, Me, COMe, and $CHF_2$;

$R^3$ is selected from the group consisting of: H, Me, and Cl; and $R^6$ is, independently at each occurrence, selected from the group consisting of: F, $NH_2$, $NHCO_2Me$, and —$CH_2NHCO_2Me$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —$CH_2$-1,3-phenylene-, —$CH_2$-1,3-phenylene-$(CH_2)_2$—, —$CH_2$-1,3-(4-F-phenylene)-, —$CH_2$-1,3-(4-F-phenylene)-$(CH_2)_2$—, —$CH_2$-1,3-phenylene-$(CH_2)_3$—, —$CH_2$-1,4-phenylene-$(CH_2)_3$—, —$CH_2$-2,6-pyridinylene-$(CH_2)_2$—, and —$CH_2$-2,6-(3-F-pyridinylene)-$(CH_2)_2$—;

Y is selected from the group consisting of: $CH_2$, O, NH, —CONH—, —NHCO—, —CONHCH$_2$—, —CONMeCH$_2$—, —OCONH—, —NHCONH—, and —$SO_2NH$—; and $R^3$ is selected from the group consisting of: H and Cl.

In another aspect, the present invention includes compounds of Formula (IIe) or (IIf) or a stereoisomer, a tautomer, a pharmaceutically acceptable salt, a solvate, or a prodrug thereof, wherein:

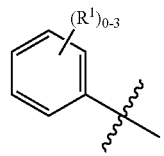

is selected from the group consisting of:

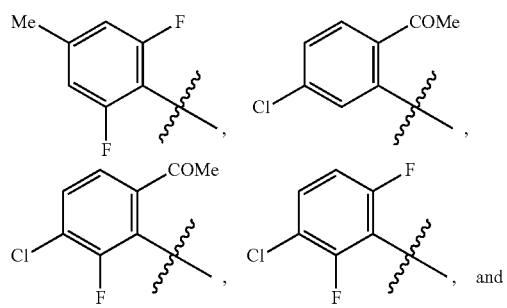

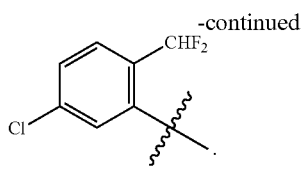

In another aspect, the present invention includes compounds of Formula (III):

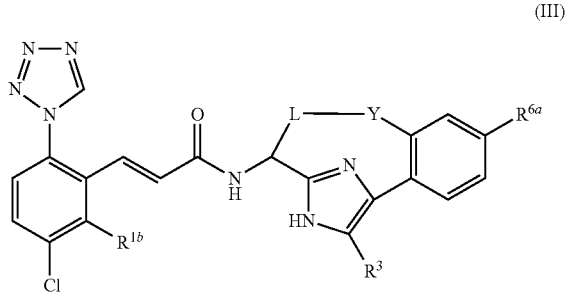

or a stereoisomer, a tautomer, a pharmaceutically acceptable salt, a solvate, or a prodrug thereof, wherein:

L is selected from the group consisting of: —CH$_2$-1,3-phenylene-, —CH$_2$-1,4-phenylene-, —CH$_2$-1,3-phenylene-(CH$_2$)$_2$—, —CH$_2$-1,3-(4-F-phenylene)-, —CH$_2$-1,4-phenylene-(CH$_2$)$_2$—, —CH$_2$-1,3-(4-F-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$—O—(CH$_2$)$_3$-1,3-phenylene-, —CH$_2$-1,3-phenylene-CONHCH$_2$—, —CH$_2$-2,6-pyridinylene-(CH$_2$)$_2$—, —CH$_2$-2,6-(3-F-pyridinylene)-(CH$_2$)$_2$—, and

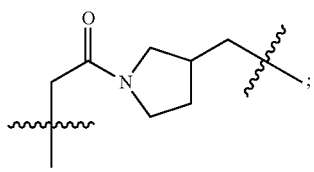 [SMILES: *CC(=O)N1CCC(C*)C1]

Y is selected from the group consisting of: CH$_2$, O, NH, NMe, —CONH—, —NHCO—, —CONHCH$_2$—, —CONMeCH$_2$—, —OCONH—, —NHCONH—, and —SO$_2$NH—;

R$^{1b}$ is selected from the group consisting of: H and F;

R$^3$ is selected from the group consisting of: H, Me, and Cl; and

R$^{6a}$ is selected from the group consisting of: H, F, NH$_2$, and NHCO$_2$Me.

In another aspect, the present invention includes compounds of Formula (III), or a stereoisomer, a tautomer, a pharmaceutically acceptable salt, a solvate, or a prodrug thereof, wherein:

L is selected from the group consisting of: —CH$_2$-1,3-phenylene-, —CH$_2$-1,3-phenylene-(CH$_2$)$_2$—, —CH$_2$-1,3-(4-F-phenylene)-, —CH$_2$-1,3-(4-F-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$-2,6-pyridinylene-(CH$_2$)$_2$—, and —CH$_2$-2,6-(3-F-pyridinylene)-(CH$_2$)$_2$—;

Y is selected from the group consisting of: CH$_2$, O, NH, —CONH—, —NHCO—, —CONHCH$_2$—, —CONMeCH$_2$—, —OCONH—, —NHCONH—, and —SO$_2$NH—;

R$^{1b}$ is selected from the group consisting of: H and F;

R$^3$ is selected from the group consisting of: H and Cl; and

R$^{6a}$ is selected from the group consisting of: H, F, NH$_2$, and NHCO$_2$Me.

In another aspect, the present invention includes compounds of Formula (III), or a stereoisomer, a tautomer, a pharmaceutically acceptable salt, a solvate, or a prodrug thereof, wherein:

L is selected from the group consisting of: —CH$_2$-1,3-phenylene-, —CH$_2$-1,3-phenylene-(CH$_2$)$_2$—, —CH$_2$-1,3-(4-F-phenylene)-(CH$_2$)$_2$—, —CH$_2$-1,3-phenylene-(CH$_2$)$_3$—, —CH$_2$-1,4-phenylene-(CH$_2$)$_3$—, —CH$_2$-2,6-pyridinylene-(CH$_2$)$_2$—, and —CH$_2$-2,6-(3-F-pyridinylene)-(CH$_2$)$_2$—;

Y is selected from the group consisting of: CH$_2$, O, NH, —CONH—, —NHCO—, —OCONH—, —NHCONH—, —CONHCH$_2$—, and —SO$_2$NH—; and R$^3$ is selected from the group consisting of: H and Cl.

In another aspect, the present invention includes compounds of Formula (V): or a stereoisomer, a tautomer, a pharmaceutically acceptable salt, a solvate, or a prodrug thereof, wherein:

ring B is selected from the group consisting of:

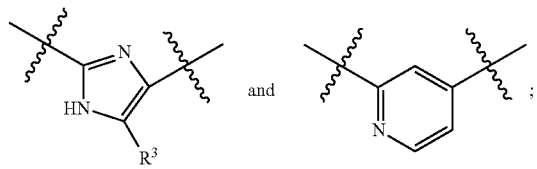

L is —CH$_2$-2,6-(3-F-pyridinylene)-(CH$_2$)$_2$—;

Y is selected from the group consisting of: CH$_2$ and —CONH—;

R$^3$ is selected from the group consisting of: H and Cl; and

R$^{6a}$ is selected from the group consisting of: H and —NHCO$_2$Me.

In another embodiment, the compounds of the present invention have Factor XIa Ki values≤10 μM.

In another embodiment, the compounds of the present invention have Factor XIa Ki values≤1 μM.

In another embodiment, the compounds of the present invention have Factor XIa Ki values≤0.5 μM.

In another embodiment, the compounds of the present invention have Factor XIa Ki values≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, dabigatran, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "Co alkyl" or "Co alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and Methods in Enzymology, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry Principles and Practice*, King, F. D., ed. The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "nL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^{1}H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-meta-chloroperbenzoic acid
CPBA
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-Y-ethylcarbodiimide
EDCI N-(3-dimthylaminopropyl)-Ar-ethylcarbodiimide hydrochloride
EDTA ethylenediaminetetraacetic acid
(S,S)-(+)-1,2-bis((2S,5S)-2,5-diethylphospholano)benzene (1,5
EtDuPhosRh(I) cyclooctadiene)rhodium(I) trifluoromethanesulfonate
$Et_3N$ or TEA triethylamine EtOAc ethyl acetate
Et₂O diethyl ether
EtOH ethanol
GMF glass microfiber filter
Grubbs (II) (1,3-bis(2,4,6-trimethylphenyl)-2-imidazolidinylidene)dichloro(phenylmethylene) (triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
H₂SO₄ sulfuric acid
K₂CO₃ potassium carbonate
KOAc potassium acetate
K₃PO₄ potassium phosphate
LAH lithium aluminum hydride
LG leaving group
LiOH lithium hydroxide
MeOH methanol
MgSO₄ magnesium sulfate
MsOH or MSA methylsulfonic acid
NaCl sodium chloride
NaH sodium hydride
NaHCO₃ sodium bicarbonate
Na₂CO₃ sodium carbonate
NaOH sodium hydroxide
Na₂SO₃ sodium sulfite
Na₂SO₄ sodium sulfate
NBS N-bromosuccinimide
NCS N-chlorosuccinimide
NH₃ ammonia
NH₄Cl ammonium chloride
NH₄OH ammonium hydroxide
OTf triflate or trifluoromethanesulfonate
Pd₂(dba)₃ tris(dibenzylideneacetone)dipalladium(0)
Pd(OAc)₂ palladium(II) acetate
Pd/C palladium on carbon
Pd(dppf)Cl₂ [1,1'-bis(diphenylphosphino)-ferrocene]dichloropalladium(II)
Ph₃PCl₂ triphenylphosphine dichloride
PG protecting group
POCl₃ phosphorus oxychloride
i-PrOH or IPA isopropanol
PS polystyrene
SEM-Cl 2-(trimethysilyl)ethoxymethyl chloride
SiO₂ silica oxide
SnCl₂ tin(II) chloride
TBAI tetra-n-butylammonium iodide
TEA triethylamine
TFA trifluoroacetic acid
THF tetrahydrofuran
TMSCHN₂ trimethylsilyldiazomethane
T3P propane phosphonic acid anhydride
TRIS tris (hydroxymethyl)aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

Imidazole derivatives useful for the synthesis of the compounds of this invention may be synthesized according to the general method outlined in Scheme 1 (Contour-Galcera et al., *Bioorg. Med. Chem. Lett.,* 11(5):741-745 (2001)). Alkylation of the potassium or cesium carboxylate of an appropriately protected or derivatized alpha amino acid 1a with a suitably substituted alpha-bromoketone 1b (ring C is aryl or heteroaryl) provides the keto ester 1c. The imidazole 1d is formed by heating the keto ester 1c to reflux in a suitable solvent, such as toluene or xylenes, in the presence of excess ammonium acetate using a Dean-Stark trap to remove water. Formation of the imidazole can also be carried out by combining the keto ester 0c and ammonium acetate in a suitable solvent, such as xylene or ethanol or a combination of solvents such as dimethylformamide and ethanol (1:1) and using microwave heating. Imidazole 1d can then be protected with as suitable protecting group. For example, imidazole 1d can be reacted with SEM-Cl, in the presence of base, such as sodium hydride or dicyclohexylmethyl amine, and in a solvent such as dimethylformamide or tetrahydrofuran to give 1e.

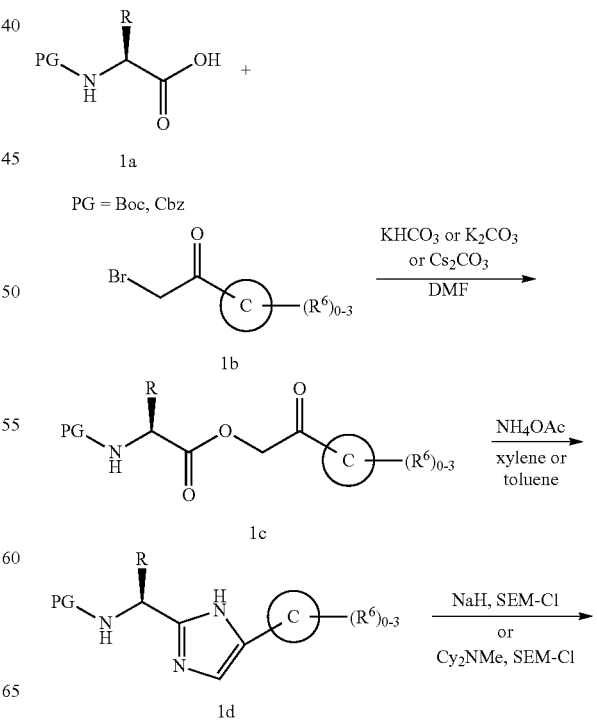

Scheme 1

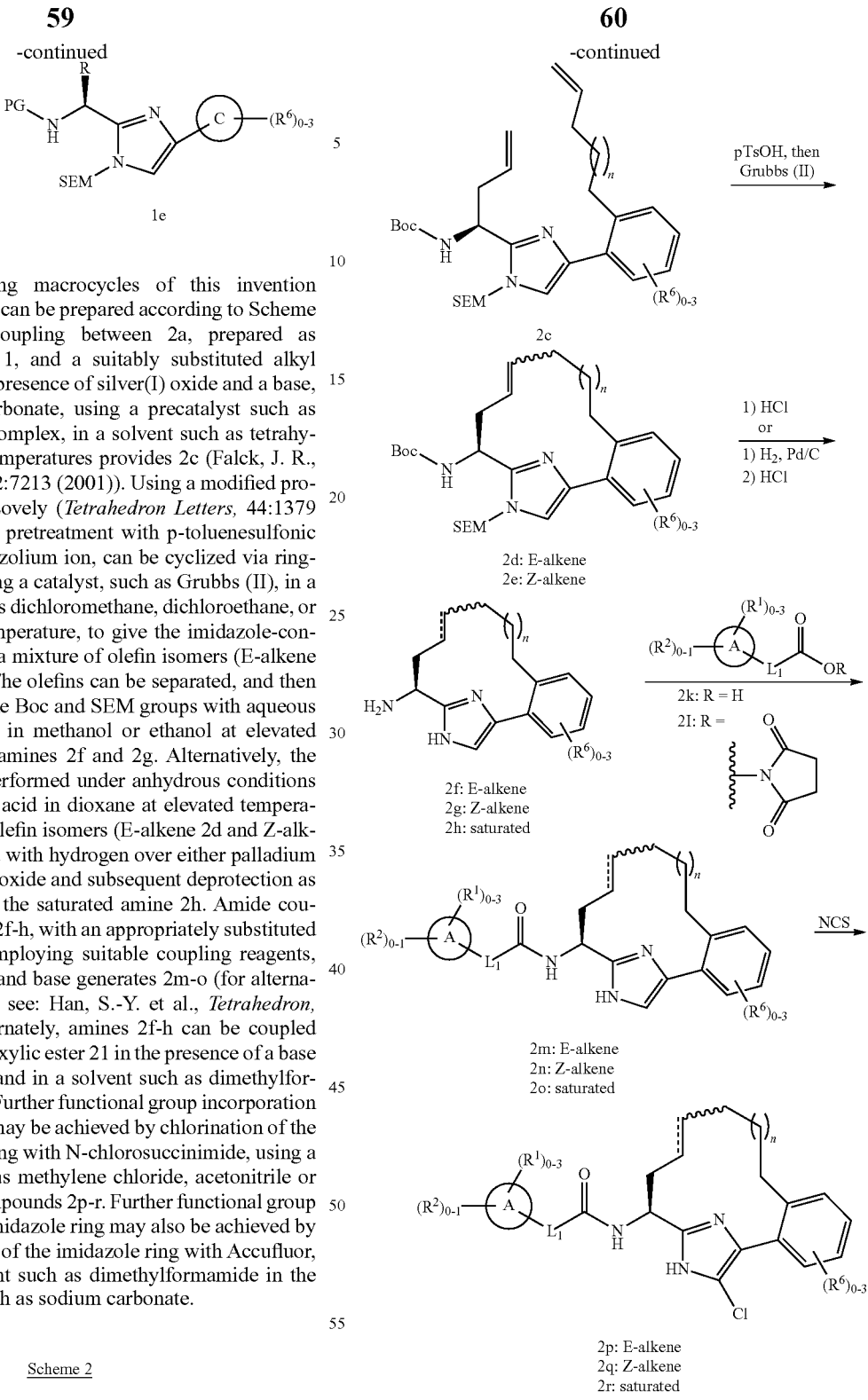

Imidazole containing macrocycles of this invention wherein Y is —CH$_2$— can be prepared according to Scheme 2. Suzuki-Miyaura coupling between 2a, prepared as described in Scheme 1, and a suitably substituted alkyl boronic acid 2b in the presence of silver(I) oxide and a base, such as potassium carbonate, using a precatalyst such as Pd(dppf)Cl$_2$.CH$_2$Cl$_2$ complex, in a solvent such as tetrahydrofuran at elevated temperatures provides 2c (Falck, J. R., *Tetrahedron Letters*, 42:7213 (2001)). Using a modified procedure described by Lovely (*Tetrahedron Letters*, 44:1379 (2003)), 2c, following pretreatment with p-toluenesulfonic acid to form the imidazolium ion, can be cyclized via ring-closing metathesis using a catalyst, such as Grubbs (II), in a suitable solvent, such as dichloromethane, dichloroethane, or toluene at elevated temperature, to give the imidazole-containing macrocycle as a mixture of olefin isomers (E-alkene 2d and Z-alkene 2e). The olefins can be separated, and then deprotection of both the Boc and SEM groups with aqueous 5M hydrochloric acid in methanol or ethanol at elevated temperature provides amines 2f and 2g. Alternatively, the deprotection can be performed under anhydrous conditions with 4M hydrochloric acid in dioxane at elevated temperatures. The mixture of olefin isomers (E-alkene 2d and Z-alkene 2e) can be reduced with hydrogen over either palladium on carbon or platinum oxide and subsequent deprotection as described above gives the saturated amine 2h. Amide coupling between amines 2f-h, with an appropriately substituted carboxylic acid 2k, employing suitable coupling reagents, such as EDCI, HOBt, and base generates 2m-o (for alternative coupling reagents see: Han, S.-Y. et al., *Tetrahedron*, 60:2447 (2004)). Alternately, amines 2f-h can be coupled with an activated carboxylic ester 2l in the presence of a base such as Hunig's base and in a solvent such as dimethylformamide to give 2m-o. Further functional group incorporation on the imidazole ring may be achieved by chlorination of the C-5 of the imidazole ring with N-chlorosuccinimide, using a suitable solvent such as methylene chloride, acetonitrile or chloroform to give compounds 2p-r. Further functional group incorporation on the imidazole ring may also be achieved by fluorination of the C-5 of the imidazole ring with Accufluor, using a suitable solvent such as dimethylformamide in the presence of a base, such as sodium carbonate.

Scheme 2

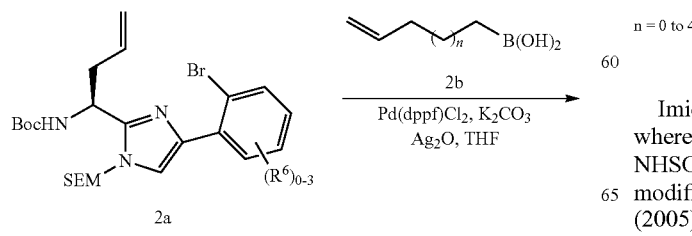

Imidazole containing macrocycles of this invention wherein Y is NH, NHC(O), NHCO$_2$, NHC(O)NH, and NHSO$_2$ can be prepared according to Scheme 3. Using a modified procedure described by Ma (*Synthesis*, 3:496 (2005)), bromide 2a can be coupled with an appropriately substituted amine 3a employing copper (I) iodide and L-proline in the presence of a base such as potassium carbonate, in a solvent such as dimethylsulfoxide at elevated temperature to give the substituted aniline 3g. Alternatively, bromide 2a can be converted to the unsubstituted aniline 3b under similar reaction conditions (Chang, S., *Chem. Commun.*, 3052 (2008)). The aniline 3b can then be coupled with an appropriately substituted carboxylic acid 3c using T3P in a solvent such as ethyl acetate or dimethylformamide to give the amide 3h. The aniline 3b can also be coupled with an appropriately substituted chloroformate 3d, isocyanate 3e, or sulfonyl chloride 3f to provide the carbamate 3k, urea 3l, and the sulfonamide 3m, respectively. Compounds of the formula 3g, 3h, and 3k-m can be converted to compounds 3n-r according to Scheme 2. For the preparation of compounds of the formulae 3n, the preferred method for removing both the Boc and SEM, as described in Scheme 2, employs anhydrous 4M hydrochloric acid in dioxane at elevated temperatures with either cysteine or O-methyl hydroxylamine as a formaldehyde scavenger.

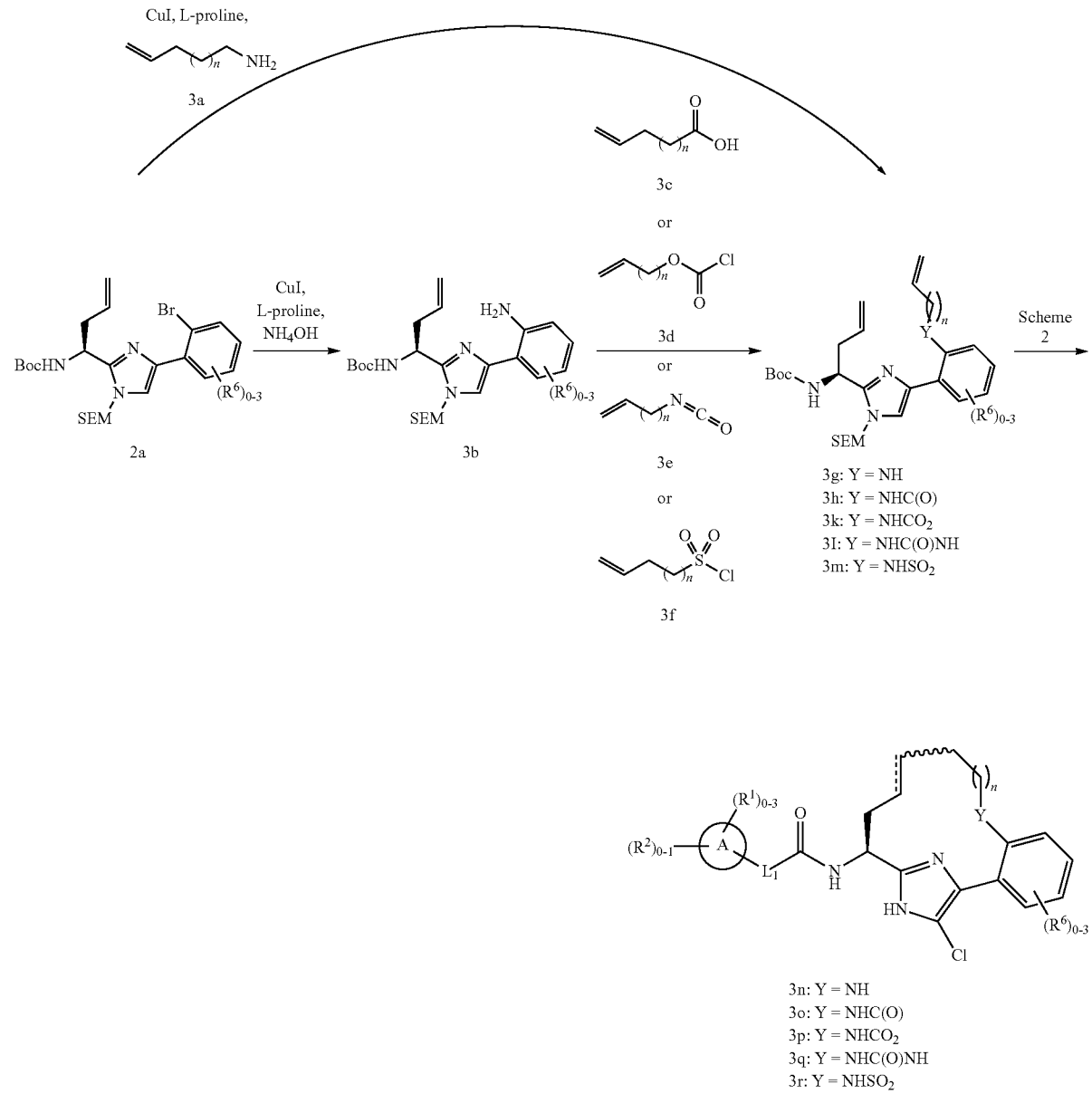

n = 0 to 4

Imidazole-containing macrocycles of this invention wherein Y is C(O)NH can be prepared according to Scheme 4. Subjecting 2a to methyllithium followed by metal-halogen exchange with n-butyllithium and quenching the intermediate anion with carbon dioxide provides the carboxylic acid 4a. Amide coupling with an appropriately substituted amine 4b, as previously described for the conversion of 3b to 3h, gives amide 4c. Amide 4c can be converted to compounds 4d-f according to Scheme 2.

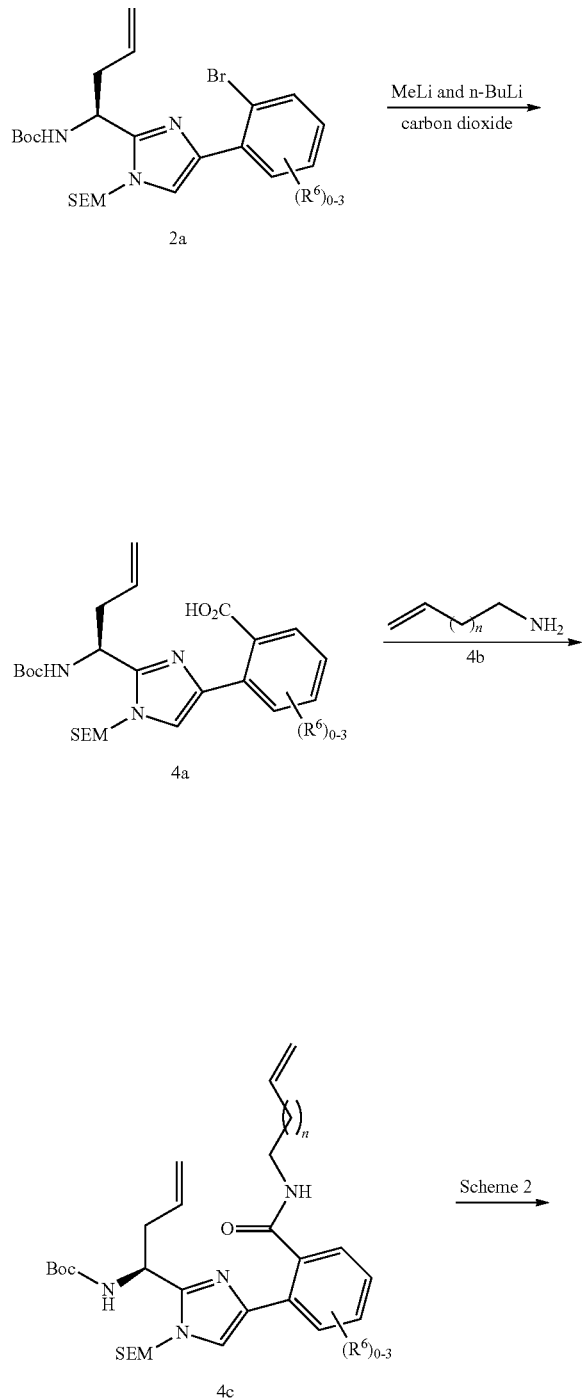

Scheme 4

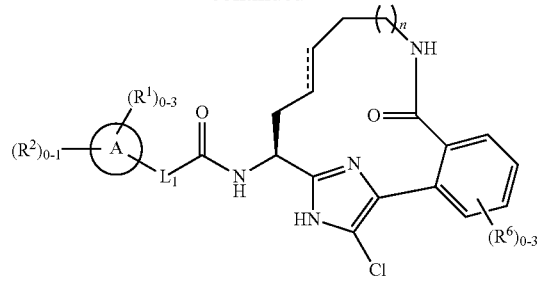

4d: E-alkene
4e: Z-alkene
4f: saturated $n = 0$ to $4$

Chiral amino acids 1a useful for the synthesis of imidazole compounds of this invention are either commercially available or can be prepared by any of a number of methods known in the art. For example, as shown in Scheme 5, didehydroamino acid derivatives of formula 5a may be reduced to provide protected (S)-amino acids of formula 5b by hydrogenation in the presence of a chiral catalyst such as (S,S)-EtDuPhosRh(I) using a modified procedure of Burk (*J. Am. Chem. Soc.,* 113:8518 (1991)). Didehydroamino acid derivatives of formula 5a can be prepared via several methods, such as for example, a Heck coupling between an aryl iodide, bromide, or triflate of formula 5c and Boc didehydroalanine benzyl ester, using a modified procedure of Carlström et al. (*Synthesis,* 414 (1989)). Alternatively, protected didehydroaminoacids of formula 5a may be prepared by Horner-Emmons type condensation of an suitably substituted aldehyde of formula 5d with Boc-methyl-2-(dimethylphosphono) glycinate, using modifications of literature procedures (Wang et al., *Tetrahedron,* 58:3101 (2002)). Protected amino acids of formula 5b may also be prepared by alkylation of methyl 2-(diphenylmethyleneamino)acetate with an appropriately substituted benzylbromide 5e in the presence of a chiral cinchonidinium catalyst in a suitable solvent, such as methylene chloride, using a procedure similar to that described by O'Donnell et al. (*Tetrahedron,* 55:6347 (1999)), followed by mild acidic workup and reprotection of the amino functionality with a Boc group according to methods known to one skilled in the art. Substitution of heteroaryl bromides or iodides for 5c, heteroaryl aldehydes for 5d, and heteroarylalkyl for 5e in Scheme 5 would lead to additional chiral amino acids useful for the synthesis of imidazole compounds of this invention.

Scheme 5

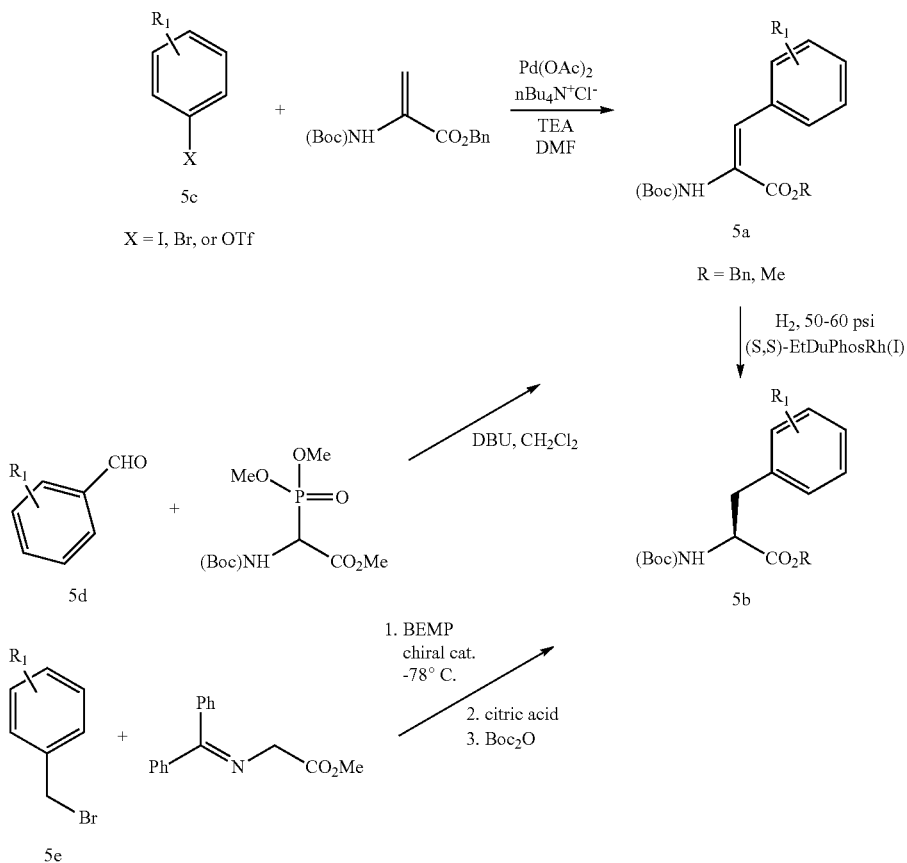

Certain 2-bromoacetophenone analogs (1b, C=aryl) that are not commercially available may be synthesized from commercially available starting materials as described in Scheme 6. Acetophenone derivatives 6a can be treated with a brominating reagent such as bromine in a solvent such chloroform to give 6b. Alternatively, acetophenone derivatives 6a can be treated with either copper (II) bromide in a solvent such as ethyl acetate at elevated temperature or phenyltrimethylammonium tribromide in a solvent such as tetrahydrofuran at low temperature to provide 6b. Benzoic acid derivatives 6c can be treated sequentially with oxalyl chloride in a suitable solvent, such as dichloromethane, containing a few drops of DMF, and then treated with trimethylsilyldiazomethane in a suitable solvent or solvent combination, such as acetonitrile and hexane. The intermediate diazoketone is isolated and treated with aqueous hydrobromic acid and dichloromethane to provide 6b. Alternatively the benzoic acid derivatives 6c can be converted to the acetophenone derivatives 6a in three steps as described in Scheme 6. Alternatively, Stille coupling between a suitably substituted aryl halide or triflate and tributyl-(1-ethoxyvinyl) stannane with a palladium catalyst, such as bis-(triphenylphosphine)palladium dichloride, in a suitable solvent, such as toluene, at elevated temperature yields the enol ether 6e. The resulting enol ether 6e can be converted to 6b with N-bromosuccinimide.

Scheme 6

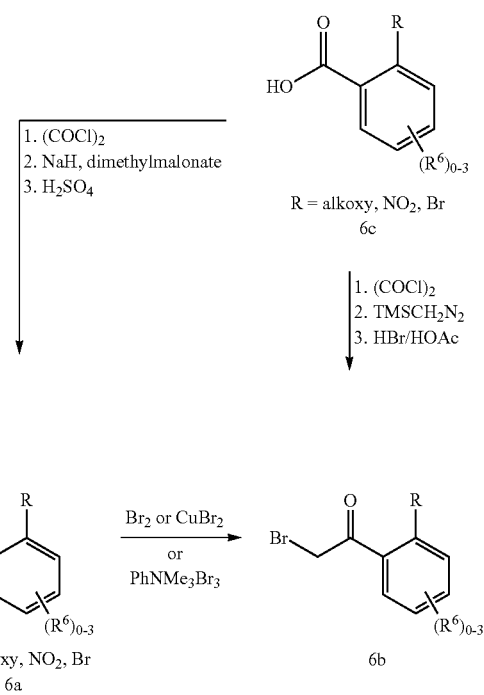

-continued

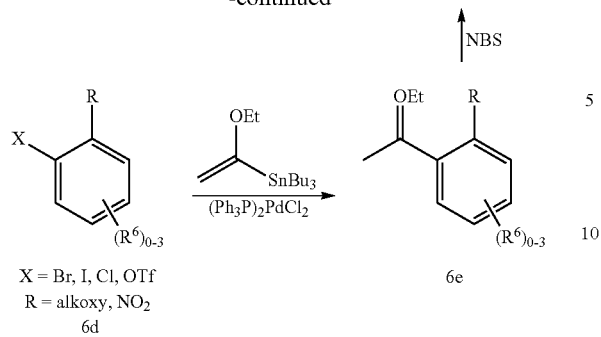

Scheme 7

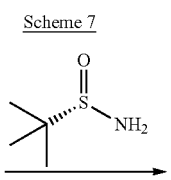

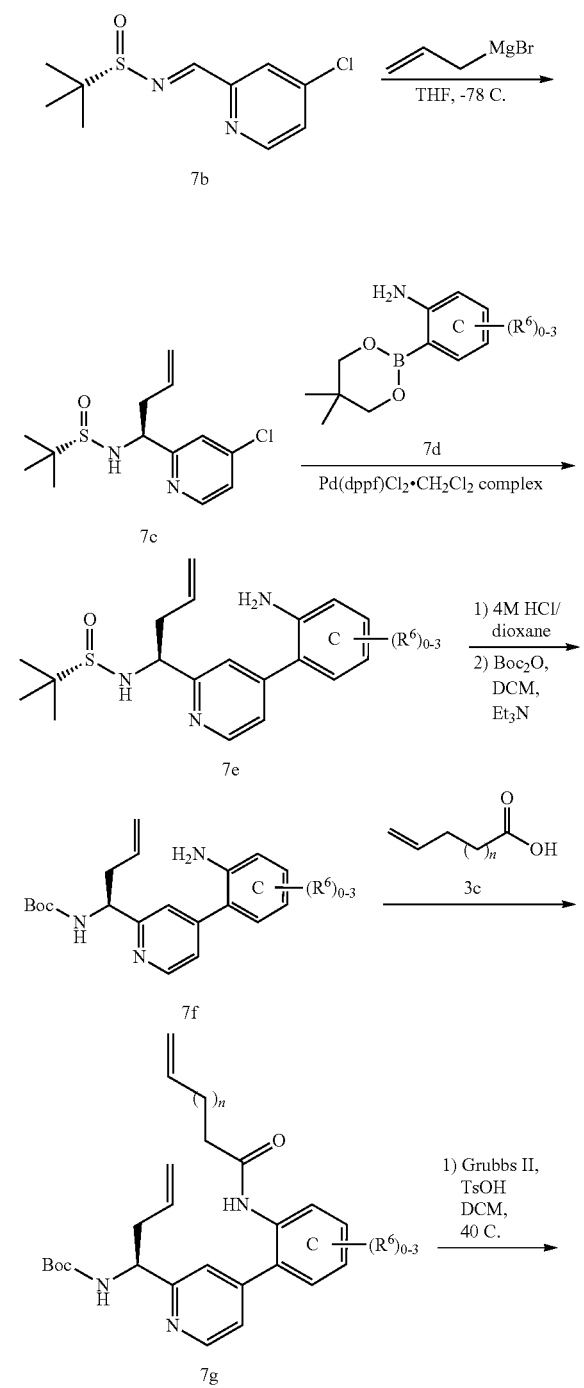

The syntheses of appropriately substituted carboxylic acids of formulae 2k, where A=aryl and where L₁=—CH₂CH₂—, —CH═CH—, —C≡C—, —OCH₂—, —S(O)$_p$CH₂—, or —CH₂NH—, useful for the synthesis of amide compounds of this invention as outlined in Scheme 2 are described in PCT International Application No. WO 2009/114677 published Sep. 17, 2009, which is incorporated in its entirety herein by reference. In addition, 1-amino-5,6,7,8-tetrahydroisoquinoline-6-carboxylic acid useful for the synthesis of amide compounds of this invention as outlined in Scheme 2 is described in U.S. Patent Application No. 2005/0282805 published Dec. 22, 2005, which is incorporated in its entirety herein by reference.

Representative pyridine (ring B=pyridine) containing macrocycles of this invention wherein Y is NHCO can be prepared as shown in Scheme 7. Condensation of aldehyde 7a, prepared according to a modified procedure described by Negi (*Synthesis*, 991 (1996)), with (S)-2-methylpropane-2-sulfinamide in the presence of anhydrous copper sulfate in a solvent such as dichloromethane gives the sulfinimine 7b (Ellman, J., *J. Org. Chem.*, 64:1278 (1999).) Using a modified procedure described by Kuduk (*Tetrahedron Letters*, 45:6641 (2004)), suitably substituted Grignard reagents, for example allylmagnesium bromide, can be added to sulfinimine 7b to give a sulfinamide 7c, as a mixture of diastereomers which can be separated at various stages of the sequence. Suzuki-Miyaura coupling between 4-chloropyridine 7c and an appropriately substituted aryl or heteroaryl boronic acid or ester 7d in the presence of a base such as potassium phosphate in a solvent mixture, such dimethylsulfoxide and water, or dimethylformamide, using a precatalyst such as Pd(dppf)Cl₂.CH₂Cl₂ complex provides 7e. Protecting group interconversion can be accomplished in two steps to give 7f. The aniline 7f can then be coupled with an appropriately substituted carboxylic acid 3c using propane phosphonic acid anhydride (T3P) to give the amide 7g. Ring closing metathesis, as described previously in Scheme 2, affords the pyridine containing macrocycle 7h, as the E-alkene. Boc deprotection on 7h with either TFA in dichloromethane or 4M hydrochloric acid in dioxane gives amine 7k. Alternatively, hydrogenation of 7h followed by Boc deprotection with TFA in dichloromethane provides amine 7l. Compounds 7k and 7l can be converted to compounds 3m and 3n according to Scheme 2.

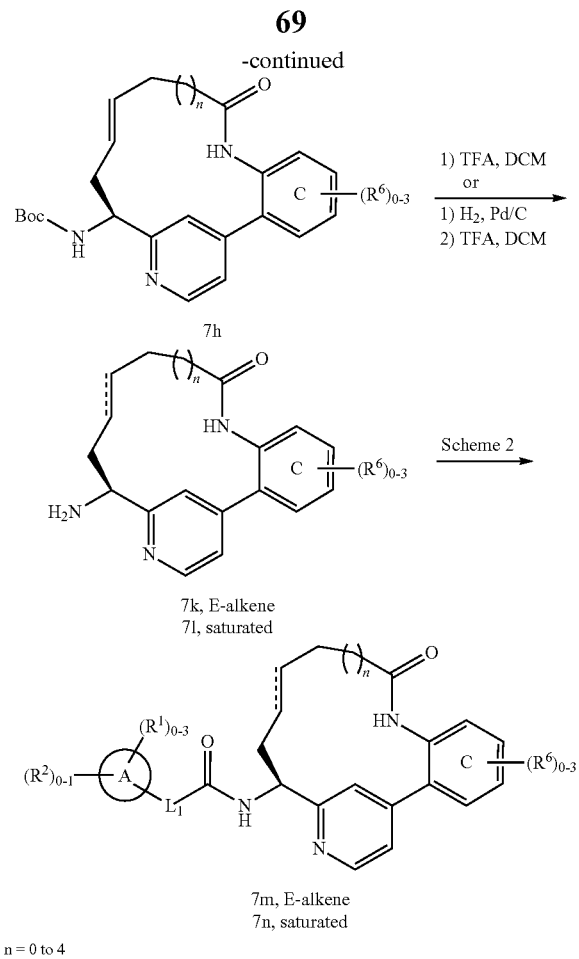

7h

7k, E-alkene
7l, saturated

7m, E-alkene
7n, saturated n = 0 to 4

Additional pyridine (ring B=pyridine) containing macrocycles of this invention wherein Y is $NHCO_2$, NHC(O)NH, and $NHSO_2$ can be prepared according to Scheme 7 by replacing 3c with an appropriately substituted chloroformate 3d, isocyanate 3e, or sulfonyl chloride 3E Additional macrocycles containing regioisomeric pyridine scaffolds to the one described in Scheme 7 can be prepared by an analogous sequence.

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., Synthesis, 1 (1976); "Pyridine and Its Derivatives", *The Chemistry of Heterocyclic Compounds*, 14(Suppl. 1-4), Abramovitch, R. A., ed., John Wiley & Sons, New York (1974); *Comprehensive Heterocyclic Chemistry*, 2:165-524, Boulton, A. J. et al., eds., Pergamon Press, New York (1984); *Comprehensive Heterocyclic Chemistry*, 5:1-300, McKillop, A., ed., Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato)diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23): 7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996).)

Representative phenyl (ring B=phenyl) containing macrocycles of this invention wherein Y is NHCO can be prepared as shown in Scheme 8. Using a modification of the procedure described by Hart (*J. Org. Chem.*, 48(3):289-294 (1983)), in situ generation of N-trimethylsilylaldimines from a suitably substituted benzaldehyde 8a and lithium bis(trimethylsilyl) amide, followed by the addition of Grignard or alkyllithium reagents 8b, for instance allylmagnesium bromide, gives after aqueous work up the amine 8c. The amine can be protected as the Boc. Compounds of the formula 8e and 8f can be prepared following the sequence described in Scheme 7, by replacing 7c with 8d.

Scheme 8

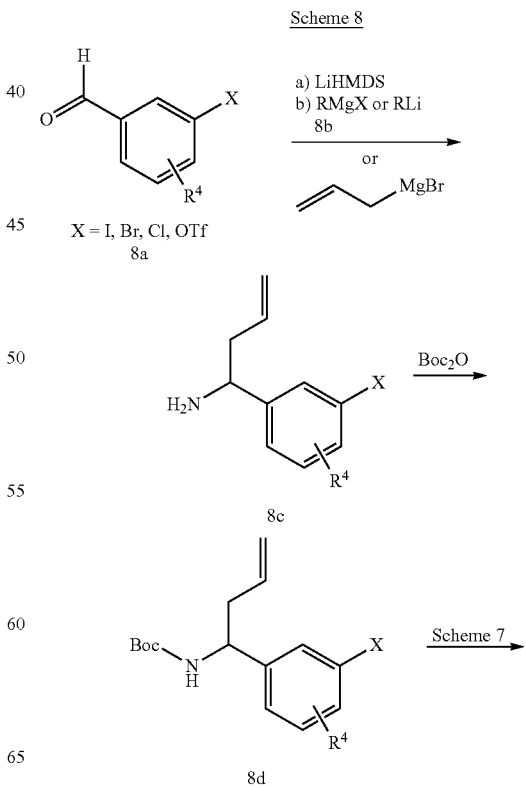

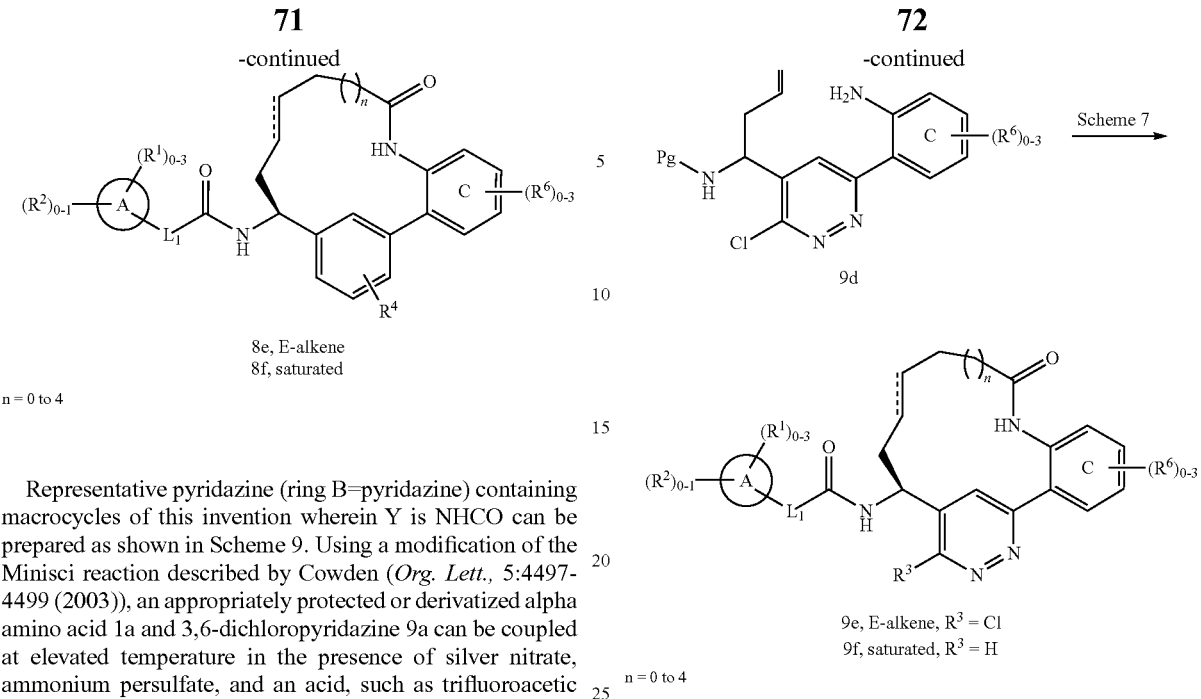

8e, E-alkene
8f, saturated n = 0 to 4

Representative pyridazine (ring B=pyridazine) containing macrocycles of this invention wherein Y is NHCO can be prepared as shown in Scheme 9. Using a modification of the Minisci reaction described by Cowden (*Org. Lett.*, 5:4497-4499 (2003)), an appropriately protected or derivatized alpha amino acid 1a and 3,6-dichloropyridazine 9a can be coupled at elevated temperature in the presence of silver nitrate, ammonium persulfate, and an acid, such as trifluoroacetic acid, in a solvent, such as water or a water/dimethylformamide mixture, to give compounds of the formulae 9b. Compound 9b wherein R=H, prepared using an appropriately protected glycine derivative of 1a, can be further functionalized by deprotonation with sec-BuLi and subsequent alkylation with an appropriately substituted alkyl halide, for instance allyl bromide, to give compound 9c. Suzuki-Miyaura coupling between chloropyridazine 9c and an appropriately substituted aryl or heteroaryl boronic acid or ester 7d in the presence of a base such as potassium phosphate in a solvent mixture, such dimethylsulfoxide and water, or dimethylformamide, using a precatalyst such as Pd(dppf)Cl₂·CH₂Cl₂ complex provides 9d. Compounds of the formula 9e and 9f can be prepared following the sequence described in Scheme 7, by replacing 7f with 9d.

9e, E-alkene, $R^3$ = Cl
9f, saturated, $R^3$ = H n = 0 to 4

Methods for the synthesis of a large variety of substituted pyridazines useful for the preparation of compounds of the present invention are well known in the art. (For examples of methods useful for the preparation of pyridazine starting materials see: "Pyridazines", *The Chemistry of Heterocyclic Compounds*, Vol. 28, Castle, R. N., ed.,
John Wiley & Sons, New York (1973); "The Pyridazines", *The Chemistry of Heterocyclic Compounds*, 57(Suppl. 1), Brown, D. J., ed., John Wiley & Sons, New York (2000); *Comprehensive Heterocyclic Chemistry II*, 6:1-93, Boulton, A. J., ed., Elsevier Science Inc., New York (1996)).

Scheme 9

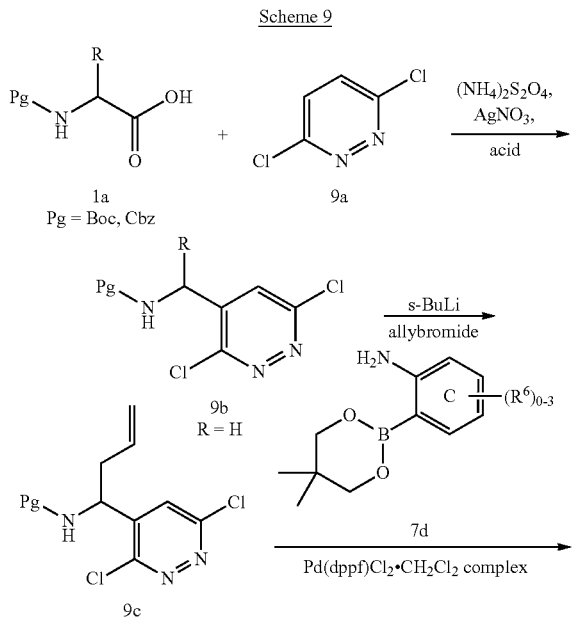

Scheme 10

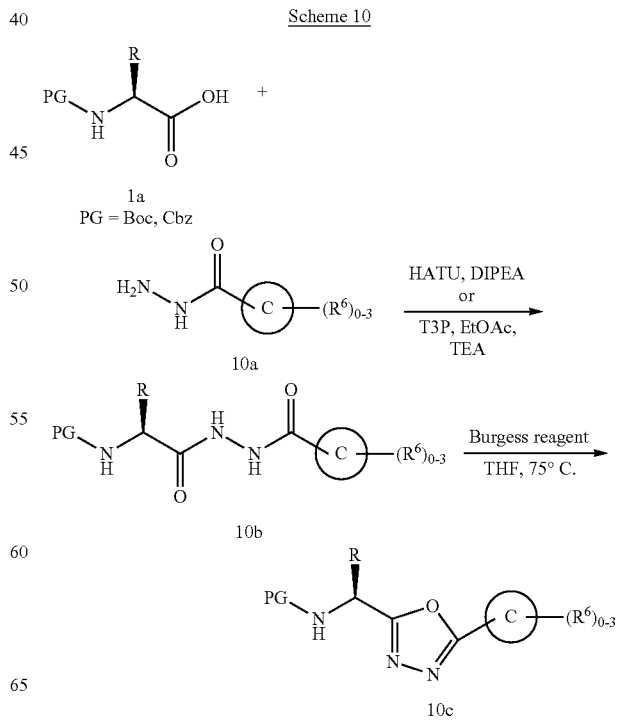

Oxadiazole derivatives useful for the synthesis of the compounds of this invention may be synthesized according to the general method outlined in Scheme 10. A suitably protected amino acid 1a is coupled to a hydrazide of formula 10a in the presence of a coupling reagent such as HATU or T3P to provide acylhydrazide 10b which is cyclized to the corresponding oxadiazole 10c by heating in the presence of Burgess reagent in a suitable solvent such as THF.

Scheme 10a

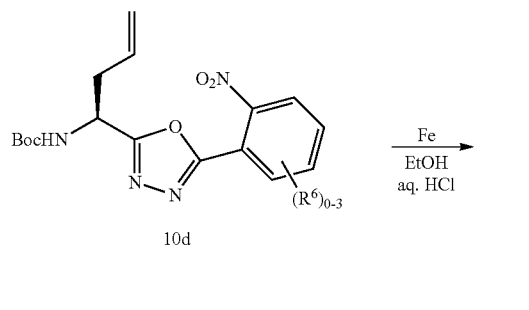

10d

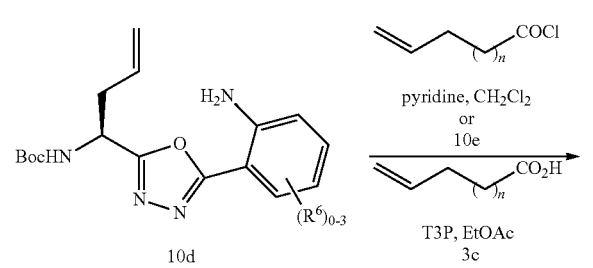

10d

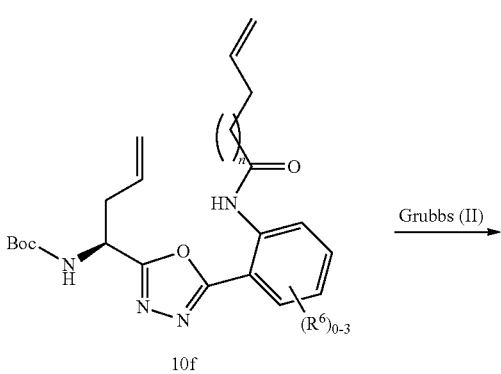

10f

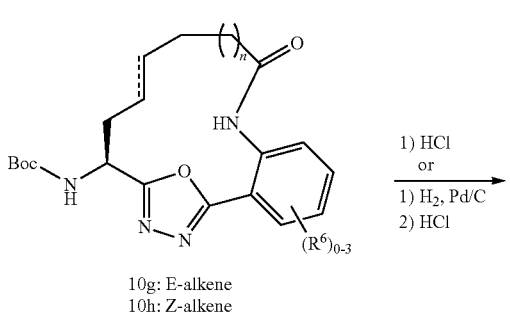

10g: E-alkene
10h: Z-alkene

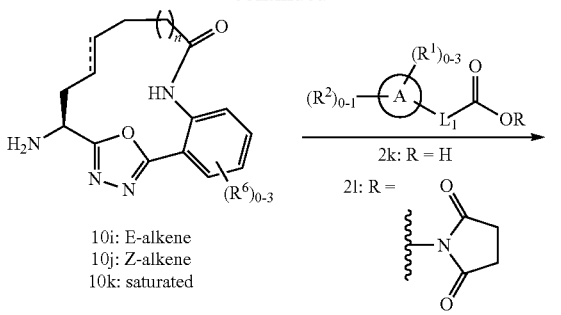

10i: E-alkene
10j: Z-alkene
10k: saturated

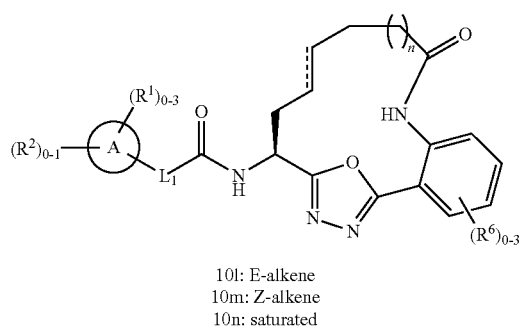

10l: E-alkene
10m: Z-alkene
10n: saturated n = 0 to 4

Representative oxadiazole (ring B=oxadiazole) containing macrocycles of this invention wherein Y is NHCO can be prepared as shown in Scheme 10a. Thus from N-Boc-allylglycine and a suitably substituted 2-nitrophenylhydrazine, compounds of formula 10d can be obtained and then converted into macrocyclic compounds of this invention using similar chemistry to that described above in Scheme 7.

It should be recognized to one skilled in the art of organic synthesis that additional macrocyclic compounds of this invention can be prepared by alternative cyclization strategies which are not limited to the ring-closing metathesis strategy described in Scheme 2. For instance, macrolactamization can also be used as described in Scheme 11. Slow addition of a solution 11a and Hunig's base in DMF to a solution BOP reagent in a mixture dichloromethane and DMF, provides macrocycle 11b. Hydrogenolysis of the Cbz provides the amine 11c. Amide coupling of the amine 11c with 2k or 2l, as described in Scheme 2, and global deprotection gives 11d.

Scheme 11

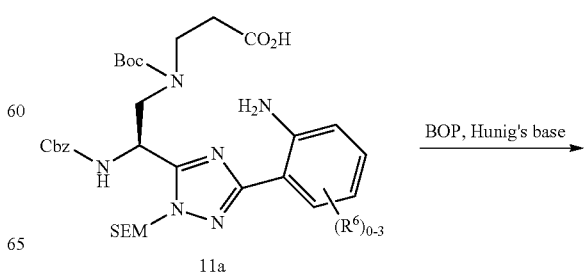

11a

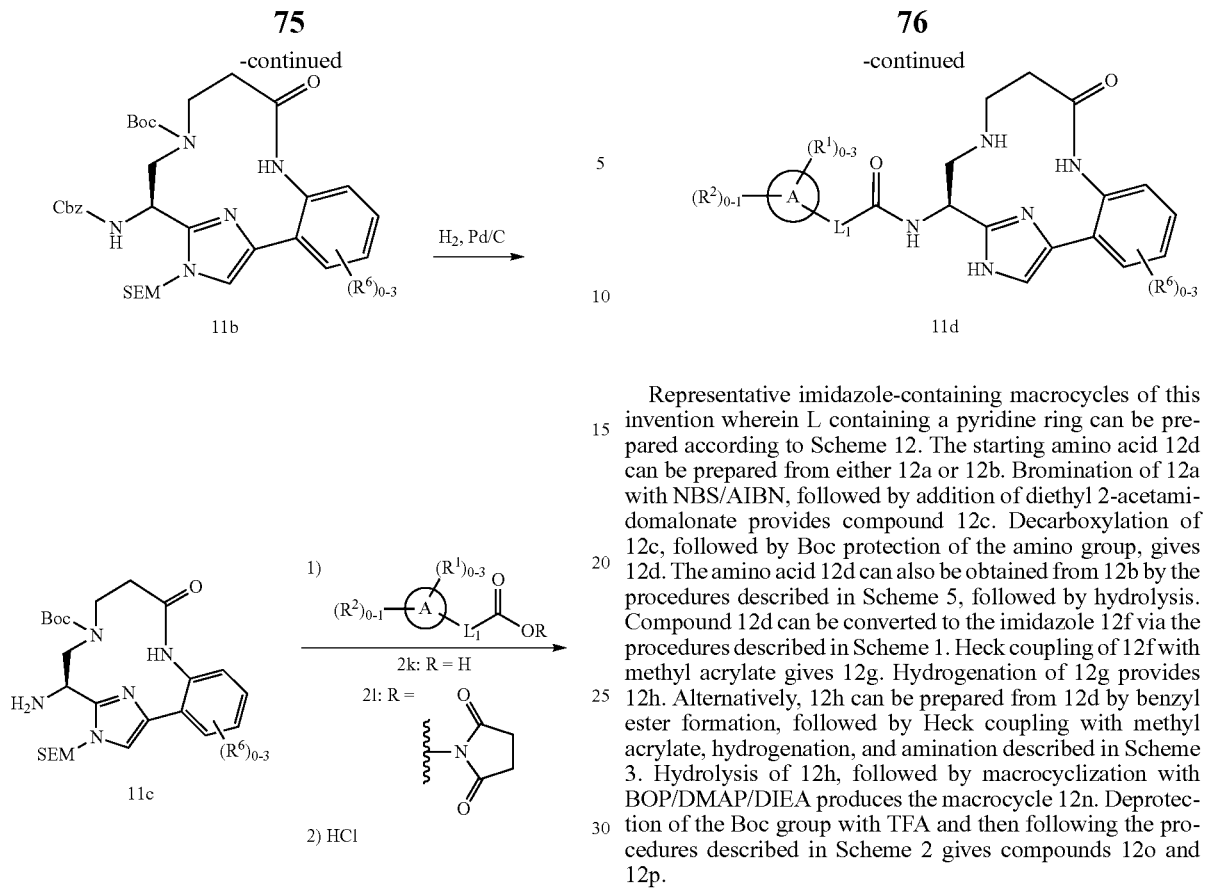

Representative imidazole-containing macrocycles of this invention wherein L containing a pyridine ring can be prepared according to Scheme 12. The starting amino acid 12d can be prepared from either 12a or 12b. Bromination of 12a with NBS/AIBN, followed by addition of diethyl 2-acetamidomalonate provides compound 12c. Decarboxylation of 12c, followed by Boc protection of the amino group, gives 12d. The amino acid 12d can also be obtained from 12b by the procedures described in Scheme 5, followed by hydrolysis. Compound 12d can be converted to the imidazole 12f via the procedures described in Scheme 1. Heck coupling of 12f with methyl acrylate gives 12g. Hydrogenation of 12g provides 12h. Alternatively, 12h can be prepared from 12d by benzyl ester formation, followed by Heck coupling with methyl acrylate, hydrogenation, and amination described in Scheme 3. Hydrolysis of 12h, followed by macrocyclization with BOP/DMAP/DIEA produces the macrocycle 12n. Deprotection of the Boc group with TFA and then following the procedures described in Scheme 2 gives compounds 12o and 12p.

Scheme 12

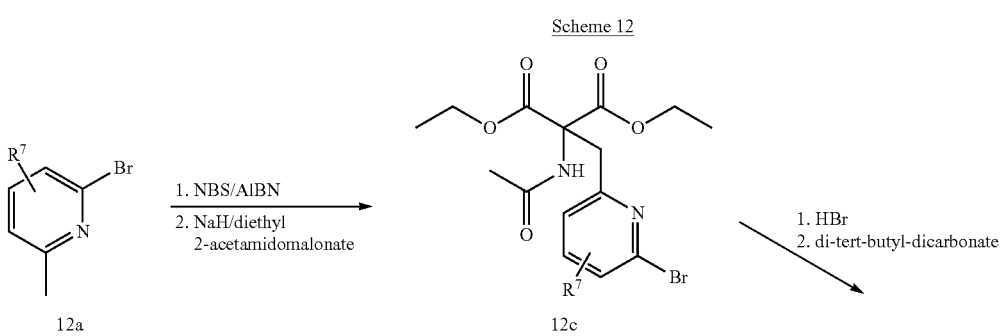

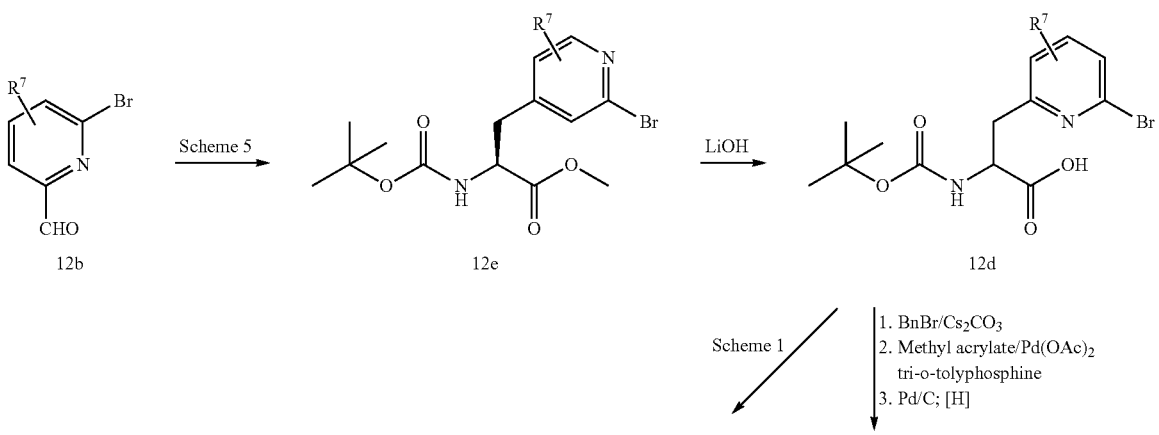

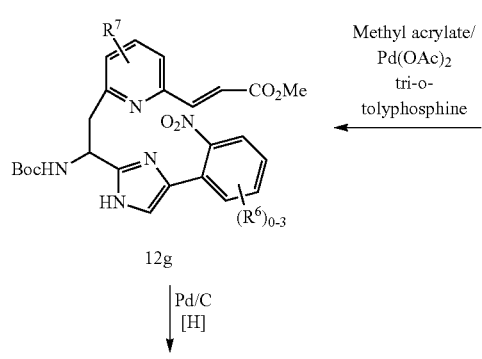

12g

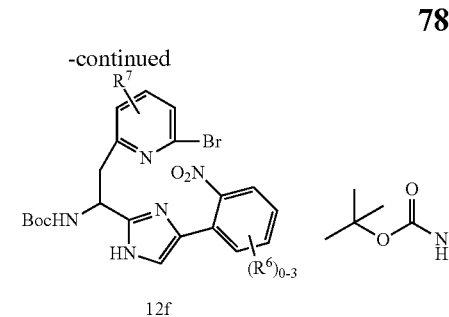

12f    12k

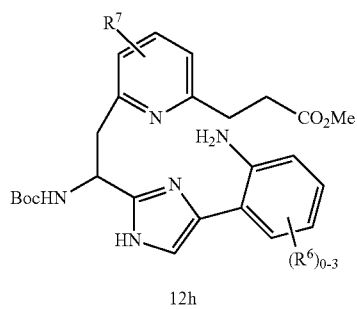

12h

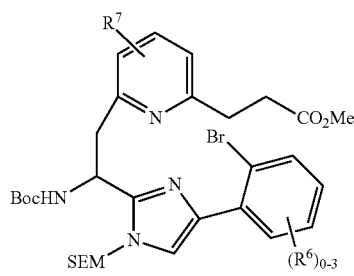

12m

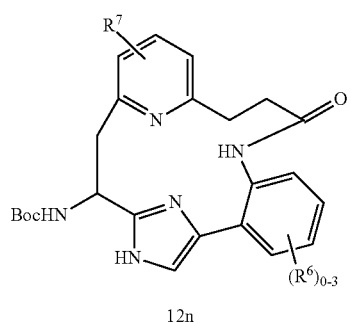

12n

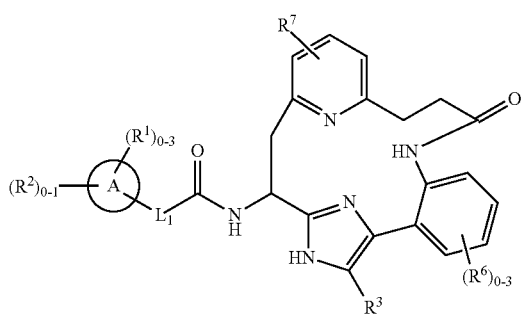

12o, R³ = H
12p, R³ = Cl

Scheme 12 can also be applied to representative imidazole-containing macrocycles of this invention wherein L containing a phenyl ring where N is replaced by CH.

Representative imidazole-containing macrocycles of this invention wherein L containing a pyrimidine ring can be prepared according to Scheme 13 and then followed the same procedures described in Scheme 12. The key amino acid derivative 13g can be prepared from 13a. Heck coupling of 13a with t-butyl acrylate gives 13c. Reduction of the methyl ester in 13c with LiBH$_4$ gives alcohol 13d, which can be oxidized to aldehyde 13e. Reaction of 13e with phosphoglycine followed the procedure in Scheme 5 produces 13f. Reduction of 13f with Duphos catalyst gives 13g, which can be used to prepared the pyrimidine macrocycles followed the procedures in Scheme 12.

Scheme 13

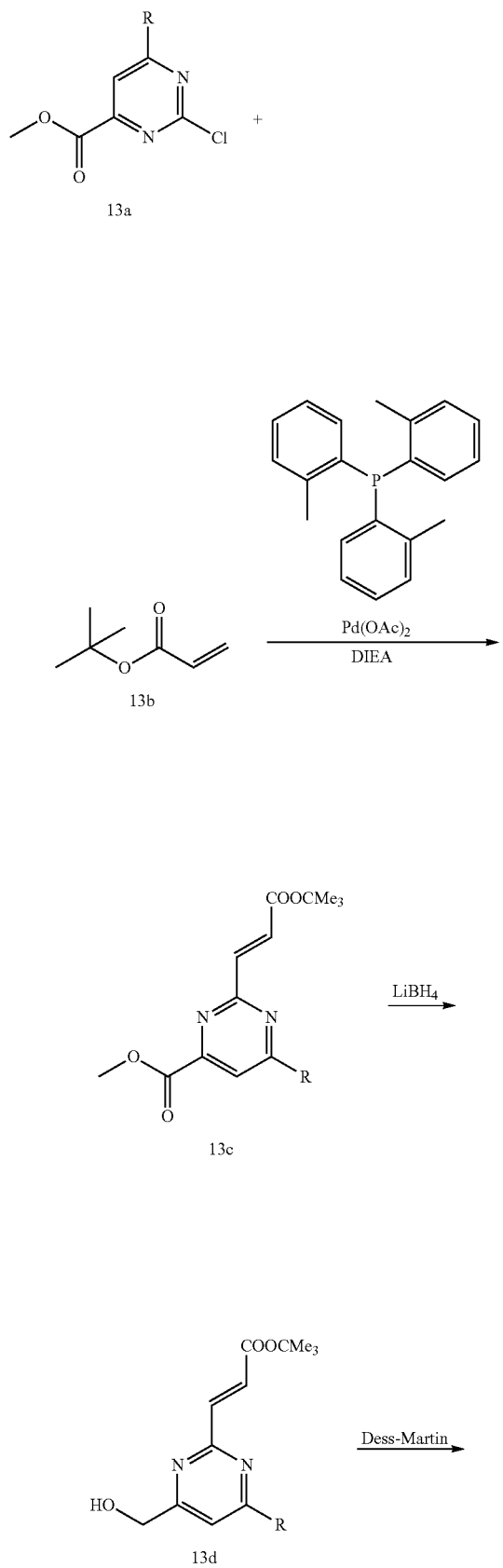

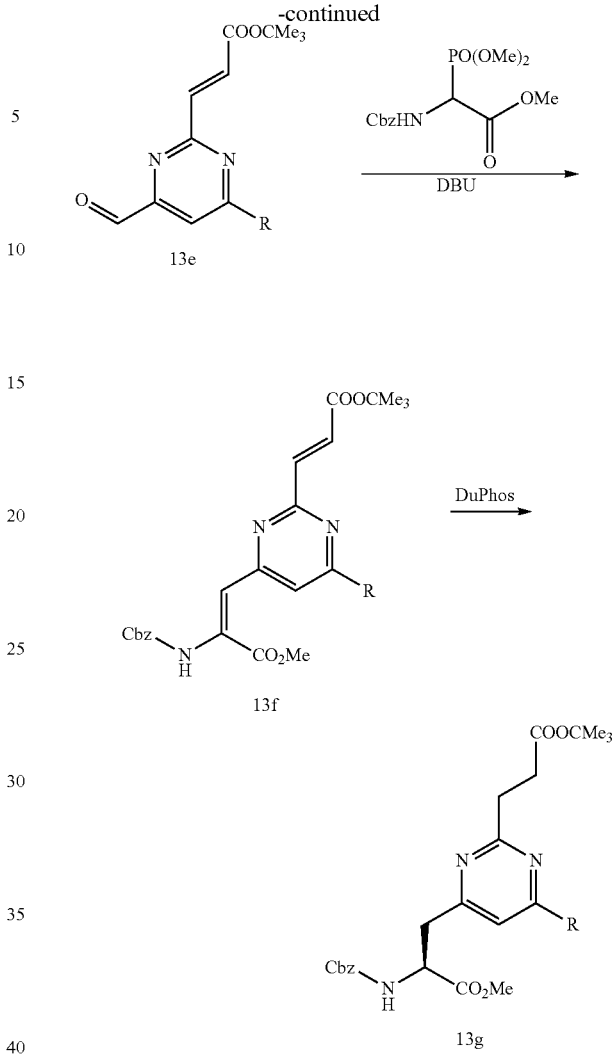

Additional imidazole containing macrocycles of this invention wherein Y is NH can be prepared according to Scheme 14. Using a modified procedure described by Ma (*Synthesis*, 3:496 (2005)), bromide 2a can be coupled with an appropriately substituted amine or amino acid ($R^7$=$CO_2H$) 14a employing copper (I) iodide and L-proline in the presence of a base such as potassium carbonate, in a solvent such as dimethylsulfoxide at elevated temperature, followed by alkylation of the carboxylic acid moiety with an alkyl iodide such as methyl iodide, gives the substituted aniline 14b. Alternatively, 14b can be prepared using a modified procedure described by Zhao (*Synthesis*, 19:3189 (2006)). Combining aniline 3b with appropriately substituted aldehydes 14c in the presence of maleic acid and allyltributyltin provides 14b. Alternatively, aniline 3b can be condensed with trifluoroacealdehyde ethyl hemiacetal followed by the addition of Grignard reagents, such as allylmagnesium bromide, which gives 14d. Compounds of the formula 14b and 14d can be converted to compounds 14e and 14f according to Scheme 2. For the preparation of compounds of the formulae 14e and 14f, the preferred method for removing both the Boc and SEM, as described in Scheme 2, employs anhydrous 4M hydrochloric acid in dioxane at elevated temperatures with either cysteine or O-methyl hydroxylamine as a formaldehyde scavenger. Further manipulation of functional groups on $R^7$ using methods known to one skilled in the art of organic synthesis will give additional compounds of the invention.

Scheme 14
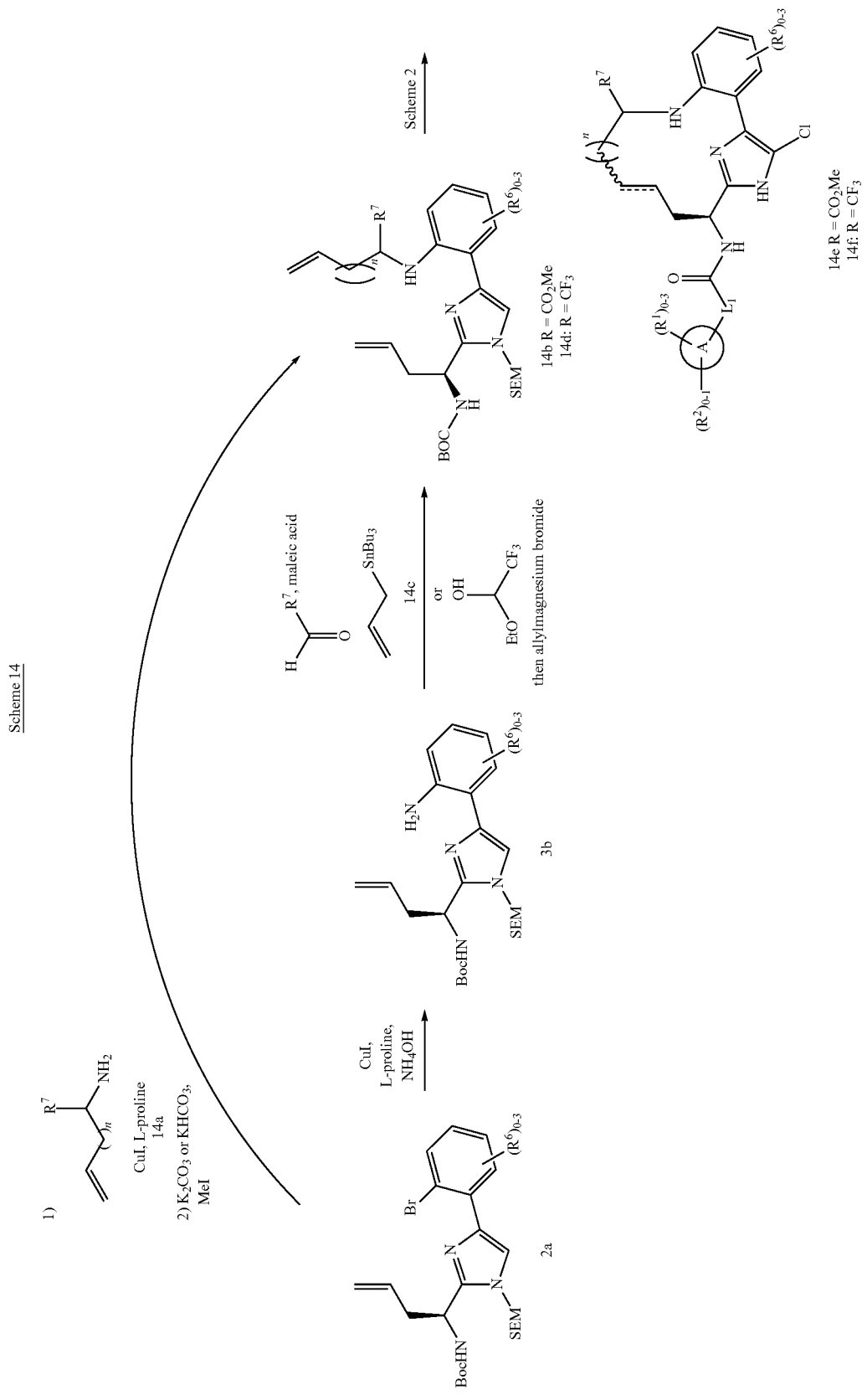
n = 0 to 4

Additional imidazole macrocycles of this invention wherein $R^3$ is CN, can be prepared according to Scheme 15. Deprotection of intermediates 15g and 15h followed by amide coupling as described above will then provide additional compounds of this invention. Further manipulation of functional groups at $R^7$ and $R^3$ using methods known to one skilled in the art of organic synthesis and as exemplified in the specific examples given below will give additional compounds of the invention.

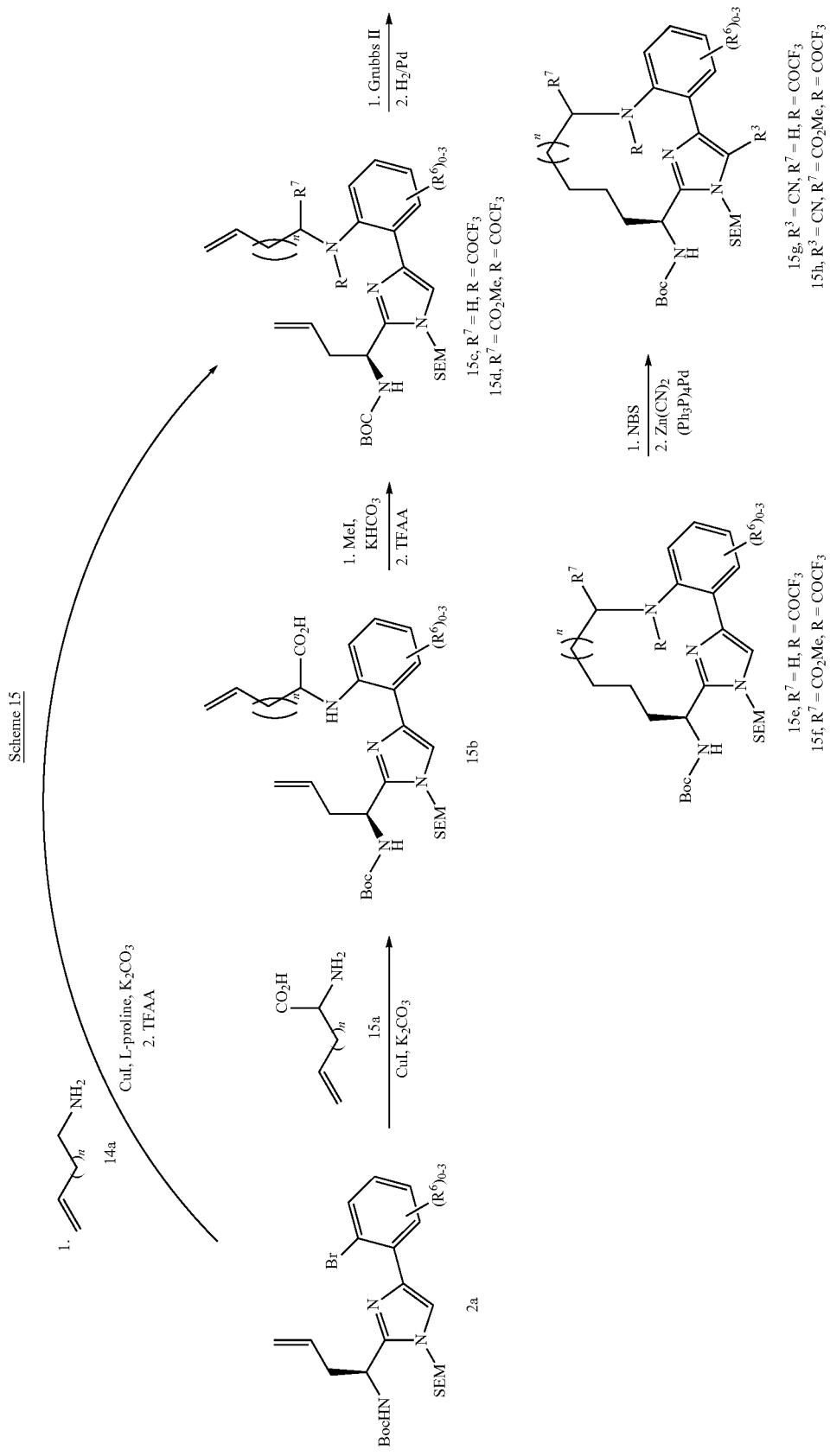

Additional imidazole containing macrocycles of this invention can be prepared according to Scheme 16. Regioselective protection of the 2,4-dibromo imidazole with SEM-Cl provides 16b. Metal-halogen exchange of 16b with n-BuLi followed by quenching with dimethylformamide affords a mixture of the C2 and C4 aldehydes. Condensation of the C2-aldehyde with (S)-2-methylpropane-2-sulfinamide in the presence of anhydrous copper sulfate in a solvent such as dichloromethane gives the sulfinimine 16c. Appropriately substituted Grignard reagents, for example allylmagnesium bromide, can be added to sulfinimine 16c to give sulfinamine 16d, as a mixture of diastereomers which can be separated at various stages of the sequence. Alternatively, the 2,4,5-tribromo imidazole 16e can be converted to 16h according to the four step sequence described above. Regioselective halogen-magnesium exchange of 16h with isopropylmagnesium chloride, followed by quenching with saturated ammonium chloride, provides 16d. Suzuki-Miyaura coupling between bromoimidazole 16d and an appropriately substituted aryl or heteroaryl boronic acid or ester 7d in the presence of a base such as potassium carbonate in a solvent, such dioxane, using a catalyst such as $Pd(tBu_3P)_2$ provides 16k. Protecting group interconversion can be accomplished in two steps to give 3b. Compound 3b can be converted to compound 3o according to Scheme 3.

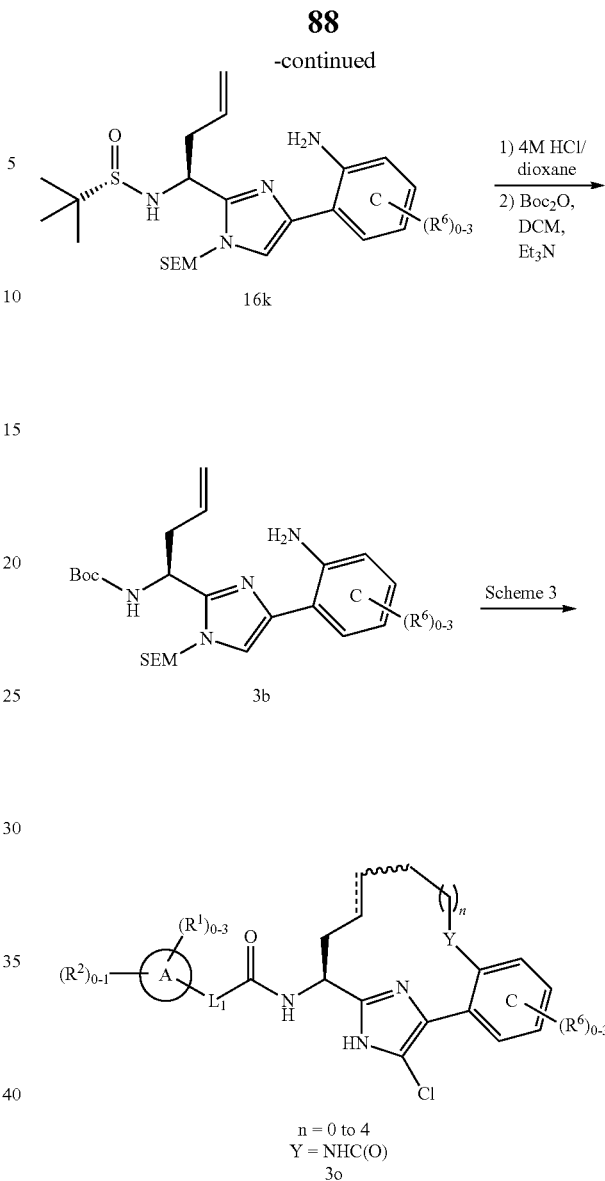

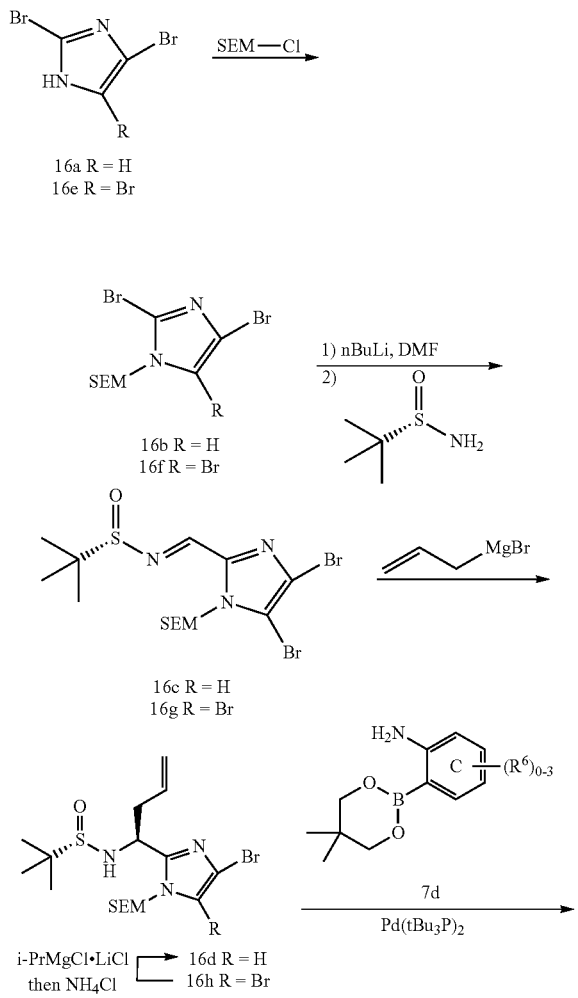

Representative pyridone (ring B=pyridone) containing macrocycles of this invention can be prepared as shown in Scheme 17. Compound 17d can be prepared in two steps according to a modified procedure described by Resmini (Resmini, M. et al., *Tetrahedron Asymmetry*, 15:1847 (2004)). A suitably substituted amino ester 17a can be converted to the corresponding β-ketophosphonate 17b by treatment with lithium dimethylmethylphosphonate. Horner-Wadsworth-Emmons reaction of 17b and a suitably substituted aldehyde 17c in the presence of base such as potassium carbonate in a solvent such as ethanol or tetrahydrofuran gives the α,β-unsaturated ketone 17d. Condensation of 17d with 1-(ethoxycarbonylmethyl)-pyrdinium chloride or 1-(carbamoylmethyl)-pyridinium chloride in the presence of ammonium acetate in a solvent such as ethanol or glacial acetic acid generates the pyridone 17e. The nitro group can be reduced to the aniline 17f with zinc and ammonium chloride in methanol. Alternatively, alkylation of the cesium salt of the pyridone 17e with methyl iodide, followed by reduction of the nitro as described above, can yield the N-Me pyridone derivative 17g. Compounds of the formula 17f and 17g can be converted to compounds 17h-k, according to Scheme 7, or to compounds 17l-m, according to Scheme 14.

Scheme 17

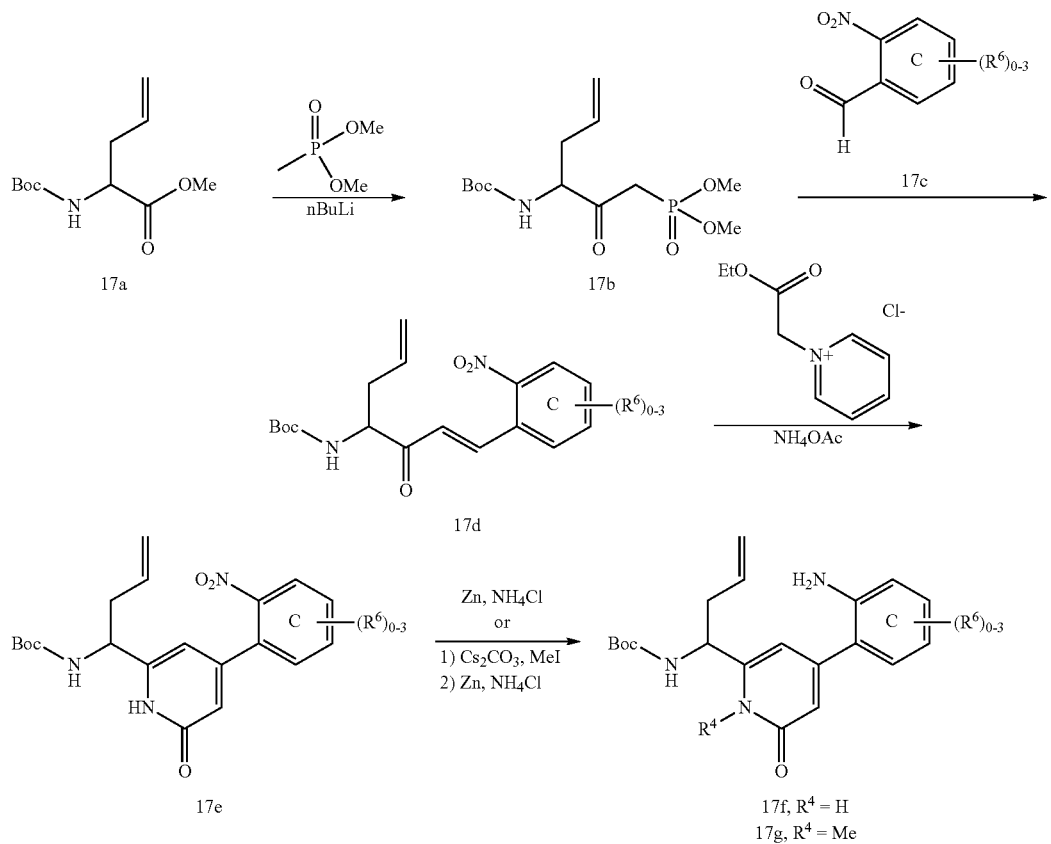

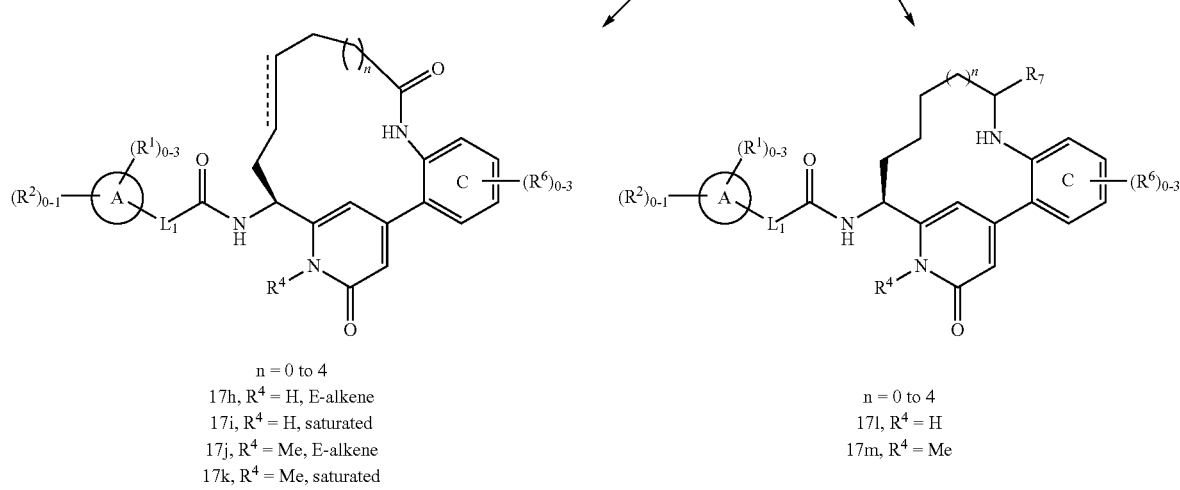

n = 0 to 4
17h, R⁴ = H, E-alkene
17i, R⁴ = H, saturated
17j, R⁴ = Me, E-alkene
17k, R⁴ = Me, saturated n = 0 to 4
17l, R⁴ = H
17m, R⁴ = Me Representative pyrimidine (ring B=pyrimidine) containing macrocycles of this invention can be prepared as shown in Scheme 18. Condensation of the β-ketoester 18b, prepared according to a modified procedure of Maibaum (*J. Org. Chem.*, 53:869(1988)), with a suitably substituted amidine under basic conditions, such as formamidine and sodium methoxide in methanol, yields the pyrimidone 18c. The pyrimidone can be converted to the chloro pyrimidine 18d in two steps with phosphorus oxychloride and then reprotection of the amine with Boc-anhydride. Alternatively, the pyrimidone can be converted directly to the corresponding triflate 18e with sodium hydride and N-phenyltrifluoromethanesulfonimide Suzuki-Miyaura coupling between 18d or 18e and an appropriately substituted aryl or heteroaryl boronic acid or ester 7d in the presence of a base such as potassium phosphate in a solvent mixture, such dimethylsulfoxide and water, or dimethylformamide, using a precatalyst such as Pd(dppf)Cl₂·CH₂Cl₂ complex provides 18f. Compounds of the formula 18f can be converted to compounds 18g-h, according to Scheme 7, or to compounds 18i, according to Scheme 14.

Scheme 18
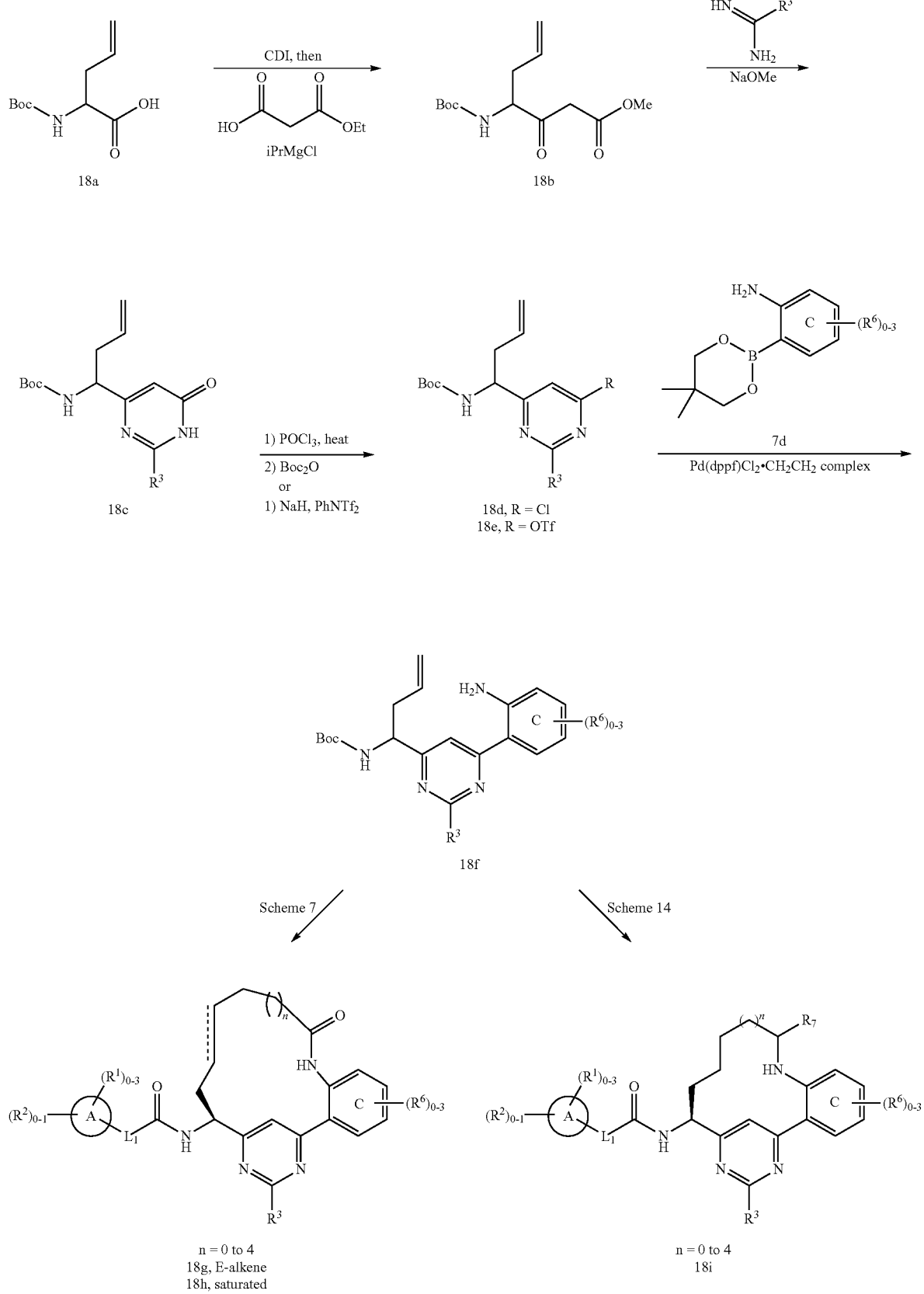

Representative pyridazinone (ring B=pyridazinone) containing macrocycles of this invention can be prepared as shown in Scheme 19. Condensation of the potassium salt of 17b with a suitably substituted α-ketoester 19a, which is either commercially available or prepared using a modified procedure described by Domagala (*Tetrahedron Lett.*, 21:4997-5000), in a solvent such as tetrahydrofuran generates the α,β-unsaturated ketone derivative which can then be condensed with a suitably substituted hydrazine derivative to give pyridazinone 19b. The nitro group can be reduced to the aniline 19c with zinc and ammonium chloride in methanol. Compounds of the formula 19c can be converted to compounds 19d according to Scheme 14.

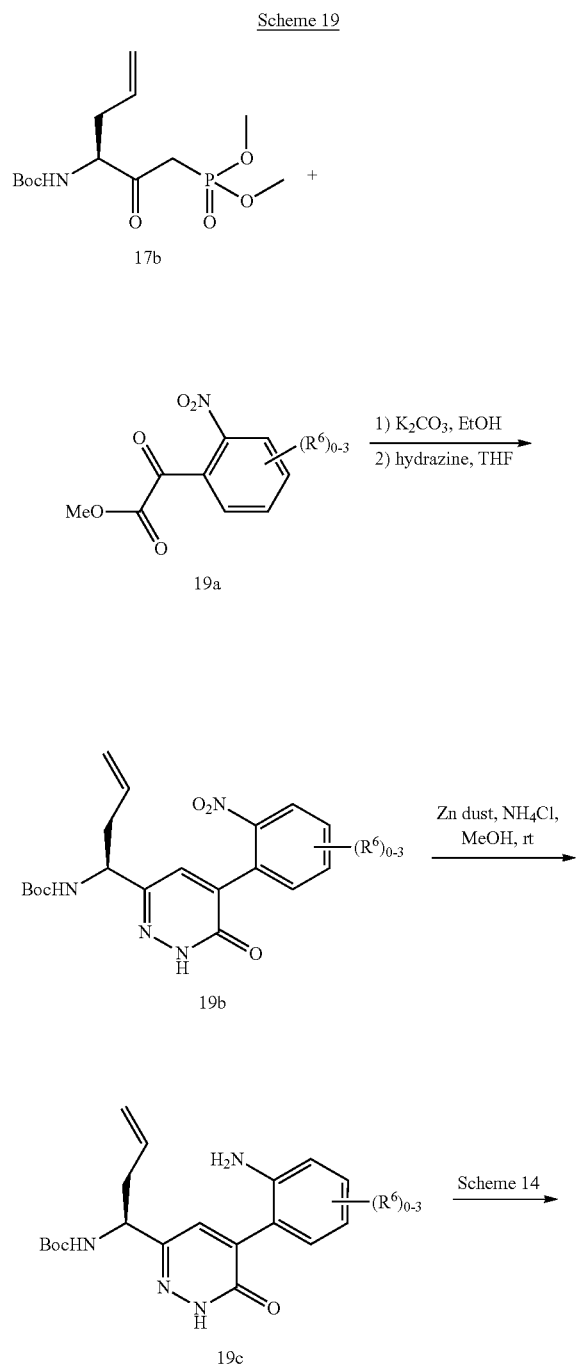

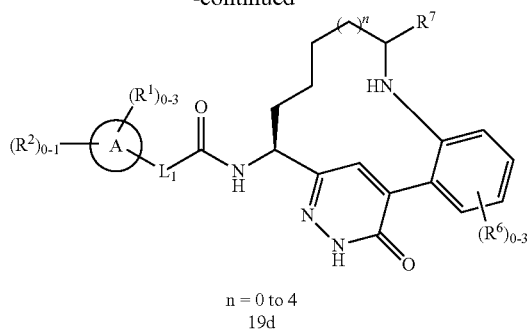

It should be recognized that additional deprotection steps and further functional group manipulations of compounds obtained via Schemes 1-19 using methods known in the art will then provide additional compounds of this invention.

Purification of intermediates and final products was carried out via either normal or reverse phase chromatography. Normal phase chromatography was carried out using prepacked $SiO_2$ cartridges eluting with either gradients of hexanes and ethyl acetate or dichloromethane and methanol unless otherwise indicated. Reverse phase preparative HPLC was carried out using C18 columns eluting with gradients of Solvent A (90% water, 10% methanol, 0.1% TFA) and Solvent B (10% water, 90% methanol, 0.1% TFA, UV 220 nm) or with gradients of Solvent A (90% water, 10% acetonitrile, 0.1% TFA) and Solvent B (10% water, 90% acetonitrile, 0.1% TFA, UV 220 nm) or with gradients of Solvent A (98% water, 2% acetonitrile, 0.05% TFA) and Solvent B (98% acetonitrile, 2% water, 0.05% TFA, UV 254 nm).

Unless otherwise stated, analysis of final products was carried out by reverse phase analytical HPLC using the Waters SunFire column (3.5 μm C18, 3.0×150 mm) Gradient elution (1.0 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm). Method B: Agilent ZORBAX® (3.5 μm C18, 4.6×75 mm) eluted at 2.5 mL/min with an 8 min gradient from 100% A to 100% B (A: 10% methanol, 89.9% water, 0.1% $H_3PO_4$; B: 10% water, 89.9% methanol, 0.1% $H_3PO_4$, UV 220 nm). Method C: Waters SunFire column (3.5 μm C18, 4.6×150 mm) eluted at 1 mL/min with a gradient from 10-100% Solvent B for 10 min and then 100% Solvent B for 5 min. (A: 0.01 M $NH_4HCO_3$ in water:methanol 95:5. B: 0.01 M $NH_4HCO_3$ in water:methanol 5:95. UV 254 nm). Method D: Waters SunFire column (3.5 μm C18, 3.0×150 mm) Gradient elution (1.0 mL/min) from 10-100% Solvent B for 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (*Hemostasis and Thrombosis, Basic Principles and Clinical Practice,* 5th Ed., p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis, pp.* 103-122, Lippincott Williams & Wilkins (2001); Schmaier, A. H., "Contact Activation", *Thrombosis and Hemorrhage, pp.* 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.,* 202:271-281 (2005); Kleinschmitz et al., *J. Exp. Med.,* 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor 1× as its normal macromolecular substrate. (Galiani, D., *Trends Cardiovasc. Med.,* 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.,* 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.,* 87:774-777 (2002); Wang et al., *J. Thromb. Haemost.,* 3:695-702 (2005)). Also, factor XI deficiency rescues the perinatal lethal phenotype of complete protein C deficiency (Chan et al., *Amer. J. Pathology,* 158:469-479 (2001)). Furthermore, baboon cross-reactive, function blocking antibodies to human factor XI protect against baboon arterial—venous shunt thrombosis (Gruber et al., Blood, 102:953-955 (2003)).

Evidence for an antithrombotic effect of small molecule inhibitors of factor XIa is also disclosed in published U.S. Patent Application No. 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide,* 2nd Ed., pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, Vol. 3 (Suppl. 1):P1228 (2005); Schumacher, W. A. et al., *European Journal of Pharmacology*, pp. 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine (Baltimore)*, 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 μM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 μM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s=I/(K_i(1+S/K_m)) \text{ for a competitive inhibitor with one binding site; or}$$

$$v_s/v_o=A+((B-A)/1+((IC_{50}/(I)_0))); \text{ and}$$

$$K_i=IC_{50}/(1+S/K_m) \text{ for a competitive inhibitor}$$

where:

$v_o$, is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXINϕ or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table 1 below lists Factor XIa Ki values measured for the following examples.

TABLE 1

| Example No. | Factor XIa Ki (nM) |
| --- | --- |
| 1 | 2983 |
| 10 | <5 |
| 86 | 2392 |

TABLE 1-continued

| Example No. | Factor XIa Ki (nM) |
| --- | --- |
| 102 | 8.16 |
| 110 | 8117 |
| 111 | 71 |
| 140 | <5 |
| 142 | 145 |
| 143 | 1309 |
| III-2 | 78 |
| III-20 | 7428 |
| III-21 | 107 |
| III-33 | 103 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h 1M) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed.

Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Ed. (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor 4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the puringergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

Intermediate 1

(E)-2,5-Dioxopyrrolidin-1-yl 3-(5-chloro-2-(1H-tetrazol-1-yl)phenyl)acrylate

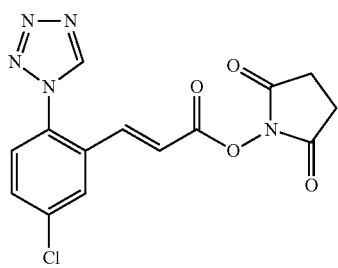 [SMILES: O=C(/C=C/c1cc(Cl)ccc1-n1cnnn1)ON1C(=O)CCC1=O]

The synthesis was described as Intermediate 1 in PCT International Application No. WO 2009/114677 published Sep. 17, 2009.

Intermediate 2

(E)-3-(5-Chloro-2-tetrazol-1-yl-phenyl)-acrylic acid

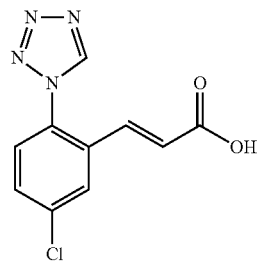 [SMILES: O=C(O)/C=C/c1cc(Cl)ccc1-n1cnnn1]

The synthesis was described as Intermediate 1B in PCT International Application No. WO 2009/114677 published Sep. 17, 2009.

Intermediate 3

(E)-3-(3-Chloro-2-fluoro-6-tetrazol-1-yl-phenyl)-acrylic acid 2,5-dioxo-pyrrolidin-1-yl ester

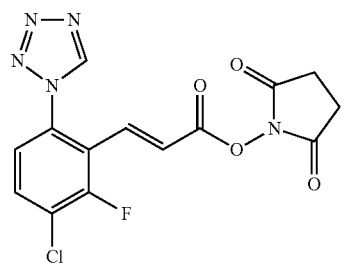 [SMILES: O=C(/C=C/c1c(-n2cnnn2)ccc(Cl)c1F)ON1C(=O)CCC1=O]

Intermediate 3A. (E)-3-(3-Chloro-2-fluoro-6-(1H-tetrazol-1-yl)phenyl)acrylic acid: The synthesis of Intermediate 3A was described as Intermediate 7 in PCT International Application No. WO 2009/114677 published Sep. 17, 2009.

Intermediate 3. To a slightly turbid mixture of Intermediate 3A (1.0 g, 3.72 mmol) in THF (18.70 mL) and DMF (1.870 mL) was added 1-hydroxypyrrolidine-2,5-dione (0.471 g, 4.09 mmol) and DIC (0.638 mL, 4.09 mmol). The reaction was stirred at rt and a white precipitate formed overtime. The solid was collected by suction filtration and washed with MeOH, water, MeOH, air-dried, and dried under vacuum to give Intermediate 3 (0.98 g, 72.0% yield), as a white solid. MS (ESI) m/z: 366.2 (M+H)+.

Intermediate 4

(E)-3-(2-Acetyl-5-chlorophenyl)acrylic acid

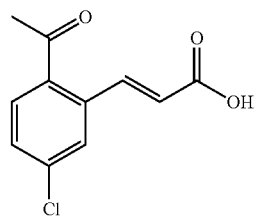

Intermediate 4A. (E)-tert-Butyl 3-(2-acetyl-5-chlorophenyl)acrylate: To a degassed solution of 1-(2-bromo-4-chlorophenyl)ethanone (1.0 g, 4.28 mmol), tributylamine (2.041 mL, 8.57 mmol), and tert-butyl acrylate (1.255 mL, 8.57 mmol) in DMF (10 mL) was added palladium on carbon (0.456 g, 0.428 mmol) and palladium(II) acetate (0.096 g, 0.428 mmol). The reaction mixture was warmed to 100° C. After 16 h, the reaction was cooled to rt. The reaction was filtered and the solid was rinsed with DMF. The filtrate was diluted with EtOAc, washed with water (2×), brine, dried over sodium sulfate, filtered and concentrated. Purification by normal phase chromatography afforded Intermediate 4A (0.760 g, 63%), as a brown oil. MS (ESI) m/z: 225.0 (M-C$_4$H$_8$+H)$^+$.

Intermediate 4. A solution of Intermediate 4A (0.048 g, 0.171 mmol) in 50% TFA/DCM (2 mL) was stirred at rt. After 1 h, the reaction was concentrated to give Intermediate 4 (0.038 g, 100% yield) as a yellow solid. The material was used without further purification. MS (ESI) m/z: 225.1 (M+H)$^+$.

Intermediate 5

1-Amino-5,6,7,8-tetrahydroisoquinoline-6-carboxylic acid

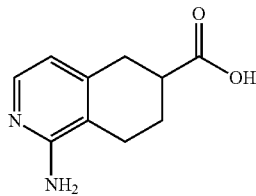 [SMILES: Nc1nccc2c1CCC(C(=O)O)C2]

The synthesis was described as Example 147, Part E in U.S. Patent Application No. 2005/0282805 published Dec. 22, 2005.

Intermediate 6

2-Bromo-1-(2-(but-3-enyloxy)phenyl)ethanone

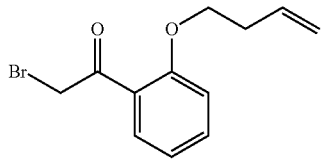

Intermediate 6A. 1-(2-But-3-enyloxy-phenyl)-ethanone: To a white suspension of potassium carbonate (15.2 g, 110 mmol) in acetone (29.4 mL) was added 5-bromobut-1-ene (3.73 mL, 36.7 mmol) and 1-(2-hydroxyphenyl)ethanone (4.42 mL, 36.7 mmol). The resulting off-white suspension was warmed to reflux and stirred overnight. The reaction was cooled to rt, filtered and the filtrate was concentrated. The residue was partitioned between water and EtOAc and the layers were separated. The aqueous layer was extracted with EtOAc (2×20 mL). The combined organic layers were washed with brine, dried over Na$_2$SO$_4$, filtered and concentrated. Purification by normal phase chromatography gave 1.12 g (15%) of Intermediate 6A, as a dark purple oil. MS (ESI) m/z: 205.2 (M+H)$^+$.

Intermediate 6. A suspension of Intermediate 6A (1.1153 g, 5.86 mmol) and copper (II) bromide (2.62 g, 11.73 mmol) in EtOAc (10.47 mL) was warmed to reflux. After 1 h, the suspension was cooled to rt, filtered, and the filtrate was concentrated to give a greenish-brown residue. The greenish-brown residue was taken up in EtOAc (100 mL) and washed with water (2×100 mL). The organic layer was then washed with brine, dried over Na$_2$SO$_4$, filtered, and concentrated. Purification by normal phase chromatography gave 0.773 g (44%) of Intermediate 6, as a yellow oil. MS (ESI) m/z: 271.1 (M+H)$^+$.

Intermediate 7

Methyl 4-(2-bromoacetyl)-3-(but-3-enyloxy)phenylcarbamate

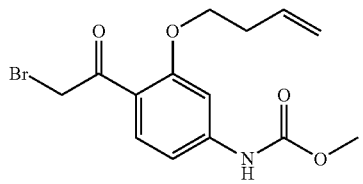 [SMILES: C=CCCOc1cc(NC(=O)OC)ccc1C(=O)CBr]

Intermediate 7A. 1-(4-Amino-2-(but-3-enyloxy)phenyl)ethanone: A suspension of 1-(4-amino-2-hydroxyphenyl)ethanone (3 g, 19.85 mmol), 4-bromobut-1-ene (6.04 mL, 59.5 mmol) and K$_2$CO$_3$ (16.46 g, 119 mmol) in acetone (30 mL) was heated in a sealed tube at 60° C. After 18 h, another 2 eq. of 4-bromobut-1-ene was added and the reaction was heated at 60° C. for 18 h. This process was repeated one more time, and the reaction was cooled to rt, diluted with EtOAc, washed with water, brine, dried over sodium sulfate, filtered and concentrated. Purification by normal phase chromatography afforded 1.055 g (14.24%) of Intermediate 7A, as a yellow solid. MS (ESI) m/z: 206.0 (M+H)$^+$.

Intermediate 7B. Methyl 4-acetyl-3-(but-3-enyloxy)phenylcarbamate: To a cooled (0° C.), clear yellow solution of Intermediate 7A (1.055 g) in DCM (9.42 mL) and pyridine (0.252 mL, 3.11 mmol) was added dropwise methyl chloroformate (0.230 mL, 2.97 mmol). The resulting yellow suspension was stirred at 0° C. for 2 h. The reaction was partitioned between EtOAc/sat. sodium bicarbonate and the layers were separated. The aqueous layer was extracted with EtOAc (1×). The combined organic layers were washed with brine, dried over sodium sulfate, filtered and concentrated to give a yellow solid. The solid was purified by trituration from DCM. The solid was collected via Buchner funnel filtration and rinsed with DCM (3×2 mL), air-dried, and dried under vacuum to give 0.91 g of Intermediate 7B as a white solid. MS (ESI) m/z: 264.0 (M+H)$^+$.

Intermediate 7 was prepared following the procedure described in Intermediate 6, by replacing Intermediate 6A with Intermediate 7B. The material was used without further purification. MS (ESI) m/z: 341.9 (M+H)$^+$ and 343.9 (M+2+H)$^+$.

Intermediate 8

[3-Bromo-4-(2-bromo-acetyl)-phenyl]-carbamic acid methyl ester

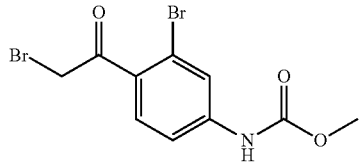 [SMILES: COC(=O)Nc1ccc(C(=O)CBr)c(Br)c1]

Intermediate 8A. 1-(4-Amino-2-bromophenyl)ethanone: (Caution, possible explosion hazard!) A clear, colorless solution of 1-(2-bromo-4-fluorophenyl)ethanone (22.8 g, 0.105 mol) in DMSO (105 mL) and ammonium hydroxide (68.2 mL, 0.526 mol) was divided into nineteen 20-mL microwave vials. The vials were sealed, microwaved at 150° C. for 1.5 h, and then cooled to rt. All the reactions were combined, partitioned between DCM and water (400 mL) and the layers were separated. The aqueous layer was extracted with DCM (2×). The combined organic layers were washed with brine, dried over sodium sulfate, filtered, and concentrated to give 35 g of Intermediate 8A as an orange oil. The material was carried onto the next step without further purification. MS (ESI) m/z: 212.4 (M+H)$^+$ and 214.4 (M+2+H)$^+$.

Intermediate 8 was prepared following the procedures described in Intermediate 7, by replacing Intermediate 7A with Intermediate 8A. MS (ESI) m/z: 352.1 (M+H)$^+$ and 354.1 (M+2+H)$^+$.

An alternative preparation of Intermediate 8 is highlighted below:

Alternative Intermediate 8A. 1-(4-Amino-2-bromophenyl)ethanone: To a solution of Intermediate 10C (19 g, 0.077 mol) in ethanol (400 mL) was added in portions tin(II) chloride (74 g, 0.39 mol). Following the addition, the reaction was heated to reflux overnight. The reaction was concentrated and the residue was dissolved in 10% aq. sodium hydroxide (200 mL). The solution was extracted with ethyl acetate (2×200 mL). The combined organic layers were washed with brine and concentrated to afford an oil. Petroleum ether (25 mL) was added to give a suspension. The petroleum ether was decanted and the solid was suspended in 20% ethyl acetate/petroleum ether. The solid was collected to afford 14 g of Intermediate 8A.

Alternative Intermediate 8B. (4-Acetyl-3-bromo-phenyl)-carbamic acid methyl ester: To a cooled (10° C.) mixture of alternative Intermediate 8A (14 g, 0.065 mol) and Hunig's base (12.7 g, 0.098 mol) in dry dioxane (140 mL) was added dropwise methyl chloroformate (7.4 g, 0.078 m). After 3 h, the reaction was quenched with water (100 mL) and then extracted with ethyl acetate (2×150 mL). The combined organic layers were washed with brine, dried over sodium sulfate, filtered, and concentrated. Purification by trituration from isopropanol provided 14 g of the alternative Intermediate 8B. MS (ESI) m/z: 271.7 (M+H)$^+$. $^1$H NMR (400 MHz, DMSO-d$_6$) δ: 2.50 (s, 3H), 3.71 (s, 3H), 7.53-7.56 (m, 1H), 7.78 (d, J=8.8 Hz, 1H), 7.86 (d, J=2.0 Hz, 1H), 10.14 (s, 1H).

Alternative Intermediate 8. To a cooled (10° C.) solution of alternative Intermediate 8B (90 g, 0.33 mol) in dry dioxane (900 mL) was added a solution of bromine (52.9 g, 0.33 mol) in dioxane (430 mL) dropwise over 1 h. After 2 h, ice cold water (500 mL) was added and the reaction was extracted with ethyl acetate (2×500 mL). The combined organic layers were washed with brine, dried over sodium sulfate, filtered, and concentrated to afford 110 g of crude product. A suspension of the crude product in ethanol (1L) was warmed to 50° C. After a clear solution formed, water (1.0 L) was added dropwise and the mixture was gradually cooled to 35° C. The precipitated solid was collected by filtration, washed with ethanol (200 mL), air-dried, and then dried at 50° C. under vacuum for 30 min to yield 70 g of alternative Intermediate 8.

Intermediate 9

Methyl 4-(2-bromoacetyl)-3-nitrophenylcarbamate

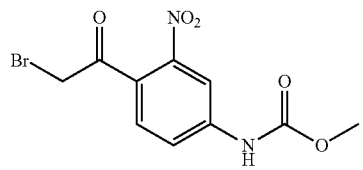 [SMILES: COC(=O)Nc1ccc(C(=O)CBr)c([N+](=O)[O-])c1]

Intermediate 9A. Methyl 4-iodo-3-nitrophenylcarbamate: To a cooled (0° C.), yellow suspension of 4-iodo-3-nitroaniline (8.46 g, 320 mmol) in DCM (320 mL) and pyridine (2.85 mL, 35.2 mmol) was added dropwise methyl chloroformate (2.61 mL, 33.6 mmol). The resulting clear, light yellow solution was stirred at 0° C. After 1.5 h, the reaction was diluted with DCM, washed with sat. NaHCO$_3$, brine, dried over MgSO$_4$, filtered and concentrated. The residue was dissolved in a minimal amount of DCM (~100 mL) and then hexane (600 mL) was added to give a yellow suspension. The suspension was filtered, and the solid was rinsed with hexane and then dried to give Intermediate 9A (10.3 g, 100%), as yellow solid. MS (ESI) m/z: 321.3 (M−H)$^-$.

Intermediate 9B. Methyl 4-(1-ethoxyvinyl)-3-nitrophenyl-carbamate: A solution of Intermediate 9A (6 g, 18.63 mmol), tributyl(1-ethoxyvinyl)stannane (7.55 mL, 22.36 mmol), and bis(triphenylphosphine)palladium(II) chloride (0.654 g, 0.932 mmol) in toluene (37.3 mL) was heated at 110° C. After 2 h, the reaction was cooled to rt. The reaction mixture was filtered through a 0.45 micron GMF, rinsing with EtOAc. The filtrate was concentrated. Purification by normal phase chromatography gave Intermediate 9B (3.59 g, 72.4% yield), as a brown solid. MS (ESI) m/z: 267.4 (M+H)$^+$.

Intermediate 9. To a slightly cloudy orange mixture of Intermediate 9B (3.59 g, 13.48 mmol) in THF (20 mL) and water (7 mL) was added NBS (2.400 g, 13.48 mmol). The resulting clear, yellow solution was stirred at rt for 20 min and then the reaction was partitioned between EtOAc/brine. The layers were separated and the organic layer washed with brine, dried over Na$_2$SO$_4$, filtered, and concentrated to afford Intermediate 9 (4.28 g, 100% yield), as a yellow foam. This material was used without further purification. MS (ESI) m/z: 317.3 (M+H)$^+$, 319.3 (M+2+H)$^+$.

Alternatively, Intermediate 9B can be hydrolyzed with aqueous 1N HCl to give the methyl ketone which can then be brominated with copper (II) bromide according to the procedure described in Intermediate 6.

Intermediate 10

2-Bromo-1-(2-bromo-4-nitrophenyl)ethanone

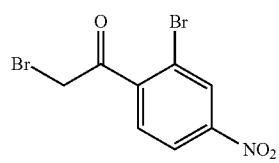 [SMILES: O=C(CBr)c1ccc([N+](=O)[O-])cc1Br]

Intermediate 10A. 2-Bromo-4-nitro-benzoic acid: To a warm (80° C.) solution of pyridine (500 mL) and water (1.0 L) was added 4-nitro-2-bromo toluene (100 g, 0.46 mol). The resulting suspension was stirred until it became a clear solution. Next, KMnO$_4$ (600 g, 3.8 mol) was added in portions over 1.5 h. The reaction was stirred overnight. The reaction mixture was cooled to RT and then 10% aq. sodium hydroxide (200 mL) was added. After 15 min, the reaction was filtered to remove the solid. The solid was rinsed with 10% aq. sodium hydroxide (5×100 mL). The filtrate was extracted with MTBE (3×250 mL). The clear aqueous layer was cooled to 10° C. and then it was acidified with concentrated HCl. The aqueous layer was extracted with MTBE (4×500 mL). The organic layers were combined, dried over sodium sulfate, filtered and concentrated to afford 72 g of Intermediate 10A. $^1$H NMR (400 MHz, DMSO-d$_6$) δ: 7.96 (d, J=8 Hz, 1H), 8.28-8.48 (m, 1H), 8.49 (d, J=2.4 Hz, 1H), 14.1 (br. s, 1H).

Intermediate 10B. 2-(2-Bromo-4-nitro-benzoyl)-malonic acid diethyl ester:

To a solution of Intermediate 10A (50 g, 0.2 mol) in toluene (500 mL) was added triethylamine (24.6 g, 0.24 mol). The reaction was cooled to 15° C. and ethyl chloroformate (24 g, 0.22 mol) was added. After 45 min, the mixed anhydride solution was cooled to 0° C.

In a separate flask: To a suspension of Mg turnings (5.4 g) in dry ether (300 mL) was added ethanol (3.0 mL), carbon tetrachloride (2.0 mL), and diethyl malonate (34 mL, 0.22 mol). The mixture was stirred at 40° C. for an hour to ensure that the magnesium dissolved completely. After the reaction became a clear solution, it was added to the cooled solution of the mixed anhydride. After 2 h, the reaction was quenched with 2N sulfuric acid (200 mL) and then extracted with ethyl acetate (4×100 mL). The combined organic layers were dried over sodium sulfate, filtered and concentrated to give 80 g of Intermediate 10B. This was used in the next step without further purification.

Intermediate 10C. 1-(2-Bromo-4-nitro-phenyl)-ethanone: A mixture of Intermediate 10B (80 g, 0.2 mol) in acetic acid (400 mL) and sulfuric acid (400 mL) was stirred at 105° C. After 3 h, the reaction was cooled to RT and then extracted with ethyl acetate (2×500 mL). The combined organic layers were washed with 20% aq. sodium hydroxide, dried over sodium sulfate, filtered and concentrated to give 43.0 g of Intermediate 10C. $^1$H NMR (400 MHz, CDCl$_3$) δ: 2.66 (s, 3H), 7.57 (d, J=8 Hz, 1H), 8.21-8.24 (dd, 1H), 8.48 (d, J=2.0 Hz, 1H).

Intermediate 10. To a cooled (10° C.) solution of the Intermediate 10C (43 g, 0.17 mol) in dry dioxane (430 mL) was added a dropwise over 1.5 h a solution of bromine (31 g) in dioxane (430 mL). The reaction was stirred for 30 min and then ice cold water (150 mL) was added. The reaction was extracted with ethyl acetate (2×200 mL). The combined organic layers were washed with brine, dried over sodium sulfate, filtered and concentrated. Purification by normal phase chromatography (petroleum ether/ethyl acetate) gave 30 g of Intermediate 10. $^1$H NMR (400 MHz, CDCl$_3$) δ 4.46 (s, 2H), 7.62 (d, J=8.4 Hz, 1H), 8.25-8.27 (dd, 1H), 8.50 (d, J=2.4 Hz, 1H).

Intermediate 11

Methyl 4-(2-bromoacetyl)-3-(pent-4-enyloxy)phenylcarbamate

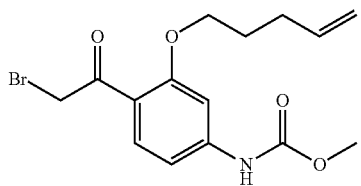 [SMILES: C=CCCCOc1cc(NC(=O)OC)ccc1C(=O)CBr]

This compound was prepared following the procedures described in Intermediate 7, by replacing 4-bromobut-1-ene with 5-bromopent-1-ene. MS (ESI) m/z: 355.9 (M+H)$^+$, 357.9 (M+2+H)$^+$.

Intermediate 12

2-(5,5-Dimethyl-1,3,2-dioxaborinan-2-yl)-5-nitrophenylamine

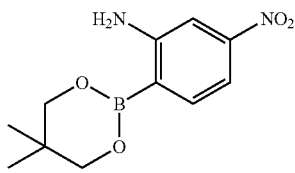 [SMILES: CC1(C)COB(c2ccc([N+](=O)[O-])cc2N)OC1]

To a flame-dried flask, equipped with a reflux condensor, containing 2-bromo-5-nitroaniline (10.0 g, 46.1 mmol), bis(neopentyl glycolato)diboron (13.01 g, 57.6 mmol), potassium acetate (13.57 g, 138 mmol), and PdCl$_2$(dppf)-CH$_2$Cl$_2$ adduct (0.941 g, 1.152 mmol) was added DMSO (132 mL). The resulting dark red-brown suspension was degassed with argon for 30 min. and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 12 as an orange solid. MS (ESI) m/z: 183.1 (M-C$_5$H$_8$+H)$^+$.

Intermediate 13

4-(5,5-Dimethyl-1,3,2-dioxaborinan-2-yl)-3-[2-(1,3-dioxo-1,3-dihydro-isoindol-2-yl)-ethoxy]-benzoic acid methyl ester

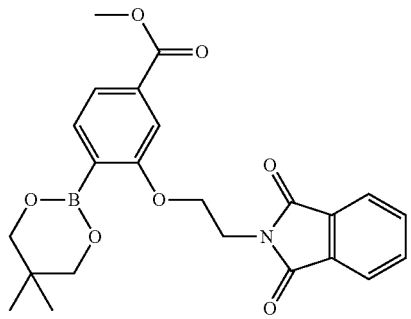 [SMILES: COC(=O)c1ccc(B2OCC(C)(C)CO2)c(OCCN2C(=O)c3ccccc3C2=O)c1]

Intermediate 13A. 4-Bromo-3-[2-(1,3-dioxo-1,3-dihydro-isoindol-2-yl)-ethoxy]-benzoic acid methyl ester: To a solution of methyl 4-bromo-3-hydroxybenzoate (2.0 g, 8.66 mmol) and 2-(2-bromoethyl)isoindoline-1,3-dione (2.419 g, 9.52 mmol) in DMF (10 mL) was added NaH (0.866 g, 21.64 mmol) in small portions at 0° C. The reaction was stirred under argon at 0° C. for 2 h. The reaction was warmed to 60° C. and stirred for 4 h. After cooling to rt, the reaction mixture was diluted with EtOAc, washed with 1M HCl, saturated NaHCO$_3$ and brine. The organic phase was dried over MgSO$_4$, filtered and concentrated. Purification by normal phase chromatography gave Intermediate 13A (0.36 g, 10.3% yield) as a white solid. MS (ESI) m/z: 404.0/406.0 (M+H)$^+$.

Intermediate 13 was prepared following the procedure described in Intermediate 12, by replacing 2-bromo-5-nitroaniline with Intermediate 13A and running the reaction in acetonitrile at 90° C. MS (ESI) m/z: 352.1 (M+H)$^+$.

Intermediate 14

[3-[(Benzyloxycarbonyl-methyl-amino)-methyl]-4-(2-bromo-acetyl)-phenyl]-carbamic acid methyl ester

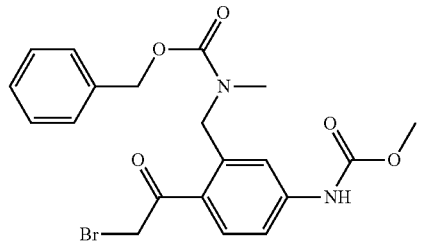 [SMILES: COC(=O)Nc1ccc(C(=O)CBr)c(CN(C)C(=O)OCc2ccccc2)c1]

Intermediate 14A. Benzyl 5-amino-2-bromobenzyl(methyl)carbamate: To a mixture of benzyl 2-bromo-5-nitrobenzyl(methyl)carbamate (3.0 g, 7.91 mmol) in MeOH (60 mL) was added ammonium chloride (2.116 g, 39.6 mmol) and zinc (2.59 g, 39.6 mmol) at 0° C. The reaction mixture was warmed up to rt and stirred under argon for 3 h. The solid was filtered off and the solvent was removed to give Intermediate 14A (2.72 g, 98% yield) as a light tan solid. MS (ESI) m/z: 350.8 (M+H)$^+$.

Intermediate 14 was prepared following the procedures described in Intermediate 9, by replacing 4-iodo-3-nitroaniline with Intermediate 14A. MS (ESI) m/z: 449.0 (M+H)$^+$.

Intermediate 15

(E)-3-(3-Chloro-2,6-difluoro-phenyl)-acrylic acid

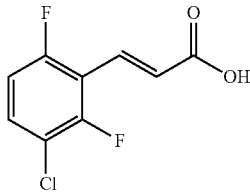 [SMILES: O=C(O)/C=C/c1c(F)ccc(Cl)c1F]

Intermediate 15A. 3-Chloro-2,6-difluorobenzaldehyde: To a solution of (3-chloro-2,6-difluorophenyl)methanol (1.07 g, 5.99 mmol) in CH$_2$Cl$_2$ (20 ml) was added Dess-Martin periodinane (3.05 g, 7.19 mmol). After 2 h, the reaction was concentrated. Purification by normal phase chromatography gave Intermediate 15A (0.94 g, 89% yield), as a white solid. MS (ESI) m/z: 177.1 (M+H)$^+$.

Intermediate 15B. (E)-tert-Butyl 3-(3-chloro-2,6-difluorophenyl)acrylate: To a solution of Intermediate 15A (0.94 g, 5.32 mmol) in THF (30 ml) were added tert-butyl 2-(dimethoxyphosphoryl)acetate (1.194 g, 5.32 mmol) and KOtBu (0.896 g, 7.99 mmol).

After 2 h, the reaction was diluted with EtOAc, washed with H$_2$O, brine, dried over MgSO$_4$, filtered and concentrated. Purification by normal phase chromatography provided Intermediate 15B (0.866 g, 59.2% yield), as a clear colorless oil. MS (ESI) m/z: 219.2 (M-$^t$Bu+H)$^+$.

Intermediate 15. To a solution of Intermediate 15B (0.866 g, 3.15 mmol) in DCM (7.0 ml) was added TFA (3.0 mL, 38.9 mmol). After 1.5 h, the reaction was concentrated and the residue was dried in vacuo to give Intermediate 15 (0.689 g, 100% yield) as an off-white solid. MS (ESI) m/z: 219.1 (M+H)$^+$.

Intermediate 16

3-[2-Amino-2-(4-chloro-pyridin-2-yl)-ethyl]-benzoic acid methyl ester, 2 TFA salt

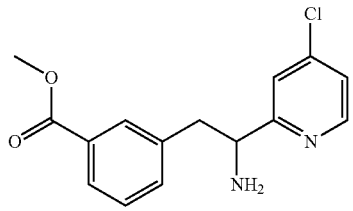 [SMILES: COC(=O)c1cccc(CC(N)c2cc(Cl)ccn2)c1]

Intermediate 16A. 4-Chloro-pyridine-2-carbonyl chloride: To a suspension of 4-chloro-pyridine-2-carboxylic acid (2.0 g, 12.8 mmol) in dichloroethane (43 mL) was added thionyl chloride (2.8 mL, 38.5 mmol) and DMF (2-3 drops). The suspension was warmed to 85° C. After 1 h, the resulting clear, yellow solution was cooled to rt and concentrated. The residue was dissolved in DCE and concentrated. This process was repeated two additional times to give a yellow liquid which crystallized upon standing to give a yellow solid.

Intermediate 16B. 3-[2-(4-Chloro-pyridin-2-yl)-2-oxo-ethyl]-benzoic acid methyl ester: (Preparation of the benzyl zinc reagent) To a flame-dried flask was added zinc powder (100 mesh, 0.570 g, 8.73 mmol). The flask was equipped with a condenser and the system was purged with argon for several minutes. Next, THF (1.75 mL) was added followed by 1,2-dibromoethane (0.075 mL, 0.87 mmol). The suspension was heated with a heat gun until a gentle bubbling was observed and the reaction was allowed to cool to rt. The above process was repeated twice. Next, TMS-Cl (0.089 mL, 0.698 mmol) was added and an exotherm was observed with bubbling. After 2 min, the zinc suspension was cooled to 0-5° C. Next, a solution of 3-bromomethyl-benzoic acid methyl ester (1.0 g, 4.36 mmol) in THF (4.4 mL) was added dropwise via syringe pump over 1 h and 45 min. (approximate rate of one drop every 6-8 sec) keeping the temperature below 5° C. Following the addition, the stirring was stopped and the zinc was allowed to settle. After 1.5 h, the supernatant was used in the next step.

To a cooled (−9° C.), solution of Intermediate 16A (0.767 g, 4.36 mmol) in THF (4.4 mL) was added dropwise the benzyl zinc reagent prepared above keeping the temperature below 5° C. during the addition. To the resulting orange solution was added tetrakis(triphenylphosphine)palladium (0) (0.126 g, 0.109 mmol) and the reaction temperature increase to 19° C. but subsided to 0-5° C. and the reaction was maintained in this temperature range. After 45 min, the reaction was quenched with 1.0 M HCl (15 mL) and then extracted with EtOAc (3×). The combined organic layers were washed with sat. sodium bicarbonate, brine, dried over sodium sulfate, filtered and concentrated to give an orange residue weighing 1.28 g. Purification by normal phase chromatography gave 0.646 g (51%) of Intermediate 16B, as a yellow, oily solid. MS (ESI) m/z: 290.20 (M+H)$^+$ and 292.20 (M+2+H)$^+$.

Intermediate 16. To an orange-yellow suspension of Intermediate 16B (0.570 g, 1.97 mmol) in methanol (7.9 mL) was added hydroxylamine hydrochloride (0.411 g, 5.91 mmol). After 16.5 h, the reaction was concentrated and then the residue was partitioned between EtOAc and sat. sodium bicarbonate. The layers were separated and the aqueous layer was extracted with EtOAc (1×). The combined organic layers were washed with brine, dried over sodium sulfate, filtered and concentrated to give 0.536 g of the oxime, as a yellow solid. To a cooled (0-5° C.) solution of oxime in TFA (4.5 mL) was added in portions zinc powder (one portion every 10 min, 0.620 g, 9.5 mmol). The reaction was allowed to warm to 15° C. and additional TFA (4.5 mL) was added to facilitate mixing. After 4.5 h, the reaction was filtered to remove the zinc, rinsing with TFA, and the resulting filtrate was concentrated to remove most of the TFA. The mixture was added dropwise to cold (0° C.) 1.0 M sodium hydroxide. The mixture was extracted with EtOAc (2×). The combined organic layers were filtered to remove the emulsion and then the filtrate was washed with brine, dried over sodium sulfate, filtered and concentrated to give an orange residue. Purification by reverse phase chromatography gave 0.409 g (39%) of Intermediate 16, as an off-white foam. MS (ESI) m/z: 291.2 (M+H)⁺ and 293.2 (M+2+H)⁺.

Intermediate 17

2-Bromo-1-(2-bromo-4-fluoro-phenyl)-ethanone

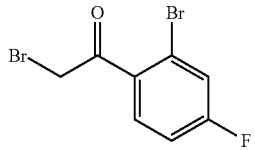 [SMILES: O=C(CBr)c1ccc(F)cc1Br]

The synthesis was described as Method A-1, Page 92 in PCT International Application No. WO 2005/014566 published Feb. 17, 2005.

Intermediate 18

(E)-3-(6-Acetyl-3-chloro-2-fluoro-phenyl)-acrylic acid

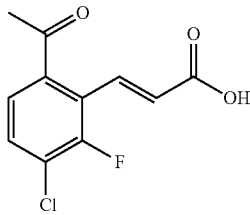 [SMILES: CC(=O)c1ccc(Cl)c(F)c1/C=C/C(=O)O]

Intermediate 18A. 2-Bromo-4-chloro-3-fluorobenzoic acid: To a cooled (−78° C.) solution of DIEA (4.9 mL, 48 mmol) in THF was added dropwise n-BuLi (132 mL, 2.3 eq, 2.5 M solution). The mixture was stirred at −30° C. for 30 min. Again the reaction mixture was cooled to −78° C., and a solution of 4-chloro-3-fluorobenzoic acid (25 g, 143 mmol) in THF was added over 1 h. The reaction was stirred at −78° C. overnight. The next day a solution of 1,2-dibromo-1,1,2,2-tetrachloroethane (87 g, 267 mmol) in THF was added and the reaction was stirred at −78° C. for further 2 h and then RT for 4 h. The reaction mixture was quenched with water, the layers were separated, and the aqueous layer washed with Et₂O. The aqueous layer was acidified with 1.5N HCl and then extracted in EtOAc (2×200 mL). The combined organic layers were dried over anhydrous Na₂SO₄, filtered and concentrated to afford Intermediate 18A (30 g, 83.3%). MS (ESI) m/z: 252.6 (M−H)⁺.

Intermediate 18B. Diethyl 2-((2-bromo-4-chloro-3-fluorophenyl)(hydroxy)methylene)malonate: To a suspension of Intermediate 18A (14.6 g, 57 mmol) in DCM (200 mL) was added thionyl chloride (6.6 mL, 88 mmol). The mixture was stirred at reflux for 3 h. The solvent was removed and the residue was dried in vacuum to give the acid chloride as a light brown solid.

To a cooled (0° C.) suspension of sodium hydride (3.66 g (60%), 91.5 mmol) in THF was added a solution of diethyl malonate (0.612 g, 3.82 mmol) in THF (5 mL). After 10 min, a solution of the acid chloride (16.4 g, 60 mmol) in THF (160 mL) was added slowly. Following the addition, the reaction was warmed to RT. After 30 min, the solvent was removed and the residue was treated with cold (0° C.) 1.2 M HCl (150 mL).

The mixture was extracted with EtOAc (3×250 mL). The combined organic layers were washed with brine, dried over Na₂SO₄, filtered and concentrated to give Intermediate 18B (20 g, 87%) as a solid. MS (ESI) m/z: 395/397 (M+H)⁺.

Intermediate 18C. 1-(2-Bromo-4-chloro-3-fluorophenyl)ethanone: A solution of Intermediate 18B (18.6 g, 47 mmol) in acetic acid (200 mL), H₂O (150 mL) and H₂SO₄ (2.0 mL) was stirred at 110° C. for 4 h. Most of the solvent was removed and the residue was diluted with EtOAc (400 mL), washed with water (5×20 mL), saturated NaHCO₃, 1N NaOH, and brine. The solvent was removed to give Intermediate 18C (10 g, 84%) as a low melting solid. ¹H NMR (400 MHz, DMSO-d₆) δ: 7.42 (q, J=6.8, 6.4 Hz, 1H), 7.24 (q, J=6.4, 5.2 Hz, 1 H), 2.5 (s, 3H).

Intermediate 18D. (E)-tert-Butyl 3-(6-acetyl-3-chloro-2-fluorophenyl)acrylate: To the mixture of Intermediate 18C (50 g, 198 mmol), tert-butyl acrylate (50.9 g, 397 mmol) and TEA (55 mL, 397 mmol) in DMF (500 mL) was added Pd(OAc)₂ (8.9 g, 39.7 mmol). The resulting mixture was stirred at 90° C. overnight. The reaction was cooled to RT, filtered, and the filtrate was concentrated. Purification by normal phase chromatography gave Intermediate 18D (30 g, 50.8%) as a light yellow solid. MS (ESI) m/z: 242.7 (M+H)⁺.

Intermediate 18. A solution of Intermediate 18D (25 g, 84 mmol) in DCM (330 mL) and TFA (330 mL) was stirred at RT. After 1.5 h, the solvent was concentrated to give Intermediate 18 (19.5 g, 97.0) as a white solid. ¹H NMR (400 MHz, DMSO-d₆) δ: 12.69 (bs, 1 H), 7.80-7.76 (m, 2 H), 7.62 (d, J=12.1 Hz, 1 H), 6.30 (dd, J=2.4, 2.0 Hz, 1 H), 2.6 (s, 3H). MS (ESI) m/z: 241 (M−H)⁺.

Intermediate 19

(E)-3-(5-Chloro-2-(difluoromethyl)phenyl)acrylic acid

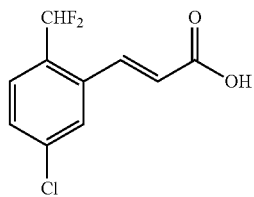 [SMILES: O=C(O)/C=C/c1cc(Cl)ccc1C(F)F]

Intermediate 19A. 2-Bromo-4-chloro-1-(difluoromethyl) benzene: To a solution of 2-bromo-4-chlorobenzaldehyde (1 g, 4.56 mmol) in DCM (15 mL) was added DAST (0.903 mL, 6.83 mmol) at 0° C. The reaction was allowed to warm to rt and stir overnight. The reaction mixture was diluted with EtOAc, washed with sat NaHCO₃ and brine. The organic phase was dried over magnesium sulfate, filtered and concentrated to give Intermediate 19A (0.88 g. 80% yield) as a clear oil. MS (ESI) m/z: 261.2 (M+Na)⁺.

Intermediate 19B. (E)-tert-Butyl 3-(5-chloro-2-(difluoromethyl)phenyl)acrylate: To a solution of Intermediate 19A (0.88 g, 3.64 mmol) in DMF (10 mL) was added tert-butyl acrylate (1.401 g, 10.93 mmol), TEA (1.270 mL, 9.11 mmol) and palladium acetate (0.082 g, 0.364 mmol). The reaction was warmed to 90° C. After 5 h, the reaction was cooled to rt and then filtered to remove the solid. The filtrate was diluted with EtOAc, washed with 1M HCl, sat NaHCO₃ and brine.

The organic phase was dried over magnesium sulfate, filtered and concentrated. Purification by normal phase chromatography gave Intermediate 19B (232 mg, 22% yield) as a tan oil. MS (ESI) m/z: 233.1 (M-tBu)+.

Intermediate 19. A solution of Intermediate 19B (232 mg, 0.804 mmol) in DCM (2.0 mL) was added TFA (2.0 mL, 26.0 mmol). The reaction was stirred under argon at rt. After 1 h, the solvent was removed and the residue was dried to give Intermediate 19 (191 mg, 100% yield) as tan solid. ¹H NMR (400 MHz, CD₃OD) δ 7.99 (dt, J=15.8, 1.5 Hz, 1H), 7.83 (s, 1H), 7.60 (d, J=8.3 Hz, 1H), 7.55-7.48 (m, 1H), 7.01 (t, J=54.6 Hz, 1H), 6.51 (d, J=15.8 Hz, 1H). ¹⁹F NMR (376 MHz, CD₃OD) δ -111.67 (s, 2F). MS (ESI) m/z: 233.1 (M+H)+.

Intermediate 24

(E)-3-(5-Chloro-2-difluoromethoxy-phenyl)-acrylic acid

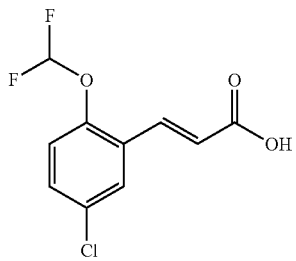 [SMILES: O=C(O)/C=C/c1cc(Cl)ccc1OC(F)F]

Intermediate 24A. (E)-3-(5-Chloro-2-difluoromethoxy-phenyl)-acrylic acid tert-butyl ester: To a cooled (0° C.) solution of potassium tert-butoxide (0.407 g, 3.63 mmol) in THF (10 mL) was added tert-butyl 2-(dimethoxyphosphoryl)acetate (0.528 mL, 2.66 mmol) and 5-chloro-2-(difluoromethoxy)benzaldehyde (0.50 g, 2.420 mmol). The reaction was allowed to warm to RT. After 4 h, the reaction was quenched with the addition of sat. ammonium chloride. The reaction was diluted with EtOAc, washed with sat. ammonium chloride, sat NaHCO₃ and brine. The organic layer was dried over sodium sulfate, filtered and concentrated. Purification by normal phase chromatography gave 550 mg (74%) of Intermediate 24A as a white solid. ¹H NMR (400 MHz, CDCl₃) δ ppm 7.77 (1H, d, J=16.31 Hz), 7.58 (1 H, d, J=2.51 Hz), 7.31 (1 H, dd, J=8.66, 2.64 Hz), 7.12 (1 H, d, J=8.78 Hz), 6.52 (1 H, t, J=72.78 Hz) 6.40 (1 H, d, J=16.31 Hz), 1.53 (9 H, s). ¹⁹F NMR (376 MHz, CDCl₃) δ ppm -81.11. MS (ESI) m/z: 327.0 (M+Na)+.

Intermediate 24. To a solution of Intermediate 24A (458 mg, 1.503 mmol) in DCM (4.0 mL) was added TFA (2.0 mL, 26.0 mmol). The reaction was stirred under argon at RT for 1 h. The solvent was removed to give Intermediate 24 as a white solid. MS (ESI) m/z: 249.0 (M+H)+.

Intermediate 25

3-(5-Chloro-2-tetrazol-1-yl-phenyl)-propionic acid

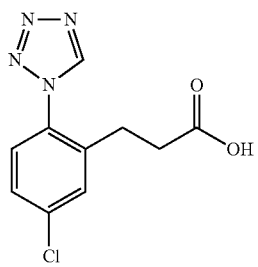 [SMILES: O=C(O)CCc1cc(Cl)ccc1-n1cnnn1]

The synthesis was described as Example 63A in PCT International Application No. WO 2007/070826 published Jun. 21, 2007.

Intermediate 40

(E)-3-(3-Chloro-2-fluoro-6-(trifluoromethyl)phenyl) acrylic acid

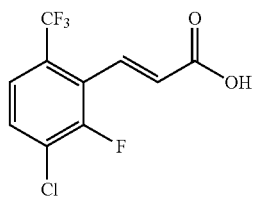 [SMILES: O=C(O)/C=C/c1c(C(F)(F)F)ccc(Cl)c1F]

Intermediate 40 was prepared following the procedures described in Intermediate 24, by replacing 5-chloro-2-(difluoromethoxy)benzaldehyde with 3-chloro-2-fluoro-6-(trifluoromethyl)benzaldehyde. MS (ESI) m/z: 292 (M+Na)+. ¹H NMR (400 MHz, CDCl₃) δ ppm 7.87 (1 H, dd, J=16.17, 2.02 Hz), 7.49-7.62 (2 H, m), 6.67 (1 H, dd, J=16.30, 1.39 Hz).

EXAMPLE 1

(E)-3-(5-Chloro-2-tetrazol-1-yl-phenyl)-N-(E)-(S)-8-oxa-16,18-diaza-tricyclo[13.2.1.0²,⁷]octadeca-1(17), 2,4,6,11,15(18)-hexaen-14-yl-acrylamide, 1 TFA salt

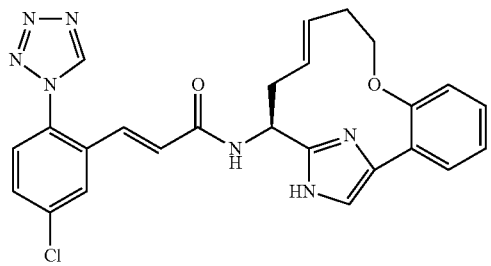 [SMILES: O=C(/C=C/c1cc(Cl)ccc1-n1cnnn1)N[C@H]1C/C=C/CCOc2ccccc2-c2c[nH]c1n2]

1A. (S)-2-tert-Butoxycarbonylamino-pent-4-enoic acid 2-(2-but-3-enyloxy-phenyl)-2-oxo-ethyl ester: A suspension of (S)-2-(tert-butoxycarbonylamino)pent-4-enoic acid (515 mg, 2.394 mmol) and potassium hydrogen carbonate (0.288 g, 2.87 mmol) in DMF (12.00 mL) was stirred at rt for 20 min. The reaction was then cooled to 0° C. and Intermediate 6 (0.773 g, 2.87 mmol) was added. The resulting yellow solution was allowed to warm to rt. After stirring overnight, the reaction was cooled to 0° C. and then poured into cold water to give a white suspension. The white suspension was then extracted with EtOAc (3×75 mL). The combined organic layers were washed with brine, dried over Na₂SO₄, filtered, and concentrated to give 1.072 g of 1A as a yellow oil. This was used without further purification. MS (ESI) m/z: 304.3 (M-C₅H₈O₂+H)+.

1B. {(S)-1-[4-(2-But-3-enyloxy-phenyl)-1H-imidazol-2-yl]-but-3-enyl}-carbamic acid tert-butyl ester: Compound 1A (1.07 g, 2.66 mmol) was dissolved in xylene (26.6 mL) and divided evenly between two 20-mL microwave vials. Next ammonium acetate (2.047 g, 26.6 mmol) was added to each vial. The vials were microwaved at 140° C. for 30 min. The resulting bright orange solutions were combined, partitioned between EtOAc and sat. NaHCO₃ and the layers were separated. The aqueous layer was extracted with EtOAc (2×100 mL). The combined organic layers were washed with brine, dried over Na₂SO₄, filtered and concentrated to give a peach residue. Purification by normal phase chromatography gave 0.626 g (62%) of 1B as a sticky, yellow solid. MS (ESI) m/z: 384.4 (M+H)⁺.

1C. {(S)-1-[4-(2-But-3-enyloxy-phenyl)-1-(2-trimethylsilanyl-ethoxymethyl)-1H-imidazol-2-yl]-but-3-enyl}-carbamic acid tert-butyl ester: To a cooled (0° C.) suspension of NaH (58.7 mg, 1.468 mmol) in DMF (2.06 mL) was added dropwise a solution of 1B (536.2 mg, 1.40 mmol) in DMF (1.3 mL). The resulting orange solution was allowed to warm to rt. After 1 h, the reaction was cooled to 0° C. and SEMCl (0.27 mL, 1.52 mmol) was added dropwise. The resulting peach solution was allowed to warm to rt. After 1 h and 45 min, the cloudy yellow mixture was cooled to 0° C. and quenched with water (20 mL). The reaction was extracted with EtOAc (3×20 mL). The combined organic layers were washed with water (3×6 mL), dried over Na₂SO₄, filtered and concentrated. Purification by normal phase chromatography gave 462.5 mg (64%) of 1C as a pale yellow oil. MS (ESI) m/z: 514.3 (M+H)⁺.

1D. [(E)-(S)-16-(2-Trimethylsilanyl-ethoxymethyl)-8-oxa-16,18-diaza-tricyclo[13.2.1.0$^{2,7}$]octadeca-1(17),2,4,6,11,15(18)-hexaen-14-yl]-carbamic acid tert-butyl ester, 1 TFA salt; and 1E. [(Z)—(S)-16-(2-Trimethylsilanyl-ethoxymethyl)-8-oxa-16,18-diaza-tricyclo[13.2.1.0$^{2,7}$]octadeca-1(17),2,4,6,11,15(18)-hexaen-14-yl]-carbamic acid tert-butyl ester, 1 TFA salt: (Flask 1): To a flame-dried RBF was added Grubbs (II) (681 mg, 0.802 mmol). The flask was degassed with argon for several minutes and then degassed DCM (10 mL) was added to give a clear, burgundy solution. (Flask 2): To a separate flame-dried RBF was added 1C (412 mg, 0.802 mmol), pTsOH monohydrate (168 mg, 0.882 mmol) and DCM (779 mL). The flask was equipped with a reflux condenser and the solution was degassed with argon for 30 min. Next, the reaction was warmed to 40° C. After 1 h, the solution of Grubbs (II) was added dropwise. After 1 h, the reaction was cooled to rt and washed with NaHCO₃, brine, dried over MgSO₄, filtered and concentrated. Purification by normal phase chromatography gave a pale, brown oil. Further purification by reverse phase chromatography gave 78.6 mg (20%) of 1D (E-alkene) as a pale brown oil and 33.2 mg (9%) of 1E (Z-alkene) as a pale, brown oil. For 1D: MS (ESI) m/z: 486.5 (M+H)⁺. For 1E: MS (ESI) m/z: 486.5 (M+H)⁺.

1F. (E)-(S)-(8-Pxa-16,18-diaza-tricyclo[13.2.1.0$^{2,7}$]octadeca-1(17),2,4,6,11,15(18)-hexaen-14-yl)amine, 2 TFA: A yellow solution of 1D (59.2 mg, 0.122 mmol) in 5M HCl (2.50 mL, 82 mmol) and EtOH (2.44 mL) was heated to 50° C. After stirring overnight, the reaction was concentrated to remove EtOH and the remaining aqueous layer was adjusted to pH>10 with sat. K₂CO₃. The reaction was extracted with EtOAc (3×). The combined organic layers were dried over Na₂SO₄, filtered and concentrated to give a brown residue. Purification by reverse phase chromatography gave 0.0246 g (42%) of 1F as a clear, colorless oil. MS (ESI) m/z: 256.3 (M+H)⁺.

1G. Example 1: To a solution of Intermediate 1 (33.5 mg, 0.096 mmol) and 1F (24.6 mg, 0.096 mmol) in DMF (0.321 mL) was added Hunig's Base (0.084 mL, 0.482 mmol). After 45 min, water was added to give a suspension. The solid was collected by filtration. Purification by reverse phase chromatography gave after concentration and lyophilization 0.0195 g (33%) of Example 1 as a white solid. ¹H NMR (400 MHz, CD₃OD) δ ppm 2.40-2.71 (m, 3 H), 2.76-2.88 (m, 1 H), 3.68-3.84 (m, 1 H), 4.21-4.42 (m, 1 H), 5.13-5.28 (m, 2 H), 5.77-5.91 (m, 1 H), 6.81 (d, J=15.9 Hz, 1 H), 7.14-7.23 (m, 2 H), 7.29 (dd, J=8.2, 1.1 Hz, 1 H), 7.47 (td, J=7.7, 1.6 Hz, 1 H), 7.55 (s, 1 H), 7.57-7.62 (m, 2 H), 7.69 (dd, J=8.8, 2.2 Hz, 1 H), 8.00 (d, J=2.2 Hz, 1 H), 9.54 (s, 1 H). MS (ESI) m/z: 488.3 (M+H)⁺. Analytical HPLC: RT=5.35 min.

EXAMPLE 2

(E)-3-(5-Chloro-2-tetrazol-1-yl-phenyl)-N—(S)-16,18-diaza-tricyclo[13.2.1.0$^{2,7}$]octadeca-1(17),2,4,6,15(18)-pentaen-14-yl-acrylamide, 1 TFA salt

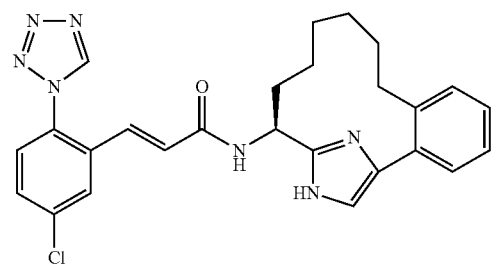 [SMILES: O=C(/C=C/c1cc(Cl)ccc1-n1cnnn1)N[C@H]1CCCCCCc2ccccc2-c2c[nH]c1n2]

2A. (S)-2-(2-Bromophenyl)-2-oxoethyl 2-(tert-butoxycarbonylamino)pent-4-enoate: To a clear, colorless solution of (S)-2-(tert-butoxycarbonylamino)pent-4-enoic acid (3.33 g, 15.47 mmol) in DMF (38.7 mL) was added potassium hydrogen carbonate (1.859 g, 18.57 mmol). The reaction was stirred for 20 min at rt and then it was cooled to 0° C. Next a solution of 2-bromo-1-(2-bromophenyl)ethanone (4.3 g, 15.47 mmol) in DMF (38.7 mL) was added dropwise and the reaction was allowed to warm to rt. After 3 h, the reaction was cooled to 0° C., poured into ice-cold water, and then extracted with EtOAc (3×). The combined organic layers were washed with water (1×), brine (1×), dried over sodium sulfate, filtered and concentrated to give 2A (6.37 g) as a yellow oil which solidified on storage in the freezer. MS (ESI) m/z: 410.2 (M–H)⁻, 412.2 (M+2–H)⁻. The material was used in the next step without further purification.

2B. (S)-tert-Butyl 1-(5-(2-bromophenyl)-1H-imidazol-2-yl)but-3-enylcarbamate: To the clear, yellow solution of 2A (6.37 g, 15.45 mmol) in xylene (155 mL) was added ammonium acetate (11.91 g, 155 mmol). The reaction mixture was heated to reflux with a Dean-Stark trap to remove water azeotropically. After 4 h, the reaction was cooled to rt, diluted with EtOAc (500 mL) and then washed with sat. sodium bicarbonate, brine, dried over sodium sulfate, filtered, and concentrated to give a brown residue. Purification by normal phase chromatography afforded 2B (2.768 g, 45.7%) as a yellow solid. MS (ESI) m/z: 392.3 (M+H)⁺, 394.3 (M+2+H)⁺.

2C. (S)-tert-Butyl 1-(4-(2-bromophenyl)-1-((2-(trimethylsilyl)ethoxy)methyl)-1H-imidazol-2-yl)but-3-enylcarbamate: To a cooled (0° C.), suspension of NaH (60% dispersion in mineral oil, 0.299 g, 7.48 mmol) in THF (10.0 mL) was added dropwise a solution of 2B (2.668 g, 6.80 mmol) in THF (15.0 mL). Gas evolution was observed. The flask containing 2B was rinsed with THF (2.2 mL) and then this solution was added to the reaction mixture. The resulting clear orange solution was stirred at 0° C. for 30 min, then SEM-Cl (1.206 mL, 6.80 mmol) was added dropwise. The resulting orange solution was maintained at 0° C. After 3 h, the reaction was quenched with sat. ammonium chloride and diluted with EtOAc (200 mL) and water. The layers were separated and the aqueous layer was extracted with EtOAc (1×). The combined organic layers were washed with brine, dried over sodium sulfate, filtered, and concentrated to give clear orange oil. Purification by normal phase chromatography gave 2C (2.76 g, 78%) as a yellow oil. MS (ESI) m/z: 522.5 (M+H)$^+$, 524.5 (M+2+H)$^+$.

2D. (S)-tert-Butyl 1-(4-(2-(pent-4-enyl)phenyl)-1-((2-(trimethylsilyl)ethoxy)methyl)-1H-imidazol-2-yl)but-3-enylcarbamate: To a flame-dried, thick-walled vial was placed 2C (1.085 g, 2.076 mmol), pent-4-enylboronic acid (0.757 g, 6.64 mmol), silver oxide (1.203 g, 5.19 mmol), potassium carbonate (1.722 g, 12.46 mmol), and PdCl$_2$(dppf)-CH$_2$Cl$_2$ adduct (0.170 g, 0.208 mmol). The vial was purged with argon for several minutes and then degassed THF (8.3 mL) was added. The vial was sealed with a teflon-coated screw cap and the black suspension was warmed to 80° C. After 16 h the reaction was cooled to rt. The reaction mixture was diluted with EtOAc, washed with water, sat. sodium bicarbonate, brine, dried over sodium sulfate, filtered and concentrated to give an orange-brown residue. Purification by normal phase chromatography yielded a clear, colorless oil which was a mixture of 2D and starting material. The material was purified further by reverse phase chromatography. The pure fractions were neutralized with sat. sodium bicarbonate and then concentrated to remove the organic solvent. The remaining residue was extracted with EtOAc (2×). The combined organic layers were washed with brine, dried over sodium sulfate, filtered and concentrated to afford 2D (0.21 g, 20%) as a clear, colorless oil. MS (ESI) m/z: 512.6 (M+H)$^+$.

2E. [(E)-(S)-16-(2-Trimethylsilanyl-ethoxymethyl)-16,18-diaza-tricyclo[13.2.1.0$^{2,7}$]octadeca-1(17),2,4,6,11,15(18)-hexaen-14-yl]-carbamic acid ten-butyl ester and 2F. [(Z)—(S)-16-(2-Trimethylsilanyl-ethoxymethyl)-16,18-diaza-tricyclo[13.2.1.0$^{2,7}$]octadeca-1(17),2,4,6,11,15(18)-hexaen-14-yl]-carbamic acid tert-butyl ester: (Flask 1): To a flame-dried flask was added Grubbs (II) (0.139 g, 0.164 mmol). The flask was degassed with argon for several minutes and then degassed DCM (2 mL) was added to give a clear, burgundy solution. (Flask 2): To a separate flame-dried RBF was added 2D (0.21 g, 0.410 mmol), p-toluenesulfonic acid monohydrate (0.086 g, 0.451 mmol) and DCM (420 mL). The flask was equipped with a reflux condenser and the solution was degassed with argon for 30 min. The reaction was heated to 40° C. After 1 h, the solution of Grubbs (II) was added dropwise. After 1 h, the reaction was cooled to rt, washed with sat. sodium bicarbonate, brine, dried over MgSO$_4$, filtered and concentrated to give a brown foam. Purification by reverse phase chromatography gave, after neutralization and extractive workup as described in 2D, 2E (0.09 g, 45.3%, E-alkene) as a yellow solid and 2F (0.035 g, 17.6%, Z-alkene) as a yellow solid. For 2E: MS (ESI) m/z: 484.6 (M+H)$^+$. For 2F: MS (ESI) m/z: 484.6 (M+H)$^+$.

2G. [(S)-16-(2-Trimethylsilanyl-ethoxymethyl)-16,18-diaza-tricyclo[13.2.1.0$^{2,7}$]octadeca-1(17),2,4,6,15(18)-pentaen-14-yl]-carbamic acid tert-butyl ester: To the solution of 2E and 2F (mixture of E/Z isomers) (0.049 g, 0.101 mmol) in MeOH (3 mL) was added 10% palladium on carbon (10.78 mg, 10.13 μmol). The reaction mixture was stirred under H$_2$-balloon. After 2 h, the reaction was filtered through a 0.45 μm glass microfiber filter (GMF) and the Pd/C was rinsed with MeOH. The filtrate was concentrated to give 2G (0.046 g, 93%) as a clear, colorless residue. MS (ESI) m/z: 486.7 (M+H)$^+$. The material was used in the next step without further purification.

2H. Example 2 was prepared by following the procedures described in step 1F, by replacing 1D with 2G; followed by step 1G. $^1$H NMR (500 MHz, 50° C., CD$_3$OD) δ ppm 9.47 (s, 1 H), 7.96 (d, J=2.2 Hz, 1 H), 7.67 (dd, J=8.8, 2.2 Hz, 1 H), 7.57 (d, J=8.8 Hz, 1 H), 7.43-7.49 (m, 3 H), 7.32-7.39 (m, 2 H), 7.18 (d, J=16.0 Hz, 1 H), 6.76 (dd, J=15.7, 3.6 Hz, 1 H), 4.99-5.04 (m, 1 H), 2.52-2.60 (m, 1 H), 2.40-2.48 (m, 1 H), 2.18-2.26 (m, 1 H), 1.84-1.90 (m, 1 H), 1.31-1.58 (m, 4 H), 1.21-1.29 (m, 2 H), 0.87-1.01 (m, 1 H), 0.40-0.54 (m, 1 H). MS (ESI) m/z: 488.0 (M+H)$^+$. Analytical HPLC: RT=5.78 min.

EXAMPLE 3

2 TFA Salt

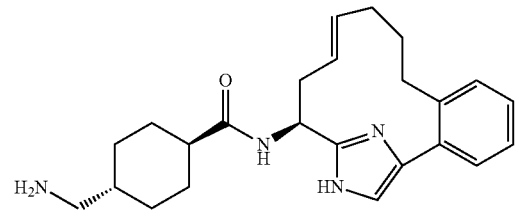 [SMILES: NC[C@H]1CC[C@H](C(=O)N[C@H]2C/C=C/CCCc3ccccc3-c3c[nH]c2n3)CC1]

3A. (E)-(S)-(16,18-Diaza-tricyclo[13.2.1.0$^{2,7}$]octadeca-1(17),2,4,6,11,15(18)-hexaen-14-yl)amine, 2 TFA salt: This compound was prepared following the procedures described in 1F, by replacing 1D with 2E. MS (ESI) m/z: 254.5 (M+H)$^+$.

3B. {4-[(E)-(S)-(16,18-Diaza-tricyclo[13.2.1.0$^{2,7}$]octadeca-1(17),2,4,6,11,15(18)-hexaen-14-yl)carbamoyl]-cyclohexylmethyl}-carbamic acid ten-butyl ester: To a solution of 3A (0.014 g, 0.029 mmol) in DMF (0.5 mL) was added (1r,4r)-4-((tert-butoxycarbonylamino)methyl)cyclohexanecarboxylic acid (8.23 mg, 0.032 mmol), EDC (0.011 g, 0.058 mmol), HOBt (8.91 mg, 0.058 mmol) and Hunig's base (0.015 g, 0.116 mmol). The reaction was stirred at rt for 16 h and then quenched with water to give a suspension. The solid was collected by filtration and then the solid was rinsed with water, air-dried, and then dried in a vacuum oven (50° C.) for 2 h to afford 3B (0.010 g, 69.8%) as white solid. MS (ESI) m/z: 293.7 (M+H)$^+$. The material was used in the next step without further purification.

3C. Example 3: To a solution of 3B (0.01 g, 0.020 mmol) in DCM (0.3 mL) was added TFA (0.3 mL, 3.89 mmol). The reaction was stirred at rt for 1 h, and then concentrated. Purification by reverse phase chromatography afforded Example 3 (0.0095 g, 73.7%) as a white solid. $^1$H NMR (500 MHz, 50° C., CD$_3$OD) δ ppm 7.40-7.45 (m, 2 H), 7.38 (s, 1 H), 7.29-7.37 (m, 2 H), 5.48-5.56 (m, 1 H), 5.07-5.15 (m, 1 H), 5.01 (dd, J=10.4, 4.9 Hz, 1 H), 2.75-2.84 (m, 3 H), 2.58-2.66 (m, 1 H), 2.43-2.51 (m, 2 H), 2.35-2.45 (m, 1 H), 1.82-2.03 (m, 6 H), 1.44-1.69 (m, 4 H), 1.20-1.30 (m, 1 H), 1.06-1.18 (m, 2 H). MS (ESI) m/z: 393.6 (M+H)$^+$. Analytical HPLC: RT=3.70 min.

EXAMPLE 8

{(S)-14-[(E)-3-(5-Chloro-2-tetrazol-1-yl-phenyl)-acryloylamino]-8-oxa-16,18-diaza-tricyclo[13.2.1.0$^{2,7}$]octadeca-1(17),2,4,6,15(18)-pentaen-5-yl}-carbamic acid methyl ester, 1 TFA salt

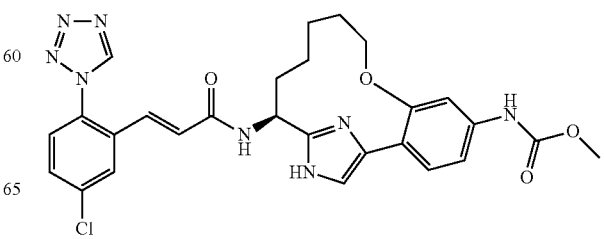

Example 8 was prepared following the procedures described in step 2A, by replacing 2-bromo-1-(2-bromophenyl)ethanone with Intermediate 7; followed by steps 2B-2C; 2E/2F-2G; 1F, by replacing ethanol with methanol and by running the reaction at 75° C.; and 1G. $^1$H NMR (500 MHz, CD$_3$OD) δ ppm 9.52 (s, 1 H), 7.98 (d, J=2.2 Hz, 1 H), 7.68 (dd, J=8.2, 2.2 Hz, 1 H), 7.59 (d, J=8.2 Hz, 1H), 7.48-7.52 (m, 2 H), 7.46 (d, J=8.2 Hz, 1 H), 7.21 (dd, J=8.8, 2.2 Hz, 1H), 7.16 (d, J=15.9 Hz, 1H), 6.78 (d, J=15.9 Hz, 1 H), 5.14 (dd, J=10.4, 6.0 Hz, 1 H), 3.82-3.88 (m, 1 H), 3.75 (s, 3H), 3.67-3.72 (m, 1 H), 2.19-2.28 (m, 1 H), 1.84-1.99 (m, 2 H), 1.46-1.62 (m, 2 H), 1.35-1.45 (m, 1 H), 1.11-1.21 (m, 1 H), 0.88-0.99 (m, 1 H). MS (ESI) m/z: 562.9 (M+H)$^+$. Analytical HPLC: RT=5.65 min.

EXAMPLE 9

{(S)-17-Chloro-14-[(E)-3-(5-chloro-2-tetrazol-1-yl-phenyl)-acryloylamino]-8-oxa-16,18-diaza-tricyclo[13.2.1.0$^{2,7}$]octadeca-1(17),2,4,6,15(18)-pentaen-5-yl}-carbamic acid methyl ester, 1 TFA salt

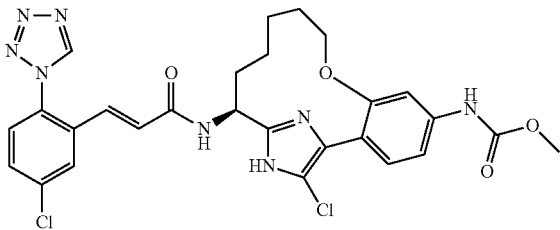 [SMILES: COC(=O)Nc1ccc2c(c1)OCCCCC[C@H](NC(=O)/C=C/c1cc(Cl)ccc1-n1cnnn1)c1nc-2c(Cl)[nH]1]

To a solution of Example 8 (0.013 g, 0.019 mmol) in acetonitrile (0.5 mL)/chloroform (0.500 mL) was added Hunig's base (6.69 µL, 0.038 mmol). The reaction was stirred at rt for 10 min, then NCS (3.08 mg, 0.023 mmol) was added. The vial was sealed with a teflon-coated screw cap and the reaction was warmed to 65° C. After 4 h, additional NCS (3.08 mg, 0.023 mmol) was added. After another 2 h, the reaction was cooled to rt and then concentrated. Purification by reverse phase chromatography afforded 0.0050 g (35.5%) of Example 9 as a yellow solid. $^1$H NMR (500 MHz, CD$_3$OD) δ ppm 9.52 (s, 1 H), 7.98 (d, J=2.2 Hz, 1 H), 7.67 (dd, J=8.5, 2.5 Hz, 1 H), 7.58 (d, J=8.3 Hz, 1 H), 7.47-7.51 (m, 2 H), 7.20 (dd, J=8.8, 2.2 Hz, 1 H), 7.15 (d, J=15.4 Hz, 1 H), 6.77 (d, J=15.4 Hz, 1 H), 5.05 (dd, J=10.4, 6.0 Hz, 1 H), 3.80-3.85 (m, 1 H), 3.75 (s, 3 H), 3.64-3.70 (m, 1 H), 2.13-2.22 (m, 1 H), 1.81-1.92 (m, 2H), 1.49-1.61 (m, 2 H), 1.30-1.41 (m, 1 H), 1.10-1.20 (m, 1 H), 0.89-1.01 (m, 1 H). MS (ESI) m/z: 597.0 (M+H)$^+$. Analytical HPLC: RT=8.09 min.

EXAMPLE 10

{(S)-14-[(E)-3-(5-Chloro-2-tetrazol-1-yl-phenyl)-acryloylamino]-9-oxo-8,16,18-triaza-tricyclo[13.2.1.0$^{2,7}$]octadeca-1(17),2,4,6,15(18)-pentaen-5-yl}-carbamic acid methyl ester, 1 TFA salt

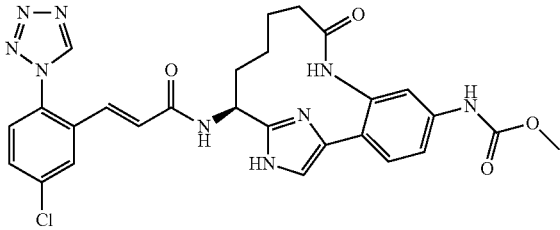 [SMILES: COC(=O)Nc1ccc2c(c1)NC(=O)CCCC[C@H](NC(=O)/C=C/c1cc(Cl)ccc1-n1cnnn1)c1nc-2c[nH]1]

10A. {3-Bromo-4-[2-((S)-1-tert-butoxycarbonylamino-but-3-enyl)-3H-imidazol-4-yl]-phenyl}-carbamic acid methyl ester: This compound was prepared following the procedures described in step 2A, by replacing 2-bromo-1-(2-bromophenyl)ethanone with Intermediate 8; followed by step 2B. MS (ESI) m/z: 467.1 (M+2+H)$^+$.

10B. {3-Bromo-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: (The following is an alternative procedure to procedure 2C). To a cooled (0° C.) solution of 10A (15 g, 32.2 mmol) in THF (77 mL) was added N,N-dicyclohexylmethylamine (7.52 mL, 35.5 mmol) followed by the dropwise addition of SEM-Cl (6.29 mL, 35.5 mmol). The reaction was stirred at 0° C. for 2 h and then it was allowed to warm slowly to rt. After 18 h, the yellow suspension was diluted with EtOAc, washed with sat. sodium bicarbonate, brine, dried over MgSO$_4$, filtered and concentrated. Purification by normal phase chromatography gave 12.24 g (63.8%) of 10B as an off-white solid. MS (ESI) m/z: 595.1 (M+H)$^+$ and 597.2 (M+2+H)$^+$.

10C. {3-Amino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: A thick-walled vial containing 10B (2 g, 3.36 mmol), copper(I) iodide (0.128 g, 0.672 mmol), L-proline (0.155 g, 1.343 mmol) and potassium carbonate (1.392 g, 10.07 mmol) in DMSO (6.72 mL) was vacuumed and back-filled with argon three times. Then 28% aq. ammonium hydroxide (0.607 mL, 4.37 mmol) was added. The vial was sealed with a teflon-coated screw cap and the reaction was warmed to 85° C. After 20 h, the reaction was cooled to rt, diluted with EtOAc, washed with water, brine, dried over sodium sulfate, filtered and concentrated. Purification by normal phase chromatography afforded 1.05 g (58.8%) of 10C as a yellow solid. MS (ESI) m/z: 532.5 (M+H)$^+$.

10C (Alternative route). Compound 10B (1.0 g, 1.679 mmol), copper(I) iodide (0.032 g, 0.168 mmol), L-proline (0.058 g, 0.504 mmol) and sodium azide (0.131 g, 2.015 mmol) were added to a 35 mL pressure tube. Next, EtOH (2.52 mL), water (0.839 mL), and 1N NaOH (0.504 mL, 0.504 mmol) were added. The reaction vessel was vacuumed and back-filled with argon three times. The pressure tube was sealed with a teflon screw cap, containing a viton O-ring, and then the reaction was warmed to 95° C. After 20 h, the reaction was cooled to rt, and additional sodium azide (0.131 g, 2.015 mmol), L-proline (0.058 g, 0.504 mmol), copper(I) iodide (0.032 g, 0.168 mmol), NaOH (0.504 mL, 0.504 mmol) and EtOH (2.52 mL) were added. The vessel was sealed and the reaction was warmed to 95° C. After another 24 h, the reaction was cooled to rt, diluted with EtOAc, washed with water, brine, dried over sodium sulfate, filtered and concentrated. Purification by normal phase chromatography gave 0.475 g (53.2%) of 10C as an orange solid. MS (ESI) m/z: 532.4 (M+H)$^+$.

10D. {3-But-3-enoylamino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: To a cooled (−10° C.) solution of Hunig's base (0.300 mL, 1.715 mmol), but-3-enoic acid (0.049 g, 0.572 mmol) and 10C (0.304 g, 0.572 mmol) in ethyl acetate (16.34 mL) was added 1-propanephosphonic acid cyclic anhydride (T3P) (50% in EtOAc, 0.674 mL, 1.143 mmol). After 5 min, the reaction was allowed to warm to rt. After 1 h at rt, the reaction was concentrated. Purification by normal phase chromatography gave 0.30 g (87%) of 10D as a yellow solid. MS (ESI) m/z: 600.3 (M+H)$^+$.

10E. [(E)-(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,11,15(18)-hexaen-5-yl]-carbamic acid methyl ester; and 10F. [(Z)—(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,11,15(18)-hexaen-5-yl]-carbamic acid methyl ester: Compound 10E, the E-alkene, and compound 10F, the Z-alkene, were prepared following the procedure described in 2E/2F, by replacing 2D with 10D. MS (ESI) m/z: 572.2 (M+H)$^+$.

10G. [(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,15(18)-pentaen-5-yl]-carbamic acid methyl ester: To a suspension of 10E (0.25 g, 0.437 mmol) in MeOH (10 mL)/EtOAc (5 mL) was added 10% palladium on carbon (0.047 g, 0.044 mmol). Hydrogen was bubbled through the reaction mixture for 5 min and then the reaction was stirred vigorously under a hydrogen atmosphere (balloon). After 24 h, the reaction was filtered through a 0.45 μm GMF, rinsing with MeOH, DCM and EtOAc. The filtrate was concentrated and purification by reverse phase chromatography afforded 0.220 g (88%) of 10G, as an off-white solid. MS (ESI) m/z: 574.4 (M+H)$^+$.

10H. ((S)-14-Amino-9-oxo-8,16,18-triaza-tricyclo[13.2.1.0$^{2,7}$]octadeca-1(17),2,4,6,15(18)-pentaen-5-yl)-carbamic acid methyl ester, 2HCl salt: A mixture of 10G (0.099 g, 0.173 mmol) and 4M HCl in dioxane (2 mL, 8.00 mmol) in a sealed tube was heated at 50° C. After 2 h, the yellow suspension was cooled to rt and then concentrated. The residue was suspended in MeOH (0.2 mL) and Et$_2$O. The solid was collected by filtration. The solid was rinsed with Et$_2$O, air-dried (very hygroscopic) to afford 0.053 g (73.8%) of 10H as a yellow solid. MS (ESI) m/z: 344.2 (M+H)$^+$.

10I. Example 10 was prepared following the procedure described in 1G, by replacing 1F with 10H. $^1$H NMR (400 MHz, CD$_3$OD) δ ppm 9.51 (s, 1 H), 7.97 (d, J=2.2 Hz, 1 H), 7.67 (dd, J=8.2, 2.2 Hz, 1 H), 7.55-7.60 (m, 2 H), 7.50 (d, J=8.2 Hz, 1 H), 7.44 (s, 1 H), 7.42 (dd, J=8.3, 2.2 Hz, 1 H), 7.13 (d, J=15.4 Hz, 1 H), 6.76 (d, J=15.9 Hz, 1 H), 5.13 (dd, J=10.2, 6.3 Hz, 1 H), 3.75 (s, 3 H), 2.42-2.52 (m, 1 H), 2.17-2.29 (m, 1H), 2.05-2.15 (m, 1 H), 1.96 (m, 1 H), 1.51-1.71 (m, 2 H), 1.36-1.49 (m, 1 H), 0.92-1.07 (m, 1H). MS (ESI) m/z: 576.3 (M+H)$^+$. Analytical HPLC: RT=4.60 min.

EXAMPLE 15

(E)-3-(5-Chloro-2-tetrazol-1-yl-phenyl)-N—((S)-9-oxo-8,16,18-triaza-tricyclo[13.2.1.0$^{2,7}$]octadeca-1(17),2,4,6,15(18)-pentaen-14-yl)-acrylamide, 1 TFA salt 15A. {(S)-1-[4-(2-Nitro-phenyl)-1-(2-trimethylsilanyl-ethoxymethyl)-1H-imidazol-2-yl]-but-3-enyl}-carbamic acid tert-butyl ester: This compound was prepared following the procedures described in step 2A, by replacing 2-bromo-1-(2-bromophenyl)ethanone with 2-bromo-1-(2-nitrophenyl)ethanone; followed by steps 2B, by replacing xylene with toluene; and 2C. MS (ESI) m/z: 489.4 (M+H)$^+$.

15B. {(S)-1-[4-(2-Amino-phenyl)-1-(2-trimethylsilanyl-ethoxymethyl)-1H-imidazol-2-yl]-but-3-enyl}-carbamic acid tert-butyl ester: To a yellow solution of 15A (1.0441 g, 2.137 mmol) in MeOH (14.15 mL) was added zinc dust (1.397 g, 21.37 mmol) and ammonium chloride (1.143 g, 21.37 mmol). The gray suspension was stirred vigorously at rt. After 1 h, the flask was equipped with a reflux condenser and the reaction was warmed to 60° C. After 1 h, the reaction was cooled to rt and allowed to stir overnight. The reaction was filtered through a 0.45 μm GMF, eluting with methanol. The filtrate was concentrated to give a yellow solid. The solid was partitioned between EtOAc and 0.5M HCl (aq). The layers were separated and the aqueous layer was extracted with EtOAc (1×). The combined organic layers were washed with sat. NaHCO$_3$, brine, dried over Na$_2$SO$_4$, filtered and concentrated to give an orange oil. Purification by normal phase chromatography gave 0.818 g (83%) of 15B as a yellow foam. MS (ESI) m/z: 459.4 (M+H)$^+$.

15C. (S)-14-Amino-8,16,18-triaza-tricyclo[13.2.1.0$^{2,7}$]octadeca-1(17),2,4,6,15(18)-pentaen-9-one, 2HCl: This compound was prepared following the procedures in step 10D, by replacing 10C with 15B; followed by steps 2E/2F; 2G, by replacing the hydrogen balloon with hydrogen (50-55 psi); and 10H. MS (ESI) m/z: 489.4 (M+H)$^+$.

15D. Example 15: A suspension of Intermediate 2 (0.074 g, 0.296 mmol), 15C (0.113 g, 0.329 mmol), EDC (0.095 g, 0.494 mmol), and HOBT (0.076 g, 0.494 mmol) in DMF (1.65 mL) and Hunig's Base (0.172 mL, 0.988 mmol) was stirred at rt overnight. Water was added to the brown solution to give a suspension. The mixture was extracted with EtOAc (2×). The organic layers were combined and washed with sat. NaHCO$_3$, brine, dried over Na$_2$SO$_4$, filtered and concentrated. Purification by reverse phase chromatography gave 0.0964 g (47%) of Example 15 as a white solid. $^1$H NMR (500 MHz, CD$_3$OD) δ ppm 0.96-1.13 (m, 1 H), 1.37-1.50 (m, 1 H), 1.51-1.72 (m, 2 H), 1.90-2.01 (m, 1 H), 2.05-2.15 (m, 1 H), 2.18-2.28 (m, 1 H), 2.44-2.50 (m, 1 H), 5.13 (dd, J=10.2, 6.3 Hz, 1 H), 6.75 (d, J=15.7 Hz, 1 H), 7.14 (d, J=15.7 Hz, 1 H), 7.31 (dd, J=7.8, 0.7 Hz, 1 H), 7.44 (td, J=7.6, 1.1 Hz, 1 H), 7.49 (s, 1 H), 7.53 (td, J=7.7, 1.4 Hz, 1 H), 7.58 (d, J=8.5 Hz, 1 H), 7.61 (dd, J=7.7, 1.4 Hz, 1 H), 7.67 (dd, J=8.5, 2.5 Hz, 1 H), 7.97 (d, J=2.2 Hz, 1 H), 9.50 (s, 1 H). MS (ESI) m/z: 503.3 (M+H)$^+$. Analytical HPLC: RT=4.72 min.

EXAMPLE 23

{(S)-14-[(E)-3-(5-Chloro-2-tetrazol-1-yl-phenyl)-acryloylamino]-11-methyl-12-oxo-11,16,18-triaza-tricyclo[13.2.1.0$^{2,7}$]octadeca-1(17),2,4,6,15(18)-pentaen-5-yl}-carbamic acid methyl ester, 1 TFA salt

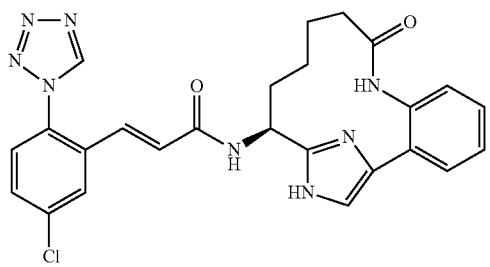 [SMILES: O=C(/C=C/c1cc(Cl)ccc1-n1cnnn1)N[C@H]1CCCCC(=O)Nc2ccccc2-c2c[nH]c1n2]

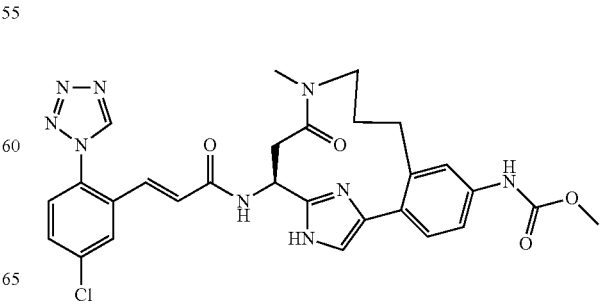

23A. (S)-3-[4-(2-Bromo-4-methoxycarbonylamino-phenyl)-1-(2-trimethylsilanyl-ethoxymethyl)-1H-imidazol-2-yl]-3-tert-butoxycarbonylamino-propionic acid benzyl ester: This compound was prepared following the procedures described in 2A, by replacing (S)-2-(tert-butoxycarbonylamino)pent-4-enoic acid with (S)-2-tert-butoxycarbonylamino-succinic acid 4-benzyl ester, by replacing 2-bromo-1-(2-bromophenyl)ethanone with Intermediate 8 and by replacing potassium hydrogen carbonate with potassium carbonate; followed by steps 2B, by replacing xylene with toluene; and 10B. MS (ESI) m/z: 703.3, 705.3 (M+H)+.

23B. Methyl-prop-2-ynyl-carbamic acid benzyl ester: To a solution of N-methylprop-2-yn-1-amine (3.50 g, 50.6 mmol) in DCM (50 mL) were added TEA (8.47 mL, 60.8 mmol) and Cbz-Cl (7.95 mL, 55.7 mmol) dropwise at 0° C. The reaction was stirred under argon at 0° C. for 1 h. The reaction mixture was diluted with CH₂Cl₂, washed with 1M HCl, saturated NaHCO₃ and brine. The organic phase was dried over MgSO₄, filtered and concentrated to give 23B (10.02 g, 97% yield) as a clear oil. MS (ESI) m/z: 204.1 (M+H)+.

23C. (S)-3-[4-{2-[3-(Benzyloxycarbonyl-methyl-amino)-prop-1-ynyl]-4-methoxycarbonylamino-phenyl}-1-(2-trimethylsilanyl-ethoxymethyl)-1H-imidazol-2-yl]-3-tert-butoxycarbonylamino-propionic acid benzyl ester: To a solution of 23A (200 mg, 0.284 mmol) in DMF (5 mL) was added 23B (69.3 mg, 0.341 mmol), CuI (10.83 mg, 0.057 mmol), TEA (0.119 mL, 0.853 mmol) and Pd(Ph₃P)₄ (32.8 mg, 0.028 mmol). The reaction was purged with argon for 3 min and then stirred under argon at 90° C. for 6 h. The reaction was cooled to rt and diluted with EtOAc. The organic layer was washed with saturated NaHCO₃ and brine, dried over MgSO₄, filtered and concentrated. The crude product was purified by normal phase chromatography to give 23C (205 mg, 87% yield) as a solid. LC-MS (ESI) m/z: 826.5 (M+H)+.

23D. (S)-3-(tert-Butoxycarbonylamino)-3-(4-(4-(methoxycarbonylamino)-2-(3-(methylamino)propyl)phenyl)-1-((2-(trimethylsilyl)ethoxy)methyl)-1H-imidazol-2-yl)propanoic acid, TFA salt: This compound was prepared following the procedure described in 2G, by replacing 2E with 23C. MS (ESI) m/z: 606.4 (M+H)+.

23E. [(S)-5-Methoxycarbonylamino-11-methyl-12-oxo-16-(2-trimethylsilanyl-ethoxymethyl)-11,16,18-triaza-tricyclo[13.2.1.0²,⁷]octadeca-1(17),2,4,6,15(18)-pentaen-14-yl]-carbamic acid tert-butyl ester: To a solution of DMAP (23.19 mg, 0.190 mmol), DIEA (0.166 mL, 0.949 mmol) and BOP (168 mg, 0.380 mmol) in DCM (20 mL) was added a solution of 23D (115 mg, 0.190 mmol) in DMF (2 mL) at rt through a syringe pump over 1.5 h. Upon addition, the reaction was stirred for another 30 min and the solvent was removed. The crude product was purified by reverse phase chromatography to give 23E (44 mg, 39.4% yield) as a solid. MS (ESI) m/z: 588.4 (M+H)+.

23F. Example 23 was prepared following the procedures described in step 1F, by replacing 1D with 23E and by replacing ethanol with methanol; followed by step 1G. ¹H NMR (400 MHz, CD₃OD, rotamers) δ ppm 9.52 (two singlets, 1H), 9.36 (s, 1H), 8.00 (d, J=1.8 Hz, 1H), 7.68 (ddd, J=8.6, 6.3, 2.3 Hz, 1H), 7.59 (dd, J=8.5, 5.5 Hz, 1H), 7.49-7.43 (m, 1H), 7.41-7.33 (m, 3H), 7.19 (two doublets, J=16.0 Hz, 1H), 6.81 (two doublets, J=15.6 Hz, 1H), 5.49 (dd, J=8.7, 4.8 Hz, 1H), 4.12 (ddd, J=7.3, 6.0, 3.7 Hz, 1H), 3.75 (two singlets, 3H), 3.55-3.43 (m, J=9.2, 7.6, 5.9 Hz, 1H), 3.00 (two singlets, 3H), 2.81 (dd, J=13.9, 4.8 Hz, 1H), 2.69-2.57 (m, 2H), 2.48-2.28 (m, 1H), 1.91-1.76 (m, 1H), 1.64-1.44 (m, 1H). LC-MS (ESI) m/z: 590.2 (M+H)+. Analytical HPLC: RT=5.328 min.

EXAMPLE 52

{(R)-15-[(E)-3-(5-Chloro-2-tetrazol-1-yl-phenyl)-acryloylamino]-9-oxo-13-oxa-8,17,19-triaza-tricyclo[14.2.1.0²,⁷]nonadeca-1(18),2,4,6,16(19)-pentaen-5-yl}-carbamic acid methyl ester, 1 TFA salt

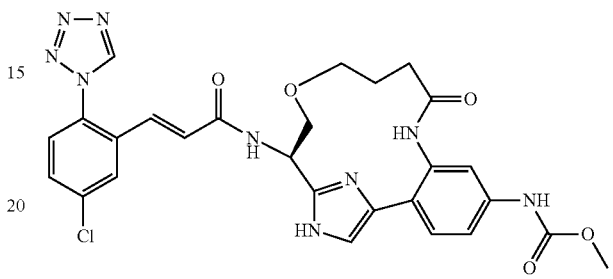

52A. (S)-3-Allyloxy-2-tert-butoxycarbonylamino-propionic acid methyl ester: This compound was prepared following a procedure described in Organic Letters, 10(17):3883 (2008). To a solution of N-(tert-butoxycarbonyl)-L-serine methyl ester (0.781 mL, 3.85 mmol) in THF (15 mL) was added allyl methyl carbonate (0.524 mL, 4.61 mmol). The solution was purged with N₂, followed by the addition of tetrakis(triphenylphosphine)palladium(0) (444 mg, 0.385 mmol). The vessel was sealed and heated at 60° C. overnight. The reaction mixture was diluted with ethyl acetate, washed with sat NaHCO₃, and brine. The organic layer was concentrated. Purification by normal phase chromatography provided 52A (550 mg, 55.2% yield) as a yellow oil. ¹H NMR (400 MHz, CDCl₃) δ ppm 5.75-5.94 (m, 1 H) 5.32-5.47 (m, 1 H) 5.11-5.29 (m, 2 H) 4.35-4.53 (m, 1 H) 3.92-4.03 (m, 2 H) 3.80-3.89 (m, 1 H) 3.76 (m, 3 H) 3.61-3.70 (m, 1 H) 1.46 (m, 9 H).

52B. (S)-3-Allyloxy-2-tert-butoxycarbonylamino-propionic acid: A solution of 52A (1000 mg, 3.86 mmol) and lithium hydroxide (486 mg, 11.57 mmol) in THF, water and MeOH was stirred at rt for 4 h. The solution was acidified using 5M HCl in water (pH~3). The mixture was extracted with EtOAc. The combined organic layers were concentrated to give 52B (0.96 g, 100% yield) as a yellow oil. MS (ESI) m/z: 146.0 (M+H-boc)+.

52C. (S)-3-Allyloxy-2-tert-butoxycarbonylamino-propionic acid 2-(2-bromo-4-nitro-phenyl)-2-oxo-ethyl ester: To a solution of 52B (0.95 g, 3.87 mmol) and Intermediate 10 (1.376 g, 4.26 mmol) in DMF (20 mL) was added potassium bicarbonate (0.465 g, 4.65 mmol). After 1.5 h at rt, the reaction was diluted with EtOAc, washed with water, saturated sodium bicarbonate solution, then brine, dried over magnesium sulfate, filtered, and concentrated to give 52C (1.82 g, 96% yield) as a thick orange oil. MS (ESI) m/z: 389.0 (M+H-boc)+.

52D. (S)-3-Allyloxy-2-tert-butoxycarbonylamino-propionic acid 2-(4-amino-2-bromo-phenyl)-2-oxo-ethyl ester: To a mixture of 52C (1700 mg, 3.49 mmol) and iron (3896 mg, 69.8 mmol) in ethanol (15 mL) and water (15.00 mL) was added 12M conc. HCl (0.204 mL, 2.442 mmol). The suspension was heated at 50° for 2 hr. The dark suspension was filtered, washed with methanol and concentrated to give 52D (1.7 g, 100%). MS (ESI) m/z: 359.0 (M+H-boc)+.

52E. (S)-3-Allyloxy-2-tert-butoxycarbonylamino-propionic acid 2-(2-bromo-4-methoxycarbonylamino-phenyl)-2-oxo-ethyl ester: To a cooled (ice bath) solution 52D (1670 mg, 3.65 mmol) and pyridine (0.325 mL, 4.02 mmol) in dichloromethane (50 mL) was added methyl chloroformate (0.297 mL, 3.83 mmol). The reaction mixture was stirred for 10 min, washed with brine, dried (MgSO$_4$) and concentrated to give 52E (1.8 g, 96% yield) as a yellow foam. MS (ESI) m/z: 417.1 (M+H-boc)$^+$.

52F. {4-[2-((R)-2-Allyloxy-1-tert-butoxycarbonylamino-ethyl)-1-(2-trimethylsilanyl-ethoxymethyl)-1H-imidazol-4-yl]-3-amino-phenyl}-carbamic acid methyl ester: This compound was prepared following the procedures described in step 1B, by replacing 1A with 52E; followed by steps 10B; and 10C (alternative). MS (ESI) m/z: 562.3 (M+H)$^+$.

52G. {3-Acryloylamino-4-[2-((R)-2-allyloxy-1-tert-butoxycarbonylamino-ethyl)-1-(2-trimethylsilanyl-ethoxymethyl)-1H-imidazol-4-yl]-phenyl}-carbamic acid methyl ester: A solution of 52F (50 mg, 0.089 mmol), and DIEA (50 µL, 0.286 mmol) in THF (2 mL) was cooled in ice bath. Acryloyl chloride (10 µL, 0.123 mmol) was added into the solution in a portion. Then, the ice bath was removed and reaction mixture was stirred for 1 hr at rt. To the reaction mixture was added sat. NaHCO$_3$ and the mixture was extracted with EtOAc. The combined organic layer were washed with brine and concentrated to provide an oily residue, which has gel like material insoluble in CH$_2$Cl$_2$. The soluble portion of the residue was purified by normal phase chromatography to give 52G (43 mg, 78% yield). MS (ESI) m/z: 616.4 (M+H)$^+$.

52H. Example 52 was prepared following the procedures described in step 2E/2F, by replacing 2D with 52G; followed by steps 2G; 10H; and 1G. $^1$H NMR (400 MHz, CDCl$_3$) δ ppm 8.94 (s, 1 H) 7.79 (s, 1 H) 7.50-7.62 (m, 1 H) 7.42 (t, J=7.91 Hz, 2 H) 7.10 (br. s., 1 H) 6.60 (d, J=15.31 Hz, 1 H) 5.22 (br. s., 1 H) 4.04-4.18 (m, 1 H) 3.92-4.02 (m, 1 H) 3.78 (s, 4 H) 3.60 (d, J=6.27 Hz, 2 H) 3.28-3.49 (m, 1 H) 2.81 (t, J=7.28 Hz, 1 H) 2.34 (s, 1 H) 2.05 (d, J=5.02 Hz, 2 H) 1.63 (br. s., 1H) 0.88 (t, J=6.90 Hz, 2 H). MS (ESI) m/z: 592.3 (M+H)$^+$. Analytical HPLC: RT=5.16 min.

EXAMPLE 72

{(S)-15-[(E)-3-(5-Chloro-2-tetrazol-1-yl-phenyl)-acryloylamino]-12-methyl-13-oxo-12,17,19-triaza-tricyclo[14.2.1.0$^{2,7}$]nonadeca-1(18),2,4,6,16(19)-pentaen-5-yl}-carbamic acid methyl ester, 1 TFA salt

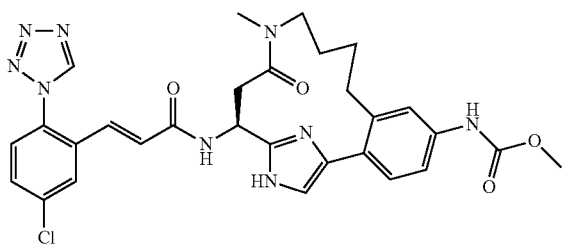 [SMILES: COC(=O)Nc1ccc2c(c1)CCCCN(C)C(=O)C[C@H](NC(=O)/C=C/c1cc(Cl)ccc1-n1cnnn1)c1nc-2c[nH]1]

72A. (S)-3-[4-(2-Allyl-4-methoxycarbonylamino-phenyl)-1-(2-trimethylsilanyl-ethoxymethyl)-1H-imidazol-2-yl]-3-tert-butoxycarbonylamino-propionic acid benzyl ester: 23A (0.30 g, 0.426 mmol), allyltributylstannane (0.282 g, 0.853 mmol), CsF (0.162 g, 1.065 mmol), Pd$_2$ dba$_3$ (0.020 g, 0.021 mmol), and tri-(tert-butyl)phosphine (0.173 g, 0.085 mmol) were added together with dioxane (10 mL). The mixture was heated to 90° C. under argon. After 2.5 h, an additional two equivalents of allyltributylstannane and CsF, and a catalytic amount of Pd$_2$ dba$_3$ and tri-(tert-butyl)phosphine were added. The mixture was stirred at 90° C. under argon for 3 h. The solvent was removed and the residue was partitioned between EtOAc and water. The EtOAc solution was washed with brine, dried over Na$_2$SO$_4$ and concentrated. The crude product was purified by normal phase chromatography to give 72A (0.26 g, 92% yield). MS (ESI) m/z: 665.3 (M+H)$^+$.

72B. (S)-3-(4-(2-Allyl-4-(methoxycarbonylamino)phenyl)-1-((2-(trimethylsilyl)ethoxy)methyl)-1H-imidazol-2-yl)-3-(tert-butoxycarbonylamino)propanoic acid: 72A (0.26 g, 0.39 mmol) was dissolved in THF (6 mL) and 2N LiOH (2 mL) was added. The mixture was stirred at rt under argon for 20 h. The solvent was removed and the residue was diluted with water and acidified to pH about 5 with 1N HCl. The mixture was extracted with EtOAc. The combined EtOAc solution was washed with brine, dried over Na$_2$SO$_4$ and concentrated to give 72B (0.24 g, 100% yield). MS (ESI) m/z: 575.3 (M+H)$^+$.

72C. {3-Allyl-4-[2-[(S)-2-(allyl-methyl-carbamoyl)-1-tert-butoxycarbonylamino-ethyl]-1-(2-trimethylsilanyl-ethoxymethyl)-1H-imidazol-4-yl]-phenyl}-carbamic acid methyl ester: To a solution of 72B in DMF (4 mL) were added PyBOP (0.26 g, 0.47 mmol), Et$_3$N (0.22 mL, 1.56 mmol), and methylallylamine (0.71 g, 0.998 mmol). The mixture was stirred at rt under argon for 1.5 h. Water was added and the mixture was extracted with EtOAc. The combined EtOAc solution was washed with brine, dried over Na$_2$SO$_4$ and concentrated. The crude product was purified by normal phase chromatography to give 72C (0.16 g, 64% yield). MS (ESI) m/z: 628.4 (M+H)$^+$.

72D. Example 72 was prepared following the procedures described in step 2E/2F, by replacing 2D with 72C; followed by steps 2G; 1F, by replacing ethanol with methanol; and 1G. $^1$H NMR (400 MHz, CD$_3$OD, rotamers) δ ppm 9.52 (s, 1H), 9.30 (s, 1H), 8.00 (dd, J=14.56 and 2.26 Hz, 1H), 7.64-7.77 (m, 1 H), 7.55-7.63 (m, 1 H), 7.46 (dd, J=10.42 and 2.13 Hz, 1 H), 7.36-7.43 (m, 1 H), 7.35 (d, J=1.25 Hz, 1 H), 7.30 (d, J=8.03 Hz, 1H), 7.21 (dd, J=15.69 and 5.14 Hz, 1H), 5.67 (m, 1H), 5.53 (m, 1H), 4.46 (m, 1H), 3.75 (two singlets, 3H), 3.47 (m, 1H), 3.28 (m, 2H), 3.25 (m, 1H), 2.92 (two singlets, 3H), 2.68 (m, 2H), 2.29 (m, 1H), 1.29 (m, 1H). LC-MS (ESI) m/z: 604.3 (M+H)$^+$. Analytical HPLC: RT=6.22/6.49 min (two rotational isomers).

EXAMPLE 79

{(S)-15-[(E)-3-(5-Chloro-2-tetrazol-1-yl-phenyl)-acryloylamino]-13-oxo-8,12,17,19-tetraaza-tricyclo[14.2.1.0$^{2,7}$]nonadeca-1(18),2,4,6,16(19)-pentaen-5-yl}-carbamic acid methyl ester, 2 TFA salt

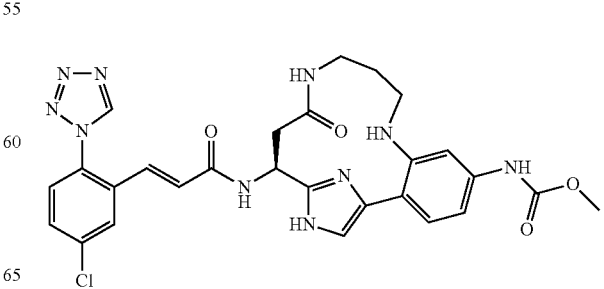

79A. (S)-Benzyl 3-(4-(2-(3-(benzyloxycarbonylamino)propylamino)-4-(methoxycarbonylamino)phenyl)-1-((2-(trimethylsilyl)ethoxy)methyl)-1H-imidazol-2-yl)-3-(tert-butoxycarbonylamino)propanoate: To a solution of 23A (200 mg, 0.284 mmol) in DMSO were added benzyl 3-aminopropylcarbamate, HCl salt (83 mg, 0.341 mmol), L-proline (6.54 mg, 0.057 mmol), CuI (5.41 mg, 0.028 mmol) and K$_2$CO$_3$ (118 mg, 0.853 mmol). The reaction was purged with argon for 3 min. The reaction was stirred at 80° C. for 16 h. The reaction was cooled to rt and then was diluted with EtOAc, washed with H$_2$O, saturated NaHCO$_3$ and brine. The organic phase was dried over MgSO$_4$, filtered and concentrated. The crude product was purified by normal phase chromatography to give 79A (47 mg, 20% yield) as a light tan solid. LC-MS (ESI) m/z: 831.4 (M+H)$^+$.

79B. Example 79 was prepared following the procedures described in step 2G, by replacing 2E with 79A; followed by steps 23E; 1F, by replacing ethanol with methanol; and 1G. $^1$H NMR (400 MHz, CD$_3$OD) δ ppm 9.52 (1 H, s), 7.99 (1 H, d, J=2.26 Hz), 7.83 (1 H, s), 7.64-7.71 (2 H, m), 7.55-7.62 (2 H, m), 7.25 (1 H, dd, J=8.53, 2.01 Hz), 7.21 (1 H, d, J=15.56 Hz), 6.74 (1 H, d, J=15.56 Hz), 5.60 (1 H, dd, J=9.29, 4.27 Hz), 3.77 (3 H, s), 3.61-3.71 (1 H, m), 3.43-3.51 (1 H, m), 3.34-3.40 (2 H, m), 2.85-2.94 (1 H, m), 2.75-2.84 (1 H, m), 2.13-2.27 (2 H, m). LC-MS (ESI) m/z: 591.2 (M+H)$^+$. Analytical HPLC: RT=4.836 min.

EXAMPLE 86

2 TFA salt

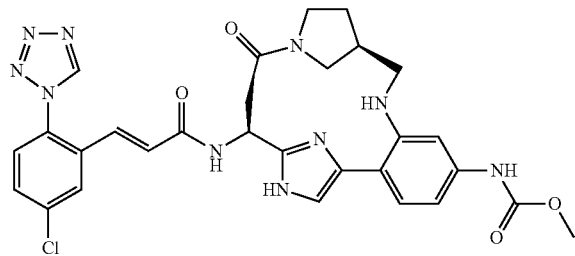 [SMILES: COC(=O)Nc1ccc2c(c1)NC[C@@H]1CCN(C1)C(=O)C[C@H](NC(=O)/C=C/c1cc(Cl)ccc1-n1cnnn1)c1nc-2c[nH]1]

Example 86 was prepared by following the procedures described in step 79A, by replacing benzyl 3-aminopropylcarbamate HCl salt with (S)-benzyl 3-(aminomethyl)pyrrolidine-1-carboxylate; followed by steps 2G; 23E; 1F, by replacing ethanol with methanol; and 1G. $^1$H NMR (conformers, 400 MHz, CD$_3$OD) δ ppm 9.50-9.60 (1 H, m), 7.91-8.15 (1 H, m), 7.47-7.86 (4 H, m), 7.14-7.39 (2 H, m), 6.58-7.02 (2 H, m), 5.50-5.84 (1 H, m), 3.55-4.53 (6 H, m), 3.37-3.53 (2 H, m), 3.10-3.23 (1 H, m), 2.73-2.84 (1 H, m), 2.57-2.72 (1 H, m), 1.64-2.48 (2 H, m), 1.21-1.46 (1 H, m). LC-MS (ESI) m/z: 617.2 (M+H)$^+$. Analytical HPLC: RT=5.481 min.

EXAMPLE 89

{(E)-17-Chloro-15-[(E)-3-(5-chloro-2-tetrazol-1-yl-phenyl)-acryloylamino]-9-oxo-8,18,19-triaza-tricyclo[14.3.1.0$^{2,7}$]icosa-1(20),2,4,6,12,16,18-heptaen-5-yl}-carbamic acid methyl ester

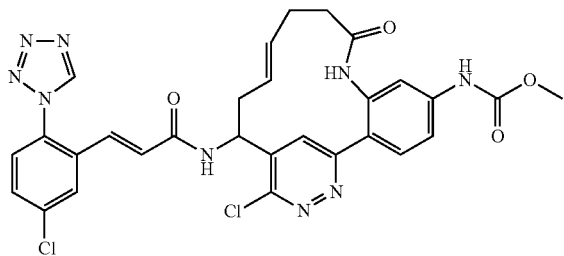 [SMILES: COC(=O)Nc1ccc2c(c1)NC(=O)CC/C=C/CC(NC(=O)/C=C/c1cc(Cl)ccc1-n1cnnn1)c1cc-2nnc1Cl]

89A. tert-Butyl 1-(3,6-dichloropyridazin-4-yl)but-3-enylcarbamate: To a cooled (−78° C.) solution of tert-butyl (3,6-dichloropyridazin-4-yl)methylcarbamate (3.28 g, 11.79 mmol) prepared by following a literature procedure (Cowden, C. J., Org. Lett., 4497-4499 (2003)) in THF (15 mL) was added TMEDA (1.780 mL, 11.79 mmol). Then sec-butyllithium (1.4M in cyclohexane, 21.06 mL, 29.5 mmol) was added dropwise at −78° C. The reaction was warmed to −40° C. over 30 min before it was cooled to −78° C. Allyl bromide (1.496 mL, 17.69 mmol) was added at −78° C. The reaction was stirred under argon at −78° C. for 30 min and then was quenched with NH$_4$Cl solution. The reaction mixture was diluted with EtOAc, washed with 1M HCl, saturated NaHCO$_3$ and brine. The organic phase was dried over MgSO$_4$, filtered and concentrated. The crude product was purified by normal phase chromatography to give 89A (1.49 g, 40% yield) as a solid. LC-MS (ESI) m/z: 318.1 (M+H)$^+$.

89B. tert-Butyl 1-(6-(2-amino-4-nitrophenyl)-3-chloropyridazin-4-yl)but-3-enylcarbamate: A flask containing 89A (1.49 g, 4.68 mmol), 2-(5,5-dimethyl-1,3,2-dioxaborinan-2-yl)-5-nitroaniline (1.756 g, 7.02 mmol) and Cs$_2$CO$_3$ (3.81 g, 11.71 mmol) was purged with argon. To it were added dioxane (40 mL), tri-tert-butylphosphine tetrafluoroborate (0.204 g, 0.702 mmol) and Pd$_2$dba$_3$ (0.429 g, 0.468 mmol) at rt. The reaction was stirred under argon at 90° C. for 3 h. The reaction was cooled to rt. The solid was filtered off and the solvent was removed to give a dark solid. The crude product was purified by normal phase chromatography to give 89B (0.66 g, 34% yield) as a dark brown solid. LC-MS (ESI) m/z: 420.2 (M+H)$^+$.

89C. tert-Butyl 1-(3-chloro-6-(4-nitro-2-pent-4-enamidophenyl)pyridazin-4-yl)but-3-enylcarbamate: To a solution of 89B (0.66 g, 1.572 mmol) in DCM (20 mL) were added TEA (0.438 mL, 3.14 mmol) and pent-4-enoyl chloride (0.208 mL, 1.886 mmol) at 0° C. The reaction was stirred under argon at 0° C. for 1.5 h. The reaction mixture was diluted with DCM, washed with 1M HCl, saturated NaHCO$_3$ and brine. The organic phase was dried over sodium sulfate, filtered and concentrated to give 89C (0.79 g, 100% yield) as a brown solid. LC-MS (ESI) m/z: 502.2 (M+H)$^+$.

89D. tert-Butyl 1-(6-(4-amino-2-pent-4-enamidophenyl)-3-chloropyridazin-4-yl)but-3-enylcarbamate: To a solution of 89C (0.79 g, 1.574 mmol) in methanol (30 mL) were added zinc powder (0.515 g, 7.87 mmol) and ammonium chloride (0.842 g, 15.74 mmol) at 0° C. The reaction was stirred under argon at rt for 4 h. The solid was filtered through a pad of CELITE® and the filtrate was concentrated to give 89D (0.74 g, 100% yield) as a dark brown solid. LC-MS (ESI) m/z: 472.4 (M+H)$^+$.

89E. {4-[5-(1-tert-Butoxycarbonylamino-but-3-enyl)-6-chloro-pyridazin-3-yl]-3-pent-4-enoylamino-phenyl}-carbamic acid methyl ester: To a solution of 89D (0.74 g, 1.568 mmol) in DCM (20 mL) and DMF (2 mL)(to make it more soluble) were added pyridine (0.254 mL, 3.14 mmol) and methyl chloroformate (0.121 mL, 1.568 mmol) at 0° C. The reaction was stirred under argon at 0° C. for 30 min. Water was added to quench the reaction. Most DCM was evaporated. The reaction mixture was diluted with EtOAc, washed with 1M HCl, saturated NaHCO$_3$ and brine. The organic phase was dried over MgSO$_4$, filtered and concentrated. The crude product was purified by normal phase chromatography to give 89E (501 mg, 60% yield) as a brown solid. LC-MS (ESI) m/z: 530.3$^+$.

89F. ((E)-17-Chloro-5-methoxycarbonylamino-9-oxo-8,18,19-triaza-tricyclo[14.3.1.0²,⁷]icosa-1(20),2,4,6,12,16,18-heptaen-15-yl)-carbamic acid tert-butyl ester: To a solution of 89E (350 mg, 0.660 mmol) in DCM (100 mL) was added Grubbs (II) (168 mg, 0.198 mmol) at rt. The solution was purged with argon for 3 min and then was stirred under argon at reflux for 1 h. Solvent was removed. The residue was dissolved in EtOAc, which was washed with water and brine. Organic phase was dried over MgSO$_4$, filtered and concentrated to give a dark solid. The crude product was purified by normal phase chromatography to give 89F (185 mg, 56% yield) as a brown solid. LC-MS (ESI) m/z: 502.3 (M+H)$^+$.

89G. Example 89 was prepared following the procedures described in step 3C, by replacing 3B with 89F; followed by step 1G. $^1$H NMR (400 MHz, MeOD) δ ppm 9.48 (s, 1H), 8.67 (d, J=4.3 Hz, 1H), 8.14 (s, 1H), 8.00 (s, 1H), 7.92 (s, 1H), 7.64 (dd, J=8.5, 1.9 Hz, 1H), 7.55 (d, J=8.6 Hz, 1H), 7.45 (dd, J=14.0, 7.6 Hz, 1H), 7.07 (d, J=15.6 Hz, 1H), 6.59 (d, J=15.8 Hz, 1H), 5.34-5.11 (m, 2H), 4.58-4.36 (m, 1H), 3.76 (s, 3H), 3.10-2.96 (m, 1H), 2.64-2.51 (m, 1H), 2.19 (dd, J=17.9, 11.0 Hz, 3H), 1.30 (t, J=7.3 Hz, 1H). LC-MS (ESI) m/z: 634.3 (M+H)$^+$. Analytical HPLC: RT=7.596 min.

EXAMPLE 94

16-Chloro-14-[(E)-3-(5-chloro-2-tetrazol-1-yl-phenyl)-acryloylamino]-12-oxo-8-oxa-11,17,18-triaza-tricyclo[13.3.1.0²,⁷]nonadeca-1(19),2,4,6,15,17-hexaene-5-carboxylic acid methyl ester

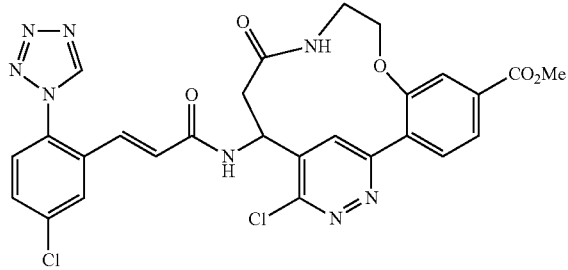 [SMILES: COC(=O)c1ccc2c(c1)OCCNC(=O)CC(NC(=O)/C=C/c1cc(Cl)ccc1-n1cnnn1)c1cc-2nnc1Cl]

94A. 4-[5-(2-Benzyloxycarbonyl-1-tert-butoxycarbonylamino-ethyl)-6-chloro-pyridazin-3-yl]-3-[2-(1,3-dioxo-1,3-dihydro-isoindol-2-yl)-ethoxy]-benzoic acid methyl ester: To a solution of benzyl 3-(tert-butoxycarbonylamino)-3-(3,6-dichloropyridazin-4-yl)propanoate (200 mg, 0.469 mmol) prepared by following a literature procedure (Cowden, C. J., Org. Leu., 4497-4499 (2003)) in dioxane (10 mL) were added Intermediate 13 (308 mg, 0.704 mmol), Cs$_2$CO$_3$ (382 mg, 1.173 mmol) and tri-tert-butylphosphine tetrafluoroborate (13.61 mg, 0.047 mmol). The solution was purged with argon for 2 min and then Pd$_2$dba$_3$ (21.48 mg, 0.023 mmol) was added. The reaction was stirred under argon at 90° C. for 2 h. The solid was filtered-off and the solvent was removed. The crude mixture was purified by normal phase chromatography to give 94A (128 mg, 38% yield) as a yellow solid. LC-MS (ESI) m/z: 715.2 (M+H)$^+$.

94B. 4-[5-(1-tert-Butoxycarbonylamino-2-carboxy-ethyl)-6-chloro-pyridazin-3-yl]-3-[2-(1,3-dioxo-1,3-dihydro-isoindol-2-yl)-ethoxy]-benzoic acid methyl ester: To a solution of 94A (128 mg, 0.179 mmol) in MeOH (5 mL) and ethyl acetate (5 mL) (more soluble in EtOAc) was added catalytic amount of 10% Pd/C. The reaction was stirred under a hydrogen balloon at rt for 3 h. The catalyst was filtered off and the solvent was removed to give 94B (102 mg, 91% yield) as a yellow solid. LC-MS (ESI) m/z: 625.2 (M+H)$^+$.

94C. 3-(2-Amino-ethoxy)-4-[5-(1-tert-butoxycarbonylamino-2-carboxy-ethyl)-6-chloro-pyridazin-3-yl]-benzoic acid methyl ester, TFA salt: To a solution of 94B (102 mg, 0.163 mmol) in EtOH (5 mL) was added hydrazine (0.1 mL, 3.19 mmol) at rt. The reaction was stirred under argon at reflux for 30 min. the solvent was removed. Purification by reverse phase chromatography gave 94C (25 mg, 25.2% yield) as a solid. LC-MS (ESI) m/z: 495.1 (M+H)$^+$.

94D. 14-tert-Butoxycarbonylamino-16-chloro-12-oxo-8-oxa-11,17,18-triaza-tricyclo[13.3.1.0²,⁷]nonadeca-1(19),2,4,6,15,17-hexaene-5-carboxylic acid methyl ester: To a solution of BOP reagent (36.3 mg, 0.082 mmol), DIEA (0.036 mL, 0.205 mmol) and DMAP (5.02 mg, 0.041 mmol) in DCM (30 mL) was added a solution of 94C (25 mg, 0.041 mmol) in DMF (2.0 mL) through a syringe pump over 2 h at rt. Upon addition, the reaction was stirred for another 30 min and the solvent was removed. The crude product was purified by reverse phase chromatography to give 94D (3.0 mg, 15.32% yield) as a tan solid. LC-MS (ESI) m/z: 477.1 (M+H)$^+$.

94E. Example 94 was prepared by following the procedures described in step 3C, by replacing 3B with 94D; followed by step 1G. $^1$H NMR (400 MHz, DMF-d$_7$) δ ppm 9.84 (1 H, s), 8.80 (1 H, d, J=8.03 Hz), 8.33 (1 H, s), 8.19-8.28 (1 H, m), 8.11 (1 H, s), 7.83 (1 H, d, J=8.28 Hz), 7.73-7.80 (4 H, m), 7.00-7.09 (1 H, m), 6.90-6.99 (1 H, m), 5.47-5.63 (1 H, m), 4.24 (2 H, dd, J=5.65, 1.88 Hz), 3.94 (3 H, s), 3.61 (2 H, t, J=5.90 Hz), 3.03-3.14 (2 H, m). LC-MS (ESI) m/z: 609.2 (M+H)$^+$. Analytical HPLC: RT=7.620 min.

EXAMPLE 97

1 TFA salt

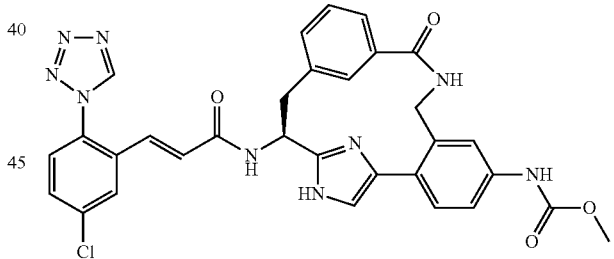

97A. (S)-Methyl 3-(2-(4-(2-bromo-4-(methoxycarbonylamino)phenyl)-1H-imidazol-2-yl)-2-(tert-butoxycarbonylamino)ethyl)benzoate: This compound was prepared following the procedures described in 2A, by replacing (S)-2-(tert-butoxycarbonylamino)pent-4-enoic acid with (S)-2-(tert-butoxycarbonylamino)-3-(3-(methoxycarbonyl)phenyl)propanoic acid and by replacing 2-bromo-1-(2-bromophenyl)ethanone with Intermediate 8; and 2B. MS (ESI) m/z: 573.0 (M+H)$^+$.

97B. (S)-Methyl 3-(2-(tert-butoxycarbonylamino)-2-(4-(2-cyano-4-(methoxycarbonylamino)phenyl)-1H-imidazol-2-yl)ethyl)benzoate: To a 20 mL microwave vial was added 97A (500 mg, 0.872 mmol), dicyanozinc (205 mg, 1.744 mmol), and DMF (7 mL). The mixture (suspension) was degassed for 5 min, and tetrakis(triphenylphosphine)palladium(0) (101 mg, 0.087 mmol) was added. The reaction mixture was heated in a microwave oven at 140° C. for 7 min.

The reaction was diluted with EtOAc (50 mL) and then washed with 2M of ammonium hydroxide, water, and brine. It was dried over Na$_2$SO$_4$, and concentrated. The residue was purified by normal phase chromatography to give a pale yellow solid (297 mg, 65.6% yield). MS (ESI) m/z: 520.0 (M+H)$^+$.

97C. (S)-3-(2-(tert-Butoxycarbonylamino)-2-(4-(2-cyano-4-(methoxycarbonylamino)phenyl)-1H-imidazol-2-yl)ethyl)benzoic acid: A solution of lithium hydroxide (21.76 mg, 0.908 mmol) in 1 mL of water was added to a solution of 97B (118 mg, 0.227 mmol) in THF (2.5 mL) at rt. The colorless solution changed to light cloudy solution upon the base addition. After 2 h, more LiOH (21.76 mg, 0.908 mmol in 1 mL of H$_2$O) was added. The mixture was stirred for another 5 h. The THF was removed and the residue was diluted with EtOAc (20 mL). 1N HCl (1.476 ml, 1.476 mmol) was added to the mixture with vigorous stirring. The organic layers were separated and the aqueous layer was extracted with EtOAc. The combined organic extracts were washed with brine, dried Na$_2$SO$_4$, concentrated, and dried in vacuo to give a pale yellow solid (116 mg, 100%). MS (ESI) m/z: 506.1 (M+H)$^+$.

97D. (S)-3-(2-(4-(2-(Aminomethyl)-4-(methoxycarbonylamino)phenyl)-1H-imidazol-2-yl)-2-(tert-butoxycarbonylamino)ethyl)benzoic acid: 97C (115 mg, 0.227 mmol) was dissolved in water and NH4OH (2:1; 12 mL). To it was added catalytic amount of Raney Ni. The mixture was placed on a hydrogenation apparatus under 55 psi for 48 h. The catalyst was removed by filtration. The filtrate was concentrated to give a white solid (116 mg, 100% yield). MS (ESI) m/z: 510.1 (M+H)$^+$.

97E. To a solution of BOP (0.195 g, 0.440 mmol) and DMAP (0.108 g, 0.880 mmol) in DCM (30 mL) and DMF (3.00 mL) at rt was added a solution of 97D (0.112 g, 0.22 mmol) and DIPEA (0.115 mL, 0.660 mmol) in DMF (7 mL) via a syringe pump over 7.5 h. To the mixture was added 0.5N HCl (30 mL), and the mixture was stirred for 10 min. The two layers were separated and the aqueous layer was extracted with DCM. The combined organic layers were washed with brine, dried over Na$_2$SO$_4$, and concentrated. It was purified by reverse phase HPLC to give the desired product (0.120 g, 90% yield) as a white solid. MS (ESI) m/z: 492.0 (M+H)$^+$.

97F. Example 97 was prepared following the procedures described in step 3C, by replacing 3B with 97E; followed by step 1G. $^1$H NMR (400 Hz, MeOH-d$_4$) δ ppm 9.58-9.50 (2 H, m), 8.00 (1 H, d, J=2.01 Hz), 7.69 (2 H, dd, J=8.53, 2.26 Hz), 7.52-7.64 (5 H, m), 7.46-7.34 (3 H, m), 7.15 (1 H, d, J=15.56 Hz), 6.81 (1H, d, J=15.56 Hz), 5.85 (1 H, s), 4.93 (1 H, m), 4.14-4.02 (2 H, m), 3.76 (3 H, s), 3.48-3.57 (1 H, m), 3.35 (1 H, td, J=3.14, 1.25 Hz). MS (ESI) m/z: 624.0 (M+H)$^+$. Analytical HPLC: RT=4.85 min.

EXAMPLE 98

1 TFA Salt

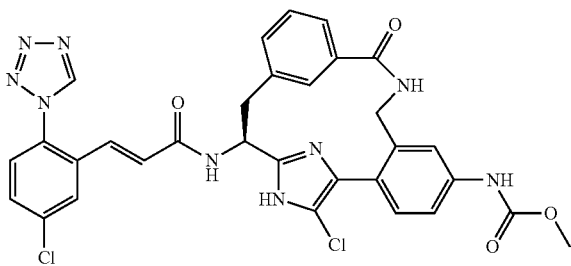 [SMILES: COC(=O)Nc1ccc2c(c1)CNC(=O)c1cccc(c1)C[C@H](NC(=O)/C=C/c1cc(Cl)ccc1-n1cnnn1)c1nc-2c(Cl)[nH]1]

98A. To a solution 97E (15 mg, 0.025 mmol) in acetonitrile (1.5 mL) was added NCS (3.97 mg, 0.030 mmol). The reaction mixture was cooled to 0-10° C., and TEA (5.18 µL, 0.037 mmol) was added. The color of the reaction changed from colorless to light brown-yellow solution upon the base addition. The reaction was completed in 10 min. The mixture was concentrated, and purified through normal phase chromatography to give the 98A (5.5 mg, 42.2% yield) as a colorless oil. MS (ESI) m/z: 526.2 (M+H)$^+$.

98B. Example 98 was prepared following the procedures described in step 3C, by replacing 3B with 98A; followed by step 1G. $^1$H NMR (400 MHz, MeOH-d$_4$)) δ ppm 9.53 (1 H, s), 9.45 (1 H, s), 8.02 (1 H, s), 7.67 (1 H, dd, J=8.53, 2.26 Hz), 7.58 (3 H, d, J=8.53 Hz), 7.41-7.51 (3 H, m), 7.31 (2 H, s), 7.14 (1 H, d, J=15.56 Hz), 6.83 (1 H, d, J=15.81 Hz), 5.82 (1 H, s), 4.85-4.89 (1 H, m), 3.93-4.03 (2 H, m), 3.75 (3 H, s), 3.15-3.27 (2H, m). MS (ESI) m/z: 658.1 (M+H)$^+$. Analytical HPLC: RT=6.97 min.

EXAMPLE 99

1 TFA Salt

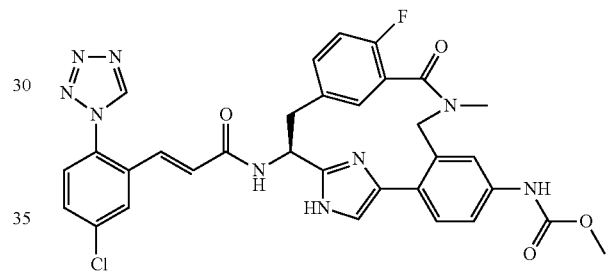

99A. Methyl 2-fluoro-5-formylbenzoate: To a solution of 2-fluoro-5-formylbenzoic acid (1.0 g, 5.65 mmol) in toluene (27 mL) and MeOH (9.14 mL, 226 mmol) was added (diazomethyl)trimethylsilane (4.24 mL, 8.48 mmol) dropwise at rt. The reaction mixture was stirred under argon at rt for 50 min. The solvent was removed to give a white solid (1.05 g, 100% yield). MS (ESI) m/z: 183.1 (M+H)$^+$.

99B. (E)-Methyl 5-(2-(tert-butoxycarbonylamino)-3-methoxy-3-oxoprop-1-enyl)-2-fluorobenzoate: To a mixture of 99A (1.05 g, 6.04 mmol) and methyl 2-(tert-butoxycarbonylamino)-2-(dimethoxyphosphoryl)acetate (1.984 g, 6.34 mmol) was added DCM (30.2 mL). It was cooled to 0° C., and DBU (1.183 mL, 7.85 mmol) was added. The mixture was warmed up to rt, and stirred for 12 h. The reaction mixture was diluted with DCM, and quenched with aq. NH$_4$Cl. The organic layer was washed with water and brine, dried over Na$_2$SO$_4$, concentrated, and dried in vacuo to give the desired product (2.3 g, 97% yield) as a yellow oil. MS (ESI) m/z: 254.2 (M-Boc+H)$^+$.

99C. (S)-Methyl 5-(2-(tert-butoxycarbonylamino)-3-methoxy-3-oxopropyl)-2-fluorobenzoate: 99B (2.3 g, 6.04 mmol) was dissolved in MeOH (30.2 mL) and (+)-1,2-bis((2S,5S)-2,5-diethyphospholano)benzene(cyclooctadien) rhodium (I) trifluoromethanesulfonate (0.153 g, 0.211 mmol) was added. The reaction mixture was placed on a hydrogenation apparatus under 50 psi for 48 h. The solvent was removed to give a light-brown oil which was used directly in the next step (2.4 g, 100% yield). MS (ESI) m/z: 256.1 (M-Boc+H)$^+$.

99D. (S)-2-(tert-Butoxycarbonylamino)-3-(4-fluoro-3-(methoxycarbonyl)phenyl)propanoic acid: A mixture of 99C (1.5 g, 3.80 mmol), MeOH (7 mL), potassium carbonate (0.788 g, 5.70 mmol), and water (7.00 mL) was heated to reflux for 3.5 h. The reaction was diluted with water (50 mL) and extracted with DCM. The aqueous layer was acidified with concentrated HCl to pH 2, and extracted with EtOAc. Combined extract was washed with brine, dried over $Na_2SO_4$, concentrated, and dried in vacuo to give 99D (910 mg, 59.7% yield) as a yellow solid. MS (ESI) m/z: 242.1 (M-Boc+H)$^+$.

99E. Example 99 was prepared following the procedures described in step 2A, by replacing (S)-2-(tert-butoxycarbonylamino)pent-4-enoic acid with 99D and by replacing 2-bromo-1-(2-bromophenyl)ethanone with Intermediate 14; followed by steps 2B; 2G; 97E; 3C; and 1G. $^1$H NMR (400 MHz, MeOH-d$_4$)) δ ppm 9.52 (s, 1 H) 8.01 (d, J=2.01 Hz, 1 H) 7.67-7.74 (m, 3 H) 7.53-7.63 (m, 4 H) 7.30 (t, J=8.91 Hz, 2 H) 7.16 (d, J=15.56 Hz, 1 H) 6.78 (d, J=15.56 Hz, 1 H) 5.80 (m, 1 H) 4.51 (d, J=14.05 Hz, 1 H) 4.09 (d, J=14.05 Hz, 1 H) 3.74 (s, 3 H) 3.35 (dt, J=3.26, 1.63 Hz, 1 H) 3.16-3.26 (m, 1 H) 2.76 (s, 3 H). MS (ESI) m/z: 656.1 (M+H)$^+$. Analytical HPLC: RT=5.53 min.

EXAMPLE 100

1 TFA Salt

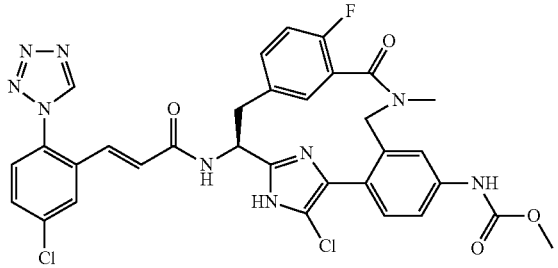 [SMILES: COC(=O)Nc1ccc2c(c1)CN(C)C(=O)c1cc(ccc1F)C[C@H](NC(=O)/C=C/c1cc(Cl)ccc1-n1cnnn1)c1nc-2c(Cl)[nH]1]

Example 100 was prepared following the procedures described in 98A, by replacing TEA with DIPEA, and by replacing 97E with Example 99. $^1$H NMR (400 MHz, MeOH-d$_4$)) δ ppm 9.50-9.56 (m, 1 H) 8.02 (d, J=2.01 Hz, 1 H) 7.64-7.70 (m, 3 H) 7.58 (d, J=8.53 Hz, 1 H) 7.45-7.52 (m, 2 H) 7.17-7.27 (m, 2 H) 7.13 (d, J=15.56 Hz, 1 H) 6.81 (d, J=15.56 Hz, 1 H) 5.87 (dd, J=6.27, 1.76 Hz, 1 H) 4.67 (dd, J=12.05, 4.52 Hz, 1 H) 4.53 (d, J=13.80 Hz, 1 H) 3.97 (d, J=13.80 Hz, 1 H) 3.76 (s, 3 H) 3.33-3.38 (m, 1 H) 3.13 (t, J=12.05 Hz, 1 H) 2.77 (s, 3 H). MS (ESI) m/z: 690.0 (M+H)$^+$. Analytical HPLC: RT=7.76 min.

EXAMPLE 101

1 TFA Salt

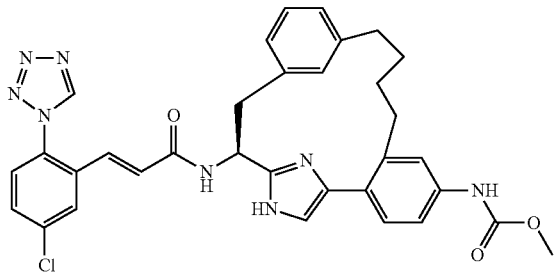 [SMILES: COC(=O)Nc1ccc2c(c1)CCCCc1cccc(c1)C[C@H](NC(=O)/C=C/c1cc(Cl)ccc1-n1cnnn1)c1nc-2c[nH]1]

101A. {3-Bromo-4-[2-[(S)-2-(3-bromo-phenyl)-1-tert-butoxycarbonylamino-ethyl]-1-(2-trimethylsilanyl-ethoxymethyl)-1H-imidazol-4-yl]-phenyl}-carbamic acid methyl ester: This compound was prepared following the procedures described in step 2A, by replacing (S)-2-(tert-butoxycarbonylamino)pent-4-enoic acid with (S)-3-(3-bromo-phenyl)-2-tert-butoxycarbonylamino-propionic acid and by replacing 2-bromo-1-(2-bromophenyl)ethanone with Intermediate 8; followed by steps 2B; and 1C. MS (ESI) m/z: 725.0 (M+H)$^+$.

101B. {3-Allyl-4-[2-[(S)-2-(3-allyl-phenyl)-1-tert-butoxycarbonylamino-ethyl]-1-(2-trimethylsilanyl-ethoxymethyl)-1H-imidazol-4-yl]-phenyl}-carbamic acid methyl ester: To a 5 mL microwave vial was placed 101A (110 mg, 0.152 mmol), 2-alkyl-4,4,5,5-tetramethyl-1,3,2-dioxaborolane (255 mg, 1.518 mmol), THF (1.5 mL), potassium carbonate (420 mg, 3.04 mmol), water (1.2 ml), and PdCl$_2$(dppf)-CH$_2$Cl$_2$Adduct (24.80 mg, 0.030 mmol). The vial was purged with argon for several minutes and sealed. The resulted mixture was heated in a microwave oven at 120° C. for 12 min. The mixture was concentrated and purified by reverse phase chromatography to give 101B (30 mg, 30.5% yield) as a brown oil. MS (ESI) m/z: 647.3 (M+H)$^+$.

101C. Example 101 was prepared following the procedures described in step 2E/2F, by replacing 2D with 101B; followed by steps 2G; 1F, by replacing ethanol with methanol as the solvent; and 1G. $^1$H NMR (400 MHz, CD$_3$OD) δ ppm 9.53 (1 H, s), 8.01 (1 H, d, J=2.26 Hz), 7.70 (1 H, dd, J=8.53, 2.26 Hz), 7.59-7.62 (1 H, m), 7.41 (1 H, s), 7.39 (1 H, s), 7.35 (1H, dd, J=8.28, 2.26 Hz), 7.24-7.31 (2 H, m), 7.18 (1 H, d, J=10.29 Hz), 7.15 (1 H, d, J=3.01 Hz), 7.08 (1 H, d, J=7.53 Hz), 6.79 (1 H, d, J=15.81 Hz), 6.46 (1 H, s), 5.10 (1 H, dd, J=11.80, 4.77 Hz), 3.73 (3 H, s), 3.52 (1 H, dd, J=12.67, 4.89 Hz), 3.10-3.17 (1 H, m), 2.51-2.63 (3 H, m), 2.36 (1 H, s), 1.73 (2 H, s), 1.22 (1 H, s), 0.96 (1H, s). MS (ESI) m/z: 623.2 (M+H)$^+$. Analytical HPLC: RT=6.99 min.

EXAMPLE 102

1 TFA Salt

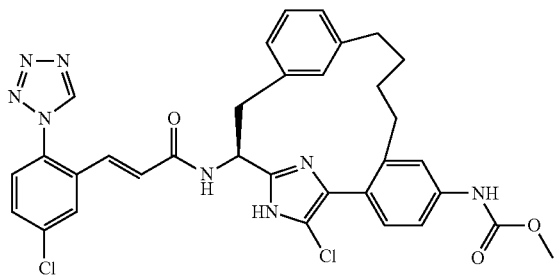 [SMILES: COC(=O)Nc1ccc2c(c1)CCCCc1cccc(c1)C[C@H](NC(=O)/C=C/c1cc(Cl)ccc1-n1cnnn1)c1nc-2c(Cl)[nH]1]

Example 102 was prepared following the procedures described in 98A, by replacing TEA with DIPEA, and by replacing 97E with Example 101. $^1$H NMR (400 MHz, MeOH-d$_4$)) δ ppm 9.54 (1 H, s), 8.02 (1 H, d, J=2.26 Hz), 7.65-7.70 (1 H, m), 7.57-7.61 (1 H, m), 7.35 (1 H, d, J=1.51 Hz), 7.29 (1 H, dd, J=8.16, 2.13 Hz), 7.23 (1 H, t, J=7.53 Hz), 7.18 (1 H, d, J=4.52 Hz), 7.14-7.16 (1 H, m), 7.06 (1 H, d, J=8.28 Hz), 7.02 (1 H, d, J=7.53 Hz), 6.81 (1 H, d, J=15.56 Hz), 6.39 (1 H, s), 4.92-4.98 (1 H, m), 3.73 (3 H, s), 3.25-3.28 (1 H, m), 3.08-3.15 (1 H, m), 2.54-2.65 (2 H, m), 2.51 (1 H, m), 2.30 (1 H, m), 1.76 (2 H, m), 1.20 (1 H, m), 0.96 (1 H, m). MS (ESI) m/z: 657.1 (M+H)$^+$. Analytical HPLC: RT=9.39 min.

EXAMPLE 103

1 TFA Salt

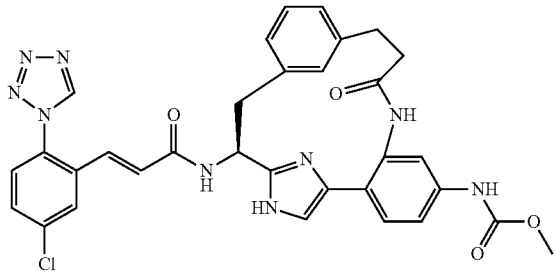 [SMILES: COC(=O)Nc1ccc2c(c1)NC(=O)CCc1cccc(c1)C[C@H](NC(=O)/C=C/c1cc(Cl)ccc1-n1cnnn1)c1nc-2c[nH]1]

103A. (4-{2-[(S)-2-(3-Bromo-phenyl)-1-tert-butoxycarbonylamino-ethyl]-1H-imidazol-4-yl}-3-nitro-phenyl)-carbamic acid methyl ester: This compound was prepared following the procedures described in step 2A, by replacing (S)-2-(tert-butoxycarbonylamino)pent-4-enoic acid with (S)-3-(3-bromo-phenyl)-2-tert-butoxycarbonylamino-propionic acid and by replacing 2-bromo-1-(2-bromophenyl)ethanone with Intermediate 9; followed by step 2B. MS (ESI) m/z: 560.0 (M+H)$^+$.

103B. (S,E)-Methyl 3-(3-(2-(tert-butoxycarbonylamino)-2-(4-(4-(methoxycarbonylamino)-2-nitrophenyl)-1H-imidazol-2-yl)ethyl)phenyl)acrylate: A mixture of 103A (180 mg, 0.321 mmol), methyl acrylate (0.087 mL, 0.964 mmol), tri-o-tolylphosphine (39.1 mg, 0.128 mmol), diacetoxypalladium (21.63 mg, 0.096 mmol), and DIEA (0.196 mL, 1.124 mmol) in Acetonitrile (0.5 mL) was degassed and purged with argon. It was placed in a microwave oven at 150° C. for 9 min. The catalyst was filtered-off and rinsed with EtOAc. The filtrate was concentrated and purified by normal phase chromatography to give 103B as an orange oil (130 mg, 71.6% yield). MS (ESI) m/z: 566.1 (M+H)$^+$.

103C. Example 103 was prepared following the procedures described in step 2G, by replacing 2E with 103B, by replacing methanol with THF, and by replacing the hydrogen balloon with hydrogen (55 psi); followed by steps 97C; 97E by using the syringe pump addition over 4 h; 3C; and 1G. $^1$H NMR (400 MHz, CD$_3$OD) δ ppm 9.52 (s, 1 H) 7.99 (d, J=2.26 Hz, 1 H) 7.66-7.71 (m, 1 H) 7.58-7.61 (m, 1 H) 7.56 (d, J=1.76 Hz, 1 H) 7.29-7.36 (m, 3 H) 7.23-7.27 (m, 2 H) 7.12-7.18 (m, 2 H) 6.76 (d, J=15.56 Hz, 1 H) 6.53 (s, 1 H) 5.08 (dd, J=11.54, 4.52 Hz, 1H) 3.74 (s, 3 H) 3.43-3.49 (m, 1 H) 3.07-3.15 (m, 1 H) 2.88-2.94 (m, 1 H) 2.82-2.87 (m, 1 H) 2.70-2.82 (m, 1 H) 2.47-2.55 (m, 1 H). MS (ESI) m/z: 638.2 (M+H)$^+$. Analytical HPLC: RT=5.59 min.

EXAMPLE 104

1 TFA salt

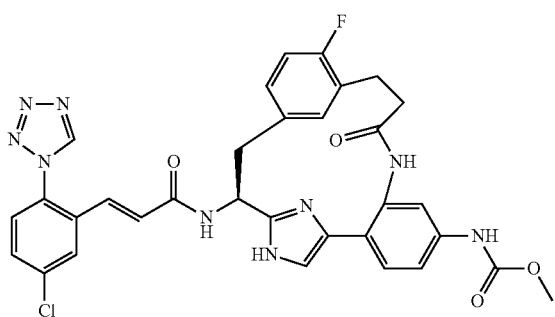 [SMILES: COC(=O)Nc1ccc2c(c1)NC(=O)CCc1cc(ccc1F)C[C@H](NC(=O)/C=C/c1cc(Cl)ccc1-n1cnnn1)c1nc-2c[nH]1]

Example 104 was prepared following the procedures described in step 2A, by replacing (S)-2-(tert-butoxycarbonylamino)pent-4-enoic acid with (S)-3-(3-bromo-4-fluorophenyl)-2-tert-butoxycarbonylamino-propionic acid and by replacing 2-bromo-1-(2-bromophenyl)ethanone with Intermediate 9; followed by steps 2B; 103B; 2G, by replacing methanol with THF, and by replacing the hydrogen balloon with hydrogen (55 psi); 97C; 97E by using the syringe pump addition over 4 h; 3C; and 1G. $^1$H NMR (400 MHz, CD$_3$OD) δ ppm 9.51 (s, 1 H) 7.99 (d, J=2.26 Hz, 1 H) 7.69 (dd, J=8.53, 2.26 Hz, 1 H) 7.58-7.62 (m, 1 H) 7.54 (d, J=1.76 Hz, 1 H) 7.33-7.38 (m, 1 H) 7.23-7.32 (m, 3 H) 7.07-7.17 (m, 2 H) 6.75 (d, J=15.56 Hz, 1 H) 6.56 (dd, J=7.03, 2.26 Hz, 1 H) 5.06 (dd, J=11.67, 4.89 Hz, 1 H) 3.75 (s, 3 H) 3.42-3.49 (m, 1 H) 2.90-3.25 (m, 2 H) 2.71-2.82 (ddd, J=15.50, 7.72, 2.38 Hz, 2 H) 2.54 (ddd, J=15.37, 10.85, 2.38 Hz, 1 H). MS (ESI) m/z: 656.3 (M+H)$^+$. Analytical HPLC: RT=5.69 min.

EXAMPLE 105

2 TFA Salt

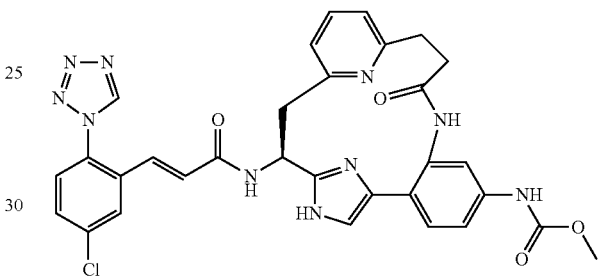

Example 105 was prepared following the procedures described in step 2A, by replacing (S)-2-(tert-butoxycarbonylamino)pent-4-enoic acid with (S)-3-(6-bromo-pyridin-2-yl)-2-tert-butoxycarbonylamino-propionic acid and by replacing 2-bromo-1-(2-bromophenyl)ethanone with Intermediate 9; followed by steps 2B; 103B; 2G, by replacing methanol with THF, and by replacing the hydrogen balloon with hydrogen (55 psi); 97C; 97E by using the syringe pump addition over 4 h; 3C; and 1G. $^1$H NMR (400 MHz, CD$_3$OD) δ ppm 9.42 (s, 1 H) 7.87 (d, J=2.26 Hz, 1 H) 7.48-7.59 (m, 4 H) 7.20-7.27 (m, 2 H) 7.10-7.17 (m, 2 H) 7.04-7.07 (m, 1 H) 6.62 (d, J=15.56 Hz, 1 H) 5.46 (dd, J=10.79, 4.77 Hz, 1 H) 3.65 (s, 3 H) 3.50-3.59 (m, 1 H) 3.36-3.44 (m, 1 H) 3.02-3.09 (m, 1 H) 2.98 (dd, J=8.03, 2.51 Hz, 1 H) 2.83-2.93 (m, 1 H) 2.66-2.75 (m, 1 H). MS (ESI) m/z: 639.2 (M+H)$^+$. Analytical HPLC: RT=4.75 min.

EXAMPLE 106

2 TFA Salt

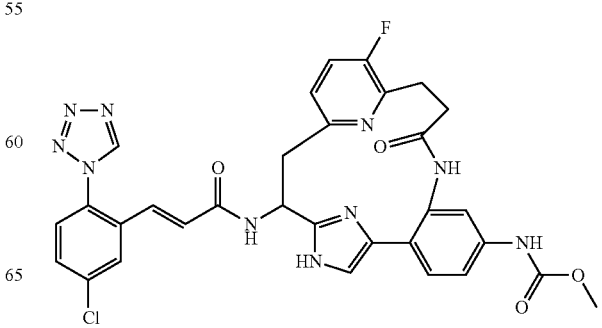

106A. Diethyl 2-acetamido-2-((6-bromo-5-fluoropyridin-2-yl)methyl)malonate: 2-Bromo-3-fluoro-6-methylpyridine (2.24 g, 11.79 mmol), NBS (2.34 g, 13.15 mmol), CCl$_4$ (40 mL), and AIBN (0.10 g, 0.609 mmol) were added together and heated to reflux under argon for 4.5 h. The CCl$_4$ was removed. The residue was dissolved in EtOAc and washed with water and brine. It was dried over Na$_2$SO$_4$, and concentrated to give 2-bromo-6-(bromomethyl)-3-fluoropyridine which was used in the next step without purification. MS (ESI) m/z: 269.9 (M+H)$^+$. NaH (0.707 g of 60% dispersion, 17.69 mmol) was placed in a three-neck flask with 15 mL of DMF. It was cooled in an ice-bath. A solution of diethyl 2-acetamidomalonate (3.59 g, 11.79 mmol) in 15 mL of DMF was added dropwise via an additional funnel White foam formed and the mixture was stirred in the ice-bath for 20 minutes after the addition. A solution of 2-bromo-6-(bromomethyl)-3-fluoropyridine in 10 mL of DMF was added through an additional funnel dropwise. The ice-bath was removed and it was stirred at rt under argon for 2 h. It was quenched with water and extracted with EtOAc. The EtOAc solution was washed with water and brine, dried over Na$_2$SO$_4$, and concentrated. It was purified by normal phase chromatography to give 106A as an off-white solid (2.39 g, 50%). MS (ESI) m/z: 405.0 (M+H)$^+$.

106B. 2-Amino-3-(6-bromo-5-fluoropyridin-2-yl)propanoic acid: 106A (2.36 g, 5.82 mmol) was suspended in 20 mL of water and 20 ml of 48% aqueous HBr was added. The mixture was heat to reflux under argon for 7 h. The solvent was removed to give 106B as an off-white solid (1.80 g, 100% yield). This material was used in the next step without further purification. MS (ESI) m/z: 263.0 (M+H)$^+$.

106C. 3-(6-Bromo-5-fluoropyridin-2-yl)-2-(tert-butoxycarbonylamino)
propanoic acid: 106B (1.53 g, 5.82 mmol) was added with 30 mL of dioxane. Aqueous 1N NaOH (30 mL) was added to form a light yellow solution. To it was added di-tert-butyl dicarbonate (2.3 g, 10.54 mmol). The mixture was stirred at rt under argon. After 30 minutes, the mixture became thick and it was hard to stir. More dioxane (20 mL) was added and the mixture was stirred for 2.5 h. The dioxane was removed. The pH of the aqueous solution was adjusted to about 4 with 1N HCl. It was then extracted with EtOAc. The EtOAc extract was washed with brine, dried over Na$_2$SO$_4$, and concentrated to give 106C as an off-white solid (1.86 g, 86%). MS (ESI) m/z: 263.0 (M+H-Boc)$^+$.

106D. tert-Butyl N-{19-fluoro-11-[(methoxycarbonyl)amino]-15-oxo-5,14,22,23-tetraazatetracyclo[16.3.1.1$^{4,7}$.0$^{8,13}$]tricosa-1(22),4(23),6,8,10,12,18,20-octaen-3-yl}carbamate: This compound was prepared following the procedures described in step 2A, by replacing (S)-2-(tert-butoxycarbonylamino)pent-4-enoic acid with 106C and by replacing 2-bromo-1-(2-bromophenyl)ethanone with Intermediate 9; followed by the steps 2B; 103B; 2G, by replacing methanol with THF and by replacing the hydrogen balloon with hydrogen (55 psi); 97C; and 97E, by using the syringe pump addition over 4 h. MS (ESI) m/z: 525.2 (M+H)$^+$.

106E. Methyl N-{3-amino-19-fluoro-15-oxo-5,14,22,23-tetraazatetracyclo[16.3.1.1$^{4,7}$.0$^{8,13}$]tricosa-1(22),4(23),6,8,10,12,18,20-octaen-11-yl}carbamate: This compound was prepared following the procedure described in 3C, by replacing 3B with 106D. MS (ESI) m/z: 425.2 (M+H)$^+$.

106F. Example 106: This compound was prepared following the procedure described in 1G by replacing 1F with 106E. $^1$H NMR (400 MHz, CD$_3$OD) δ ppm 9.43 (s, 1 H) 9.41 (s, 1 H) 7.86 (d, J=2.26 Hz, 1 H) 7.58 (dd, J=8.53, 2.26 Hz, 1 H) 7.47-7.52 (m, 2 H) 7.31-7.37 (m, 1 H) 7.18-7.27 (m, 3 H) 7.14 (s, 1 H) 7.08 (d, J=15.81 Hz, 1 H) 6.60 (d, J=15.56 Hz, 1 H) 5.44 (dd, J=11.04, 4.77 Hz, 1 H) 3.66 (s, 3 H) 3.51-3.58 (m, 1 H) 3.37-3.45 (m, 1 H) 3.02-3.13 (m, 1 H) 2.86-2.96 (m, 2 H) 2.71-2.80 (m, 1 H). MS (ESI) m/z: 657.2 (M+H)$^+$. Analytical HPLC: RT=5.52 min.

EXAMPLE 107

Enantiomer A, 2 TFA Salt

EXAMPLE 108

Enantiomer B, 2 TFA Salt

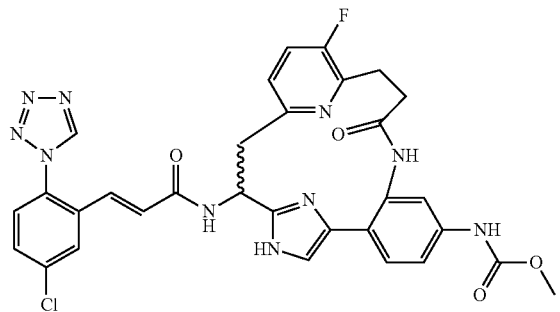 [SMILES: COC(=O)Nc1ccc2c(c1)NC(=O)CCc1nc(ccc1F)CC(NC(=O)/C=C/c1cc(Cl)ccc1-n1cnnn1)c1nc-2c[nH]1]

Example 106 was separated by Chiral HPLC(CHIRALCEL® OD-H ODH, Isocratic, 70% B over 20 min. A=Heptane with 0.1% DEA, B=MeOH/EtOH (50:50) with 0.1% DEA) to give Example 107 and Example 108. Example 107: $^1$H NMR (400 MHz, acetonitrile-d$_3$) δ ppm 9.03 (s, 1 H) 8.83 (d, J=8.03 Hz, 1 H) 7.78-7.81 (m, 2 H) 7.49-7.55 (m, 2 H) 7.42 (d, J=8.53 Hz, 1 H) 7.18-7.26 (m, 3 H) 7.00-7.06 (m, 2 H) 6.97 (d, J=15.56 Hz, 1 H) 6.58 (d, J=15.56 Hz, 1 H) 5.74 (td, J=8.85, 5.65 Hz, 1 H) 3.62 (s, 3 H) 3.37-3.47 (m, 2 H) 2.92-3.04 (m, 2 H) 2.82-2.92 (m, 1 H) 2.77 (td, J=7.72, 3.39 Hz, 1 H). MS (ESI) m/z: 657.2 (M+H)$^+$. Analytical HPLC: RT=5.35 min. Example 108: $^1$H NMR (400 MHz, acetonitrile-d$_3$) δ ppm 9.03 (s, 1 H) 8.78 (d, J=8.03 Hz, 1 H) 7.76-7.84 (m, 2 H) 7.49-7.55 (m, 2 H) 7.42 (d, J=8.53 Hz, 1 H) 7.18-7.26 (m, 3 H) 7.00-7.06 (m, 2 H) 6.97 (d, J=15.56 Hz, 1 H) 6.58 (d, J=15.56 Hz, 1 H) 5.74 (td, J=8.85, 5.65 Hz, 1 H) 3.61 (s, 3 H) 3.37-3.47 (m, 2 H) 2.92-3.04 (m, 2 H) 2.82-2.92 (m, 1 H) 2.76 (td, J=7.72, 3.39 Hz, 1H). MS (ESI) m/z: 657.2 (M+H)$^+$. Analytical HPLC: RT=5.46 min.

EXAMPLE 109

1 TFA Salt

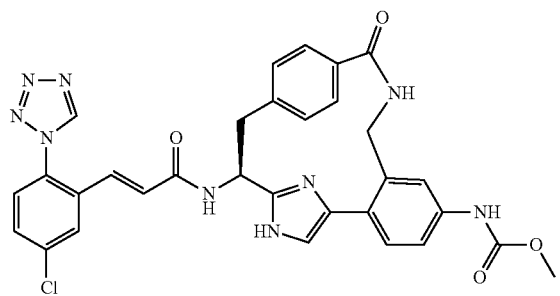 [SMILES: COC(=O)Nc1ccc2c(c1)CNC(=O)c1ccc(cc1)C[C@H](NC(=O)/C=C/c1cc(Cl)ccc1-n1cnnn1)c1nc-2c[nH]1]

Example 109 was prepared following the procedures described in step 2A, by replacing (S)-2-(tert-butoxycarbonylamino)pent-4-enoic acid with 4-((S)-2-tert-Butoxycarbonylamino-2-carboxy-ethyl)-benzoic acid methyl ester and by replacing 2-bromo-1-(2-bromophenyl)ethanone with Intermediate 8; followed by steps 2B; 97B-E; 3C; and 1G. $^1$H NMR (400 MHz, CD$_3$OD) δ ppm 9.54 (1 H, s), 8.02 (1 H, d, J=2.26 Hz), 7.90 (2 H, d, J=8.28 Hz), 7.71 (1 H, dd, J=8.53, 2.26 Hz), 7.59-7.63 (1 H, m), 7.43 (2 H, s), 7.31-7.37 (3 H, m), 7.16-7.25 (2 H, m), 6.81 (1 H, d, J=15.56 Hz), 5.35 (1 H, dd, J=12.05, 5.27 Hz), 3.68-3.78 (2 H, m), 3.64 (3 H, s), 3.35 (1 H, ddd, J=3.58, 2.26, 1.94 Hz), 3.23-3.27 (1 H, m). MS (ESI) m/z: 624.3 (M+H)$^+$. Analytical HPLC: RT=5.92 min.

EXAMPLE 110

1 TFA Salt

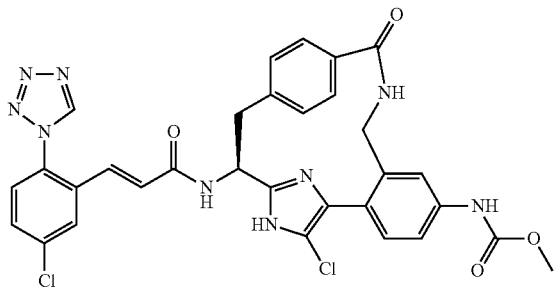 [SMILES: COC(=O)Nc1ccc2c(c1)CNC(=O)c1ccc(cc1)C[C@H](NC(=O)/C=C/c1cc(Cl)ccc1-n1cnnn1)c1nc-2c(Cl)[nH]1]

Example 110 was prepared following the procedures described in 98A, by replacing TEA with DIPEA, and by replacing 97E with Example 109. $^1$H NMR (400 MHz, CD$_3$OD) δ ppm 9.54 (1 H, s), 8.03 (1 H, d, J=2.01 Hz), 7.84 (2 H, d, J=8.28 Hz), 7.65-7.71 (1 H, m), 7.57-7.61 (1 H, m), 7.27-7.38 (4 H, m), 7.15-7.21 (2 H, m), 6.84 (1H, d, J=15.56 Hz), 5.19 (1 H, dd, J=11.80, 5.02 Hz), 3.63 (3 H, s), 3.45-3.51 (2 H, m), 3.17-3.27 (2 H, m). MS (ESI) m/z: 659.1 (M+H)$^+$. Analytical HPLC: RT=8.58 min.

EXAMPLE 111

1 TFA Salt

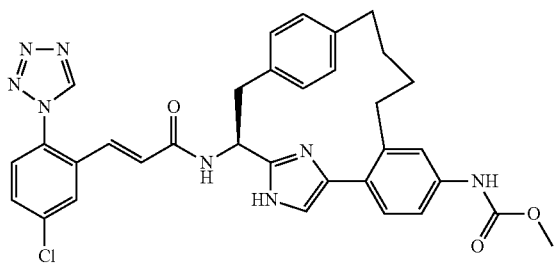 [SMILES: COC(=O)Nc1ccc2c(c1)CCCCc1ccc(cc1)C[C@H](NC(=O)/C=C/c1cc(Cl)ccc1-n1cnnn1)c1nc-2c[nH]1]

Example 111 was prepared following the procedures described in Example 101, by replacing (S)-3-(3-bromo-phenyl)-2-tert-butoxycarbonylamino-propionic acid with (S)-3-(4-bromo-phenyl)-2-tert-butoxycarbonylamino-propionic acid in 101A. $^1$H NMR (400 MHz, CD$_3$OD) δ ppm 9.52 (1 H, s), 8.01 (1 H, d, J=2.26 Hz), 7.69 (1 H, dd, J=8.53, 2.26 Hz), 7.58-7.62 (1 H, m), 7.44 (1 H, d, J=1.00 Hz), 7.26-7.32 (4 H, m), 7.09-7.18 (2 H, m), 6.98 (1 H, s), 6.77 (1 H, d, J=15.56 Hz), 6.71 (1 H, d, J=1.00 Hz), 5.15 (1 H, dd, J=11.29, 6.53 Hz), 3.73 (3 H, s), 3.65-3.40 (H, dd, J=12.42, 6.65 Hz), 3.07 (1 H, t, J=12.05 Hz), 2.79 (1 H, m), 2.60 (1 H, m), 1.86-1.98 (3 H, m), 1.63-1.70 (1 H, m), 1.39-1.50 (1 H, m). MS (ESI) m/z: 623.1 (M+H)$^+$. Analytical HPLC: RT=7.09 min.

EXAMPLE 112

1 TFA Salt

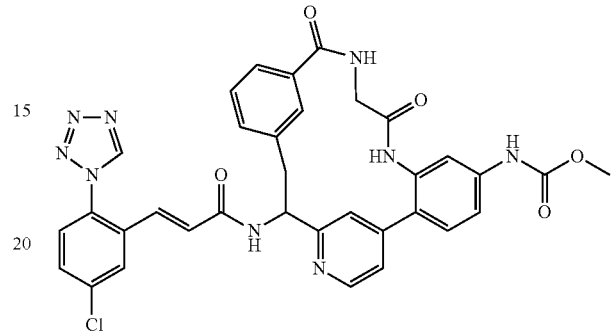

112A. 3-(2-{4-[2-(2-Benzyloxycarbonylamino-acetylamino)-4-nitro-phenyl]-pyridin-2-yl}-2-tert-butoxycarbonylamino-ethyl)-benzoic acid methyl ester: This compound was prepared by following the procedures described in step 89B, by replacing 89A with Intermediate 16; followed by step 10D, by replacing but-3-enoic acid with 2-(benzyloxycarbonylamino)acetic acid and by replacing Hunig's base with TEA. MS (ESI) m/z: 684.3 (M+H)$^+$.

112B. 3-(2-{4-[4-Amino-2-(2-benzyloxycarbonylaminoacetylamino)-phenyl]-pyridin-2-yl}-2-tert-butoxycarbonylamino-ethyl)-benzoic acid methyl ester: To a solution of 112A (87 mg, 0.127 mmol) in MeOH (10 mL) were added NH$_4$Cl (68.1 mg, 1.272 mmol) and SnCl$_2$.2H$_2$O (144 mg, 0.636 mmol) at rt. The reaction was stirred under argon at rt for 5 h. The solid was filtered off and the solvent was removed to give 112B as a yellow solid in quantitative yield. MS (ESI) m/z: 654.3 (M+H)$^+$.

112C. Example 112 was prepared following the procedures described in step 89E, by replacing 89D with 112B; followed by steps 72B; 2G; 94D; 3C; and 1G. $^1$H NMR (400 MHz, CD$_3$OD) δ ppm 9.52 (s, 1H), 8.88-8.35 (m, 2H), 7.99 (d, J=1.9 Hz, 1H), 7.66 (dd, J=8.5, 2.3 Hz, 1H), 7.59 (t, J=9.8 Hz, 2H), 7.55-7.35 (m, 4H), 7.37-7.21 (m, 1H), 7.14 (t, J=13.8 Hz, 2H), 6.83 (d, J=15.2 Hz, 1H), 6.73-6.21 (m, 1H), 5.36 (dd, J=11.9, 5.4 Hz, 1H), 4.37-3.80 (m, 1H), 3.75 (s, 3H), 3.42-3.20 (m, 2H). LC-MS (ESI) m/z: 678.2 (M+H)$^+$. Analytical HPLC: RT=6.258 min.

EXAMPLE 114

1 TFA Salt

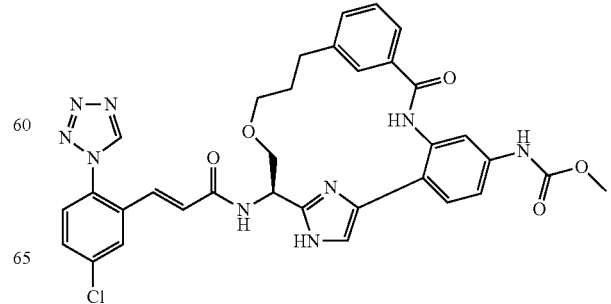

Example 114 was prepared following the procedures described in step 10D, by replacing 10C with 52F and by replacing but-3-enoic acid with 3-vinylbenzoic acid; followed by steps 2E/2F; 2G; 10H; and 1G. $^1$H NMR (400 MHz, CD$_3$OD) δ ppm 9.36-9.68 (m, 2 H) 8.23 (br. s., 1 H) 7.83-8.03 (m, 1 H) 7.08-7.76 (m, 10 H) 6.95 (br. s., 1 H) 5.49 (s, 1 H) 3.87-4.18 (m, 2 H) 3.66-3.89 (m, 3 H) 2.64-2.95 (m, 2 H) 1.99-2.22 (m, 1 H) 1.71-1.92 (m, 1 H). MS (ESI) m/z: 668.4 (M+H)$^+$. Analytical HPLC: RT=6.75 min.

EXAMPLE 139

(2E)-3-[5-Chloro-2-(1H-1,2,3,4-tetrazol-1-yl)phenyl]-N-{19-fluoro-15-oxo-5,14,22,23-tetraazatetracyclo[16.3.1.1$^{4,7}$.0$^{8,13}$]tricosa-1(22),4(23),6,8,10,12,18,20-octaen-3-yl}prop-2-enamide, 2 TFA salt

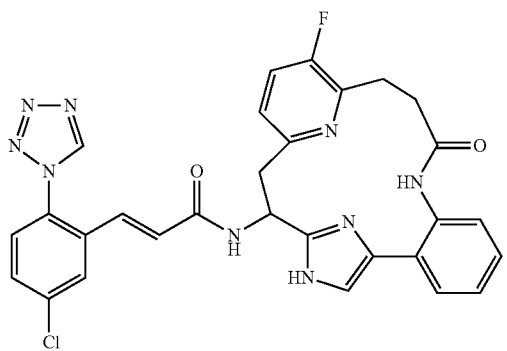 [SMILES: O=C(/C=C/c1cc(Cl)ccc1-n1cnnn1)NC1Cc2ccc(F)c(n2)CCC(=O)Nc2ccccc2-c2c[nH]c1n2]

139A. Ethyl 3-(6-bromo-5-fluoropyridin-2-yl)-2-(diphenylmethyleneamino)propanoate: 139A was prepared by following a literature procedure (Ansari, A. M. et al., *Synthetic Communications*, 38:2330-2340 (2008)) using 2-bromo-6-(bromomethyl)-3-fluoropyridine synthesized according to the procedure described in 106A. MS (ESI) m/z: 455.1 (M+H)$^+$.

139B. Ethyl 3-(6-bromo-5-fluoropyridin-2-yl)-2-(tert-butoxycarbonylamino) propanoate. To a flask containing 139A (1.703 g, 3.74 mmol) in water (10 mL) was added TFA (5.0 mL, 64.9 mmol) at rt. The reaction was stirred under argon at rt for 3 h. Solvent was removed to give a brown oil. MS (ESI) m/z: 292.9 (M+H)$^+$. To a suspension of the above oil in ethyl acetate (30 mL) were added TEA (2.61 mL, 18.70 mmol) and BOC$_2$O (0.955 mL, 4.11 mmol) at rt. The reaction was stirred under argon at rt for 1.5 h. The reaction mixture was diluted with EtOAc, washed with 1M HCl, sat NaHCO$_3$ and brine. The organic phase was dried over magnesium sulfate, filtered and concentrated. The crude product was purified by normal phase chromatography to give 139B (884 mg, 60% overall yield over 4 steps from 2-bromo-3-fluoro-6-methylpyridine) as a tan oil. $^1$H NMR (400 MHz, CDCl$_3$) δ ppm 7.33 (1 H, d, J=8.03 Hz), 7.12 (1 H, dd, J=8.03, 3.26 Hz), 5.37 (1 H, d, J=5.77 Hz), 4.62 (1 H, d, J=6.02 Hz), 4.15-4.28 (2 H, m), 3.28 (2 H, d, J=3.76 Hz), 1.42 (9 H, s), 1.26 (3H, t, J=7.03 Hz). $^{19}$F NMR (376 MHz, CDCl$_3$) δ ppm −115.64 (1 F, s). MS (ESI) m/z: 391.0/393.0 (M+H)$^+$.

139C. (E)-tert-Butyl 3-(6-(2-(tert-butoxycarbonylamino)-3-ethoxy-3-oxopropyl)-3-fluoropyridin-2-yl)acrylate. 139C was prepared following the procedure described in 103B by replacing methyl acrylate with tert-butyl acrylate. $^1$H NMR (400 MHz, CDCl$_3$) δ ppm 7.77 (1 H, dd, J=15.56, 1.51 Hz), 7.34 (1 H, dd, J=9.54, 8.53 Hz), 7.12 (1 H, dd, J=8.41, 3.64 Hz), 6.92 (1 H, d, J=15.56 Hz), 5.67 (1 H, d, J=7.53 Hz), 4.57-4.77 (1 H, m), 4.07-4.25 (2 H, m), 3.21-3.42 (2 H, m), 1.54 (9 H, s), 1.43 (9 H, s), 1.23 (3 H, t, J=7.03 Hz). $^{19}$F NMR (376 MHz, CDCl$_3$) δ ppm −127.70 (1F, s). MS (ESI) m/z: 439.1 (M+H)$^+$.

139D. 3-(6-(3-tert-Butoxy-3-oxopropyl)-5-fluoropyridin-2-yl)-2-(tert-butoxycarbonylamino)propanoic acid. To a solution of 139C (0.68 g, 1.551 mmol) in THF (10 mL) and water (3 mL) was added LiOH (0.074 g, 3.10 mmol) at 0° C. The reaction was stirred under argon at 0° C. for 2 hrs. 1.0 N HCl (3.1 mL) was added to neutralize the reaction. The reaction mixture was diluted with EtOAc, washed with H$_2$O and brine. The organic phase was dried over magnesium sulfate, filtered and concentrated to give a tan solid of (E)-3-(6-(3-tert-butoxy-3-oxoprop-1-enyl)-5-fluoropyridin-2-yl)-2-(tert-butoxycarbonylamino)propanoic acid. MS (ESI) m/z: 411.1 (M+H)$^+$. To the above obtained intermediate were added catalytic amount of 10% Pd/C and MeOH (15 mL). The reaction mixture was stirred under a hydrogen balloon at rt for 1 h. Catalyst was filtered off and solvent was removed to give 139D as a tan solid. MS (ESI) m/z: 413.1 (M+H)$^+$.

139E. tert-Butyl 3-(6-(2-(tert-butoxycarbonylamino)-2-(4-(2-nitrophenyl)-1H-imidazol-2-yl)ethyl)-3-fluoropyridin-2-yl)propanoate. 139A was prepared following the procedure described in 2A and 2B by replacing (S)-2-(tert-butoxycarbonylamino)pent-4-enoic acid with 139D in 2A.

139F. 3-(6-(2-(tert-Butoxycarbonylamino)-2-(4-(2-nitrophenyl)-1H-imidazol-2-yl)ethyl)-3-fluoropyridin-2-yl)propanoic acid. To a solution of 139E (220 mg, 0.396 mmol) in DCM (7 mL) was added TFA (3.0 mL, 38.9 mmol) at rt. The reaction was stirred under argon at rt for 1.5 h. Solvent was removed to give a brown solid, which was used without further purification. MS (ESI) m/z: 400.1 (M+H)$^+$. The above obtained product was dissolved in dioxane (15 mL), to which were added NaOH (1.980 mL, 1.980 mmol) and BOC$_2$O (0.138 mL, 0.594 mmol) at rt. After stirred for 2 h, MS showed the reaction was complete. The reaction mixture was diluted with EtOAc, washed with 1M HCl and brine. The organic phase was dried over magnesium sulfate, filtered and concentrated to give 139F as a tan oil. MS (ESI) m/z: 500.1 (M+H)$^+$.

139G. 3-(6-(2-(4-(2-Aminophenyl)-1H-imidazol-2-yl)-2-(tert-butoxycarbonylamino)ethyl)-3-fluoropyridin-2-yl)propanoic acid, TFA salt. 139G was prepared according to the procedure described in 15B. The crude product was purified by reverse phase chromatography to give 139G as a brown solid. MS (ESI) m/z: 470.1 (M+H)$^+$.

139H. Example 139 was prepared following the procedure described in 23E, 1G and 3C, by replacing 23D with 139G. $^1$H NMR (400 MHz, CD$_3$OD) δ ppm 9.50 (1 H, s), 7.96 (1 H, d, J=2.26 Hz), 7.67 (1 H, dd, J=8.53, 2.26 Hz), 7.56-7.61 (1 H, m), 7.48-7.54 (1 H, m), 7.41-7.48 (2 H, m), 7.34-7.40 (1 H, m), 7.25-7.34 (3 H, m), 7.18 (1 H, d, J=15.56 Hz), 6.70 (1 H, d, J=15.56 Hz), 5.55 (1 H, dd, J=11.04, 4.77 Hz), 3.59-3.70 (1 H, m), 3.46-3.57 (1 H, m), 3.12-3.21 (1 H, m), 2.94-3.07 (2 H, m), 2.80-2.90 (1 H, m). $^{19}$F NMR (376 MHz, CD$_3$OD) δ ppm −77.55 (11.8F, s, TFA), −130.00 (1F, s). MS (ESI) m/z: 584.2 (M+H)+. Analytical HPLC: RT=5.756 min.

EXAMPLE 140

Methyl N-{3-[(2E)-3-(2-acetyl-5-chlorophenyl)prop-2-enamido]-19-fluoro-15-oxo-5,14,22,23-tetraazatetracyclo[16.3.1.1$^{4,7}$.0$^{8,13}$]tricosa-1(22),4(23),6,8,10,12,18,20-octaen-11-yl}carbamate, 2 TFA salt

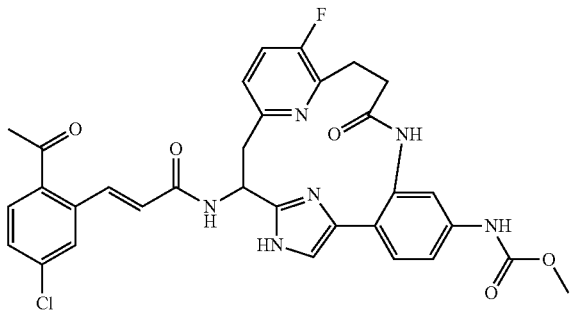 [SMILES: COC(=O)Nc1ccc2c(c1)NC(=O)CCc1nc(ccc1F)CC(NC(=O)/C=C/c1cc(Cl)ccc1C(C)=O)c1nc-2c[nH]1]

Example 140 was prepared following the procedure described in 1G, by replacing 1F with 106E, by replacing Intermediate 1 with Intermediate 4 and by using EDC, HOBt, and triethylamine. $^1$H NMR (400 MHz, CD$_3$OD) δ ppm 9.42 (s, 1 H) 7.89 (d, J=15.81 Hz, 1 H) 7.79 (d, J=8.28 Hz, 1 H) 7.53 (d, J=2.01 Hz, 1 H) 7.47 (d, J=1.76 Hz, 1 H) 7.41 (dd, J=8.28, 2.01 Hz, 1 H) 7.29-7.36 (m, 1 H) 7.19-7.27 (m, 3 H) 7.14 (s, 1 H) 6.39 (d, J=15.56 Hz, 1 H) 5.48 (dd, J=11.04, 4.77 Hz, 1H) 3.64 (s, 3 H) 3.52-3.60 (m, 1 H) 3.42 (dd, J=14.18, 11.17 Hz, 1H) 3.03 (d, J=10.04 Hz, 1 H) 2.84-2.95 (m, 2 H) 2.70-2.80 (m, 1 H) 2.48 (s, 3 H). MS (ESI) m/z: 631.2 (M+H)+. Analytical HPLC: RT=6.0 min.

EXAMPLE 141

Methyl N-{3-[(2E)-3-(2-acetyl-5-chloro-6-fluorophenyl)prop-2-enamido]-19-fluoro-15-oxo-5,14,22,23-tetraazatetracyclo[16.3.1.1$^{4,7}$.0$^{8,13}$]tricosa-1(22),4(23),6,8,10,12,18,20-octaen-11-yl}carbamate, 2 TFA salt

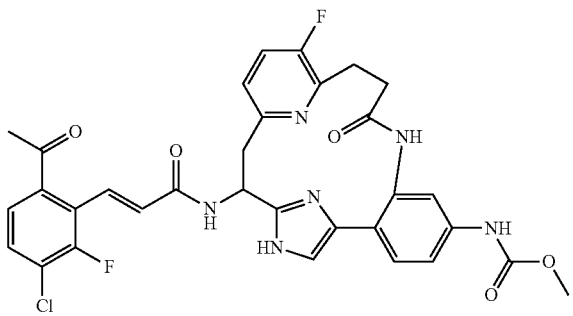 [SMILES: COC(=O)Nc1ccc2c(c1)NC(=O)CCc1nc(ccc1F)CC(NC(=O)/C=C/c1c(C(C)=O)ccc(Cl)c1F)c1nc-2c[nH]1]

Example 141 was prepared following the procedure described in 1G, by replacing 1F with 106E, by replacing Intermediate 1 with Intermediate 18 and by using EDC, HOBt, and triethylamine. $^1$H NMR (400 MHz, CD$_3$OD) δ ppm 7.68-7.76 (m, 2 H) 7.60-7.67 (m, 2 H) 7.43-7.50 (m, 1 H) 7.33-7.41 (m, 3 H) 7.28 (s, 1 H) 6.64 (dd, J=16.06, 2.01 Hz, 1 H) 5.61 (dd, J=11.29, 4.77 Hz, 1 H) 3.78 (s, 3 H) 3.65-3.73 (m, 1 H) 3.55 (dd, J=14.18, 11.17 Hz, 1 H) 3.14-3.24 (m, 1 H) 2.98-3.09 (m, 2 H) 2.84-2.93 (m, 1 H) 2.61 (s, 3 H). MS (ESI) m/z: 649.2 (M+H)+. Analytical HPLC: RT=6.1 min.

EXAMPLE 142

Methyl N-{3-[(2,6-difluoro-4-methylbenzene)amido]-19-fluoro-15-oxo-5,14,22,23-tetraazatetracyclo[16.3.1.1$^{4,7}$.0$^{8,13}$]tricosa-1(22),4(23),6,8,10,12,18,20-octaen-11-yl}carbamate, 2 TFA salt

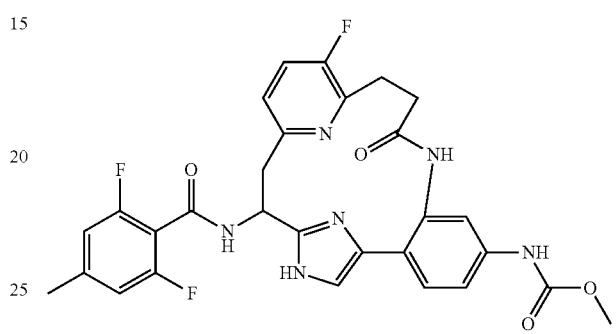

Example 142 was prepared following the procedure described in 1G, by replacing 1F with 106E, by replacing Intermediate 1 with 2,6-difluoro-4-methylbenzoic acid and by using EDC, HOBt, and triethylamine $^1$H NMR (400 MHz, CD$_3$CN) δ ppm 7.86 (s, 1 H) 7.43 (d, J=1.76 Hz, 1 H) 7.27-7.34 (m, 1 H) 7.22-7.27 (m, 2 H) 7.16 (dd, J=8.41, 3.89 Hz, 1 H) 7.11-7.13 (m, 1 H) 6.78 (d, J=9.03 Hz, 2 H) 5.78-5.85 (m, 1 H) 3.62 (s, 3 H) 3.52 (d, J=7.78 Hz, 2 H) 2.98-3.08 (m, 1 H) 2.89-2.97 (m, 1 H) 2.72-2.84 (m, 2 H) 2.26 (s, 3 H). MS (ESI) m/z: 579.1 (M+H)+. Analytical HPLC: RT=5.6 min.

EXAMPLE 143

Methyl N-{19-fluoro-3-[(4-methylcyclohexane)amido]-15-oxo-5,14,22,23-tetraazatetracyclo[16.3.1.1$^{4,7}$.0$^{8,13}$]tricosa-1(22),4(23),6,8,10,12,18,20-octaen-11-yl}carbamate, 2 TFA salt

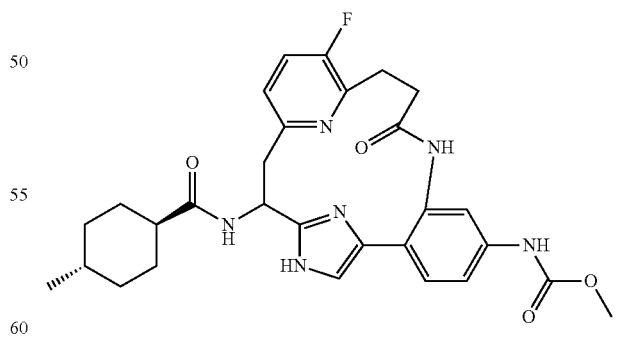

Example 143 was prepared following the procedure described in 1G, by replacing 1F with 106E, by replacing Intermediate 1 with (1r,4r)-4-methylcyclohexanecarboxylic acid and by using EDC, HOBt, and triethylamine. $^1$H NMR (400 MHz, CD$_3$OD) δ ppm 7.60 (d, J=1.25 Hz, 1 H) 7.42-7.49 (m, 1 H) 7.34-7.39 (m, 2 H) 7.29-7.34 (m, 1 H) 7.25 (s, 1 H)

5.44 (dd, J=11.54, 4.77 Hz, 1 H) 3.78 (s, 3 H) 3.54-3.63 (m, 1 H) 3.46 (dd, J=14.05, 11.54 Hz, 1 H) 3.14-3.23 (m, 1 H) 2.97-3.07 (m, 2 H) 2.83-2.91 (m, 1 H) 2.22 (ddd, J=12.23, 8.85, 3.51 Hz, 1 H) 1.75-1.86 (m, 3 H) 1.42-1.52 (m, 2 H) 1.32-1.42 (m, 1 H) 0.95-1.06 (m, 2 H) 0.92 (d, J=6.53 Hz, 3 H). MS (ESI) m/z: 549.2 (M+H)⁺. Analytical HPLC: RT=6.0 min.

EXAMPLE 146

(2E)-N-{6-Chloro-19-fluoro-15-oxo-5,14,22,23-tetraazatetracyclo[16.3.1.1$^{4,7}$.0$^{8,13}$]tricosa-1(22),4 (23),6,8,10,12,18,20-octaen-3-yl}-3-[5-chloro-2-(1H-1,2,3,4-tetrazol-1-yl)phenyl]prop-2-enamide, 2 TFA salt

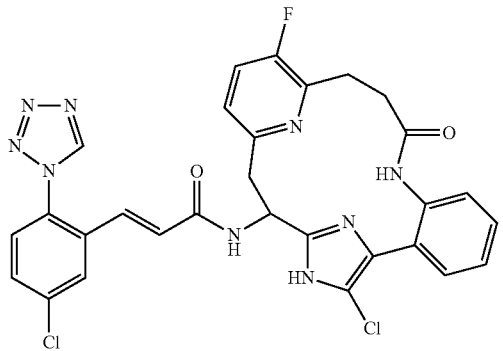 [SMILES: O=C(/C=C/c1cc(Cl)ccc1-n1cnnn1)NC1Cc2ccc(F)c(n2)CCC(=O)Nc2ccccc2-c2nc1[nH]c2Cl]

Example 146 was prepared following the procedure described in Example 9, by replacing Example 8 with Example 139 and by running the reaction at rt. ¹H NMR (400 MHz, CD₃OD) δ ppm 9.51 (1 H, s), 7.98 (1 H, d, J=2.26 Hz), 7.66 (1 H, dd, J=8.53, 2.26 Hz), 7.57 (1 H, d, J=8.53 Hz), 7.50 (1 H, dd, J=7.65, 1.38 Hz), 7.38-7.47 (2 H, m), 7.33 (1 H, td, J=7.59, 1.38 Hz), 7.30 (1 H, dd, J=7.91, 0.88 Hz), 7.23 (1 H, dd, J=8.28, 3.76 Hz), 7.17 (1 H, d, J=15.56 Hz), 6.75 (1H, d, J=15.56 Hz), 5.49 (1 H, dd, J=10.16, 4.64 Hz), 3.52 (1 H, dd, J=14.31, 4.52 Hz), 3.44 (1 H, dd, J=14.31, 10.29 Hz), 3.03-3.17 (2 H, m), 2.91 (2 H, t, J=6.02 Hz). MS (ESI) m/z: 618.1 (M+H)⁺. Analytical HPLC: RT=7.368 min.

EXAMPLE 147

Methyl N-{3-[(2E)-3-(3-chloro-2,6-difluorophenyl) prop-2-enamido]-19-fluoro-15-oxo-5,14,22,23-tetraazatetracyclo[16.3.1.1$^{4,7}$.0$^{8,13}$]tricosa-1(22),4(23), 6,8,10,12,18,20-octaen-11-yl}carbamate, 2 TFA salt

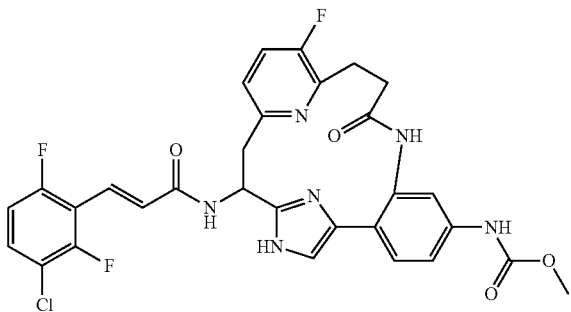 [SMILES: COC(=O)Nc1ccc2c(c1)NC(=O)CCc1nc(ccc1F)CC(NC(=O)/C=C/c1c(F)ccc(Cl)c1F)c1nc-2c[nH]1]

Example 147 was prepared following the procedure described in 1G, by replacing 1F with 106E, by replacing Intermediate 1 with Intermediate 15 and by using EDC, HOBt, and Hunig's base. ¹H NMR (400 MHz, CD₃OD) δ ppm 9.55 (s, 1 H) 7.68 (d, J=16.06 Hz, 1 H) 7.53-7.63 (m, 2 H) 7.43-7.50 (m, 1 H) 7.32-7.41 (m, 3 H) 7.28 (s, 1 H) 7.09-7.16 (m, 1 H) 7.01 (d, J=16.06 Hz, 1 H) 5.61 (dd, J=11.29, 4.77 Hz, 1 H) 3.78 (s, 3 H) 3.69 (dd, J=14.18, 4.64 Hz, 1 H) 3.55 (dd, J=14.05, 11.29 Hz, 1 H) 3.14-3.25 (m, 1 H) 2.98-3.09 (m, 2 H) 2.85-2.93 (m, 1 H). MS (ESI) m/z: 625.1 (M+H)⁺. Analytical HPLC: RT=6.07 min.

EXAMPLE 148

Methyl N-{6-chloro-19-fluoro-15-oxo-3-[(2E)-3-(3-chloro-2,6-difluorophenyl)prop-2-enamido]-5,14,22, 23-tetraazatetracyclo[16.3.1.1$^{4,7}$.0$^{8,13}$]tricosa-1(22),4 (23),6,8,10,12,18,20-octaen-11-yl}carbamate, 2 TFA salt

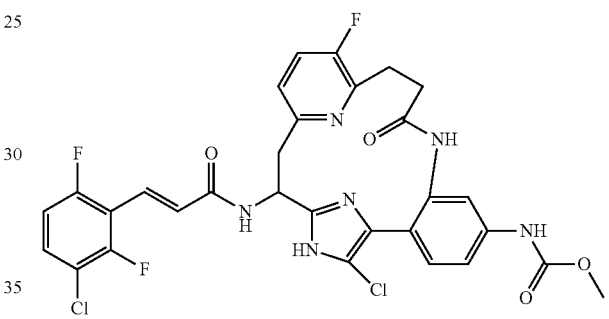

148A. tert-Butyl N-{6-chloro-19-fluoro-11-[(methoxycarbonyl)amino]-15-oxo-5,14,22,23-tetraazatetracyclo [16.3.1.1$^{4,7}$.0$^{8,13}$]tricosa-1(22),4(23),6,8,10,12,18,20-octaen-3-yl}carbamate: This compound was prepared by following the procedure described in Example 9, by replacing Example 8 with 106D and lowering the reaction temperature to 10-20 deg. MS (ESI) m/z: 559.1 (M+H)⁺.

148B. Methyl N-{3-amino-6-chloro-19-fluoro-15-oxo-5, 14,22,23-tetraazatetracyclo[16.3.1.1$^{4,7}$.0$^{8,13}$]tricosa-1(22),4 (23),6,8,10,12,18,20-octaen-11-yl}carbamate: This compound was prepared by following the procedure described in 3C, by replacing 3B with 148A. MS (ESI) m/z: 459.1 (M+H)⁺.

148C. Example 148 was prepared following the procedure described in 1G, by replacing 1F with 148B, by replacing Intermediate 1 with Intermediate 15 and by using EDC, HOBt, and Hunig's base. ¹H NMR (400 MHz, CD₃OD) δ ppm 7.56 (d, J=16.06 Hz, 1 H) 7.40-7.51 (m, 2 H) 7.27-7.37 (m, 2 H) 7.20 (ddd, J=14.81, 8.53, 3.01 Hz, 2 H) 6.95-7.03 (m, 1 H) 6.90 (d, J=16.06 Hz, 1 H) 5.41 (dd, J=10.79, 4.52 Hz, 1 H) 3.66 (s, 3 H) 3.44-3.51 (m, 1 H) 3.31-3.41 (m, 1 H) 3.01-3.11 (m, 1 H) 2.97 (d, J=7.28 Hz, 1 H) 2.74-2.86 (m, 2 H). MS (ESI) m/z: 659.1 (M+H)⁺. Analytical HPLC: RT=8.05 min.

EXAMPLE 149

Methyl N-{6-chloro-3-[(2,6-difluoro-4-methylbenzene)amido]-19-fluoro-15-oxo-5,14,22,23-tetraazatetracyclo[16.3.1.1^{4,7}.0^{8,13}]tricosa-1(22),4(23),6,8,10,12,18,20-octaen-11-yl}carbamate, 2 TFA salt

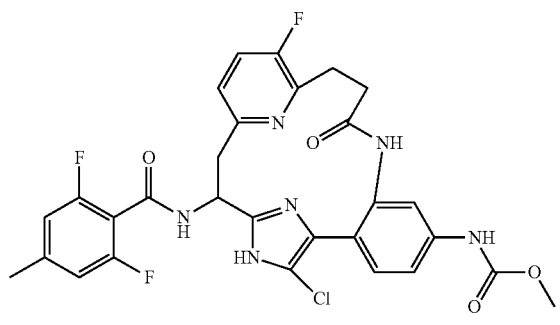

Example 149 was prepared following the procedure described in 1G, by replacing 1F with 148B, by replacing Intermediate 1 with 2,6-difluoro-4-methylbenzoic acid and by using EDC, HOBt, and Hunig's base. $^1$H NMR (400 MHz, CD$_3$OD) δ ppm 7.61 (d, J=1.76 Hz, 1 H) 7.41-7.50 (m, 2 H) 7.29-7.39 (m, 2 H) 6.92 (d, J=9.03 Hz, 2 H) 5.61 (dd, J=11.29, 5.02 Hz, 1 H) 3.78 (s, 3 H) 3.53-3.64 (m, 2 H) 3.11-3.21 (m, 1 H) 2.99-3.10 (m, 1 H) 2.87-2.98 (m, 2 H) 2.40 (s, 3 H). MS (ESI) m/z: 613.1 (M+H)$^+$. Analytical HPLC: RT=7.12 min.

EXAMPLE 150

Methyl N-{6-chloro-19-fluoro-3-[(4-methylcyclohexane)amido]-15-oxo-5,14,22,23-tetraazatetracyclo[16.3.1.1^{4,7}.0^{8,13}]tricosa-1(22),4(23),6,8,10,12,18,20-octaen-11-yl}carbamate, 2 TFA salt

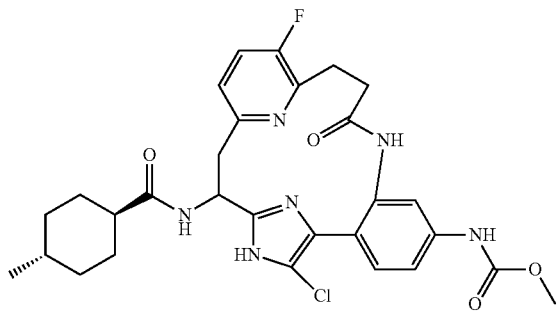

Example 150 was prepared following the procedure described in 1G, by replacing 1F with 148B, by replacing Intermediate 1 with (1r,4r)-4-methylcyclohexanecarboxylic acid and by using EDC, HOBt, and Hunig's base. $^1$H NMR (400 MHz, CD$_3$OD) δ ppm 7.61 (s, 1 H) 7.42-7.49 (m, 1 H) 7.32-7.41 (m, 2 H) 7.29 (dd, J=8.28, 3.76 Hz, 1 H) 5.33 (dd, J=11.04, 4.77 Hz, 1 H) 3.78 (s, 3 H) 3.47-3.57 (m, 1 H) 3.40 (dd, J=14.05, 11.04 Hz, 1 H) 3.13-3.23 (m, 1 H) 2.96-3.06 (m, 2 H) 2.80-2.89 (m, 1 H) 2.18-2.28 (m, 1 H) 1.86 (s, 1 H) 1.74-1.83 (m, 3 H) 1.44-1.53 (m, 2 H) 1.35-1.42 (m, 1 H) 0.95-1.06 (m, 2 H) 0.92 (d, J=6.53 Hz, 3 H). MS (ESI) m/z: 583.1 (M+H)$^+$. Analytical HPLC: RT=7.47 min.

EXAMPLE 151

2 TFA Salt

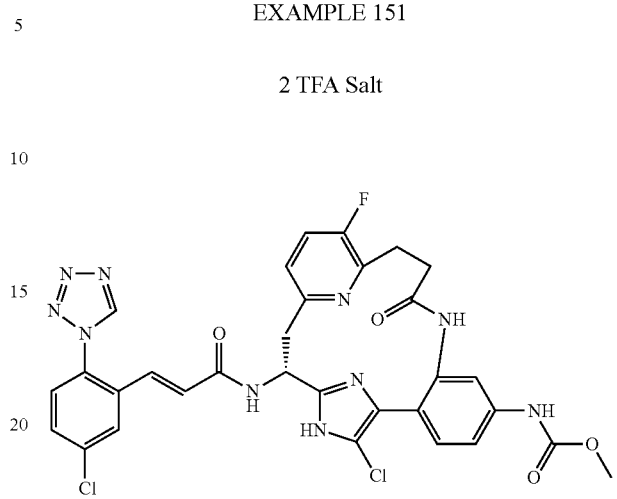

Example 151 was prepared following the procedure described in Example 9 by replacing Example 8 with 107 and lowering the reaction temperature to 10-20 deg. $^1$H NMR (400 MHz, CD$_3$OD) δ ppm 9.53 (s, 1 H) 7.99 (d, J=2.26 Hz, 1 H) 7.65-7.70 (m, 1 H) 7.57-7.62 (m, 2 H) 7.37-7.47 (m, 2 H) 7.31-7.35 (m, 1 H) 7.27 (dd, J=8.28, 3.76 Hz, 1 H) 7.19 (d, J=15.56 Hz, 1 H) 6.76 (d, J=15.56 Hz, 1 H) 5.49 (dd, J=10.54, 4.77 Hz, 1 H) 3.74-3.80 (m, 3 H) 3.52-3.59 (m, 1 H) 3.42-3.50 (m, 1 H) 3.12-3.21 (m, 1 H) 3.03 (s, 1 H) 2.86-2.96 (m, 2 H). MS (ESI) m/z: 691.1 (M+H)$^+$. Analytical HPLC: RT=6.93 min.

EXAMPLE 157

2 TFA Salt

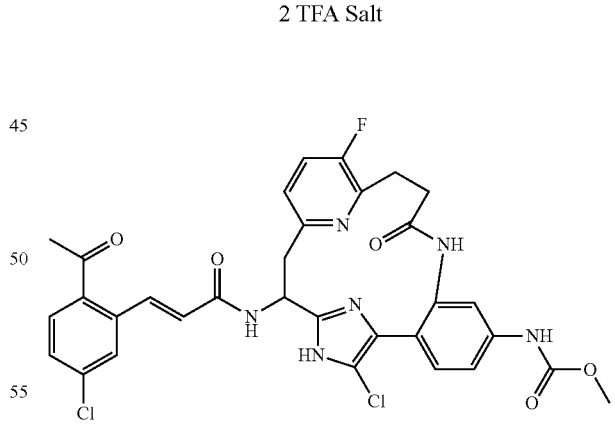

Example 157 was prepared following the procedures described in 1G, by replacing 1F with 148B, by replacing Intermediate 1 with Intermediate 4 and by using EDC, HOBt, and Hunig's base. $^1$H NMR (400 MHz, CD$_3$OD) δ ppm 7.98 (d, J=15.81 Hz, 1 H) 7.87 (d, J=8.53 Hz, 1 H) 7.62 (d, J=2.01 Hz, 1 H) 7.56 (d, J=2.01 Hz, 1 H) 7.49 (dd, J=8.28, 2.01 Hz, 1 H) 7.39-7.45 (m, 1 H) 7.33-7.38 (m, 1 H) 7.26-7.32 (m, 2 H) 6.50 (d, J=15.56 Hz, 1 H) 5.49 (dd, J=10.54, 4.77 Hz, 1 H) 3.73 (s, 3 H) 3.52-3.61 (m, 1 H) 3.40-3.49 (m, 1 H) 3.09-3.19

(m, 1 H) 2.91-3.03 (m, 2 H) 2.79-2.89 (m, 1 H) 2.55-2.60 (m, 3 H). MS (ESI) m/z: 665.1 (M+H)⁺. Analytical HPLC: RT=7.38 min.

EXAMPLE 158

2 TFA Salt

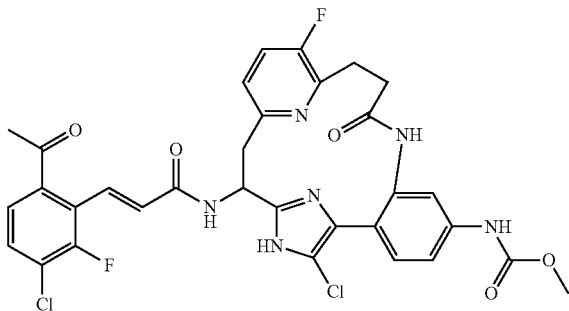

Example 158 was prepared following the procedures described in 1G, by replacing 1F with 148B, by replacing Intermediate 1 with Intermediate 18 and by using EDC, HOBt, and Hunig's base. $^1$H NMR (400 MHz, CD$_3$OD) δ ppm 7.56-7.66 (m, 2 H) 7.49-7.55 (m, 2 H) 7.29-7.38 (m, 2 H) 7.19-7.26 (m, 2 H) 6.55 (dd, J=16.06, 2.01 Hz, 1 H) 5.42 (dd, J=10.79, 4.52 Hz, 1 H) 3.67 (s, 3 H) 3.45-3.54 (m, 1 H) 3.33-3.42 (m, 1 H) 3.05 (d, J=1.76 Hz, 1 H) 2.90-2.98 (m, 1 H) 2.83 (ddd, J=19.20, 8.66, 2.76 Hz, 2H) 2.50 (s, 3H). MS (ESI) m/z: 683.1 (M+H)⁺. Analytical HPLC: RT=7.56 min.

EXAMPLE 162

2 TFA Salt

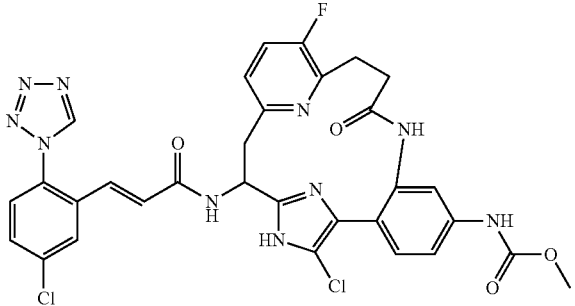 [SMILES: COC(=O)Nc1ccc2c(c1)NC(=O)CCc1nc(ccc1F)C[C@@H](NC(=O)/C=C/c1cc(Cl)ccc1-n1cnnn1)c1nc-2c(Cl)[nH]1]

Example 162 was prepared following the procedures described in 1G, by replacing 1F with 148B. $^1$H NMR (400 MHz, CD$_3$OD) δ ppm 9.40 (s, 1H) 7.85 (d, J=2.26 Hz, 1H) 7.51-7.57 (m, 1 H) 7.44-7.49 (m, 2 H) 7.23-7.34 (m, 2 H) 7.13-7.22 (m, 2 H) 7.05 (d, J=15.56 Hz, 1 H) 6.62 (d, J=15.56 Hz, 1 H) 5.33 (dd, J=10.67, 4.64 Hz, 1 H) 3.64 (s, 3 H) 3.40-3.47 (m, 1 H) 3.28-3.37 (m, 1 H) 2.98-3.09 (m, 1 H) 2.85-2.95 (m, 1 H) 2.79-2.84 (m, 1 H) 2.70-2.77 (m, 1 H). MS (ESI) m/z: 691.0 (M+H)⁺. Analytical HPLC: RT=7.13 min.

EXAMPLE 163

2 TFA Salt

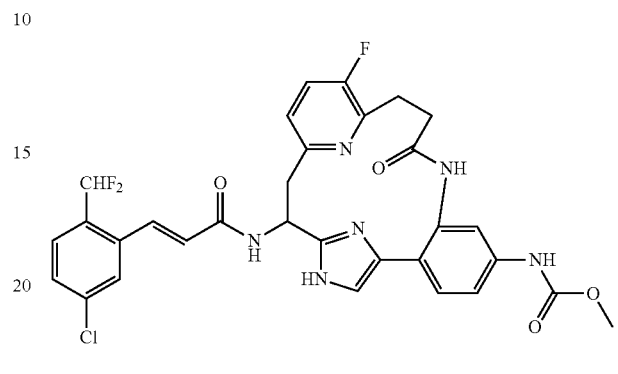

Example 163 was prepared following the procedure described in 1G, by replacing 1F with 106E, by replacing Intermediate 1 with Intermediate 19 and by using EDC, HOBt, and Hunig's base. $^1$H NMR (400 MHz, CD$_3$OD) δ ppm 7.92 (d, J=15.56 Hz, 1 H) 7.75 (s, 1 H) 7.54-7.62 (m, 2 H) 7.47-7.53 (m, 1 H) 7.38-7.45 (m, 1 H) 7.29-7.36 (m, 3 H) 7.24 (s, 1 H) 6.97 (s, 1 H) 6.67 (d, J=15.56 Hz, 1 H) 5.59 (dd, J=10.92, 4.89 Hz, 1 H) 3.74 (s, 3 H) 3.61-3.69 (m, 1 H) 3.49-3.59 (m, 1 H) 3.10-3.20 (m, 1 H) 2.94-3.05 (m, 2 H) 2.80-2.89 (m, 1 H). MS (ESI) m/z: 639.1 (M+H)⁺. Analytical HPLC: RT=6.74 min.

EXAMPLE 164

2 TFA Salt

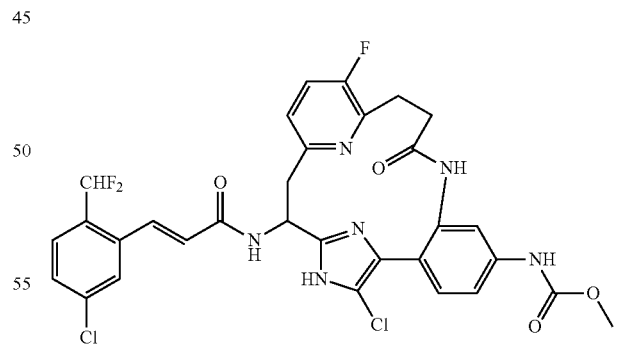

Example 164 was prepared following the procedures described in 1G, by replacing 1F with 148B, by replacing Intermediate 1 with Intermediate 19 and by using EDC, HOBt, and Hunig's base. $^1$H NMR (400 MHz, CD$_3$OD) δ ppm 7.95 (d, J=15.56 Hz, 1 H) 7.80 (s, 1 H) 7.58-7.65 (m, 2 H) 7.50-7.58 (m, 1 H) 7.40-7.47 (m, 2 H) 7.34 (dd, J=8.53, 2.26 Hz, 1 H) 7.27 (dd, J=8.28, 3.76 Hz, 1 H) 7.03 (m, 1 H) 6.73 (d, J=15.56 Hz, 1 H) 5.56 (dd, J=10.29, 4.52 Hz, 1 H)

3.77 (s, 3 H) 3.54-3.62 (m, 1 H) 3.45-3.53 (m, 1 H) 3.10-3.21 (m, 2 H) 2.92-2.98 (m, 2 H). MS (ESI) m/z: 673.0 (M+H)+. Analytical HPLC: RT=8.73 min.

EXAMPLE 165

2 TFA Salt

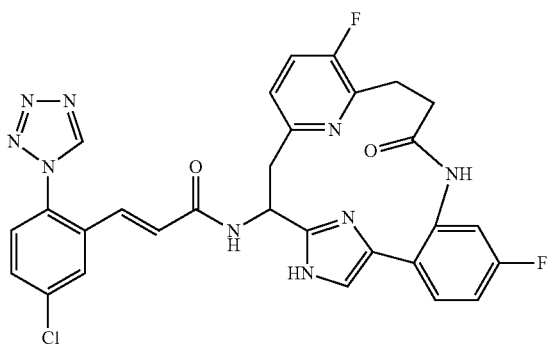 [SMILES: O=C(/C=C/c1cc(Cl)ccc1-n1cnnn1)NC1Cc2ccc(F)c(n2)CCC(=O)Nc2cc(F)ccc2-c2c[nH]c1n2]

165A. 2-Bromo-1-(2-bromo-4-fluorophenyl)ethanone. To a 20 mL microwave vial was added of 1-(2-bromo-4-fluorophenyl)ethanone (1.15 g, 5.19 mmol), copper(II) bromide (2.320 g, 10.39 mmol), and ethyl acetate (12 ml) The mixture (suspension) was heated in microwave at 120° C. for 17 min (fixed hold time). Reaction was filtered via Buchner funnel to remove solid. The solid was rinsed with EtOAc. The clear, green filtrate was washed with water (2×10 mL), brine, dried over anh. Na$_2$SO$_4$, filtered and concentrated, and purified through normal phase chromatography to give 165A (1.02 g, 66.4% yield) as a colorless oil. MS (ESI) m/z: 295.0 (M−H).

165B. Benzyl 3-(6-bromo-5-fluoropyridin-2-yl)-2-(tert-butoxycarbonylamino) propanoate. To a clear, pale yellow solution of 106C (1.3 g, 3.58 mmol) in MeOH (13.5 mL)/Water (1.485 mL) was added Cesium carbonate (0.676 g, 2.076 mmol). The reaction was stirred for 20 min at rt. The solvent was removed, and remaining water in the cesium salt of SM was further reduced by repeated azeotropic distillation with toluene. The resulting dry salt was dissolved in DMF (10 mL). (bromomethyl)benzene (0.553 mL, 4.65 mmol) was added, and the resulting mixture was stirred at rt under Ar. for 2 hrs. To the reaction mixture was added ice-cold water, and then extracted with EtOAc. The organic layer was washed with water (2×), brine (1×), dried over anh. Na$_2$SO$_4$, filtered, concentrated, and purified through normal phase chromatography to give 165B (1.62 g, 100% yield) as a colorless oil. MS (ESI) m/z: 453.0 (M+H)+.

165C. (E)-Methyl 3-(6-(3-(benzyloxy)-2-(tert-butoxycarbonylamino)-3-oxopropyl)-3-fluoropyridin-2-yl)acrylate. This compound was prepared following the procedure described in 103B, by replacing 103A with 165B. MS (ESI) m/z: 459.1 (M+H)+.

165D. 2-(tert-Butoxycarbonylamino)-3-(5-fluoro-6-(3-methoxy-3-oxopropyl)pyridin-2-yl)propanoic acid. This compound was prepared following the procedure described in 10F, by replacing 10E with 165C and by replacing the hydrogen balloon with hydrogen (55 psi). MS (ESI) m/z: 371.1 (M+H)+.

165E. 2-(2-Bromo-4-fluorophenyl)-2-oxoethyl 2-(tert-butoxycarbonylamino)-3-(5-fluoro-6-(3-methoxy-3-oxopropyl)pyridin-2-yl)propanoate. This compound was prepared following the procedure described in 2A, by replacing (5)-2-(tert-butoxycarbonylamino)pent-4-enoic acid with 165D and by replacing 2-bromo-1-(2-bromophenyl)ethanone with 165A. MS (ESI) m/z: 585.0 (M+H)+.

165F. tert-Butyl N-(11,19-difluoro-15-oxo-5-{[2-(trimethylsilyl)ethoxy]methyl}-5,14,22,23-tetraazatetracyclo[16.3.1.1$^{4,7}$.0$^{8,13}$]tricosa-1(22),4(23),6,8,10,12,18,20-octaen-3-yl)carbamate. This compound was prepared following the procedures described in 2B, by replacing 2A with 165E; 10B; 10C; 97C; 97E. MS (ESI) m/z: 600.2 (M+H)+.

165G. 3-Amino-11,19-difluoro-5,14,22,23-tetraazatetracyclo[16.3.1.1$^{4,7}$.0$^{8,13}$]tricosa-1(22),4(23),6,8,10,12,18,20-octaen-15-one. This compound was prepared following the procedures described in 10H by replacing 10G with 165F. MS (ESI) m/z: 370.0 (M+H)+.

165H. Example 165: This compound was prepared following the procedures described in 1G by replacing 1F with 165G. $^1$H NMR (400 MHz, CD$_3$OD) δ ppm 9.58 (s, 1 H) 8.04 (d, J=2.26 Hz, 1 H) 7.74 (dd, J=8.53, 2.26 Hz, 1 H) 7.63-7.68 (m, 1 H) 7.48-7.58 (m, 2 H) 7.34-7.41 (m, 2 H) 7.15-7.27 (m, 3 H) 6.79 (d, J=15.56 Hz, 1 H) 5.60 (dd, J=11.04, 4.77 Hz, 1 H) 3.67-3.76 (m, 1 H) 3.58 (dd, J=14.05, 11.29 Hz, 1 H) 3.19-3.28 (m, 1 H) 3.02-3.14 (m, 2 H) 2.87-2.96 (m, 1H). MS (ESI) m/z: 602.1 (M+H)+. Analytical HPLC: RT=5.98 min.

EXAMPLE 166

2 TFA Salt

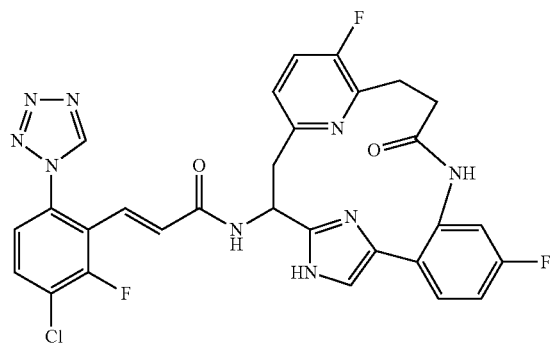 [SMILES: O=C(/C=C/c1c(-n2cnnn2)ccc(Cl)c1F)NC1Cc2ccc(F)c(n2)CCC(=O)Nc2cc(F)ccc2-c2c[nH]c1n2]

Example 166 was prepared following the procedures described in 1G by replacing 1F with 165G, and by replacing Intermediate 1 with Intermediate 3. $^1$H NMR (400 MHz, CD$_3$OD) δ ppm 9.59 (s, 1 H) 7.83-7.89 (m, 1 H) 7.48-7.58 (m, 3 H) 7.38 (dd, J=8.41, 3.64 Hz, 1 H) 7.35 (s, 1 H) 7.11-7.22 (m, 3 H) 6.80 (d, J=15.81 Hz, 1 H) 5.59 (dd, J=11.17, 4.89 Hz, 1 H) 3.65-3.74 (m, 1 H) 3.52-3.61 (m, 1 H) 3.18-3.28 (m, 1 H) 3.02-3.13 (m, 2 H) 2.87-2.96 (m, 1 H). MS (ESI) m/z: 620.0 (M+H)+. Analytical HPLC: RT=5.97 min.

Unless otherwise stated, the compounds listed in the following tables can be prepared by one skilled in the art of organic synthesis using the procedures described above.

TABLE III-1

Examples III-1 to III-15:

| Ex. # | R | R³ | R⁶ᵃ | LCMS [M + H]⁺ | HPLC RT (min.) |
|---|---|---|---|---|---|
| III-1 (S) | 1-(4-chloro-2-(prop-1-en-1-yl)phenyl)-1H-tetrazol-5-yl | Cl | F | 636.0 | 7.78 |
| III-2 (S) | trans-4-ethylcyclohexyl | Cl | NHCO₂Me | 597.1 | 8.32 |
| III-3 (S) | 2,6-difluoro-4-methoxyphenyl | Cl | NHCO₂Me | 629.0 | 7.19 |
| III-4 (S) | 2-acetyl-5-chlorophenyl(prop-1-en-1-yl) | Cl | NHCO₂Me | 665.0 | 7.39 |
| III-5 (R) | 2-acetyl-5-chlorophenyl(prop-1-en-1-yl) | Cl | NHCO₂Me | 665.0 | 7.28 |
| III-6 (S) | 2-(difluoromethoxy)-5-chlorophenyl(prop-1-en-1-yl) | Cl | NHCO₂Me | 689.2 | 8.17 |
| III-7 (S) | 2,6-difluoro-3-chlorophenyl(prop-1-en-1-yl) | Cl | NHCO₂Me | 659.0 | 7.95 |
| III-8 (R) | 2,6-difluoro-3-chlorophenyl(prop-1-en-1-yl) | Cl | NHCO₂Me | 659.0 | 7.96 |
| III-9 (S) | 2,6-difluoro-3-methylphenyl(prop-1-en-1-yl) | Cl | NHCO₂Me | 613.0 | 7.45 |
| III-10 (R) | 2,6-difluoro-3-methylphenyl(prop-1-en-1-yl) | Cl | NHCO₂Me | 613.0 | 7.42 |
| III-11 | 2-cyano-5-chlorophenyl(prop-1-en-1-yl) | Cl | NHCO₂Me | 648.2 | 7.46 |

TABLE III-1-continued

Examples III-1 to III-15:

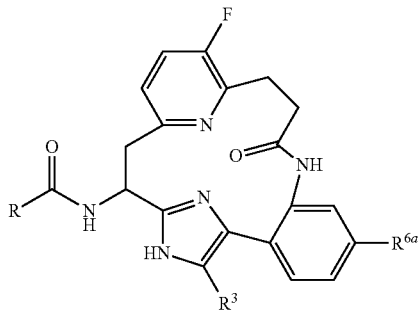

| Ex. # | R | R³ | R⁶ᵃ | LCMS [M + H]⁺ | HPLC RT (min.) |
|---|---|---|---|---|---|
| III-12 | Me, phenyl with Cl (2-Me-5-Cl styryl-dimethyl) | Cl | NHCO₂Me | 637.2 | 8.03 |
| III-13 | tetrazolyl-phenyl-Cl styryl-dimethyl | H | NHCO₂Me | 671.3 | 6.13 |
| III-14 (R) | CN-phenyl-Cl styryl-dimethyl | Cl | NHCO₂Me | 648.2 | 7.87 |
| III-15 (S) | CN-phenyl-Cl styryl-dimethyl | Cl | NHCO₂Me | 648.2 | 7.89 |

TABLE III-2

Examples III-16 to III-21:

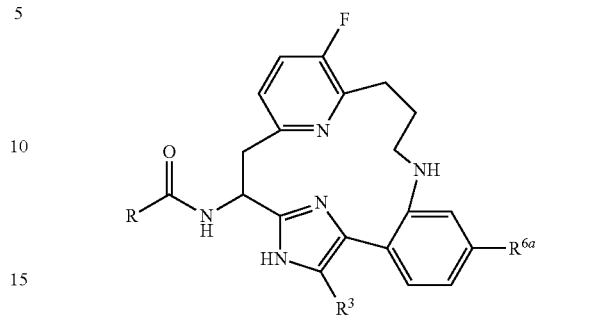

| Ex. # | R | R³ | R⁶ᵃ | LCMS [M + H]⁺ | HPLC RT (min.) |
|---|---|---|---|---|---|
| III-16 | tetrazolyl-phenyl-Cl styryl-dimethyl | H | F | 588.1 | 6.67 |
| III-17 | tetrazolyl-phenyl-Cl styryl-dimethyl | Cl | NHCO₂Me | 677.1 | 7.33 |
| III-18 (R) | tetrazolyl-phenyl-Cl styryl-dimethyl | Cl | NHCO₂Me | 677.2 | 7.77 |
| III-19 (S) | tetrazolyl-phenyl-Cl styryl-dimethyl | Cl | NHCO₂Me | 677.2 | 7.77 |

TABLE III-2-continued

Examples III-16 to III-21:

| Ex. # | R | R³ | R⁶ᵃ | LCMS [M+H]⁺ | HPLC RT (min.) |
|---|---|---|---|---|---|
| III-20 (R) | tetrazolyl-(chlorophenyl)-propenyl | Cl | NHMe | 633.2 | 6.45 |
| III-21 (S) | tetrazolyl-(chlorophenyl)-propenyl | Cl | NHMe | 633.2 | 6.43 |

III-30

Methyl N-[(3S)-3-[(2E)-3-[5-Chloro-2-(1H-1,2,3,4-tetrazol-1-yl)phenyl]prop-2-enamido]-20-(dimethylamino)-15-oxo-5,14,19,22,23-pentaazatetracyclo[16.3.1.1⁴,⁷.0⁸,¹³]tricosa-1(22),4(23),6,8,10,12,18,20-octaen-11-yl]carbamate

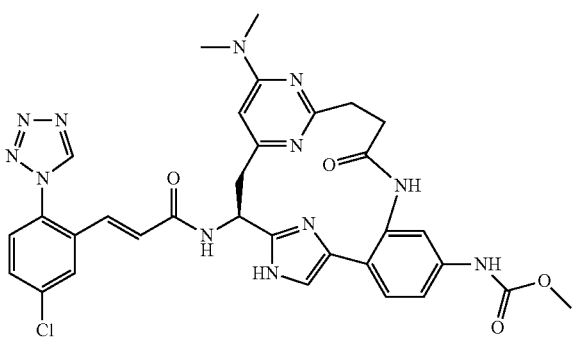 [SMILES: COC(=O)Nc1ccc2c(c1)NC(=O)CCc1nc(cc(N(C)C)n1)C[C@H](NC(=O)/C=C/c1cc(Cl)ccc1-n1cnnn1)c1nc-2c[nH]1]

III-30A (E)-Methyl 2-(3-tert-butoxy-3-oxoprop-1-enyl)-6-(dimethylamino)pyrimidine-4-carboxylate: To a solution of methyl 2-chloro-6-) dimethylamino)pyrimidine-4-carboxylate (0.8 g, 3.71 mmol) in CH₃CN (10 mL) was added tert-butyl acrylate (1.62 mL, 11.13 mmol), DIEA (2.59 mL, 14.84 mmol), tri-o-tolylphosphine (0.34 g, 1.11 mmol), and palladium acetate (0.167 g, 0.74 mmol). The reaction was heated in a microwave oven at 145° C. for 10 min. The mixture was diluted with EtOAc, filtered through CELITE®, washed CELITE® with EtOAc, and concentrated. Purification by normal phase chromatography gave (E)-methyl 2-(3-tert-butoxy-3-oxoprop-1-enyl)-6-(dimethylamino) pyrimidine-4-carboxylate (680 mg, 60% yield). MS (ESI) m/z: 308.2 (M+H)⁺.

III-30B. (E)-tert-Butyl 3-(4-(dimethylamino)-6-(hydroxymethyl)pyrimidin-2-yl)acrylate: (E)-Methyl 2-(3-tert-butoxy-3-oxoprop-1-enyl)-6-(dimethylamino)pyrimidine-4-carboxylate (1.91 g, 6.21 mmol) was suspended with diethyl ether (50 mL). Solid lithium borohydride (0.165 g, 6.84 mmol) was added portion wise. The mixture was stirred at RT under argon for 10 min. The color of the mixture changed from yellow to orange. The reaction was cooled to 0-10° C. and stirred for 1 h. It was quenched with water. EtOAc was added and the mixture was stirred for 20 min. The two layers were separated. The organic layer was washed with water and brine, dried over sodium sulfate, concentrated, and dried under vacuum to giving the desired product (1.72 g, 6.16 mmol, 99% yield) as a yellow solid. MS (ESI) m/z: 280.2 (M+H)⁺.

III-30C. (E)-tert-Butyl 3-(4-(dimethylamino)-6-formylpyrimidin-2-yl)acrylate: (E)-tert-Butyl 3-(4-(dimethylamino)-6-(hydroxymethyl)pyrimidin-2-yl)acrylate (1.72 g, 6.16 mmol) was dissolved in ethyl acetate (Volume: 50 mL). Dess-Martin Periodinane (3.40 g, 8.00 mmol) was added. The mixture was stirred at RT under argon for 20 min, and then at 0-10° C. for 20 min. To the reaction mixture was added another 50 mg of Dess-Martin periodinane. The reaction was stirred at 10° C.-20° C. for 30 min. It was filtered through CELITE® and washed CELITE® with EtOAc. The EtOAc solution was concentrated. Purification by normal phase chromatography gave the title compound (1.3 g, 76% yield). MS (ESI) m/z: 310.2 (M+H+ MeOH)⁺.

III-30D. Methyl 2-(benzyloxycarbonylamino)-3-(2-((E)-3-tert-butoxy-3-oxoprop-1-enyl)-6-(dimethylamino)pyrimidin-4-yl)acrylate: Cbz-phosphonoglycine (1.660 g, 5.01 mmol) was dissolved in CH₂Cl₂ (12 mL) and cooled in an ice-bath. DBU (1.511 mL, 10.02 mmol) was added and the mixture was stirred for 5 minutes. A slurry of (E)-tert-butyl 3-(4-(dimethylamino)-6-formylpyrimidin-2-yl)acrylate (1.39 g, 5.01 mmol) in DCM (12.00 mL) was added. The ice-bath was removed and the mixture was stirred at RT under argon for 1.5 h. The reaction mixture was diluted with CH₂Cl₂, washed with water and brine, dried over sodium sulfate, concentrated, and purified by normal phase chromatography giving the desired product (MS (ESI) m/z: 483.3 (M+H)⁺.

III-30E. (S)-Methyl 2-(benzyloxycarbonylamino)-3-(2-(3-tert-butoxy-3-oxopropyl)-6-(dimethylamino)pyrimidin-4-yl)propanoate: Methyl 2-(benzyloxycarbonylamino)-3-(2-((E)-3-tert-butoxy-3-oxoprop-1-enyl)-6-(dimethylamino)pyrimidin-4-yl)acrylate (2.0 g, 4.14 mmol) was suspended in MeOH (50 mL), and [S,S] Et DuPhos Rh[I] (0.150 g, 0.207 mmol) was added. The mixture was purged with N₂ and then placed under 55 psi of H₂ for 22 hrs. The suspension changed to clear solution after 3 hrs. It was concentrated and dried under vacuum to give the desired product (2.017 g, 4.14 mmol, 100% yield). MS (ESI) m/z: 487.3 (M+H)⁺.

III-30F. (S)-2-(Benzyloxycarbonylamino)-3-(2-(3-tert-butoxy-3-oxopropyl)-6-(dimethylamino)pyrimidin-4-yl)

propanoic acid: (S)-Methyl 2-(benzyloxycarbonylamino)-3-(2-(3-tert-butoxy-3-oxopropyl)-6-(dimethylamino)pyrimidin-4-yl)propanoate (2.014 g, 4.14 mmol) was dissolved in THF (15 mL). A solution of lithium hydroxide (0.218 g, 9.11 mmol) in water (5.00 mL) was added. The mixture was stirred at RT under argon for 1.5 h. To the reaction mixture was added 1N HCl to adjust the pH to ~7. The THF was removed and it was extracted with EtOAc. The combined organic mixture was dried over sodium sulfate, concentrated, and dried under vacuum to give the desired product (2.1 g, 3.93 mmol, 95% yield) as a yellow foam. MS (ESI) m/z: 473.3 $(M+H)^+$.

III-30G. (S)-2-(2-Bromo-4-(methoxycarbonylamino)phenyl)-2-oxoethyl 2-(benzyloxycarbonylamino)-3-(2-(3-tert-butoxy-3-oxopropyl)-6-(dimethylamino)pyrimidin-4-yl)propanoate: To a clear solution of (S)-2-(benzyloxycarbonylamino)-3-(2-(3-tert-butoxy-3-oxopropyl)-6-(dimethylamino)pyrimidin-4-yl)propanoic acid (2.1 g, 4.00 mmol) in DMF (16.00 ml) was added $KHCO_3$ (0.521 g, 5.20 mmol) and water (0.2 mL). The reaction mixture was stirred for 20~30 min at RT and then cooled to 0° C. A solution of methyl 3-bromo-4-(2-bromoacetyl)phenylcarbamate (1.614 g, 4.60 mmol) in DMF (3 mL) was added dropwise and the mixture was allowed to warm to RT over 20 min. The reaction was stirred at RT for 80 min, and ice-water was added to give a white suspension. The mixture was warmed to RT, and then extracted with EtOAc. The organic layer was washed with water and brine, dried over sodium sulfate, filtered, concentrated, and dried under vacuum to give the desired product (3.6 g, 3.88 mmol, 97% yield) as a yellow foam. MS (ESI) m/z: 742.4 $(M+H)^+$, 744.4 $(M+2+H)^+$.

III-30H. (S)-tert-Butyl 3-(4-(2-(benzyloxycarbonylamino)-2-(4-(2-bromo-4-(methoxycarbonylamino)phenyl)-1H-imidazol-2-yl)ethyl)-6-(dimethylamino)pyrimidin-2-yl)propanoate: To the clear, yellow solution of the product from part III-30G (3.6 g, 3.88 mmol) in toluene (50 mL) was added ammonium acetate (8.97 g, 116 mmol). The reaction mixture was heated to reflux for 4 h. The reaction was cooled to RT, diluted with EtOAc (500 mL) and then washed with saturated sodium bicarbonate and brine. It was dried over sodium sulfate, filtered, and concentrated to give a brown residue. Purification by normal phase chromatography afforded the desired product (0.97 g, 34.6%) as yellow foam. MS (ESI) m/z: 722.4 $(M+H)^+$, 724.4 $(M+2+H)^+$.

III-30I. (S)-tert-Butyl 3-(4-(2-(benzyloxycarbonylamino)-2-(4-(2-bromo-4-(methoxycarbonylamino)phenyl)-1-((2-(trimethylsilyl)ethoxy)methyl)-1H-imidazol-2-yl)ethyl)-6-(dimethylamino)pyrimidin-2-yl)propanoate: (S)-tert-Butyl 3-(4-(2-(benzyloxycarbonylamino)-2-(4-(2-bromo-4-(methoxycarbonylamino)phenyl)-1H-imidazol-2-yl)ethyl)-6-(dimethylamino)pyrimidin-2-yl)propanoate (610 mg, 0.844 mmol) was dissolved in THF (7035 µl) and cooled to 0° C. To the reaction was added N,N-dicyclohexylmethylamine (221 µl, 1.013 mmol) followed by dropwise (over 5 min) addition of SEM-Cl (284 µl, 1.604 mmol). The reaction mixture was allowed warm to RT and stirred at RT for 70 min. It was quenched with water, and concentrated to remove the THF. The residue was dissolved in ethyl acetate and washed with aqueous sodium bicarbonate, water, and then brine. The organic layer was dried over sodium sulfate, concentrated, and dried under vacuum to give the desired product (0.85 g, 118% yield) as a yellow viscous oil. MS (ESI) m/z: 854.5 $(M+H)^+$.

III-30J. (S)-tert-Butyl 3-(4-(2-(4-(2-amino-4-(methoxycarbonylamino)phenyl)-1-((2-(trimethylsilyl)ethoxy)methyl)-1H-imidazol-2-yl)-2-(benzyloxycarbonylamino)ethyl)-6-(dimethylamino)pyrimidin-2-yl)propanoate, 2 TFA salt: (S)-tert-Butyl 3-(4-(2-(benzyloxycarbonylamino)-2-(4-(2-bromo-4-(methoxycarbonylamino)phenyl)-1-((2-(trimethylsilyl)ethoxy)methyl)-1H-imidazol-2-yl)ethyl)-6-(dimethylamino)pyrimidin-2-yl)propanoate (72 mg, 0.084 mmol) was dissolved in DMSO (1 ml). L-Proline (5.83 mg, 0.051 mmol), Copper(I) iodide (4.82 mg, 0.025 mmol), and potassium carbonate (35.0 mg, 0.253 mmol) were added. The mixture was purged with argon for a few minutes and ammonium hydroxide (9.86 µl, 0.253 mmol) was added. The mixture was sealed and heated at 70° C. in an oil-bath for 3 h. The product was purified by reverse phase chromatography (17.17 mg, 20% yield) as a brown oil. MS (ESI) m/z: 789.7 $(M+H)^+$.

III-30K. (S)-3-(4-(2-(4-(2-Amino-4-(methoxycarbonylamino)phenyl)-1-((2-(trimethylsilyl)ethoxy)methyl)-1H-imidazol-2-yl)-2-(benzyloxycarbonylamino)ethyl)-6-(dimethylamino)pyrimidin-2-yl)propanoic acid, 2 TFA salt: (S)-tert-Butyl 3-(4-(2-(4-(2-amino-4-(methoxycarbonylamino)phenyl)-1-((2-(trimethylsilyl)ethoxy)methyl)-1H-imidazol-2-yl)-2-(benzyloxycarbonylamino)ethyl)-6-(dimethylamino)pyrimidin-2-yl)propanoate, 2 TFA (120 mg, 0.118 mmol) and L-cysteine (71.5 mg, 0.590 mmol) were dissolved in DCM (5 ml)/TFA (1.667 ml). The mixture was stirred at RT under Ar for 1 h. the mixture was concentrated, and purified by reverse phase chromatography (65 mg, 57.3% yield) as a light brown oil. MS (ESI) m/z: 733.6 $(M+H)^+$.

III-30L. Methyl N-[(3S)-3-[(2E)-3-[5-chloro-2-(1H-1,2,3,4-tetrazol-1-yl)phenyl]prop-2-enamido]-20-(dimethylamino)-15-oxo-5,14,19,22,23-pentaazatetracyclo[16.3.1.1$^{4,7}$.0$^{8,13}$]tricosa-1(22),4(23),6,8,10,12,18,20-octaen-11-yl]carbamate: To a solution of BOP (74.8 mg, 0.169 mmol) and DMAP (34.7 mg, 0.284 mmol) in DCM (25 mL) and DMF (2.5 mL) at RT was added a solution of (S)-3-(4-(2-(4-(2-amino-4-(methoxycarbonylamino)phenyl)-1-((2-(trimethylsilyl)ethoxy)methyl)-1H-imidazol-2-yl)-2-(benzyloxycarbonylamino)ethyl)-6-(dimethylamino)pyrimidin-2-yl)propanoic acid, 2 TFA (65 mg, 0.068 mmol) and DIEA (0.083 mL, 0.473 mmol) in DMF (2 mL) via a syringe pump over 3.5 h. The mixture was stirred at RT for 60 min. It was concentrated to remove DCM. The residue was partitioned between EtOAc/water. The two layers were separated. The organic layer was washed with water, concentrated, and purified by reverse phase chromatography (25 mg, 44.6% yield) as a white solid. MS (ESI) m/z: 715.6 $(M+H)^+$.

III-30M. Methyl N-[(3S)-3-amino-20-(dimethylamino)-15-oxo-5-{[2-(trimethylsilyl)ethoxy]methyl}-5,14,19,22,23-pentaazatetracyclo[16.3.1.1$^{4,7}$.0$^{8,13}$]tricosa-1(22),4(23),6,8,10,12,18,20-octaen-11-yl]carbamate: The product from part III-30L (20 mg, 0.024 mmol) was dissolved in MeOH (3 mL). Catalytic amount of Pd 10% activated carbon (3 mg) was added. The mixture was placed under a balloon of $H_2$ for 70 min. It was filtered to remove the catalyst. The filtrate was concentrated and dried under vacuum to give the desired product (14.71 mg, 74.6% yield) as a solid. MS (ESI) m/z: 581.5 $(M+H)^+$.

III-30N. Methyl N-[(3S)-3-amino-20-(dimethylamino)-15-oxo-5-{[2-(trimethylsilyl)ethoxy]methyl}-5,14,19,22,23-pentaazatetracyclo[16.3.1.1^{4,7}.0^{8,13}]tricosa-1(22),4(23),6,8,10,12,18,20-octaen-11-yl]carbamate: The mixture of the product from part III-30M (10 mg, 0.017 mmol) and HCl (0.6 mL, 2.400 mmol) (4M in 1,4-dioxane) in a sealed tube was heated at 65° C. for 1 h, and then cooled to RT. The suspension was dissolved in MeOH. It was concentrated, and dried under vacuum to give the desired product (9.6 mg, 100% yield) as an off-white solid. MS (ESI) m/z: 451.4 (M+H)+.

Example III-30: To a solution of the product from part III-30N (9.52 mg, 17 mmol) in DMF (1 mL) was added (E)-2,5-dioxopyrrolidin-1-yl 3-(5-chloro-2-(1H-tetrazol-1-yl)phenyl)acrylate (5.91 mg, 17 mmol) at RT, and then added DIPEA (0.036 mL, 0.204 mmol) dropwise at 0-10° C. The cooling-bath was removed after 10 min, and reaction mixture was stirred at RT under argon for 2 h. The crude product was purified by reverse phase chromatography (7.0 mg, 45.0% yield) as a white solid. $^1$H NMR (400 MHz, CD$_3$OD) δ ppm 9.56 (s, 1 H) 8.03 (d, J=2.01 Hz, 1H) 7.68-7.77 (m, 2 H) 7.58-7.67 (m, 1 H) 7.32-7.42 (m, 3 H) 7.21 (d, J=15.56 Hz, 1 H) 6.82-6.92 (m, 2 H) 5.51-5.62 (m, 1 H) 3.76 (s, 3 H) 3.51-3.62 (m, 1 H) 3.22-3.31 (m, 7 H) 3.01-3.13 (m, 2 H) 2.72-2.94 (m, 2 H). MS (ESI) m/z: 683.5 (M+H)+. Analytical HPLC: RT=4.36 min.

TABLE III-3

Examples III-22 to III-30:

| Ex. # | R | R$^3$ | R$^{6a}$ | R$^{7a}$ | LCMS [M + H]+ | HPLC RT (min.) |
|---|---|---|---|---|---|---|
| III-22 | (1-(4-chloro-2-((E)-3-methylbut-1-en-1-yl)phenyl)-1H-tetrazol-5-yl) | H | NHCO$_2$Me | Me | 654.3 | 4.31 |
| III-23 (S) | (1-(4-chloro-2-((E)-3-methylbut-1-en-1-yl)phenyl)-1H-tetrazol-5-yl) | H | NHCO$_2$Me | Me | 654.3 | 4.36 |
| III-24 (S) | (2,6-difluoro-4-methylphenyl, with methyl branch) | H | NHCO$_2$Me | Me | 576.3 | 4.37 |
| III-25 (S) | (2,6-difluoro-4-methylphenyl, with methyl branch) | Cl | NHCO$_2$Me | Me | 610.3 | 5.10 |

TABLE III-3-continued
Examples III-22 to III-30:
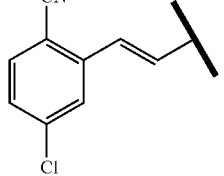
| Ex. # | R | $R^3$ | $R^{6a}$ | $R^{7a}$ | LCMS [M + H]⁺ | HPLC RT (min.) |
|---|---|---|---|---|---|---|
| III-26 (S) | 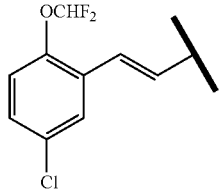 | Cl | NHCO₂Me | Me | 645.3 | 5.82 |
| III-27 (S) | 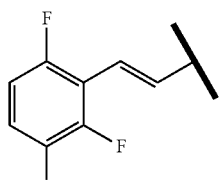 | Cl | NHCO₂Me | Me | 686.3 | 7.05 |
| III-28 (S) | 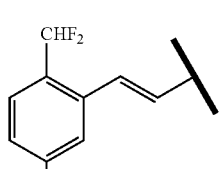 | Cl | NHCO₂Me | Me | 656.3 | 6.90 |
| III-29 (S) | 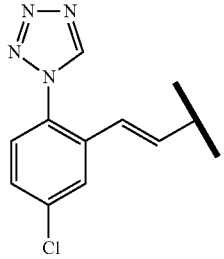 | Cl | NHCO₂Me | Me | 670.3 | 6.91 |
| III-30 (S) |  | H | NHCO₂Me | N(Me)₂ | 683.5 | 4.36 |

III-31

Methyl N-{3-[(2E)-3-[5-chloro-2-(1H-1,2,3,4-tetra-zol-1-yl)phenyl]prop-2-enamido]-19-fluoro-15-oxo-23-oxa-5,14,22-triazatetracyclo[16.3.1.1^{4,7}.0^{8,13}]tricosa-1(22),4,6,8,10,12,18,20-octaen-11-yl}carbamate

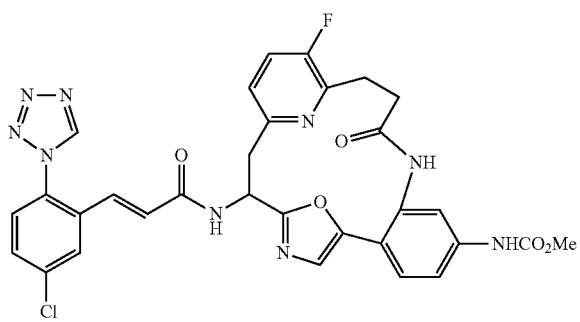

III-31A. 2-Amino-1-(2-bromo-4-nitrophenyl)ethanone, HCl salt: To a solution of 2-bromo-1-(2-bromo-4-nitrophenyl)ethanone (1.12 g, 3.47 mmol) in acetonitrile (15 mL) was added sodium diformylamide (0.396 g, 4.16 mmol) at RT. The reaction suspension was stirred under argon at RT for 2 hrs. Then the reaction was warmed up and filtered. Solid was washed with warm acetonitrile. Solvent was removed from filtrate to give a dark tar. LC-MS (ESI) m/z: 286.9 (M+H)$^+$. To the above obtained product was added 25 mL 4N HCl (aq.) solution and the mixture was heated up to reflux. After stirring for 1 hr, the reaction was allowed to stir at RT over night. Solvent was removed to give a yellow solid, which was used without further purification. LC-MS (ESI) m/z: 258.9/261.0 (M+H)$^+$.

III-31B. Methyl 3-(6-(3-(2-(2-bromo-5-nitrophenyl)-2-oxoethylamino)-2-(tert-butoxycarbonylamino)-3-oxopropyl)-3-fluoropyridin-2-yl)propanoate: To a solution of 2-(tert-butoxycarbonylamino)-3-(5-fluoro-6-(3-methoxy-3-oxopropyl)pyridin-2-yl)propanoic acid (393 mg, 1.061 mmol) in DMF (10 mL) were added EDC (264 mg, 1.379 mmol) and HOBt (211 mg, 1.379 mmol), DIEA (0.185 mL mg, 1.061 mmol). After stirred at RT for 5 min, a solution of III-31A (314 mg, 1.061 mmol) and DIEA (0.185 mL mg, 1.061 mmol) (prepared by adding DIEA into amino ketone solution in 3 mL DMF, which turned dark immediately upon addition of DIEA) was added at RT. The dark solution was stirred under argon at RT for 1 h. The reaction mixture was diluted with EtOAc, washed with 1M HCl (1×15 mL) and brine (2×15 mL). The organic phase was dried over sodium sulfate, filtered and concentrated. The crude product was purified by normal phase chromatography to give III-31B 145 mg (22.5% yield). LC-MS (ESI) m/z: 611.0/613.0 (M+H)$^+$.

III-31C. Methyl 3-(6-(2-(5-(2-bromo-4-nitrophenyl)oxazol-2-yl)-2-(tert-butoxycarbonylamino)ethyl)-3-fluoropyridin-2-yl)propanoate: To a solution of III-31B (145 mg, 0.237 mmol) in DCM (8 mL) was added Burgess reagent (283 mg, 1.186 mmol) at RT. The reaction was stirred under argon at RT and turned dark red. After stirred over night, the reaction was heated up to reflux (~45° C. oil bath) for 2 hrs. The reaction was cooled to RT. The reaction mixture was diluted with DCM, washed with H$_2$O and brine.

The organic phase was dried over sodium sulfate, filtered and concentrated. The crude product was purified by normal phase chromatography to give III-31C 64 mg (46% yield) LC-MS (ESI) m/z: 593.0/594.9 (M+H)$^+$.

III-31D. Methyl 3-(6-(2-(5-(2-bromo-4-(methoxycarbonylamino)phenyl)oxazol-2-yl)-2-(tert-butoxycarbonylamino)ethyl)-3-fluoropyridin-2-yl)propanoate: To a solution of III-31C (64 mg, 0.108 mmol) in MeOH (5 mL) were added NH$_4$Cl (57.7 mg, 1.079 mmol) and zinc dust (70.5 mg, 1.079 mmol) at RT. The reaction was stirred under argon at RT for 2.5 hrs. Solid was filtered and solvent was removed from filtrate to give a white solid. LC-MS (ESI) m/z: 563.0/565.0 (M+H)$^+$. Thus obtained solid was dissolved in DCM (10 mL), to which were added pyridine (0.044 mL, 0.539 mmol) and methyl chloroformate (8.35 μL, 0.108 mmol) at 0° C. After stirred for 15 min, water was added to quench the reaction. The reaction mixture was diluted with DCM, washed with 1M HCl and brine. The organic phase was dried over sodium sulfate, filtered and concentrated. The crude product was purified by normal phase chromatography to give III-31D 63.6 mg (95% yield). LC-MS (ESI) m/z: 621.0/623.0 (M+H)$^+$.

III-31E. Methyl 3-(6-(2-(5-(2-amino-4-(methoxycarbonylamino)phenyl)oxazol-2-yl)-2-(tert-butoxycarbonylamino)ethyl)-3-fluoropyridin-2-yl)propanoate: To a solution of III-31D (63 mg, 0.101 mmol) in DMSO (1.5 mL) were added NaN$_3$ (19.77 mg, 0.304 mmol), L-proline (5.84 mg, 0.051 mmol), CuI (19.31 mg, 0.101 mmol) and K$_2$CO$_3$ (42.0 mg, 0.304 mmol) at RT. The reaction was stirred under argon at 90° C. After 11 hrs. The reaction was cooled to RT. The reaction mixture was diluted with EtOAc and water Ammonium hydroxide solution was added to make the aqueous phase clear. Organic phase was separated and further washed with brine (2×). The organic phase was dried over sodium sulfate, filtered and concentrated to give a solid mixture of desired product and the corresponding azide intermediate in about 1:1 ratio 49 mg. LC-MS (ESI) m/z: 558.1 (M+H)$^+$.

III-31F. 3-(6-(2-(5-(2-Amino-4-(methoxycarbonylamino)phenyl)oxazol-2-yl)-2-(tert-butoxycarbonylamino)ethyl)-3-fluoropyridin-2-yl)propanoic acid, TFA salt:

To a solution of III-32E in THF/H$_2$O was added LiOH (1.074 mg, 0.045 mmol) at 0° C. The reaction was stirred under argon at 0° C. for 2 hrs. The reaction mixture was neutralized with 1.0M HCl and most solvent was removed. The crude product was purified by reverse phase chromatography to give III-31F 25 mg (85%). LC-MS (ESI) m/z: 544.1 (M+H)$^+$.

III-31G. tert-Butyl N-{19-fluoro-11-[(methoxycarbonyl)amino]-15-oxo-23-oxa-5,14,22-triazatetracyclo[16.3.1.1$^{4,7}$.0$^{8,13}$]tricosa-1(22),4,6,8,10,12,18,20-octaen-3-yl}carbamate: To a solution of DMAP (11.24 mg, 0.092 mmol) and BOP (61.0 mg, 0.138 mmol) in DCM (40 mL) was added a solution of III-31F (25 mg, 0.046 mmol) and DIEA (0.040 mL, 0.230 mmol) in DMF (2 mL) at RT through a syringe pump. After stirring over night, solvent was removed. The crude product was purified by reverse phase chromatography to give III-31G 5.5 mg (23%). LC-MS (ESI) m/z: 526.1 (M+H)$^+$.

Example III-31: To a solution of III-31G (5.5 mg, 10.47 μmol) in DCM (1.5 mL) was added TFA (0.5 mL, 6.49 mmol) at RT. The reaction was stirred under argon at RT for 1 hr. Solvent was removed and residue was dried in vacuo. Thus obtained intermediate was dissolved in DMF (1 mL), to which were added (E)-2,5-dioxopyrrolidin-1-yl 3-(5-chloro-2-(1H-tetrazol-1-yl)phenyl)acrylate (3.64 mg, 10.47 μmol) and DIEA (0.05 mL, 0.286 mmol). The reaction was stirred at RT for 12 hrs. The crude product was purified by reverse phase chromatography to give III-31 as a white solid. $^1$H NMR (400 MHz, CD$_3$OD) δ ppm 9.43 (1 H, s), 7.92 (1 H, d, J=2.26 Hz), 7.58 (1 H, dd, J=8.41, 2.13 Hz), 7.46-7.53 (2 H, m), 7.32 (1 H, d, J=8.28 Hz), 7.27 (1 H, dd, J=8.28, 1.76 Hz), 7.20 (1 H, t, J=8.91 Hz), 7.10 (1 H, d, J=15.81 Hz), 7.00 (1 H, s), 6.97 (1 H, dd, J=8.66, 3.39 Hz), 6.69 (1 H, d, J=15.56 Hz), 5.86 (1 H, dd, J=10.16, 4.89 Hz), 5.80-5.93 (1 H, m), 3.66 (3 H, s), 3.37-3.44 (2 H, m), 3.29-3.35 (2 H, m), 3.16-3.19 (1 H, m), 2.78-2.85 (1 H, m). $^{19}$F NMR (376 MHz, CD$_3$OD) δ ppm)-77.21 (TFA, s), −130.84 (1 F, s). LC-MS (ESI) m/z: 658.1 (M+H)$^+$. Analytical HPLC: RT=7.681 min.

TABLE III-4

Examples III-31 to III-37:

| Ex. # | Structure | LCMS [M + H]+ | HPLC RT (min) |
|---|---|---|---|
| III-31 | 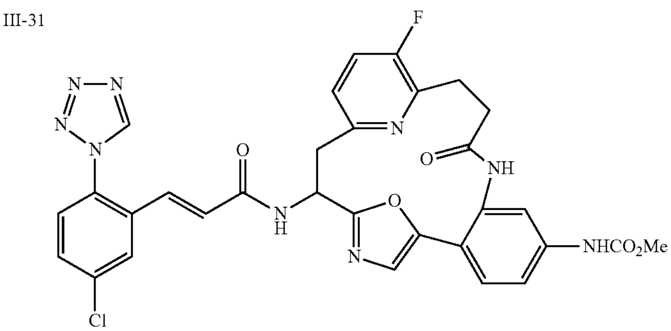 | 658.1 | 7.68 |
| III-32 | 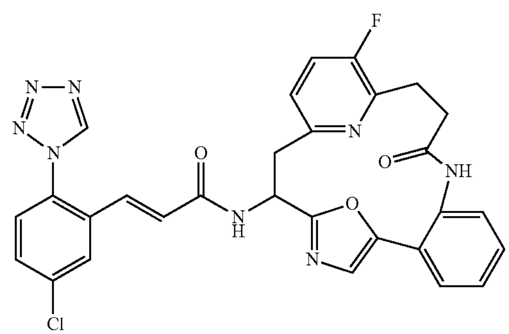 [SMILES: O=C(/C=C/c1cc(Cl)ccc1-n1cnnn1)NC1Cc2ccc(F)c(n2)CCC(=O)Nc2ccccc2C2=CN=C1O2] | 585.0 | 7.85 |
| III-33 | 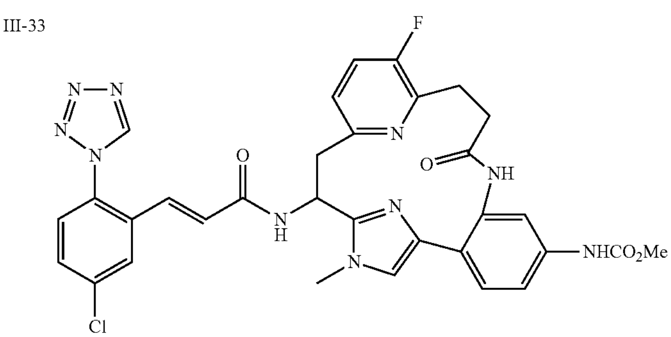 | 671.3 | 5.03 |
| III-34 | 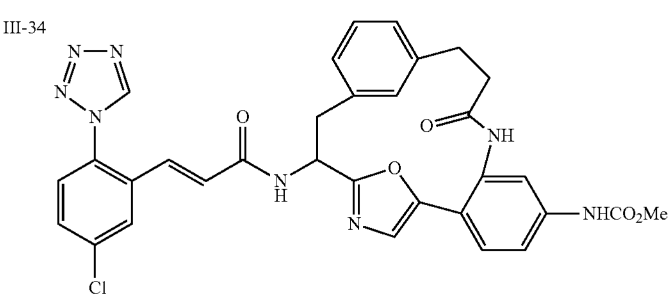 | 640.2 | 5.35 |

TABLE III-4-continued

Examples III-31 to III-37:

| Ex. # | Structure | LCMS [M + H]+ | HPLC RT (min) |
|---|---|---|---|
| III-35 | 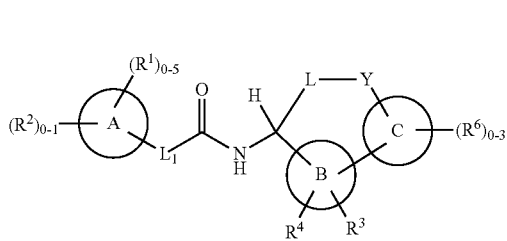 | 667.3 | 5.27 |
| III-36 | 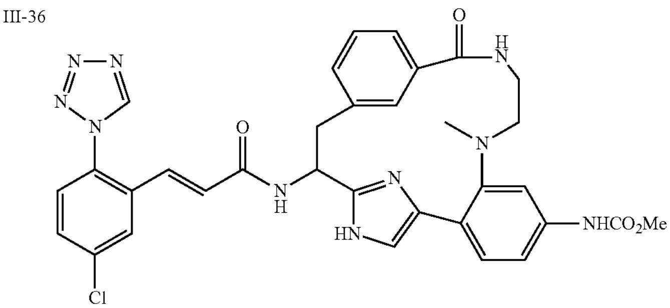 | 667.3 | 5.37 |
| III-37 | 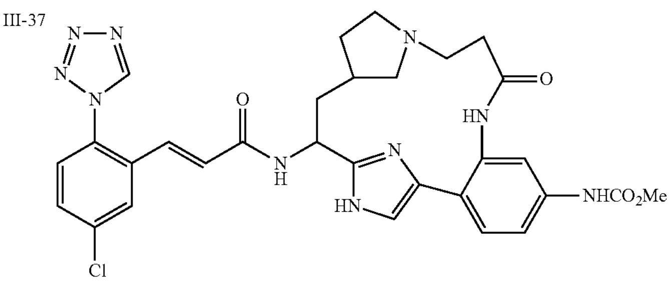 | 632.2 | 3.94 |

What is claimed is:

1. A compound of Formula (I):

(I)

or a stereoisomer, a tautomer, a pharmaceutically acceptable salt thereof, wherein:
  ring A is phenyl;
  ring B is imidazolyl;
  ring C is phenyl;
  $L_1$ is independently selected from the group consisting of:
    a bond, —CHR$^5$—, —CHR$^5$CHR$^5$—, —CR$^5$═CR$^5$—, —C≡C—, —OCH$_2$—, —CHR$^5$NH—, —CH$_2$O—, —SCH$_2$—, —SO$_2$CH$_2$—, —CH$_2$NH—, and —CR$^5$R$^5$—;
  L is independently selected from the group consisting of:
    —C$_{1-6}$ alkylene-(aryl)-C$_{0-4}$ alkylene-, and —C$_{1-6}$ alkylene-(5- to 6-membered heterocycle)-C$_{0-4}$ alkylene-; wherein said heterocycle comprises: carbon atoms and 1-4 heteroatoms selected from N, NH, N(C$_{1-4}$ alkyl), O, and S(O)p; wherein said alkylene is substituted with 0-2 R$^7$ and optionally one or more of the carbon atoms of said alkylene may be replaced by O, S, NH, N(C$_{1-4}$ alkyl), CO, CONH, NHCO, OCONH, NHCO$_2$, SO$_2$NH, NHSO$_2$, CON(C$_{1-4}$ alkyl), or N(C$_{1-4}$ alkyl)CO; wherein said aryl and heterocycle are substituted with 0-2 R$^{7a}$;
  Y is independently selected from the group consisting of: CH$_2$, CH(C$_{1-4}$ alkyl), C(C$_{1-4}$ alkyl)$_2$, O, S, NH, N(C$_{1-4}$ alkyl), N(CO$_2$(C$_{1-4}$ alkyl)), —CONH—, —NHCO—, —CONHCH$_2$—, —CON(C$_{1-4}$ alkyl)CH$_2$—, —OCONH—, —OCON(C$_{1-4}$ alkyl)-, —NHCONH—, —SO$_2$NH—, —NHCO$_2$—, and —NHSO$_2$—;
  R$^1$ is, independently at each occurrence, selected from the group consisting of: halogen, C$_{1-6}$ alkyl, C$_{1-4}$ alkoxy, C$_{1-4}$ alkylthio, OH, C$_{1-4}$haloalkyl, OCH$_2$F, OCHF$_2$, OCF$_3$, CN, NH$_2$, —NH(C$_{1-4}$ alkyl), —N(C$_{1-4}$ alkyl)$_2$, —CO$_2$ $_{(C1-4}$ alkyl), —CO(C$_{1-4}$ alkyl), —CH$_2$NH$_2$, —CONH$_2$, —CONH(C$_{1-4}$ alkyl), —CH$_2$NHCO$_2$(C$_{1-4}$ alkyl), —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, and phenyl substituted with 0-2 R$^a$;

R$^2$ is independently a 5- to 7-membered heterocycle comprising carbon atoms and 1-4 heteroatoms selected from N, NH, N(C$_{1-4}$ alkyl), O, and S(O)p, wherein said heterocycle is substituted with 0-2 R$^{2a}$;

R$^{2a}$ is, independently at each occurrence, selected from the group consisting of: halogen, C$_{1-4}$ alkyl, —CH$_2$OH, C$_{1-4}$ alkoxy, OH, CF$_3$, OCF$_3$, CN, NH$_2$, CO$_2$H, CO$_2$(C$_{1-4}$ alkyl), COC$_{1-4}$ alkyl, —CONH$_2$, —CONH(C$_{1-4}$ alkyl), —CON(C$_{1-4}$ alkyl)$_2$, —SO$_2$(C$_{1-4}$ alkyl), —SO$_2$NH$_2$, —SO$_2$NH(C$_{1-4}$ alkyl), and —SO$_2$N(C$_{1-4}$ alkyl)$_2$;

R$^3$ is independently selected from the group consisting of: H, halogen, OH, NH$_2$, CN, CF$_3$, C$_{1-4}$ alkyl, C$_{1-4}$ alkoxy, —CH$_2$OH, CO$_2$H, CO$_2$(C$_{1-4}$ alkyl), —C(O)NH$_2$, —C(O)NH(C$_{1-4}$ alkyl), —C(O)N(C$_{1-4}$ alkyl)$_2$, —CH$_2$CO$_2$H, and C$_{3-6}$ cycloalkyl;

R$^4$ is independently selected from the group consisting of: H, and C$_{1-4}$ alkyl;

R$^5$ is, independently at each occurrence, selected from the group consisting of: H, halogen, OH, and C$_{1-4}$ alkyl;

R$^6$ is, independently at each occurrence, selected from the group consisting of: halogen, C$_{1-4}$ alkyl, CN, OH, CF$_3$, CO$_2$H, CO$_2$(C$_{1-4}$ alkyl), —CH$_2$CO$_2$H, —(CH$_2$)$_2$CO$_2$H, —CH$_2$CO$_2$(C$_{1-4}$ alkyl), —(CH$_2$)$_2$CO$_2$(C$_{1-4}$ alkyl), NH$_2$, NH(C$_{1-4}$alkyl), —CH$_2$NH$_2$, —NHCO(C$_{1-4}$ alkyl), —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$CH$_2$CH(C$_{1-4}$ alkyl)O(C$_{1-4}$ alkyl), —NHCO$_2$(CH$_2$)$_2$OH, —NHCO$_2$(CH$_2$)$_2$NH$_2$, —NHCO$_2$CH$_2$CO$_2$H, —CH$_2$NHCO$_2$(C$_{1-4}$ alkyl), —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$NH(CH$_2$)$_2$OH, —SO$_2$NH(CH$_2$)$_2$O(C$_{1-4}$ alkyl), —C(O)NH(CH$_2$)$_2$O(C$_{1-4}$alkyl), —CONH$_2$, —CONH(C$_{1-4}$ alkyl), —CON(C$_{1-4}$ alkyl)$_2$, —CH$_2$CONH$_2$, and

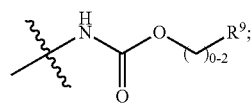

R$^7$ and R$^{7a}$ are, independently at each occurrence, selected from the group consisting of: halogen, OH, NH$_2$, CH$_2$NH$_2$, CH$_2$F, CHF$_2$, CF$_3$, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$O(CH$_2$)$_{1-4}$O(C$_{1-4}$ alkyl), CO$_2$H, CO$_2$(C$_{1-4}$ alkyl), CH$_2$CO$_2$H, CH$_2$CO$_2$(C$_{1-4}$ alkyl), CONH$_2$, CONH(C$_{1-4}$ alkyl), CON(C$_{1-4}$ alkyl)$_2$, —OCO(C$_{1-4}$ alkyl), —CON(C$_{1-4}$ alkyl)(CH$_2$)$_2$N(C$_{1-4}$ alkyl)$_2$, C$_{1-4}$ alkyl, —(CO)$_{0-1}$(CH$_2$)$_{0-1}$ aryl, and —(CO)$_{0-1}$(CH$_2$)$_{0-1}$-(4- to 6-membered heterocycle comprising carbon atoms and 1-4 heteroatoms selected from N, NH, N(C$_{1-4}$ alkyl), O, and S(O)p; wherein said aryl and heterocycle are substituted with 0-2 R$^8$;

R$^8$ is, independently at each occurrence, selected from the group consisting of: halogen, OH, CHF$_2$, CF$_3$, C$_{1-4}$ alkoxy, CH$_2$OH, CO$_2$H, CO$_2$(C$_{1-4}$ alkyl), CONH$_2$, and C$_{1-4}$ alkyl;

R$^9$ is a 4- to 6-membered heterocycle comprising: carbon atoms and 14 heteroatoms selected from N, NH, N(C$_{1-4}$ alkyl), N(CO$_2$(C$_{1-4}$ alkyl)), O, and S(O)p;

R$^a$ is, independently at each occurrence, selected from the group consisting of: halogen, OH, CF$_3$, C$_{1-4}$ alkoxy, and C$_{1-4}$ alkyl;

p is, independently at each occurrence, selected from the group consisting of: 0, 1, and 2.

2. The compound of claim 1, or a stereoisomer, a tautomer, a pharmaceutically acceptable salt thereof, wherein:
ring A is phenyl;

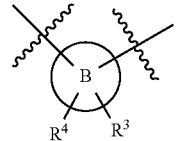

is

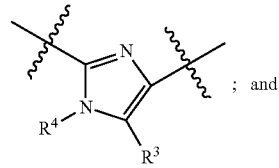
; and

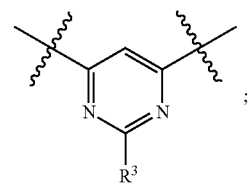
;

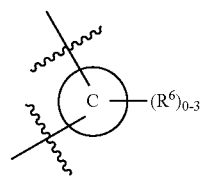

is

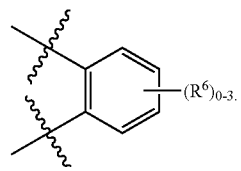

3. A compound of Formula (II):

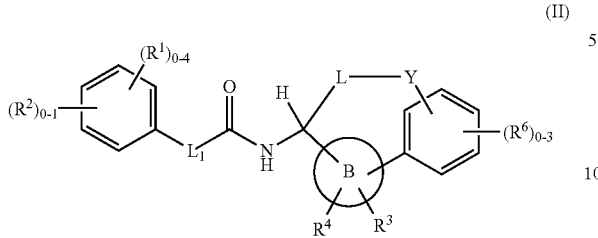

or a stereoisomer, a tautomer, a pharmaceutically acceptable salt thereof, wherein:

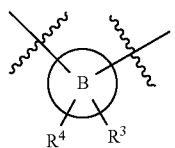

is

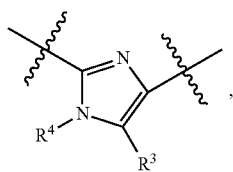

$L_1$ is independently selected from the group consisting of: a bond, —$CHR^5CHR^5$—, —$CR^5$=$CHR^5$—, —C≡C—, —$OCH_2$—, —$CHR^5NH$—, —$CH_2O$—, —$SCH_2$—, —$SO_2CH_2$—, —$CH_2NH$—, and —$CR^5R^5$—;

L is independently selected from the group consisting of: —$C_{1-6}$ alkylene-(aryl)—$C_{0-4}$ alkylene-, and —$C_{1-6}$ alkylene-(5- to 6-membered heterocycle) -$C_{0-4}$ alkylene-; wherein said heterocycle comprises: carbon atoms and 1-4 heteroatoms selected from N, NH, N($C_{1-4}$ alkyl), O, and S(O)p; wherein said alkylene is substituted with 0-2 $R^7$ and optionally one or more of the carbon atoms of said alkylene may be replaced by O, S, NH, N($C_{1-4}$ alkyl), CO, CONH, NHCO, OCONH, $SO_2NH$, or CON($C_{1-4}$ alkyl); wherein said aryl and heterocycle are substituted with 0-2 $R^{7a}$;

Y is independently selected from the group consisting of: $CH_2$, CH($C_{1-4}$ alkyl), C($C_{1-4}$ alkyl)$_2$, O, S, NH, N($C_{1-4}$ alkyl), N($CO_2$($C_{1-4}$ alkyl)), —CONH—, —NHCO—, —$CONHCH_2$—, —CON($C_{1-4}$ alkyl)$CH_2$—, —OCONH—, —OCON($C_{1-4}$ alkyl)-, —NHCONH—, and —$SO_2NH$—;

$R^1$ is, independently at each occurrence, selected from the group consisting of: halogen, $C_{1-6}$ alkyl, $C_{1-4}$ alkoxy, $C_{1-4}$ alkylthio, OH, $CH_2F$, $CHF_2$, $CF_3$, $OCH_2F$, $OCHF_2$, $OCF_3$, CN, $NH_2$, NH($C_{1-4}$ alkyl), N($C_{1-4}$ alkyl)$_2$, $CO_2$($C_{1-4}$ alkyl), CO($C_{1-4}$ alkyl), —$OCH_2CO_2H$, —$CH_2NH_2$, —$CONH_2$, —CONH($C_{1-4}$ alkyl), —$CH_2NHCO_2$($C_{1-4}$ alkyl), —$SO_2NH_2$, and —C(=NH)$NH_2$;

$R^2$ is independently a 5- to 6-membered heterocycle comprising carbon atoms and 1-4 heteroatoms selected from N, NH, O, and S(O)p, wherein said heterocycle is substituted with 0-2 $R^{2a}$;

$R^{2a}$ is, independently at each occurrence, selected from the group consisting of: halogen, $C_{1-4}$ alkyl, —$CH_2OH$, $C_{1-4}$ alkoxy, OH, $CF_3$, $OCF_3$, CN, $NH_2$, $CO_2H$, $CO_2$($C_{1-4}$ alkyl), $COC_{1-4}$ alkyl, —$CONH_2$, —CONH($C_{1-4}$ alkyl), and —CON($C_{1-4}$ alkyl)$_2$;

$R^3$ is independently selected from the group consisting of: H, halogen, OH, $NH_2$, CN, $CF_3$, $C_{1-4}$ alkyl, $C_{1-4}$ alkoxy, —$CH_2OH$, $CO_2H$, $CO_2$($C_{1-4}$ alkyl), —C(O) $NH_2$, —C(O)NH($C_{1-4}$ alkyl), —C(O)N($C_{1-4}$ alkyl)$_2$, and —$CH_2CO_2H$;

$R^4$ is independently selected from the group consisting of: H and $C_{1-4}$ alkyl;

$R^5$ is, independently at each occurrence, selected from the group consisting of: H, halogen, OH, and $C_{1-4}$ alkyl;

$R^6$ is, independently at each occurrence, selected from the group consisting of: halogen, $C_{1-4}$ alkyl, CN, OH, $CF_3$, $CO_2H$, $CO_2$($C_{1-4}$ alkyl), —$CH_2CO_2H$, —($CH_2$)$_2CO_2H$, —$CH_2CO_2$($C_{1-4}$ alkyl), —($CH_2$)$_2CO_2$($C_{1-4}$ alkyl), $NH_2$, NH($C_{1-4}$alkyl), —$CH_2NH_2$, —NHCO($C_{1-4}$ alkyl), —$NHCO_2$($C_{1-4}$ alkyl), —$NHCO_2$($CH_2$)$_2$O($C_{1-4}$ alkyl), —$NHCO_2$($CH_2$)$_3$O($C_{1-4}$ alkyl), —$NHCO_2CH_2$CH($C_{1-4}$ alkyl)O($C_{1-4}$ alkyl), —$NHCO_2$($CH_2$)$_2$OH, —$NHCO_2$($CH_2$)$_2NH_2$, —$NHCO_2CH_2CO_2H$, —$CH_2NHCO_2$($C_{1-4}$ alkyl), —NHC(O)NH($C_{1-4}$ alkyl), —NHC(O)N($C_{1-4}$ alkyl)$_2$, —$NHSO_2$($C_{1-4}$ alkyl), —$SO_2NH$($CH_2$)$_2OH$, —$SO_2NH$($CH_2$)$_2$O($C_{1-4}$ alkyl), —C(O)NH($CH_2$)$_2$O($C_{1-4}$ alkyl), $CONH_2$, CONH($C_{1-4}$ alkyl), CON($C_{1-4}$ alkyl)$_2$, —$CH_2CONH_2$, and

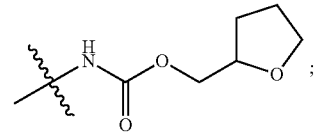 [SMILES: *NC(=O)OCC1CCCO1]

$R^7$ and $R^{7a}$ are, independently at each occurrence, selected from the group consisting of: halogen, OH, $CHF_2$, $CF_3$, N($C_{1-4}$ alkyl)$_2$, $C_{1-4}$ alkoxy, $CH_2OH$, $CH_2O$($C_{1-4}$ alkyl), $CO_2H$, $CO_2$($C_{1-4}$ alkyl), $CH_2CO_2H$, $CH_2CO_2$($C_{1-4}$ alkyl), $CONH_2$, CONH($C_{1-4}$ alkyl), CON($C_{1-4}$ alkyl)$_2$, —OCO ($C_{1-4}$ alkyl), —CON($C_{1-4}$ alkyl )($CH_2$)$_2$N ($C_{1-4}$ alkyl)$_2$, $C_{1-4}$ alkyl), and —(CO)$_{0-1}$-(4- to 6-membered heterocycle comprising carbon atoms and 1-4 heteroatoms selected from N, NH, N($C_{1-4}$ alkyl), O, and S(O)p; wherein said heterocycle is substituted with 0-2 $R^8$;

$R^8$ is, independently at each occurrence, selected from the group consisting of: halogen, OH, $CHF_2$, $CF_3$, $C_{1-4}$ alkoxy, and $C_{1-4}$ alkyl; and p is, independently at each occurrence, selected from the group consisting of: 0, 1, and 2.

4. The compound of claim 3 having Formula (IIb):

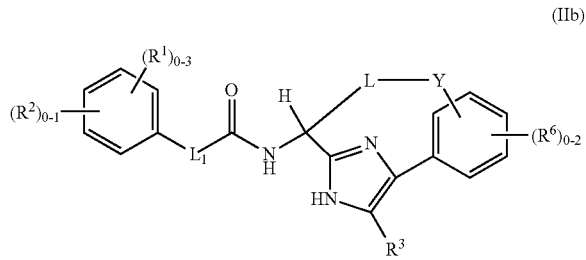

or a stereoisomer, a tautomer, a pharmaceutically acceptable salt thereof.

5. The compound of claim 3 having or Formula (IId):

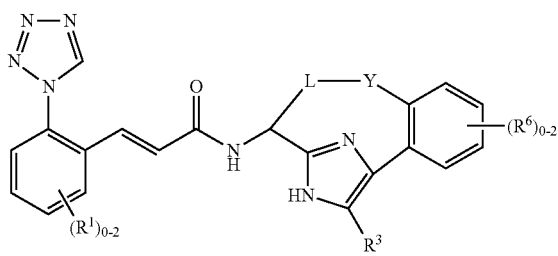

(IId)

or a stereoisomer, a tautomer, a pharmaceutically acceptable salt thereof.

6. The compound of claim 3, having Formula (II), a stereoisomer, a tautomer, a pharmaceutically acceptable salt thereof, wherein:

$L_1$ is independently selected from the group consisting of: a bond, —$CH_2CH_2$—, —CH=CH—, —C(Me)=CH—, —C≡C—, and —$CH_2NH$—;

L is independently selected from the group consisting of: —$(CH_2)_{1-2}$-(phenylene)-$(CH_2)_{0-3}$—, —$CH_2O(CH_2)_{1-4}$-(phenylene)-$(CH_2)_{0-3}$—, —$(CH_2)_{1-2}$-(phenylene)-CONH$(CH_2)_{0-2}$—, —$(CH_2)_{1-2}$-phenylene-CON($C_{1-4}$ alkyl)$(CH_2)_{0-2}$—, —$(CH_2)_{1-2}$-(pyridinylene)-$(CH_2)_{0-3}$—, —$CH_2$-pyrimidinylene-$(CH_2)_{0-3}$—,

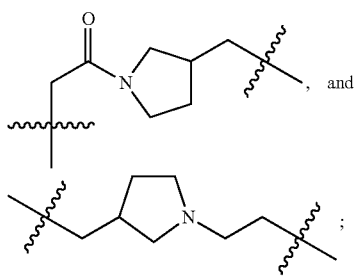

, and

;

wherein each ring moiety is substituted with 0-2 $R^{7a}$;

Y is independently selected from the group consisting of: $CH_2$, CH($C_{1-4}$ alkyl), C($C_{1-4}$ alkyl)$_2$, O, S, NH, N($C_{1-4}$ alkyl), N(CO$_2$($C_{1-4}$ alkyl)), —CONH—, —NHCO—, —CONHCH$_2$—, —CON($C_{1-4}$ alkyl)CH$_2$—, —OCONH—, —NHCONH—, and —SO$_2$NH—;

$R^1$ is, independently at each occurrence, selected from: halogen, CN, OH, CH$_2$F, CHF$_2$, CF$_3$, OCH$_2$F, OCHF$_2$, OCF$_3$, $C_{1-4}$ alkyl, $C_{1-4}$ alkoxy, CO($C_{1-4}$ alkyl), NH$_2$, NH($C_{1-4}$ alkyl), N($C_{1-4}$ alkyl)$_2$, —C(=NH),NH$_2$, —C(O)NH$_2$, —CH$_2$NH$_2$, —CH$_2$NHCO$_2$($C_{1-4}$ alkyl), and —SO$_2$NH$_2$;

$R^3$ is independently selected from the group consisting of: H, halogen, OH, NH$_2$, CN, CF$_3$, $C_{1-4}$ alkyl, $C_{1-4}$ alkoxy, —CH$_2$OH, CO$_2$H, CO$_2$($C_{1-4}$ alkyl), —C(O)NH$_2$, —C(O)NH($C_{1-4}$ alkyl), —C(O)N($C_{1-4}$ alkyl)$_2$, and —CH$_2$CO$_2$H; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —(CH$_2$)$_2$CO$_2$H, —CH$_2$CO$_2$($C_{1-4}$ alkyl), —(CH$_2$)$_2$CO$_2$($C_{1-4}$ alkyl), NH$_2$, —CH$_2$NH$_2$, —NHCO($C_{1-4}$ alkyl), —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$CH$_2$CH($C_{1-4}$ alkyl)O ($C_{1-4}$ alkyl), —NHCO$_2$(CH$_2$)$_2$OH, —NHCO$_2$(CH$_2$)$_2$NH$_2$, —NHCO$_2$CH$_2$CO$_2$H, —CH$_2$NHCO$_2$($C_{1-4}$ alkyl), —NHC(O)NH($C_{1-4}$ alkyl), —NHC(O)N($C_{1-4}$ alkyl)$_2$, —NHSO$_2$($C_{1-4}$ alkyl), —SO$_2$NH(CH$_2$)$_2$OH, —SO$_2$NH (CH$_2$)$_2$O($C_{1-4}$ alkyl), CONH$_2$, CONH($C_{1-4}$ alkyl), CON ($C_{1-4}$ alkyl)$_2$, and

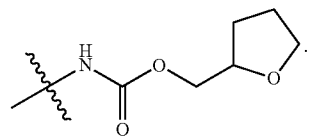

7. The compound of claim 4 having Formula (IIb), or a stereoisomer, a tautomer, a pharmaceutically acceptable salt thereof, wherein:

$L_1$ is independently selected from the group consisting of: a bond, —CH$_2$CH$_2$— and —CH=CH—;

$R^1$ is, independently at each occurrence, selected from the group consisting of: halogen, CN, $C_{1-4}$ alkyl, OH, $C_{1-4}$ alkoxy, CH$_2$F, CHF$_2$, CF$_3$, OCH$_2$F, OCHF$_2$, OCF$_3$, CO($C_{1-4}$ alkyl), NH$_2$, NH($C_{1-4}$ alkyl), N($C_{1-4}$ alkyl)$_2$, —CH$_2$NH$_2$, —CH$_2$NHCO$_2$($C_{1-4}$ alkyl), and —C(=NH),NH$_2$;

$R^3$ is independently selected from the group consisting of: H, halogen, CN, CF$_3$, CO$_2$H, CO$_2$($C_{1-4}$ alkyl), and $C_{1-4}$ alkyl; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —CH$_2$CO$_2$($C_{1-4}$ alkyl), NH$_2$, —CH$_2$NH$_2$, —NHCO($C_{1-4}$ alkyl), —NHCO$_2$($C_{1-4}$ alkyl), —CH$_2$NHCO$_2$($C_{1-4}$ alkyl), —CONH$_2$, —NHCO$_2$(CH$_2$)$_2$OH, —NHCO$_2$(CH$_2$)$_2$O ($C_{1-4}$ alkyl), —NHCO$_2$CH$_2$CO$_2$H, —NHCO$_2$CH$_2$CH ($C_{1-4}$ alkyl)O($C_{1-4}$ alkyl), and

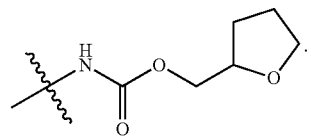

8. The compound of claim 5 having Formula (IId), or a stereoisomer, a tautomer, a pharmaceutically acceptable salt thereof, wherein:

L is independently selected from the group consisting of: —CH$_2$-phenylene-(CH$_2$)$_{0-3}$—, —CH$_2$O(CH$_2$)$_{2-4}$-phenylene-(CH$_2$)$_{0-1}$—, —CH$_2$-phenylene-CONH (CH$_2$)$_{0-2}$—, —CH$_2$-phenylene-CON($C_{1-4}$ alkyl) (CH$_2$)$_{0-2}$—, —CH$_2$-pyridinylene-(CH$_2$)$_{0-3}$—, —CH$_2$-pyrimidinylene-(CH$_2$)$_{0-3}$—,

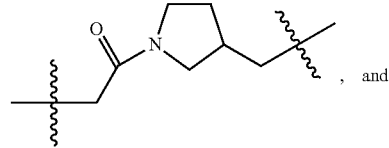

, and

-continued

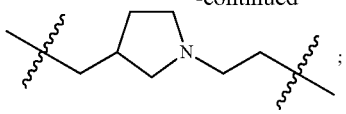

wherein each ring moiety is substituted with 0-1 $R^{7a}$;

Y is independently selected from the group consisting of: $CH_2$, O, NH, $N(C_{1-4}$ alkyl), $N(CO_2(C_{1-4}$ alkyl)), —CONH—, —NHCO—, —CONHCH$_2$—, —CON($C_{1-4}$ alkyl)CH$_2$—, —OCONH—, —NHCONH—, and —SO$_2$NH—; and $L_1$ is independently selected from the group consisting of: a bond and —CH=CH—;

$R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, $NH_2$, $N(C_{1-4}$ alkyl)$_2$, —CH$_2$NH$_2$, —CH$_2$NHCO$_2$($C_{1-4}$ alkyl), and —C(=NH),NH$_2$;

$R^3$ is independently selected from the group consisting of: H, halogen, $C_{1-4}$ alkyl, and CN;

$R^6$ is, independently at each occurrence, selected from the group consisting of: halogen, $NH_2$, $CO_2H$, $CO_2(C_{1-4}$ alkyl), $CONH_2$, $CONH(C_{1-4}$ alkyl), $CON(C_{1-4}$ alkyl)$_2$, —NHCO$_2$($C_{1-4}$ alkyl), —CH$_2$NHCO$_2$($C_{1-4}$ alkyl), —NHCO$_2$CH$_2$CO$_2$H, —NHCO$_2$(CH$_2$)$_2$OH, —NHCO$_2$(CH$_2$)$_2$O($C_{1-4}$ alkyl), —NHCO$_2$CH$_2$CH($C_{1-4}$ alkyl)O($C_{1-4}$ alkyl), and

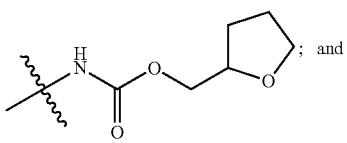; and $R^{7a}$ is independently selected from the group consisting of: halogen, $C_{1-4}$ alkyl, and $N(C_{1-4}$ alkyl)$_2$.

9. A compound of Formula (III) or Formula (IIIa):

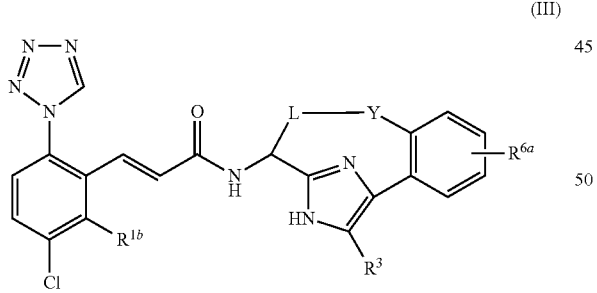

(III)

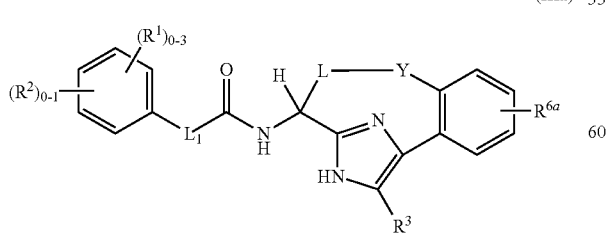

(IIIa)

or a stereoisomer, a tautomer, a pharmaceutically acceptable salt thereof, wherein:

L is independently selected from the group consisting of:

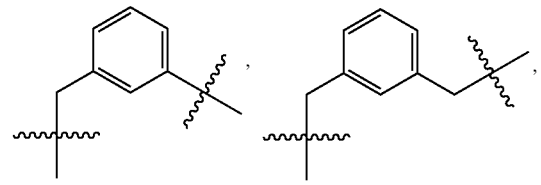

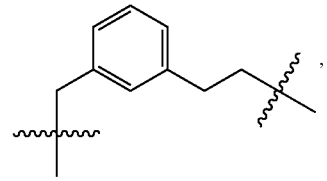

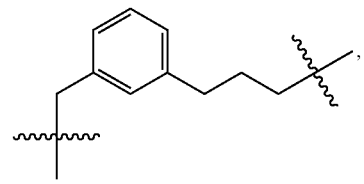

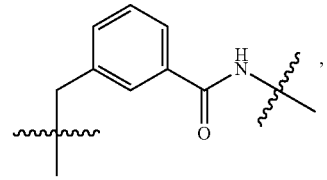

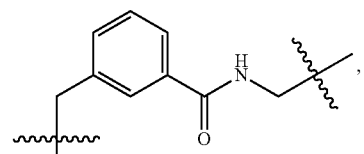

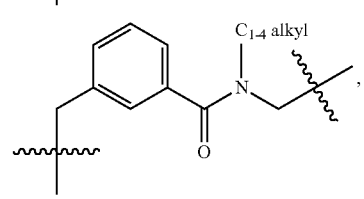

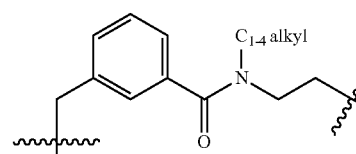

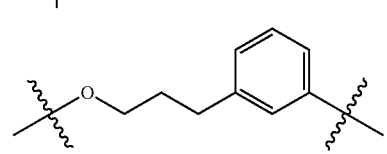

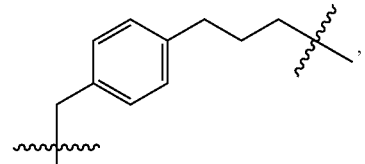

-continued

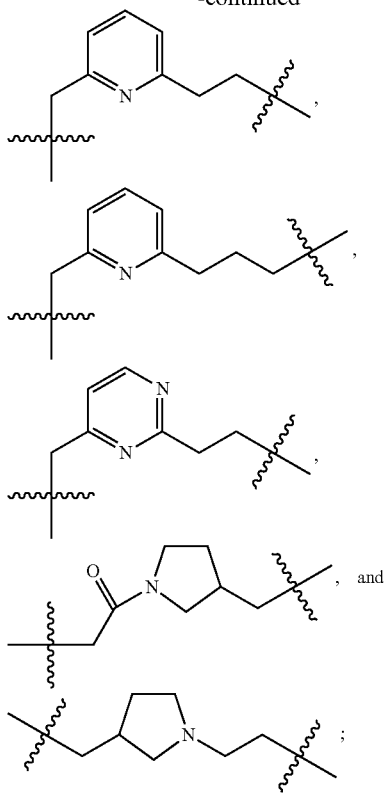

wherein each ring moiety is substituted with 0-1 $R^{7a}$;
Y is independently selected from the group consisting of: $CH_2$, O, NH, $N(C_{1-4}$ alkyl), $N(CO_2(C_{1-4}$ alkyl)), —CONH—, —NHCO—, —CONHCH$_2$—, —CON($C_{1-4}$ alkyl)CH$_2$—, —OCONH—, —NHCONH—, and —SO$_2$NH—;
$L_1$ is independently selected from the group consisting of: a bond and —CH=CH—;
$R^1$ is, independently at each occurrence, selected from the group consisting of: halogen, $C_{1-4}$ alkyl, OH, $C_{1-4}$ alkoxy, CO($C_{1-4}$ alkyl), CN, $CH_2F$, $CHF_2$, $OCHF_2$, $NH_2$, $N(C_{1-4}$ alkyl)$_2$, —$CH_2NH_2$, —$CH_2NHCO_2(C_{1-4}$ alkyl), and —C(=NH),$NH_2$;
$R^{1b}$ is independently selected from the group consisting of: H and halogen;
$R^2$ is independently a 5-membered heterocycle selected from: triazolyl and tetrazolyl;
$R^3$ is independently selected from the group consisting of: H, halogen, $C_{1-4}$ alkyl, and CN;
$R^{6a}$ is independently selected from the group consisting of: H, halogen, $NH_2$, $CO_2H$, $CONH_2$, $CO_2(C_{1-4}$ alkyl), —NHCO$_2$($C_{1-4}$ alkyl), —NHCO$_2$(CH$_2$)$_2$OH, —NHCO$_2$(CH$_2$)$_2$O($C_{1-4}$ alkyl), —NHCO$_2$CH$_2$CO$_2$H, —NHCO$_2$CH$_2$CH($C_{1-4}$ alkyl)O($C_{1-4}$ alkyl), and

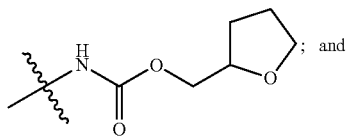 ; and $R^{7a}$ is independently selected from the group consisting of: halogen, $C_{1-4}$ alkyl, and $N(C_{1-4}$ alkyl)$_2$.

10. A compound of Formula (IIIb) or Formula (IIIc):

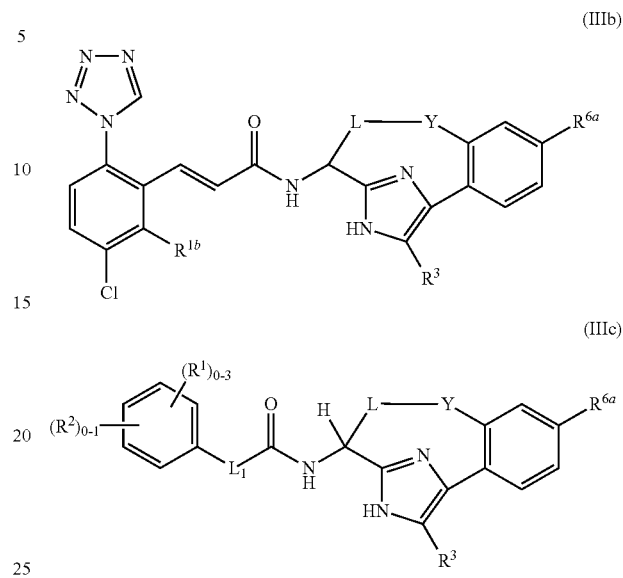

or a stereoisomer, a tautomer, a pharmaceutically acceptable salt thereof, wherein:

L is independently selected from the group consisting of:

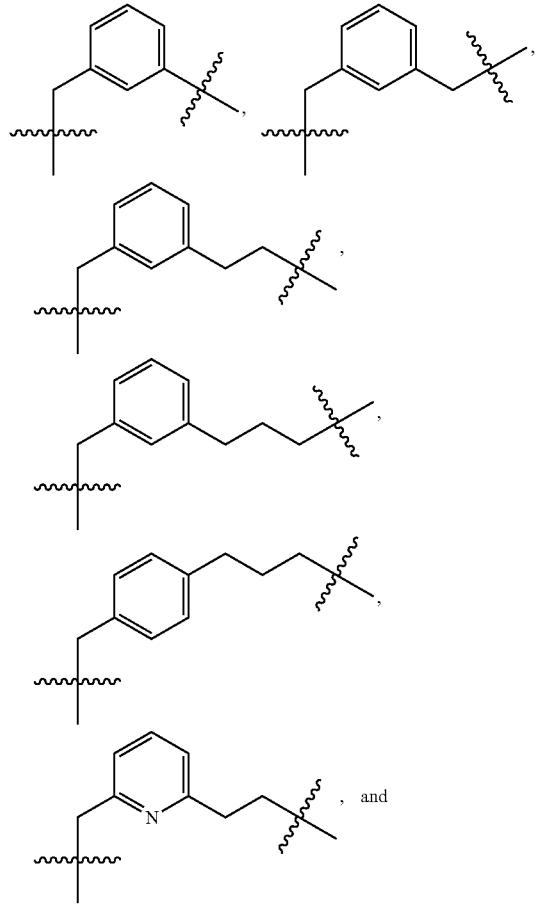

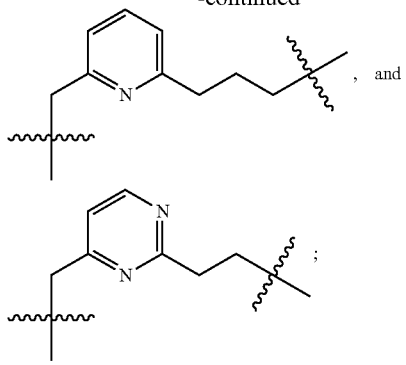, and ;

wherein each ring moiety is substituted with 0-1 $R^{7a}$;

Y is independently selected from the group consisting of: $CH_2$, O, NH, —CONH—, —NHCO—, —CONHCH$_2$—, —CON($C_{1-4}$ alkyl)CH$_2$—, —OCONH—, —NHCONH—, and —SO$_2$NH—;

Lhd 1 is independently selected from the group consisting of: a bond and —CH=CH—;

$R^1$ is, independently at each occurrence, selected from the group consisting of: halogen, $C_{1-4}$ alkyl, OH, $C_{1-4}$ alkoxy, CO($C_{1-4}$ alkyl), CN, $CH_2F$, $CHF_2$, $OCHF_2$, —CH$_2$NH$_2$, —CH$_2$NHCO$_2$($C_{1-4}$ alkyl), and —C(=NH),NH2;

$R^{1b}$ is independently selected from the group consisting of: H and halogen;

$R^3$ is independently selected from the group consisting of: H, halogen, $C_{1-4}$ alkyl, and CN;

Rhu 6a is independently selected from the group consisting of: H, halogen, NH$_2$, CO$_2$H, CONH$_2$, —NHCO$_2$($C_{1-4}$ alkyl), —NHCO$_2$(CH$_2$)$_2$OH, —NHCO$_2$(CH$_2$)$_2$O($C_{1-4}$ alkyl), —NHCO$_2$CH$_2$CH($C_{1-4}$ alkyl)O($C_{1-4}$ alkyl), and

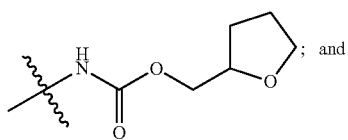 [SMILES: *NC(=O)OCC1CCCO1]; and $R^{7a}$ is independently selected from the group consisting of: halogen, $C_{1-4}$ alkyl, and N($C_{1-4}$ alkyl)$_2$.

11. A compound of Formula (IIIc):

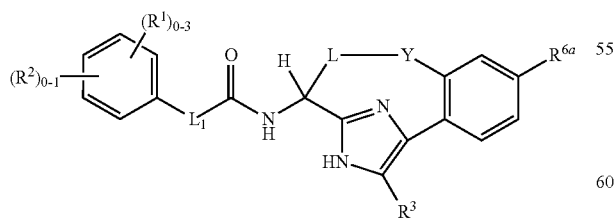

(IIIc)

or a stereoisomer, a tautomer, a pharmaceutically acceptable salt thereof, wherein:

L-Y is independently selected from the group consisting of:

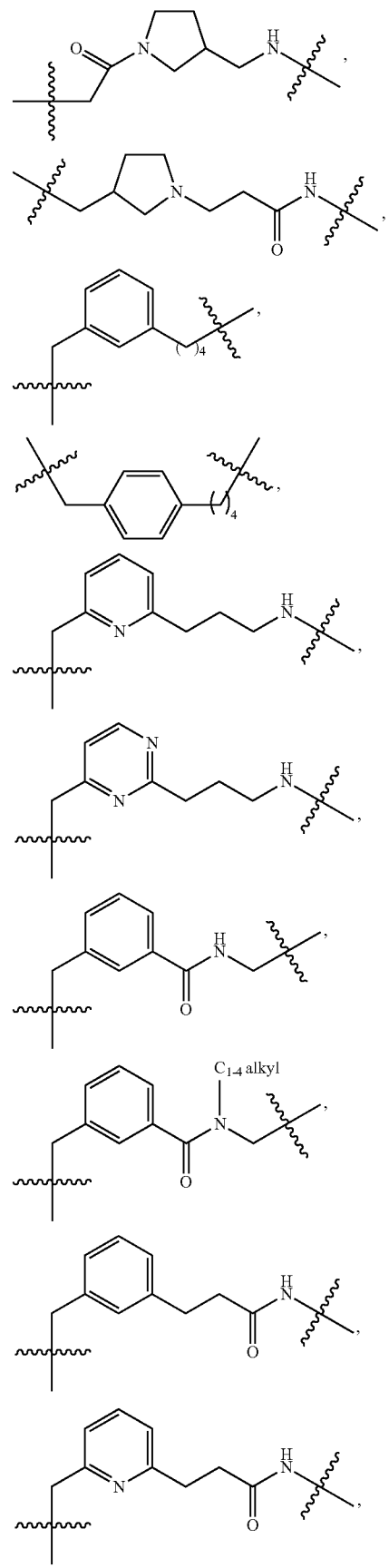

-continued

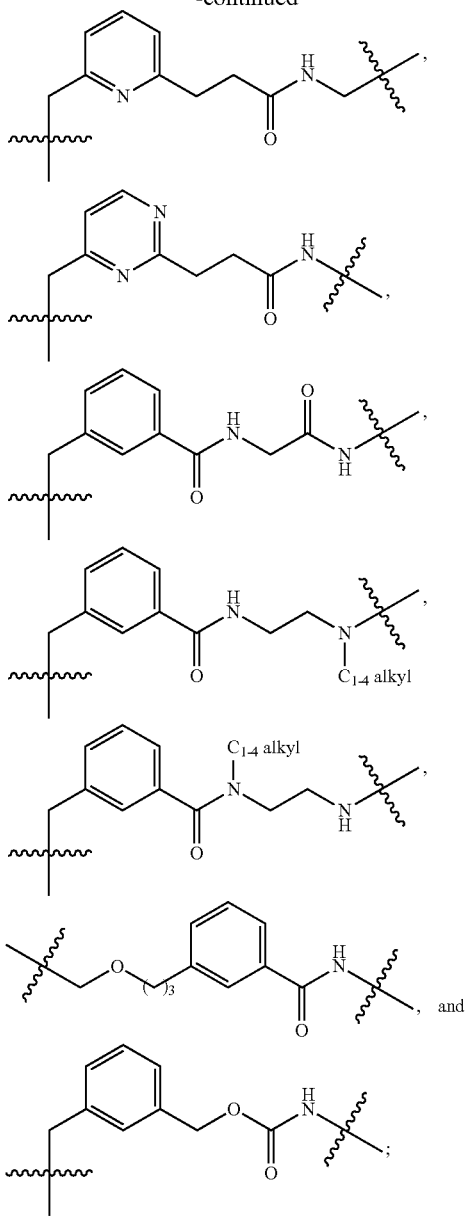

wherein each ring moiety is substituted with 0-1 $R^{7a}$;
$L_1$ is independently selected from the group consisting of: a bond and —CH=CH—;
$R^1$ is, independently at each occurrence, selected from the group consisting of: halogen, $C_{1-4}$ alkyl, $C_{1-4}$ alkoxy, CO($C_{1-4}$ alkyl), CN, $CHF_2$, and $OCHF_2$;
$R^{1b}$ is independently selected from the group consisting of: H and halogen;
$R^2$ is independently a 5-membered heterocycle selected from: pyrazolyl, imidazolyl, triazolyl, and tetrazolyl;
$R^3$ is independently selected from the group consisting of: H and halogen;
$R^{6a}$ is independently selected from the group consisting of: H, halogen, NH($C_{1-4}$ alkyl), and $NHCO_2$($C_{1-4}$ alkyl); and
$R^{7a}$ is independently selected from the group consisting of: halogen, $C_{1-4}$ alkyl, N($C_{1-4}$ alkyl)$_2$.

12. The compound of claim 11 or a stereoisomer, a tautomer, a pharmaceutically acceptable salt thereof, wherein:

L-Y is independently selected from the group consisting of:

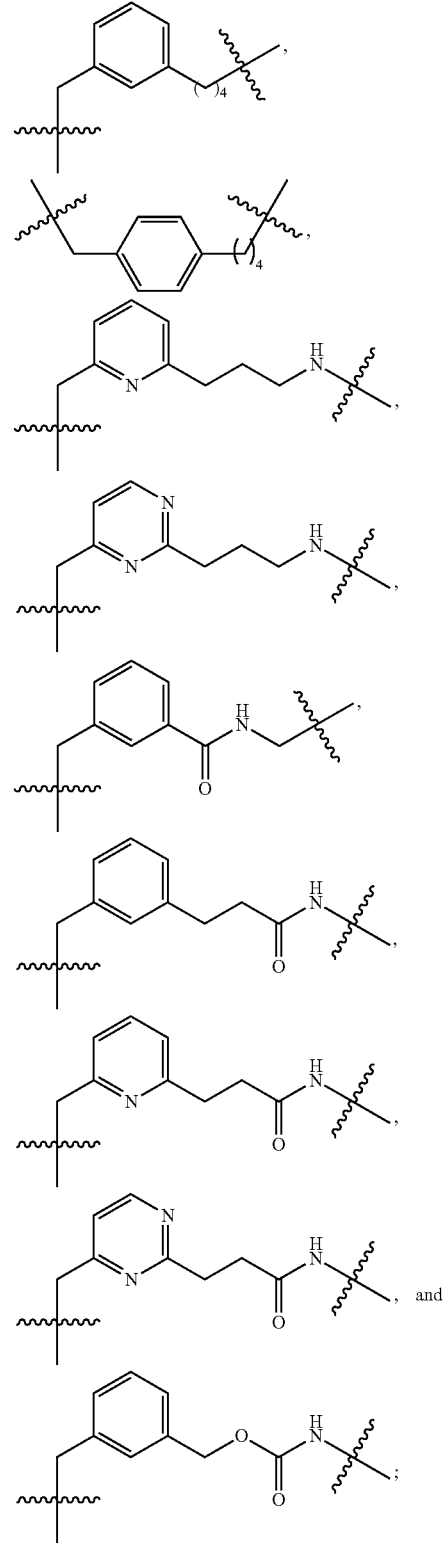

wherein each ring moiety is substituted with 0-1 $R^{7a}$;
$R^2$ is independently triazolyl or tetrazolyl; and
$R^{6a}$ is independently selected from the group consisting of: H, halogen, and $NHCO_2$($C_{1-4}$ alkyl).

13. The compound of claim 11 or a stereoisomer, a tautomer, a pharmaceutically acceptable salt thereof, wherein:

L-Y is independently selected from the group consisting of:

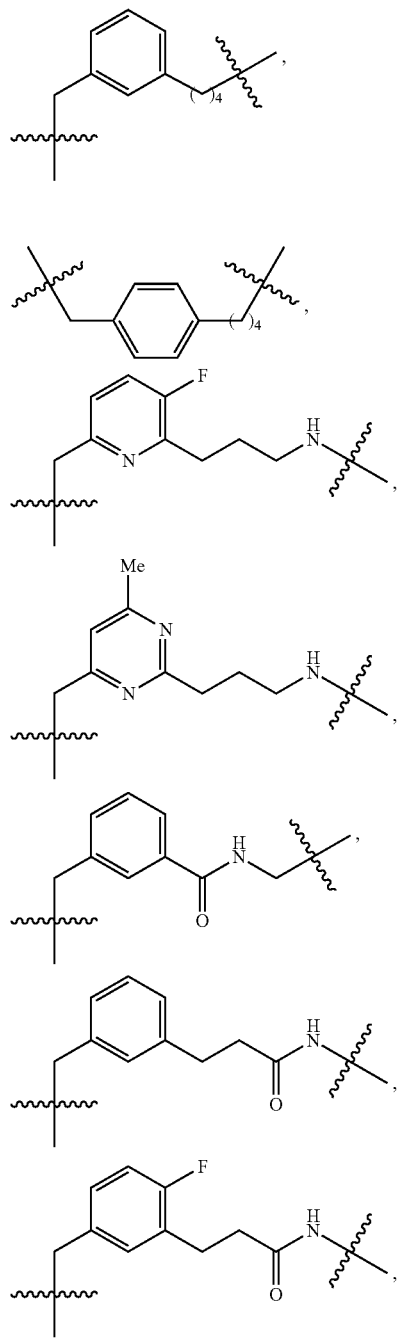

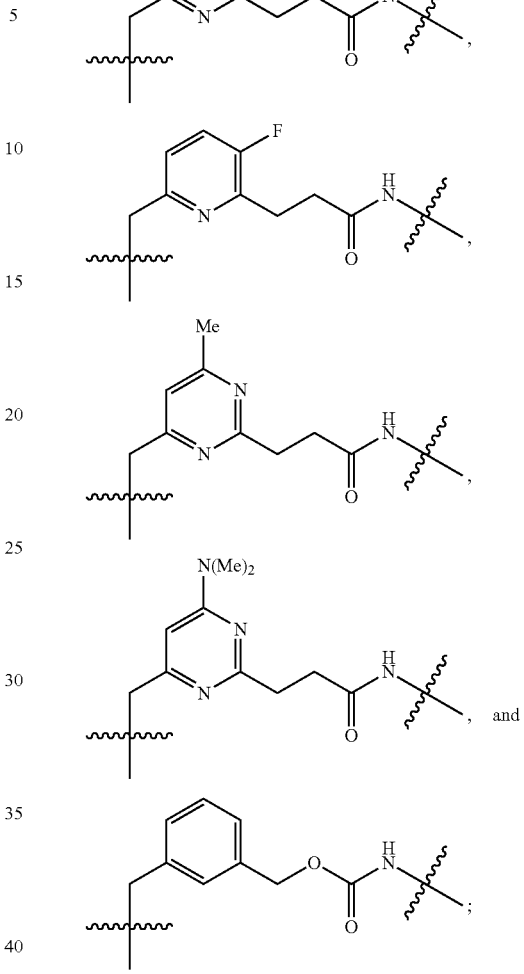

$R^1$ is independently selected from the group consisting of: F, Cl, Me, OMe, COMe, CN, $CHF_2$, and $OCHF_2$;

$R^{1b}$ is independently selected from the group consisting of: H and F;

$R^2$ is tetrazolyl;

$R^3$ is independently selected from the group consisting of: H and Cl; and $R^{6a}$ is independently selected from the group consisting of: H, F, and $NHCO_2Me$.

14. A pharmaceutical composition comprising a pharmaceutically acceptable carrier and at least one of the compounds of claim 1.

UNITED STATES PATENT AND TRADEMARK OFFICE
CERTIFICATE OF CORRECTION

PATENT NO.         : 8,828,983 B2
APPLICATION NO.    : 13/577666
DATED              : September 9, 2014
INVENTOR(S)        : Mimi L. Quan et al.

It is certified that error appears in the above-identified patent and that said Letters Patent is hereby corrected as shown below:

In the Claims:

Claim 1:

Column 182, line 65, change "$_{(C1-4}$ alkyl)," to -- ($C_{1-4}$ alkyl), --.

Column 183, line 3, change "$R^{a;}$" to -- $R^a$; --.

Column 183, line 4, change "$R^2$is" to -- $R^2$ is --.

Column 183, line 34, change "($C_{l-4}$ alkyl)," to -- ($C_{1-4}$ alkyl), --.

Column 184, line 2, change "14" to -- 1-4 --.

Claim 2:

Column 184, lines 37 to 44, after " 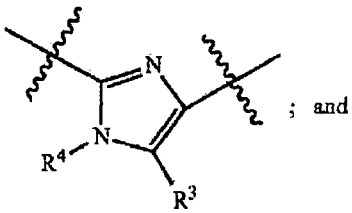 ", delete

" 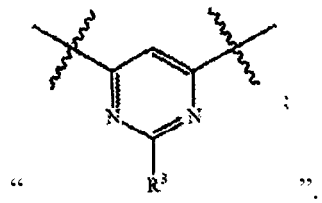 ".

Claim 3:

Column 186, line 12, change "—C(O) NH$_2$," to -- —C(O)NH$_2$, --.

Column 186, line 44, change "$C_{1-4}$ alkyl)," to -- $C_{1-4}$ alkyl, --.

Claim 5:

Column 187, line 1, after "having", delete "or".

Signed and Sealed this
Seventh Day of April, 2015

Michelle K. Lee
*Director of the United States Patent and Trademark Office*

In the Claims:

Claim 6:

Column 187, line 53, change "—C(=NH),NH$_2$," to -- —C(=NH)NH$_2$, --.

Claim 7:

Column 188, line 27, change "—C(=NH),NH$_2$;" to -- —C(=NH)NH$_2$; --.

Claim 8:

Column 189, line 20, change "—C(=NH),NH$_2$;" to -- —C(=NH)NH$_2$; --.

Claim 10:

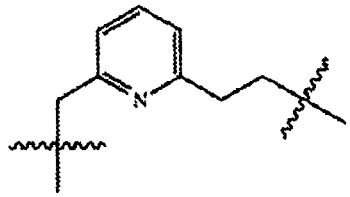

Column 192, line 63, after " ", delete "and".

Column 193, line 23, change "Lhd 1" to -- L$_1$ --.

Column 193, line 25, change "R$^1$is," to -- R$^1$ is, --.

Column 193, line 29, change "—C(=NH),NH2;" to -- —C(=NH)NH$_2$; --.

Column 193, line 35, change "Rhu 6a" to -- R$^{6a}$ --.

Claim 11:

Column 195, line 50, change "L$_1$is" to -- L$_1$ is --.

Column 195, line 52, change "R$^1$is" to -- R$^1$ is --.

Claim 12:

Column 196, line 66, change "R$^6$a" to -- R$^{6a}$ --.